(12) United States Patent
Bacac et al.

(10) Patent No.: US 11,013,801 B2
(45) Date of Patent: May 25, 2021

(54) TREATMENT METHOD

(71) Applicant: Hoffmann-La Roche Inc., Little Falls, NJ (US)

(72) Inventors: Marina Bacac, Schlieren (CH); Stefan Evers, Schlieren (CH); Christian Klein, Schlieren (CH); Pavel Pisa, Schlieren (CH); Eva Rossmann, Basel (CH); Jose Saro, Schlieren (CH); Pablo Umana, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/371,891

(22) Filed: Dec. 7, 2016

(65) Prior Publication Data

US 2017/0209573 A1     Jul. 27, 2017

(30) Foreign Application Priority Data

Dec. 9, 2015   (EP) .................. 15198715
Jun. 2, 2016   (EP) .................. 16172739
Oct. 10, 2016  (EP) .................. 16193151

(51) Int. Cl.
| | | |
|---|---|---|
| A61K 39/00 | (2006.01) | |
| A61K 39/395 | (2006.01) | |
| C07K 16/30 | (2006.01) | |
| C07K 16/28 | (2006.01) | |

(52) U.S. Cl.
CPC .... *A61K 39/39558* (2013.01); *A61K 39/3955* (2013.01); *A61K 39/39583* (2013.01); *C07K 16/2809* (2013.01); *C07K 16/2887* (2013.01); *C07K 16/3007* (2013.01); *A61K 2039/505* (2013.01); *A61K 2039/507* (2013.01); *A61K 2039/54* (2013.01); *A61K 2039/545* (2013.01); *C07K 2317/31* (2013.01); *C07K 2319/00* (2013.01); *C07K 2319/24* (2013.01)

(58) Field of Classification Search
CPC .............................. A61K 2039/505
See application file for complete search history.

(56) References Cited

U.S. PATENT DOCUMENTS

| | | |
|---|---|---|
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,737,086 B2 | 5/2004 | Gutierrez et al. |
| 6,809,185 B1 | 10/2004 | Schoonjans et al. |
| 7,235,641 B2 | 6/2007 | Kufer et al. |
| 7,332,581 B2 | 2/2008 | Presta |
| 7,695,936 B2 | 4/2010 | Carter et al. |
| 8,227,577 B2 | 7/2012 | Klein et al. |
| 8,236,308 B2 | 8/2012 | Kischel et al. |
| 8,242,247 B2 | 8/2012 | Klein et al. |
| 8,642,742 B2 | 2/2014 | Hofer et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,846,042 B2 | 9/2014 | Zhou |
| 8,969,526 B2 | 3/2015 | Baehner et al. |
| 9,068,008 B2 | 6/2015 | Mossner et al. |
| 9,206,260 B2 | 12/2015 | Hofer et al. |
| 9,266,938 B2 | 2/2016 | Ast et al. |
| 9,266,967 B2 | 2/2016 | Klein et al. |
| 9,382,323 B2 | 7/2016 | Brinkmann et al. |
| 9,447,159 B2 | 9/2016 | Ast et al. |
| 9,526,797 B2 | 12/2016 | Gerdes et al. |
| 2002/0004587 A1 | 1/2002 | Miller et al. |
| 2006/0115475 A1 | 6/2006 | Carton et al. |
| 2007/0071675 A1 | 3/2007 | Wu et al. |
| 2007/0111281 A1 | 5/2007 | Sondermann et al. |
| 2007/0219133 A1 | 9/2007 | Lazar et al. |
| 2008/0241152 A1 | 10/2008 | Alitalo et al. |
| 2009/0162359 A1 | 6/2009 | Klein et al. |
| 2009/0162360 A1 | 6/2009 | Klein et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |

(Continued)

FOREIGN PATENT DOCUMENTS

| | | |
|---|---|---|
| EA | 015009 B1 | 4/2011 |
| EP | 0404097 B1 | 9/1996 |

(Continued)

OTHER PUBLICATIONS

García-Muñoz et al. (Immunotherapy. Mar. 1, 2018; 10 (6): 491-9).*
Jiang et al. (J. Biol. Chem. Feb. 11, 2005; 280 (6): 4656-4662).*
Riemer et al. (Mol. Immunol. 2005; 42: 1121-1124).*
FDA Drug Safety Document: GAZYVA™ [obinutuzumab] (Reference ID: 3400019) (last revised Nov. 2013); pp. 1-15.*
Peng et al. (PLoS One. 2012; 7 (5): e36412; pp. 1-14).*
Hassan, R. et al. et al., "Pretreatment with rituximab does not inhibit the human immune response against the immunogenic protein LMB-1" Clin Cancer Res 10:16-18 (Jan. 1, 2004).

(Continued)

*Primary Examiner* — Stephen L Rawlings
(74) *Attorney, Agent, or Firm* — Clark & Elbing LLP; Karen L. Elbing

(57) ABSTRACT

The present invention relates to methods of treating a disease, and methods for reduction of the formation of anti-drug antibodies (ADAs) in response to the administration of a therapeutic agent. The invention further relates to methods of treating a disease, particularly a B-cell proliferative disorder, and methods for reduction of adverse effects in response to the administration of a therapeutic agent, particularly a T-cell activating therapeutic agent.

28 Claims, 17 Drawing Sheets

Specification includes a Sequence Listing.

(56) References Cited

U.S. PATENT DOCUMENTS

| | | |
|---|---|---|
| 2010/0316645 A1 | 12/2010 | Imhof-Jung et al. |
| 2011/0293613 A1 | 12/2011 | Brinkmann et al. |
| 2012/0149876 A1 | 6/2012 | von Kreudenstein et al. |
| 2012/0225071 A1 | 9/2012 | Klein et al. |
| 2012/0251531 A1 | 10/2012 | Baehner et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0166661 A1 | 6/2015 | Chen et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145340 A1 | 5/2016 | Borges et al. |
| 2016/0145354 A1 | 5/2016 | Bacac et al. |
| 2016/0175397 A1 | 6/2016 | Umana et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |
| 2018/0134798 A1 | 5/2018 | Chu et al. |
| 2018/0312589 A1 | 11/2018 | Bacac et al. |

FOREIGN PATENT DOCUMENTS

| | | |
|---|---|---|
| EP | 1870459 A1 | 12/2007 |
| EP | 1870459 A4 | 9/2010 |
| EP | 2261258 A1 | 12/2010 |
| EP | 2578230 A1 | 4/2013 |
| EP | 2647707 A1 | 10/2013 |
| EP | 2647707 A4 | 4/2014 |
| EP | 1870459 B1 | 6/2016 |
| JP | 2012-528092 A | 11/2012 |
| JP | 2014-534806 A | 12/2014 |
| TW | 201321413 A | 6/2013 |
| TW | 201326212 A | 7/2013 |
| WO | WO-91/01990 A1 | 2/1991 |
| WO | WO-91/03493 A1 | 3/1991 |
| WO | WO-93/01161 A1 | 1/1993 |
| WO | WO-93/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | WO-02/09573 A2 | 2/2002 |
| WO | WO-2005/044859 A2 | 5/2005 |
| WO | WO-2005/044859 A3 | 8/2005 |
| WO | WO-2005/086875 A2 | 9/2005 |
| WO | WO-2006/082515 A2 | 8/2006 |
| WO | WO-2007/024715 A2 | 3/2007 |
| WO | WO-2007/042261 A2 | 4/2007 |
| WO | WO-2007/071422 A2 | 6/2007 |
| WO | WO-2007/071426 A1 | 6/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | 2009/134738 A1 | 11/2009 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/023787 A1 | 3/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/143545 A1 | 11/2011 |
| WO | WO-2012/058768 A1 | 5/2012 |
| WO | WO-2012/058768 A8 | 6/2012 |
| WO | WO-2012/073985 A1 | 6/2012 |
| WO | 2012/107417 A1 | 8/2012 |
| WO | 2012/117002 A1 | 9/2012 |
| WO | WO-2012/130831 A1 | 10/2012 |
| WO | WO-2012/146628 A1 | 11/2012 |
| WO | WO-2012/154530 A1 | 11/2012 |
| WO | WO-2012/158818 A2 | 11/2012 |
| WO | WO-2012/162067 A2 | 11/2012 |
| WO | WO-2013/012414 A1 | 1/2013 |
| WO | WO-2013/026831 A1 | 2/2013 |
| WO | WO-2013/026832 A1 | 2/2013 |
| WO | WO-2013/026833 A1 | 2/2013 |
| WO | WO-2013/026837 A1 | 2/2013 |
| WO | WO-2013/096291 A2 | 6/2013 |
| WO | WO-2013/157953 A1 | 10/2013 |
| WO | WO-2013/157954 A1 | 10/2013 |
| WO | WO-2014/022540 A1 | 2/2014 |
| WO | WO-2014/028560 A2 | 2/2014 |
| WO | WO-2014/047231 A1 | 3/2014 |
| WO | 2014/056783 A1 | 4/2014 |
| WO | WO-2014/028560 A3 | 5/2014 |
| WO | WO-2014/081955 A1 | 5/2014 |
| WO | WO-2014/122143 A1 | 8/2014 |
| WO | WO-2014/122144 A1 | 8/2014 |
| WO | WO-2014/122251 A2 | 8/2014 |
| WO | WO-2014/131694 A1 | 9/2014 |
| WO | WO-2014/131711 A1 | 9/2014 |
| WO | WO-2014/141152 A2 | 9/2014 |
| WO | WO-2014/153002 A1 | 9/2014 |
| WO | WO-2014/122251 A3 | 10/2014 |
| WO | WO-2014/167022 A1 | 10/2014 |
| WO | WO-2014/141152 A3 | 12/2014 |
| WO | WO-2014/191113 A1 | 12/2014 |
| WO | WO-2014/191113 A8 | 2/2015 |
| WO | 2015/095410 A1 | 6/2015 |
| WO | WO-2015/101588 A1 | 7/2015 |
| WO | WO-2015/150447 A1 | 10/2015 |
| WO | WO-2016/020065 A1 | 2/2016 |

(56) References Cited

FOREIGN PATENT DOCUMENTS

| WO | WO-2016/020309 A1 | 2/2016 |
|---|---|---|
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/179003 A1 | 11/2016 |
| WO | WO-2017/021450 A1 | 2/2017 |
| WO | WO-2018/093821 A1 | 5/2018 |

OTHER PUBLICATIONS

Klein et al., "Epitope interactions of monoclonal antibodies targeting CD20 and their relationship to functional properties" mABs 5(1):22-33 ( 2013).
Mossoba et al., "Pentostatin Plus Cyclophosphamide Safely and Effectively Prevents Immunotoxin Immunogenicity in Murine Hosts" Clinical Cancer Research 17:3697-3705 ( 2011).
Onda et al., "Tofacitinib Suppresses Antibody Responses to Protein Therapeutics in Murine Hosts" J Immunol 193:48-55 ( 2014).
PCT ISA for PCT/EP2016/079800.
Siegall et al., "Prevention of Immunotoxin-Induced Immunogenicity by Coadministration with CTLA4Ig Enhances Antitumor Efficacy" J Immunol 159:5168-5173 ( 1997).
Van Oers et al., "CD20 antibodies: type II to tango?" Blood 119:5061-5063 ( 2012).
Atwell et al., "Stable heterodimers from remodeling the domain interface of a homodimer using a phage display library," J Mol Biol. 270(1):26-35 (1997).
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).
Carter, "Bispecific human IgG by design," J Immunol Methods. 248(1-2):7-15 (2001).
Chan et al., "Variable region domain exchange in human IgGs promotes antibody complex formation with accompanying structural changes and altered effector functions," Mol Immunol. 41(5):527-38 (2004).
Edelman et al., "The covalent structure of an entire gammaG immunoglobulin molecule," Proc Natl Acad Sci U S A. 63(1):78-85 (1969).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).

Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Oshimi et al., "Increased lysis of patient CD10-positive leukemic cells by T cells coated with anti-CD3 Fab' antibody cross-linked to anti-CD10 Fab' antibody," Blood. 77(5)1044-9 (1991).
Pessano et al., "The T3/T cell receptor complex: antigenic distinction between the two 20-kd T3 (T3-delta and T3-epsilon) subunits," EMBO J. 4(2):337-44 (1985).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BiTE antibody that engages patient-derived T cells," J Immunother. 34(8):597-605 (2011).
Tutt et al., "Trispecific F(ab')3 derivatives that use cooperative signaling via the TCR/CD3 complex and CD2 to activate and redirect resting cytotoxic T cells," J Immunol. 147(1):60-9 (1991).
Wolf et al., "BiTEs: bispecific antibody constructs with unique anti-tumor activity," Drug Discov Today. 10(18):1237-44 (2005).
Zhu et al., "Identification of heavy chain residues in a humanized anti-CD3 antibody important for efficient antigen binding and T cell activation," J Immunol. 155(4):1903-10 (1995).
Freeman et al., "Pattern of cytokine release in patients with chronic lymphocytic leukaemia treated with obinutuzumab and possible relationship with development of infusion related reactions (IRR)," Br J Haematol. 169(Suppl 1):64 Abstract 154 (2015).
Freeman et al., "4674 Pattern of Cytokine Release in Patients with Chronic Lymphocytic Leukemia Treated with Obinutuzumab and Possible Relationship with Development of Infusion Related Reactions (IRR)," 56th ASH Annual Meeting and Exposition, Dec. 6-9, San Francisco, CA. Blood. 124(21): Abstract 4674 (2014) (3 pages).
Freeman et al., "Cytokine release in patients treated with obinutuzumab, a glycoengineered type II anti-CD20 antibody and possible relationship with development of infusion related reactions in patients with chronic lymphocytic leukaemia," Br J Haematol. 165(Suppl 1):70 Abstract 168 (2014).
Freeman et al., "Cytokine release in patients with CLL treated with obinutuzumab and possible relationship with infusion-related reactions," Blood. 126(24):2646-9 (2015).
Xu et al., "Cytokine release syndrome in cancer immunotherapy with chimeric antigen receptor engineered T cells," Cancer Lett. 343(2):172-8 (2014).
Written Opinion for International Patent Application No. PCT/EP2016/079800, dated Jul. 31, 2017 (14 pages).
Caldas et al., "Humanization of the anti-CD18 antibody 6.7: An unexpected effect of a framework residue in binding to antigen," Mol Immunol. 39(15):941-52 (2003).
Casset et al., "A peptide mimetic of an anti-CD4 monoclonal antibody by rational design," Biochem Biophys Res Commun. 307(1):198-205 (2003).

(56) References Cited

OTHER PUBLICATIONS

Chang et al., "Loop-sequence features and stability determinants in antibody variable domains by high-throughput experiments," Structure. 22(1):9-21 (2014).

Chien et al., "Significant structural and functional change of an antigen-binding site by a distant amino acid substitution: proposal of a structural mechanism," Proc Natl Acad Sci U S A. 86(14):5532-6 (1989).

Chin et al., "Immune intervention with monoclonal antibodies targeting CD152 (CTLA-4) for autoimmune and malignant diseases," Chang Gung Med J. 31(1):1-15 (2008).

Conaghan et al., "Targeted killing of colorectal cancer cell lines by a humanised IgG1 monoclonal antibody that binds to membrane-bound carcinoembryonic antigen," Br J Cancer. 98(7):1217-25 (2008).

De Pascalis et al., "Grafting of "abbreviated" complementarity-determining regions containing specificity-determining residues essential for ligand contact to engineer a less immunogenic humanized monoclonal antibody," J Immunol. 169(6):3076-84 (2002).

Giusti et al., "Somatic diversification of S107 from an antiphosphocholine to an anti-DNA autoantibody is due to a single base change in its heavy chain variable region," Proc Natl Acad Sci U S A. 84(9):2926-30 (1987).

Graves et al., "Antagonistic and agonistic anti-canine CD28 monoclonal antibodies: tools for allogeneic transplantation," Transplantation. 91(8):833-40 (2011).

Güssow et al., "Humanization of monoclonal antibodies," Methods Enzymol. 203:99-121 (1991).

Holm et al., "Functional mapping and single chain construction of the anti-cytokeratin 8 monoclonal antibody TS1," Mol Immunol. 44(6):1075-84 (2007).

Huehls et al., "Bispecific T-cell engagers for cancer immunotherapy," Immunol Cell Biol. 93(3):290-6 (2015).

Jiang et al., "A novel peptide isolated from a phage display peptide library with trastuzumab can mimic antigen epitope of HER-2," J Biol Chem. 280(6):4656-62 (2005).

Klein et al., Chapter 62: Obinutuzumab (Gazyva®), a Novel Glycoengineered Type II CD20 Antibody for the Treatment of Chronic Lymphocytic Leukemia and Non-Hodgkin's Lymphoma. *Handbook of Therapeutic Antibodies, Second Edition*. Stefan Dubel and Janice M. Reichert, 1695-1732 (2014) (38 pages).

MacCallum et al., "Antibody-antigen interactions: contact analysis and binding site topography," J Mol Biol. 262(5):732-45 (1996).

MacLean et al., "Anti-CD3:anti-IL-2 receptor-bispecific mAb-mediated immunomodulation. Low systemic toxicity, differential effect on lymphoid tissue, and inhibition of cell-mediated hypersensitivity," J Immunol. 155(7):3674-82 (1995).

Mariuzza et al., "The structural basis of antigen-antibody recognition," Annu Rev Biophys Biophys Chem. 16:139-59 (1987).

Mössner et al., "Increasing the efficacy of CD20 antibody therapy through the engineering of a new type II anti-CD20 antibody with enhanced direct and immune effector cell-mediated B-cell cytotoxicity," Blood. 115(22):4393-402 (2010) (11 pages).

Neumaier et al., "Cloning of the genes for T84.66, an antibody that has a high specificity and affinity for carcinoembryonic antigen, and expression of chimeric human/mouse T84.66 genes in myeloma and Chinese hamster ovary cells," Cancer Res. 50(7):2128-34 (1990) (8 pages).

Peng et al., "The CEA/CD3-bispecific antibody MEDI-565 (MT111) binds a nonlinear epitope in the full-length but not a short splice variant of CEA," PLoS One. 7(5):e36412 (2012) (14 pages).

Plückthun, Antibodies from *Escherichia coli. The Pharmacology of Monoclonal Antibodies*. Rosenberg & Moore, 269-315 (1994).

Riemer et al., "Matching of trastuzumab (Herceptin) epitope mimics onto the surface of Her-2/neu—a new method of epitope definition," Mol Immunol. 42(9):1121-4 (2005).

Rudikoff et al., "Single amino acid substitution altering antigen-binding specificity," Proc Natl Acad Sci U S A. 79(6):1979-83 (1982).

Sauerborn et al., "Antibody response against Betaferon® in immune tolerant mice: involvement of marginal zone B-cells and CD4+ T-cells and apparent lack of immunological memory," J Clin Immunol. 33(1):255-63 (2013) (9 pages).

Stancovski et al., "Mechanistic aspects of the opposing effects of monoclonal antibodies to the ERBB2 receptor on tumor growth," Proc Natl Acad Sci U S A. 88(19):8691-5 (1991).

Stewart et al., "Humanisation and characterisation of PR1A3, a monoclonal antibody specific for cell-bound carcinoembryonic antigen," Cancer Immunol Immunother. 47(6):299-306 (1999).

Strop et al., "Generating bispecific human IgG1 and IgG2 antibodies from any antibody pair," J Mol Biol. 420(3):204-19 (2012).

Vajdos et al., "Comprehensive functional maps of the antigen-binding site of an anti-ErbB2 antibody obtained with shotgun scanning mutagenesis," J Mol Biol. 320(2):415-28 (2002).

Winkler et al., "Changing the antigen binding specificity by single point mutations of an anti-p24 (HIV-1) antibody," J Immunol. 165(8):4505-14 (2000).

Wu et al., "Humanization of a murine monoclonal antibody by simultaneous optimization of framework and CDR residues," J Mol Biol. 294(1):151-62 (1999).

Yazaki et al., "Humanization of the anti-CEA T84.66 antibody based on crystal structure data," Protein Eng Des Sel. 17(5):481-9 (2004).

Yu et al., "Rationalization and design of the complementarity determining region sequences in an antibody-antigen recognition interface," PLoS One. 7(3):e33340 (2012) (15 pages).

International Search Report and Written Opinion for International Patent Application No. PCT/EP2014/053489, dated Jun. 5, 2014 (14 pages).

International Search Report and Written Opinion for International Patent Application No. PCT/EP2014/053490, dated Jun. 10, 2014 (16 pages).

International Preliminary Report on Patentability for International Patent Application No. PCT/EP2014/053490, dated Sep. 1, 2015 (11 pages).

International Search Report and Written Opinion for International Patent Application No. PCT/EP2016/073171, dated Dec. 20, 2016 (13 pages).

\* cited by examiner

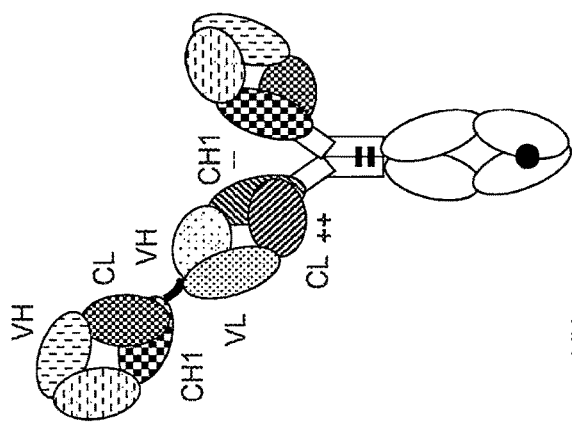
FIG. 6G  FIG. 6H  FIG. 6I  FIG. 6J
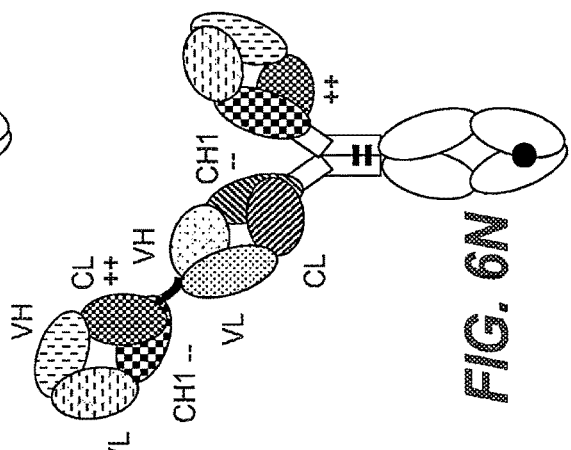
FIG. 6K  FIG. 6L  FIG. 6M  FIG. 6N

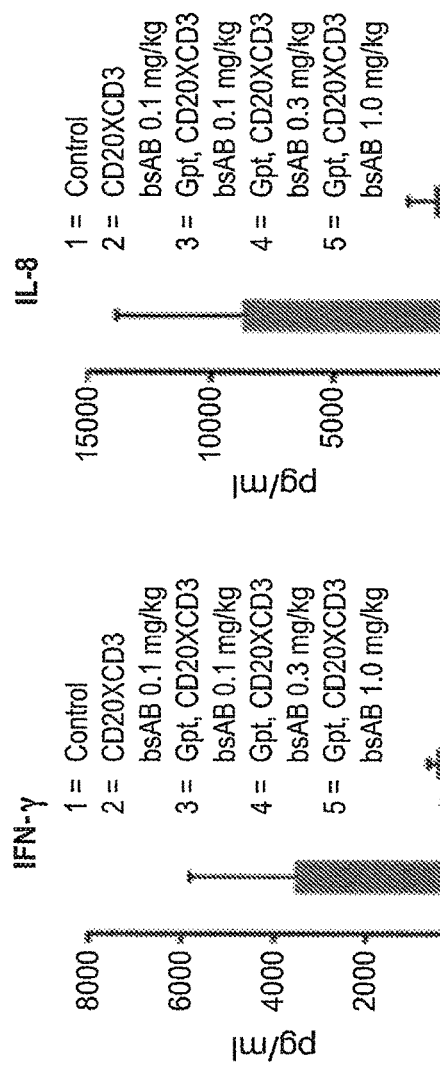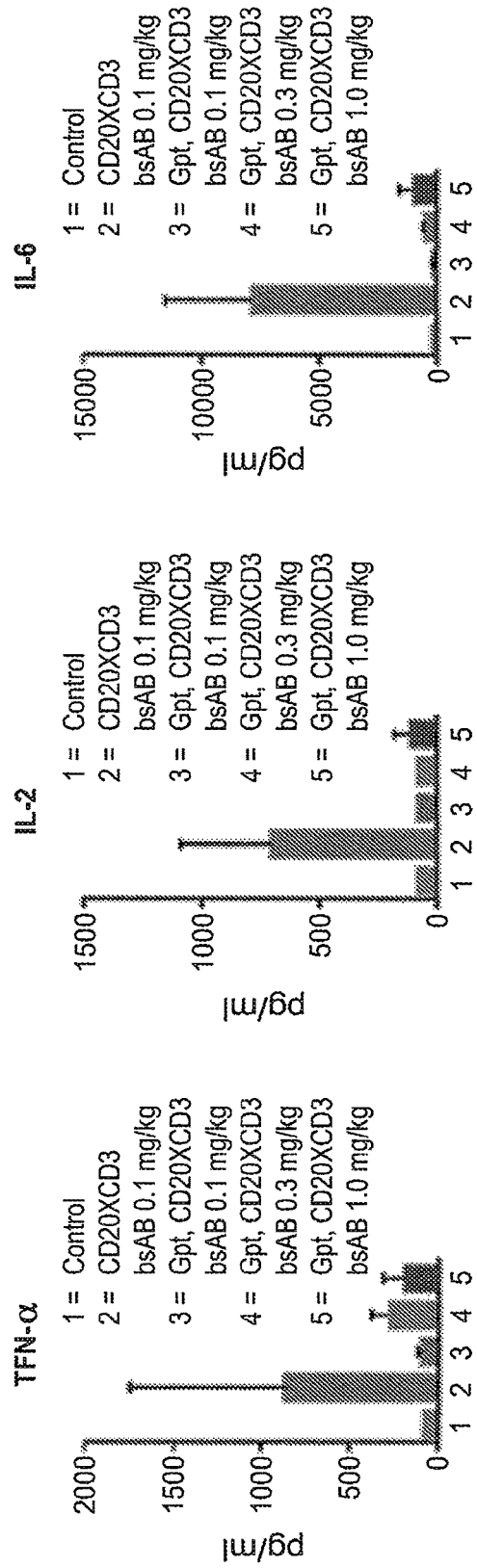

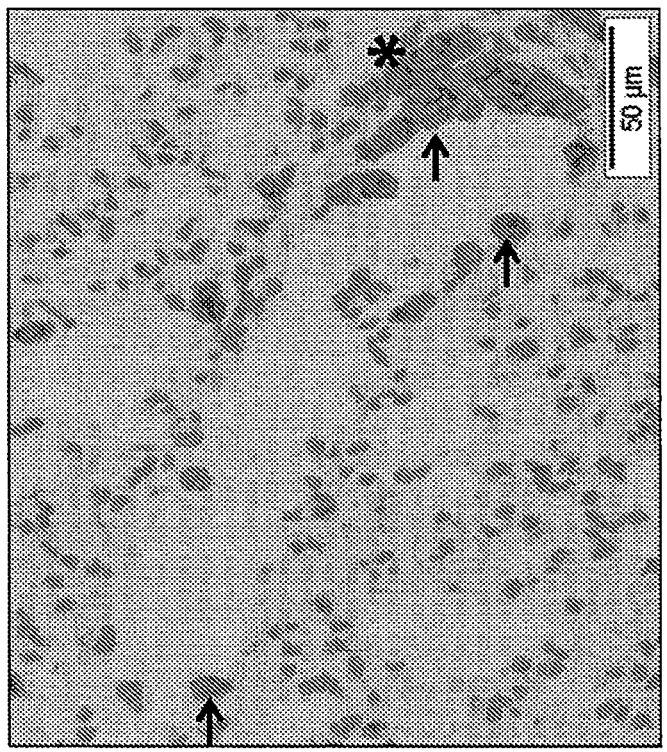
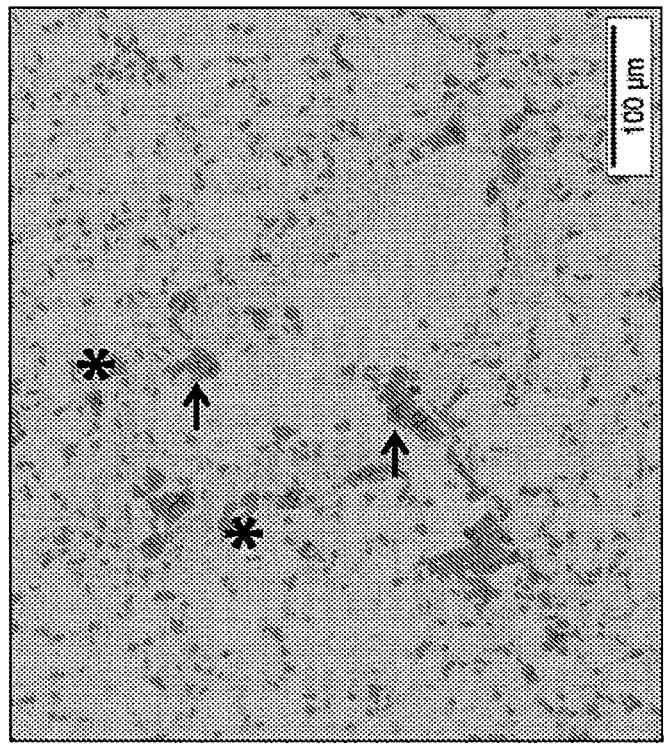
FIG. 13A
FIG. 13B

SEQUENCE LISTING

```
<160> NUMBER OF SEQ ID NOS: 150

<210> SEQ ID NO 1
<211> LENGTH: 297
<212> TYPE: PRT
<213> ORGANISM: Homo sapiens

<400> SEQUENCE: 1

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205
```

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Glu Gln Thr Ile
225                 230                 235                 240

Glu Ile Lys Glu Val Val Gly Leu Thr Glu Thr Ser Ser Gln Pro
                245                 250                 255

Lys Asn Glu Glu Asp Ile Glu Ile Pro Ile Gln Glu Glu Glu
                260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 2
<211> LENGTH: 112
<212> TYPE: PRT
<213> ORGANISM: Mus musculus

<400> SEQUENCE: 2

Gly Pro Glu Leu Val Lys Pro Gly Ala Ser Val Lys Ile Ser Cys Lys
1               5                   10                  15

Ala Ser Gly Tyr Ala Phe Ser Tyr Ser Trp Met Asn Trp Val Lys Leu
                20                  25                  30

Arg Pro Gly Gln Gly Leu Glu Trp Ile Gly Arg Ile Phe Pro Gly Asp
            35                  40                  45

Gly Asp Thr Asp Tyr Asn Gly Lys Phe Lys Gly Lys Ala Thr Leu Thr
        50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
            100                 105                 110

<210> SEQ ID NO 3
<211> LENGTH: 103
<212> TYPE: PRT
<213> ORGANISM: Mus musculus

<400> SEQUENCE: 3

Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
                20                  25                  30

Gln Lys Pro Gly Gln Ser Pro Gln Leu Leu Ile Tyr Gln Met Ser Asn
            35                  40                  45

Leu Val Ser Gly Val Pro Asp Arg Phe Ser Ser Gly Ser Gly Thr
        50                  55                  60

Asp Phe Thr Leu Arg Ile Ser Arg Val Glu Ala Glu Asp Val Gly Val
65                  70                  75                  80

Tyr Tyr Cys Ala Gln Asn Leu Glu Leu Pro Tyr Thr Phe Gly Gly Gly
                85                  90                  95

Thr Lys Leu Glu Ile Lys Arg
            100

<210> SEQ ID NO 4

```
<211> LENGTH: 5
<212> TYPE: PRT
<213> ORGANISM: Artificial Sequence
<220> FEATURE:
<223> OTHER INFORMATION: CD20 HCDR1

<400> SEQUENCE: 4

Tyr Ser Trp Ile Asn
1               5

<210> SEQ ID NO 5
<211> LENGTH: 17
<212> TYPE: PRT
<213> ORGANISM: Artificial Sequence
<220> FEATURE:
<223> OTHER INFORMATION: CD20 HCDR2

<400> SEQUENCE: 5

Arg Ile Phe Pro Gly Asp Gly Asp Thr Asp Tyr Asn Gly Lys Phe Lys
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: CD20 HCDR3

<400> SEQUENCE: 6

Asn Val Phe Asp Gly Tyr Trp Leu Val Tyr
1               5                   10

<210> SEQ ID NO 7
<211> LENGTH: 16
<212> TYPE: PRT
<213> ORGANISM: Artificial Sequence
<220> FEATURE:
<223> OTHER INFORMATION: CD20 LCDR1

<400> SEQUENCE: 7

Arg Ser Ser Lys Ser Leu Leu His Ser Asn Gly Ile Thr Tyr Leu Tyr
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: CD20 LCDR2

<400> SEQUENCE: 8

Gln Met Ser Asn Leu Val Ser
1               5

<210> SEQ ID NO 9
<211> LENGTH: 9
<212> TYPE: PRT
<213> ORGANISM: Artificial Sequence
<220> FEATURE:
<223> OTHER INFORMATION: CD20 LCDR3

<400> SEQUENCE: 9

Ala Gln Asn Leu Glu Leu Pro Tyr Thr
1               5
```

```
<210> SEQ ID NO 10
<211> LENGTH: 119
<212> TYPE: PRT
<213> ORGANISM: Artificial Sequence
<220> FEATURE:
<223> OTHER INFORMATION: CD20 VH

<400> SEQUENCE: 10

Gln Val Gln Leu Val Gln Ser Gly Ala Glu Val Lys Pro Gly Ser
1               5                   10                  15

Ser Val Lys Val Ser Cys Lys Ala Ser Gly Tyr Ala Phe Ser Tyr
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: CD20 VL

<400> SEQUENCE: 11

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Arg Thr Val
        115

<210> SEQ ID NO 12
<211> LENGTH: 133
<212> TYPE: PRT
<213> ORGANISM: Homo sapiens

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

```
                    20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 13
<211> LENGTH: 133
<212> TYPE: PRT
<213> ORGANISM: Artificial Sequence
<220> FEATURE:
<223> OTHER INFORMATION: IL2v

<400> SEQUENCE: 13

Ala Pro Ala Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Gly Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 14
<211> LENGTH: 5
<212> TYPE: PRT
<213> ORGANISM: Artificial Sequence
<220> FEATURE:
<223> OTHER INFORMATION: CEA HCDR1

<400> SEQUENCE: 14

Glu Phe Gly Met Asn
 1               5

<210> SEQ ID NO 15
<211> LENGTH: 17
<212> TYPE: PRT
<213> ORGANISM: Artificial Sequence
<220> FEATURE:
```

-continued

```
<223> OTHER INFORMATION: CEA HCDR2

<400> SEQUENCE: 15

Trp Ile Asn Thr Lys Thr Gly Glu Ala Thr Tyr Val Glu Glu Phe Lys
1               5                   10                  15
Gly

<210> SEQ ID NO 16
<211> LENGTH: 12
<212> TYPE: PRT
<213> ORGANISM: Artificial Sequence
<220> FEATURE:
<223> OTHER INFORMATION: CEA HCDR3

<400> SEQUENCE: 16

Trp Asp Phe Ala Tyr Tyr Val Glu Ala Met Asp Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: CEA LCDR1

<400> SEQUENCE: 17

Lys Ala Ser Ala Ala Val Gly Thr Tyr Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: CEA LCDR2

<400> SEQUENCE: 18

Ser Ala Ser Tyr Arg Lys Arg
1               5

<210> SEQ ID NO 19
<211> LENGTH: 10
<212> TYPE: PRT
<213> ORGANISM: Artificial Sequence
<220> FEATURE:
<223> OTHER INFORMATION: CEA LCDR3

<400> SEQUENCE: 19

His Gln Tyr Tyr Thr Tyr Pro Leu Phe Thr
1               5                   10

<210> SEQ ID NO 20
<211> LENGTH: 121
<212> TYPE: PRT
<213> ORGANISM: Artificial Sequence
<220> FEATURE:
<223> OTHER INFORMATION: CEA VH

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45
```

```
Gly Trp Ile Asn Thr Lys Thr Gly Glu Ala Thr Tyr Val Glu Glu Phe
        50                  55                  60

Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
            115                 120

<210> SEQ ID NO 21
<211> LENGTH: 108
<212> TYPE: PRT
<213> ORGANISM: Artificial Sequence
<220> FEATURE:
<223> OTHER INFORMATION: CEA VL

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Lys Ala Ser Ala Ala Val Gly Thr Tyr
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Lys Arg Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Tyr Thr Tyr Pro Leu
                 85                  90                  95

Phe Thr Phe Gly Gln Gly Thr Lys Leu Glu Ile Lys
            100                 105

<210> SEQ ID NO 22
<211> LENGTH: 598
<212> TYPE: PRT
<213> ORGANISM: Artificial Sequence
<220> FEATURE:
<223> OTHER INFORMATION: CEA IL2v HC

<400> SEQUENCE: 22

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Phe
                 20                  25                  30

Gly Met Asn Trp Val Arg Gln Ala Pro Gly Gln Gly Leu Glu Trp Met
             35                  40                  45

Gly Trp Ile Asn Thr Lys Thr Gly Glu Ala Thr Tyr Val Glu Glu Phe
         50                  55                  60

Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
```

```
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                    180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Cys Arg Asp Glu Leu Thr Lys Asn Gln Val Ser
                355                 360                 365
Leu Trp Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Gly Gly Gly Ser Gly Gly Gly Ser Gly Gly Gly Gly
        450                 455                 460
Ser Ala Pro Ala Ser Ser Thr Lys Lys Thr Gln Leu Gln Leu Glu
465                 470                 475                 480
His Leu Leu Leu Asp Leu Gln Met Ile Leu Asn Gly Ile Asn Asn Tyr
                485                 490                 495
Lys Asn Pro Lys Leu Thr Arg Met Leu Thr Ala Lys Phe Ala Met Pro
                500                 505                 510
Lys Lys Ala Thr Glu Leu Lys His Leu Gln Cys Leu Glu Glu Glu Leu
                515                 520                 525
Lys Pro Leu Glu Glu Val Leu Asn Gly Ala Gln Ser Lys Asn Phe His
530                 535                 540
```

-continued

```
Leu Arg Pro Arg Asp Leu Ile Ser Asn Ile Asn Val Ile Val Leu Glu
545                 550                 555                 560

Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Ala Gln Ser
            580                 585                 590

Ile Ile Ser Thr Leu Thr
        595

<210> SEQ ID NO 23
<211> LENGTH: 451
<212> TYPE: PRT
<213> ORGANISM: Artificial Sequence
<220> FEATURE:
<223> OTHER INFORMATION: CEA HC

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
            325                 330                 335

Glu Lys Thr Ile Ser Lys Ala Lys Gly Gln Pro Arg Glu Pro Gln Val
        340                 345                 350

Cys Thr Leu Pro Pro Ser Arg Asp Glu Leu Thr Lys Asn Gln Val Ser
    355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 24
<211> LENGTH: 215
<212> TYPE: PRT
<213> ORGANISM: Artificial Sequence
<220> FEATURE:
<223> OTHER INFORMATION: CEA LC

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210             215

<210> SEQ ID NO 25
<211> LENGTH: 117
<212> TYPE: PRT
<213> ORGANISM: Artificial Sequence
<220> FEATURE:
<223> OTHER INFORMATION: FAP VH

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 26
<211> LENGTH: 108
<212> TYPE: PRT
<213> ORGANISM: Artificial Sequence
<220> FEATURE:
<223> OTHER INFORMATION: FAP VL

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 27
<211> LENGTH: 594
<212> TYPE: PRT
<213> ORGANISM: Artificial Sequence
<220> FEATURE:
<223> OTHER INFORMATION: FAP IL2v HC

<400> SEQUENCE: 27

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

```
                420                 425                 430
His Asn His Tyr Thr Gln Lys Ser Leu Ser Leu Ser Pro Gly Gly Gly
            435                 440                 445

Gly Gly Ser Gly Gly Gly Ser Gly Gly Gly Ser Ala Pro Ala
450                 455                 460

Ser Ser Ser Thr Lys Thr Gln Leu Gln Leu Glu His Leu Leu Leu
465                 470                 475                 480

Asp Leu Gln Met Ile Leu Asn Gly Ile Asn Asn Tyr Lys Asn Pro Lys
                485                 490                 495

Leu Thr Arg Met Leu Thr Ala Lys Phe Ala Met Pro Lys Lys Ala Thr
            500                 505                 510

Glu Leu Lys His Leu Gln Cys Leu Glu Glu Glu Leu Lys Pro Leu Glu
        515                 520                 525

Glu Val Leu Asn Gly Ala Gln Ser Lys Asn Phe His Leu Arg Pro Arg
    530                 535                 540

Asp Leu Ile Ser Asn Ile Asn Val Ile Val Leu Glu Leu Lys Gly Ser
545                 550                 555                 560

Glu Thr Thr Phe Met Cys Glu Tyr Ala Asp Glu Thr Ala Thr Ile Val
                565                 570                 575

Glu Phe Leu Asn Arg Trp Ile Thr Phe Ala Gln Ser Ile Ile Ser Thr
            580                 585                 590

Leu Thr
```

<210> SEQ ID NO 28
<211> LENGTH: 447
<212> TYPE: PRT
<213> ORGANISM: Artificial Sequence
<220> FEATURE:
<223> OTHER INFORMATION: FAP HC

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 29
<211> LENGTH: 215
<212> TYPE: PRT
<213> ORGANISM: Artificial Sequence
<220> FEATURE:
<223> OTHER INFORMATION: FAP LC

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110
```

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 30
<211> LENGTH: 225
<212> TYPE: PRT
<213> ORGANISM: Homo sapiens

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 31
<211> LENGTH: 20
<212> TYPE: PRT

<213> ORGANISM: Homo sapiens

<400> SEQUENCE: 31

Met Tyr Arg Met Gln Leu Leu Ser Cys Ile Ala Leu Ser Leu Ala Leu
1               5                   10                  15

Val Thr Asn Ser
            20

<210> SEQ ID NO 32
<211> LENGTH: 5
<212> TYPE: PRT
<213> ORGANISM: Artificial Sequence
<220> FEATURE:
<223> OTHER INFORMATION: CD3 HCDR1

<400> SEQUENCE: 32

Thr Tyr Ala Met Asn
1               5

<210> SEQ ID NO 33
<211> LENGTH: 19
<212> TYPE: PRT
<213> ORGANISM: Artificial Sequence
<220> FEATURE:
<223> OTHER INFORMATION: CD3 HCDR2

<400> SEQUENCE: 33

Arg Ile Arg Ser Lys Tyr Asn Asn Tyr Ala Thr Tyr Tyr Ala Asp Ser
1               5                   10                  15

Val Lys Gly

<210> SEQ ID NO 34
<211> LENGTH: 14
<212> TYPE: PRT
<213> ORGANISM: Artificial Sequence
<220> FEATURE:
<223> OTHER INFORMATION: CD3 HCDR3

<400> SEQUENCE: 34

His Gly Asn Phe Gly Asn Ser Tyr Val Ser Trp Phe Ala Tyr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: CD3 LCDR1

<400> SEQUENCE: 35

Gly Ser Ser Thr Gly Ala Val Thr Thr Ser Asn Tyr Ala Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: CD3 LCDR2

<400> SEQUENCE: 36

Gly Thr Asn Lys Arg Ala Pro
1               5

<210> SEQ ID NO 37

```
<211> LENGTH: 9
<212> TYPE: PRT
<213> ORGANISM: Artificial Sequence
<220> FEATURE:
<223> OTHER INFORMATION: CD3 LCDR3

<400> SEQUENCE: 37

Ala Leu Trp Tyr Ser Asn Leu Trp Val
1               5

<210> SEQ ID NO 38
<211> LENGTH: 125
<212> TYPE: PRT
<213> ORGANISM: Artificial Sequence
<220> FEATURE:
<223> OTHER INFORMATION: CD3 VH

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 39
<211> LENGTH: 109
<212> TYPE: PRT
<213> ORGANISM: Artificial Sequence
<220> FEATURE:
<223> OTHER INFORMATION: CD3 VL

<400> SEQUENCE: 39

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 40
<211> LENGTH: 215
```

```
<212> TYPE: PRT
<213> ORGANISM: Artificial Sequence
<220> FEATURE:
<223> OTHER INFORMATION: CEA CD3 bsAb LC(CEA)

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 41
<211> LENGTH: 214
<212> TYPE: PRT
<213> ORGANISM: Artificial Sequence
<220> FEATURE:
<223> OTHER INFORMATION: CEA CD3 bsAb LC(CD3)

<400> SEQUENCE: 41

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110
```

```
Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 42
<211> LENGTH: 694
<212> TYPE: PRT
<213> ORGANISM: Artificial Sequence
<220> FEATURE:
<223> OTHER INFORMATION: CEA CD3 bsAB HC(CEA-CD3-Fc)

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Gly Gly Gly Gly Ser Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255
```

```
Cys Ala Ala Ser Gly Phe Thr Phe Ser Thr Tyr Ala Met Asn Trp Val
            260                 265                 270

Arg Gln Ala Pro Gly Lys Gly Leu Glu Trp Val Ser Arg Ile Arg Ser
            275                 280                 285

Lys Tyr Asn Asn Tyr Ala Thr Tyr Tyr Ala Asp Ser Val Lys Gly Arg
            290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
            325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ala Ser Val Ala Ala Pro Ser Val
            355                 360                 365

Phe Ile Phe Pro Pro Ser Asp Glu Gln Leu Lys Ser Gly Thr Ala Ser
370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
            405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
            435                 440                 445

Val Thr His Gln Gly Leu Ser Ser Pro Val Thr Lys Ser Phe Asn Arg
            450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
            485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
            515                 520                 525

Val Glu Val His Asn Ala Lys Thr Lys Pro Arg Glu Glu Gln Tyr Asn
            530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
            565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
            595                 600                 605

Gln Val Ser Leu Trp Cys Leu Val Lys Gly Phe Tyr Pro Ser Asp Ile
            610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
            645                 650                 655

Leu Thr Val Asp Lys Ser Arg Trp Gln Gln Gly Asn Val Phe Ser Cys
            660                 665                 670
```

Ser Val Met His Glu Ala Leu His Asn His Tyr Thr Gln Lys Ser Leu
            675                 680                 685

Ser Leu Ser Pro Gly Lys
        690

<210> SEQ ID NO 43
<211> LENGTH: 451
<212> TYPE: PRT
<213> ORGANISM: Artificial Sequence
<220> FEATURE:
<223> OTHER INFORMATION: CEA CD3 bsAB HC(CEA-Fc)

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

```
Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 44
<211> LENGTH: 672
<212> TYPE: PRT
<213> ORGANISM: Artificial Sequence
<220> FEATURE:
<223> OTHER INFORMATION: CD20 VH-CH1(EE)-CD3 VL-CH1-Fc (knob, P329G
      LALA)

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
    210                 215                 220

Gly Gly Gly Ser Gly Gly Gly Gly Ser Gln Ala Val Val Thr Gln Glu
225                 230                 235                 240
```

-continued

```
Pro Ser Leu Thr Val Ser Pro Gly Gly Thr Val Leu Thr Cys Gly
            245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
            275                 280                 285

Arg Ala Pro Gly Thr Pro Ala Arg Phe Ser Gly Ser Leu Leu Gly Gly
            290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
            355                 360                 365

Leu Gly Cys Leu Val Lys Asp Tyr Phe Pro Glu Pro Val Thr Val Ser
    370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
            405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
            435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
            610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655
```

```
Glu Ala Leu His Asn His Tyr Thr Gln Lys Ser Leu Ser Leu Ser Pro
            660                 665                 670
```

<210> SEQ ID NO 45
<211> LENGTH: 447
<212> TYPE: PRT
<213> ORGANISM: Artificial Sequence
<220> FEATURE:
<223> OTHER INFORMATION: CD20 VH-CH1(EE)-Fc (hole, P329G LALA)

<400> SEQUENCE: 45

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350
```

```
Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 46
<211> LENGTH: 219
<212> TYPE: PRT
<213> ORGANISM: Artificial Sequence
<220> FEATURE:
<223> OTHER INFORMATION: CD20 VL-CL(RK)

<400> SEQUENCE: 46

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 47
<211> LENGTH: 232
<212> TYPE: PRT
<213> ORGANISM: Artificial Sequence
<220> FEATURE:
<223> OTHER INFORMATION: CD3 VH-CL

<400> SEQUENCE: 47
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230

<210> SEQ ID NO 48
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 48

Asp Tyr Ile Met His
1               5

<210> SEQ ID NO 49
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 49

Tyr Ile Asn Pro Tyr Asn Asp Gly Ser Lys Tyr Thr Glu Lys Phe Gln
1               5                   10                  15

Gly

<210> SEQ ID NO 50
<211> LENGTH: 12
<212> TYPE: PRT
<213> ORGANISM: Artificial Sequence
```

```
<220> FEATURE:
<223> OTHER INFORMATION: CD19 HCDR3

<400> SEQUENCE: 50

Gly Thr Tyr Tyr Tyr Gly Ser Ala Leu Phe Asp Tyr
1               5                   10

<210> SEQ ID NO 51
<211> LENGTH: 16
<212> TYPE: PRT
<213> ORGANISM: Artificial Sequence
<220> FEATURE:
<223> OTHER INFORMATION: CD19 LCDR1

<400> SEQUENCE: 51

Lys Ser Ser Gln Ser Leu Glu Asn Pro Asn Gly Asn Thr Tyr Leu Asn
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 52

Arg Val Ser Lys Arg Phe Ser
1               5

<210> SEQ ID NO 53
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 53

Leu Gln Leu Thr His Val Pro Tyr Thr
1               5

<210> SEQ ID NO 54
<211> LENGTH: 121
<212> TYPE: PRT
<213> ORGANISM: Artificial Sequence
<220> FEATURE:
<223> OTHER INFORMATION: CD19 VH

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly
                100                 105                 110

Gln Gly Thr Thr Val Thr Val Ser Ser
```

-continued

```
            115                 120

<210> SEQ ID NO 55
<211> LENGTH: 112
<212> TYPE: PRT
<213> ORGANISM: Artificial Sequence
<220> FEATURE:
<223> OTHER INFORMATION: CD19 VL

<400> SEQUENCE: 55

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Pro
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

<210> SEQ ID NO 56
<211> LENGTH: 449
<212> TYPE: PRT
<213> ORGANISM: Artificial Sequence
<220> FEATURE:
<223> OTHER INFORMATION: CD19 VH-CH1(EE)-Fc(hole, P329G LALA)

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Ser Ala Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

Pro Ser Ser Ser Leu Gly Thr Gln Thr Tyr Ile Cys Asn Val Asn His
            195                 200                 205

Lys Pro Ser Asn Thr Lys Val Asp Glu Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
            325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro

<210> SEQ ID NO 57
<211> LENGTH: 674
<212> TYPE: PRT
<213> ORGANISM: Artificial Sequence
<220> FEATURE:
<223> OTHER INFORMATION: CD19 VH-CH1(EE)-CD3 VL-CH1-Fc(knob, P329G LALA)

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly

```
                100             105                 110
Gln Gly Thr Thr Val Thr Val Ser Ser Ala Ser Thr Lys Gly Pro Ser
            115                 120             125
Val Phe Pro Leu Ala Pro Ser Ser Lys Ser Thr Ser Gly Gly Thr Ala
            130                 135             140
Ala Leu Gly Cys Leu Val Glu Asp Tyr Phe Pro Glu Pro Val Thr Val
145                 150                 155                 160
Ser Trp Asn Ser Gly Ala Leu Thr Ser Gly Val His Thr Phe Pro Ala
                165                 170             175
Val Leu Gln Ser Ser Gly Leu Tyr Ser Leu Ser Ser Val Val Thr Val
            180                 185             190
Pro Ser Ser Ser Leu Gly Thr Gln Thr Tyr Ile Cys Asn Val Asn His
            195                 200             205
Lys Pro Ser Asn Thr Lys Val Asp Glu Lys Val Glu Pro Lys Ser Cys
            210                 215             220
Asp Gly Gly Gly Ser Gly Gly Gly Ser Gln Ala Val Val Thr
225                 230                 235                 240
Gln Glu Pro Ser Leu Thr Val Ser Pro Gly Gly Thr Val Thr Leu Thr
                245                 250             255
Cys Gly Ser Ser Thr Gly Ala Val Thr Thr Ser Asn Tyr Ala Asn Trp
            260                 265             270
Val Gln Glu Lys Pro Gly Gln Ala Phe Arg Gly Leu Ile Gly Gly Thr
            275                 280             285
Asn Lys Arg Ala Pro Gly Thr Pro Ala Arg Phe Ser Gly Ser Leu Leu
            290                 295             300
Gly Gly Lys Ala Ala Leu Thr Leu Ser Gly Ala Gln Pro Glu Asp Glu
305                 310                 315                 320
Ala Glu Tyr Tyr Cys Ala Leu Trp Tyr Ser Asn Leu Trp Val Phe Gly
                325                 330             335
Gly Gly Thr Lys Leu Thr Val Leu Ser Ser Ala Ser Thr Lys Gly Pro
            340                 345             350
Ser Val Phe Pro Leu Ala Pro Ser Ser Lys Ser Thr Ser Gly Gly Thr
            355                 360             365
Ala Ala Leu Gly Cys Leu Val Lys Asp Tyr Phe Pro Glu Pro Val Thr
            370                 375             380
Val Ser Trp Asn Ser Gly Ala Leu Thr Ser Gly Val His Thr Phe Pro
385                 390                 395                 400
Ala Val Leu Gln Ser Ser Gly Leu Tyr Ser Leu Ser Ser Val Val Thr
                405                 410             415
Val Pro Ser Ser Ser Leu Gly Thr Gln Thr Tyr Ile Cys Asn Val Asn
            420                 425             430
His Lys Pro Ser Asn Thr Lys Val Asp Lys Lys Val Glu Pro Lys Ser
            435                 440             445
Cys Asp Lys Thr His Thr Cys Pro Pro Cys Pro Ala Pro Glu Ala Ala
            450                 455             460
Gly Gly Pro Ser Val Phe Leu Phe Pro Pro Lys Pro Lys Asp Thr Leu
465                 470                 475                 480
Met Ile Ser Arg Thr Pro Glu Val Thr Cys Val Val Val Asp Val Ser
                485                 490             495
His Glu Asp Pro Glu Val Lys Phe Asn Trp Tyr Val Asp Gly Val Glu
            500                 505             510
Val His Asn Ala Lys Thr Lys Pro Arg Glu Glu Gln Tyr Asn Ser Thr
            515                 520             525
```

```
Tyr Arg Val Val Ser Val Leu Thr Val Leu His Gln Asp Trp Leu Asn
            530                 535                 540

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
            580                 585                 590

Ser Leu Trp Cys Leu Val Lys Gly Phe Tyr Pro Ser Asp Ile Ala Val
            595                 600                 605

Glu Trp Glu Ser Asn Gly Gln Pro Glu Asn Asn Tyr Lys Thr Thr Pro
            610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
                660                 665                 670

Ser Pro

<210> SEQ ID NO 58
<211> LENGTH: 219
<212> TYPE: PRT
<213> ORGANISM: Artificial Sequence
<220> FEATURE:
<223> OTHER INFORMATION: CD19 VL-CL(RK)

<400> SEQUENCE: 58

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Pro
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 59
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 59

```
Asp Tyr Ile Met His
1               5
```

<210> SEQ ID NO 60
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 60

```
Tyr Ile Asn Pro Tyr Asn Asp Gly Ser Lys Tyr Thr Glu Lys Phe Gln
1               5                   10                  15

Gly
```

<210> SEQ ID NO 61
<211> LENGTH: 12
<212> TYPE: PRT
<213> ORGANISM: Artificial Sequence
<220> FEATURE:
<223> OTHER INFORMATION: CD19 HCDR3

<400> SEQUENCE: 61

```
Gly Thr Tyr Tyr Tyr Gly Pro Gln Leu Phe Asp Tyr
1               5                   10
```

<210> SEQ ID NO 62
<211> LENGTH: 16
<212> TYPE: PRT
<213> ORGANISM: Artificial Sequence
<220> FEATURE:
<223> OTHER INFORMATION: CD19 LCDR1

<400> SEQUENCE: 62

```
Lys Ser Ser Gln Ser Leu Glu Thr Ser Thr Gly Thr Thr Tyr Leu Asn
1               5                   10                  15
```

<210> SEQ ID NO 63
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 63

```
Arg Val Ser Lys Arg Phe Ser
1               5
```

<210> SEQ ID NO 64
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 64

```
Leu Gln Leu Leu Glu Asp Pro Tyr Thr
1               5
```

<210> SEQ ID NO 65
<211> LENGTH: 121
<212> TYPE: PRT
<213> ORGANISM: Artificial Sequence
<220> FEATURE:
<223> OTHER INFORMATION: CD19 VH

<400> SEQUENCE: 65

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110

Gln Gly Thr Thr Val Thr Val Ser Ser
        115                 120
```

<210> SEQ ID NO 66
<211> LENGTH: 112
<212> TYPE: PRT
<213> ORGANISM: Artificial Sequence
<220> FEATURE:
<223> OTHER INFORMATION: CD19 VL

<400> SEQUENCE: 66

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110
```

<210> SEQ ID NO 67
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 67

```
Asp Tyr Ile Met His
1               5

<210> SEQ ID NO 68
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 68

Tyr Ile Asn Pro Tyr Asn Asp Gly Ser Lys Tyr Thr Glu Lys Phe Gln
1               5                   10                  15

Gly

<210> SEQ ID NO 69
<211> LENGTH: 12
<212> TYPE: PRT
<213> ORGANISM: Artificial Sequence
<220> FEATURE:
<223> OTHER INFORMATION: CD19 HCDR3

<400> SEQUENCE: 69

Gly Thr Tyr Tyr Tyr Gly Ser Ala Leu Phe Asp Tyr
1               5                   10

<210> SEQ ID NO 70
<211> LENGTH: 16
<212> TYPE: PRT
<213> ORGANISM: Artificial Sequence
<220> FEATURE:
<223> OTHER INFORMATION: CD19 LCDR1

<400> SEQUENCE: 70

Lys Ser Ser Gln Ser Leu Glu Ser Ser Thr Gly Asn Thr Tyr Leu Asn
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 71

Arg Val Ser Lys Arg Phe Ser
1               5

<210> SEQ ID NO 72
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 72

Leu Gln Leu Ile Asp Tyr Pro Val Thr
1               5

<210> SEQ ID NO 73
<211> LENGTH: 121
<212> TYPE: PRT
<213> ORGANISM: Artificial Sequence
<220> FEATURE:
<223> OTHER INFORMATION: CD19 VH

<400> SEQUENCE: 73
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly
            100                 105                 110

Gln Gly Thr Thr Val Thr Val Ser Ser
            115                 120

<210> SEQ ID NO 74
<211> LENGTH: 112
<212> TYPE: PRT
<213> ORGANISM: Artificial Sequence
<220> FEATURE:
<223> OTHER INFORMATION: CD19 VL

<400> SEQUENCE: 74

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Ser Ser
            20                  25                  30

Thr Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Ile Asp Tyr Pro Val Thr Phe Gly Gln Gly Thr Lys Leu Glu Ile Lys
            100                 105                 110

<210> SEQ ID NO 75
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 75

Asp Tyr Ile Met His
1               5

<210> SEQ ID NO 76
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 76

Tyr Ile Asn Pro Tyr Asn Asp Gly Ser Lys Tyr Thr Glu Lys Phe Gln
1               5                   10                  15

Gly

<210> SEQ ID NO 77
<211> LENGTH: 12
<212> TYPE: PRT
<213> ORGANISM: Artificial Sequence
<220> FEATURE:
<223> OTHER INFORMATION: CD19 HCDR3

<400> SEQUENCE: 77

Gly Thr Tyr Tyr Tyr Gly Ser Glu Leu Phe Asp Tyr
1               5                   10

<210> SEQ ID NO 78
<211> LENGTH: 16
<212> TYPE: PRT
<213> ORGANISM: Artificial Sequence
<220> FEATURE:
<223> OTHER INFORMATION: CD19 LCDR1

<400> SEQUENCE: 78

Lys Ser Ser Gln Ser Leu Glu Thr Ser Thr Gly Asn Thr Tyr Leu Asn
1               5                   10                  15

<210> SEQ ID NO 79
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 79

Arg Val Ser Lys Arg Phe Ser
1               5

<210> SEQ ID NO 80
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 80

Leu Gln Ala Thr His Ile Pro Tyr Thr
1               5

<210> SEQ ID NO 81
<211> LENGTH: 121
<212> TYPE: PRT
<213> ORGANISM: Artificial Sequence
<220> FEATURE:
<223> OTHER INFORMATION: CD19 VH

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

-continued

```
Gln Gly Arg Val Thr Met Thr Ser Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Gly Thr Tyr Tyr Tyr Gly Ser Glu Leu Phe Asp Tyr Trp Gly
            100                 105                 110

Gln Gly Thr Thr Val Thr Val Ser Ser
            115                 120
```

<210> SEQ ID NO 82
<211> LENGTH: 112
<212> TYPE: PRT
<213> ORGANISM: Artificial Sequence
<220> FEATURE:
<223> OTHER INFORMATION: CD19 VL

<400> SEQUENCE: 82

```
Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Glu Thr Ser
             20                  25                  30

Thr Gly Asn Thr Tyr Leu Asn Trp Tyr Leu Gln Lys Pro Gly Gln Ser
         35                  40                  45

Pro Gln Leu Leu Ile Tyr Arg Val Ser Lys Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Ala
                 85                  90                  95

Thr His Ile Pro Tyr Thr Phe Gly Gln Gly Thr Lys Leu Glu Ile Lys
            100                 105                 110
```

<210> SEQ ID NO 83
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 83

```
Asp Tyr Ile Thr His
 1               5
```

<210> SEQ ID NO 84
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 84

```
Tyr Ile Asn Pro Tyr Asn Asp Gly Ser Lys Tyr Thr Glu Lys Phe Gln
 1               5                  10                  15

Gly
```

<210> SEQ ID NO 85
<211> LENGTH: 12
<212> TYPE: PRT
<213> ORGANISM: Artificial Sequence
<220> FEATURE:
<223> OTHER INFORMATION: CD19 HCDR3

```
<400> SEQUENCE: 85

Gly Thr Tyr Tyr Tyr Gly Pro Asp Leu Phe Asp Tyr
1               5                   10

<210> SEQ ID NO 86
<211> LENGTH: 16
<212> TYPE: PRT
<213> ORGANISM: Artificial Sequence
<220> FEATURE:
<223> OTHER INFORMATION: CD19 LCDR1

<400> SEQUENCE: 86

Lys Ser Ser Gln Ser Leu Glu Thr Ser Thr Gly Asn Thr Tyr Leu Asn
1               5                   10                  15

<210> SEQ ID NO 87
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 87

Arg Val Ser Lys Arg Phe Ser
1               5

<210> SEQ ID NO 88
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 88

Leu Gln Leu Thr His Val Pro Tyr Thr
1               5

<210> SEQ ID NO 89
<211> LENGTH: 121
<212> TYPE: PRT
<213> ORGANISM: Artificial Sequence
<220> FEATURE:
<223> OTHER INFORMATION: CD19 VH

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Thr His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Asp Leu Phe Asp Tyr Trp Gly
            100                 105                 110

Gln Gly Thr Thr Val Thr Val Ser Ser
        115                 120
```

```
<210> SEQ ID NO 90
<211> LENGTH: 112
<212> TYPE: PRT
<213> ORGANISM: Artificial Sequence
<220> FEATURE:
<223> OTHER INFORMATION: CD19 VL
<220> FEATURE:
<221> NAME/KEY: misc_feature
<222> LOCATION: (107)..(107)
<223> OTHER INFORMATION: Xaa can be any naturally occurring amino acid

<400> SEQUENCE: 90

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Xaa Lys Leu Glu Ile Lys
            100                 105                 110

<210> SEQ ID NO 91
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 91

Asp Tyr Ile Met His
1               5

<210> SEQ ID NO 92
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 92

Tyr Ile Asn Pro Tyr Asn Asp Gly Ser Lys Tyr Thr Glu Lys Phe Gln
1               5                   10                  15

Gly

<210> SEQ ID NO 93
<211> LENGTH: 12
<212> TYPE: PRT
<213> ORGANISM: Artificial Sequence
<220> FEATURE:
<223> OTHER INFORMATION: CD19 HCDR3

<400> SEQUENCE: 93

Gly Thr Tyr Tyr Tyr Gly Ser Ala Leu Phe Asp Tyr
1               5                   10

<210> SEQ ID NO 94
<211> LENGTH: 16
<212> TYPE: PRT
```

```
<213> ORGANISM: Artificial Sequence
<220> FEATURE:
<223> OTHER INFORMATION: CD19 LCDR1

<400> SEQUENCE: 94

Lys Ser Ser Gln Ser Leu Glu Thr Ser Thr Gly Asn Thr Tyr Leu Asn
1               5                   10                  15

<210> SEQ ID NO 95
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 95

Arg Val Ser Lys Arg Phe Ser
1               5

<210> SEQ ID NO 96
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 96

Leu Gln Pro Gly His Tyr Pro Gly Thr
1               5

<210> SEQ ID NO 97
<211> LENGTH: 121
<212> TYPE: PRT
<213> ORGANISM: Artificial Sequence
<220> FEATURE:
<223> OTHER INFORMATION: CD19 VH

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly
            100                 105                 110

Gln Gly Thr Thr Val Thr Val Ser Ser
        115                 120

<210> SEQ ID NO 98
<211> LENGTH: 112
<212> TYPE: PRT
<213> ORGANISM: Artificial Sequence
<220> FEATURE:
<223> OTHER INFORMATION: CD19 VL

<400> SEQUENCE: 98
```

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Pro
                85                  90                  95

Gly His Tyr Pro Gly Thr Phe Gly Gln Gly Thr Lys Leu Glu Ile Lys
            100                 105                 110
```

<210> SEQ ID NO 99
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 99

```
Asp Tyr Ile Met His
1               5
```

<210> SEQ ID NO 100
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 100

```
Tyr Ile Asn Pro Tyr Asn Asp Gly Ser Lys Tyr Thr Glu Lys Phe Gln
1               5                   10                  15

Gly
```

<210> SEQ ID NO 101
<211> LENGTH: 12
<212> TYPE: PRT
<213> ORGANISM: Artificial Sequence
<220> FEATURE:
<223> OTHER INFORMATION: CD19 HCDR3

<400> SEQUENCE: 101

```
Gly Thr Tyr Tyr Tyr Gly Pro Gln Leu Phe Asp Tyr
1               5                   10
```

<210> SEQ ID NO 102
<211> LENGTH: 16
<212> TYPE: PRT
<213> ORGANISM: Artificial Sequence
<220> FEATURE:
<223> OTHER INFORMATION: CD19 LCDR1

<400> SEQUENCE: 102

```
Lys Ser Ser Gln Ser Leu Glu Thr Ser Thr Gly Asn Thr Tyr Leu Asn
1               5                   10                  15
```

<210> SEQ ID NO 103
<211> LENGTH: 7
<212> TYPE: PRT

```
<213> ORGANISM: Artificial Sequence
<220> FEATURE:
<223> OTHER INFORMATION: CD19 LCDR2

<400> SEQUENCE: 103

Arg Val Ser Lys Arg Phe Ser
1               5

<210> SEQ ID NO 104
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 104

Leu Gln Leu Asp Ser Tyr Pro Asn Thr
1               5

<210> SEQ ID NO 105
<211> LENGTH: 121
<212> TYPE: PRT
<213> ORGANISM: Artificial Sequence
<220> FEATURE:
<223> OTHER INFORMATION: CD19 VH

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
                100                 105                 110

Gln Gly Thr Thr Val Thr Val Ser Ser
            115                 120

<210> SEQ ID NO 106
<211> LENGTH: 112
<212> TYPE: PRT
<213> ORGANISM: Artificial Sequence
<220> FEATURE:
<223> OTHER INFORMATION: CD19 VL

<400> SEQUENCE: 106

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
                20                  25                  30

Thr Gly Asn Thr Tyr Leu Asn Trp Tyr Leu Gln Lys Pro Gly Gln Ser
            35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Leu Gln Leu
                    85                  90                  95

Asp Ser Tyr Pro Asn Thr Phe Gly Gln Gly Thr Lys Leu Glu Ile Lys
                100                 105                 110

<210> SEQ ID NO 107
<211> LENGTH: 5
<212> TYPE: PRT
<213> ORGANISM: Artificial Sequence
<220> FEATURE:
<223> OTHER INFORMATION: CD19 HCDR1

<400> SEQUENCE: 107

Asp Tyr Ile Met His
1               5

<210> SEQ ID NO 108
<211> LENGTH: 17
<212> TYPE: PRT
<213> ORGANISM: Artificial Sequence
<220> FEATURE:
<223> OTHER INFORMATION: CD19 HCDR2

<400> SEQUENCE: 108

Tyr Ile Asn Pro Tyr Asn Asp Gly Ser Lys Tyr Thr Glu Lys Phe Gln
1               5                   10                  15

Gly

<210> SEQ ID NO 109
<211> LENGTH: 12
<212> TYPE: PRT
<213> ORGANISM: Artificial Sequence
<220> FEATURE:
<223> OTHER INFORMATION: CD19 HCDR3

<400> SEQUENCE: 109

Gly Thr Tyr Tyr Tyr Gly Ser Glu Leu Phe Asp Tyr
1               5                   10

<210> SEQ ID NO 110
<211> LENGTH: 16
<212> TYPE: PRT
<213> ORGANISM: Artificial Sequence
<220> FEATURE:
<223> OTHER INFORMATION: CD19 LCDR1

<400> SEQUENCE: 110

Lys Ser Ser Gln Ser Leu Glu Thr Ser Thr Gly Asn Thr Tyr Leu Asn
1               5                   10                  15

<210> SEQ ID NO 111
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 111

Arg Val Ser Lys Arg Phe Ser
1               5

<210> SEQ ID NO 112
<211> LENGTH: 9
<212> TYPE: PRT
```

```
<213> ORGANISM: Artificial Sequence
<220> FEATURE:
<223> OTHER INFORMATION: CD19 LCDR3

<400> SEQUENCE: 112

Leu Gln Leu Thr His Glu Pro Tyr Thr
1               5

<210> SEQ ID NO 113
<211> LENGTH: 121
<212> TYPE: PRT
<213> ORGANISM: Artificial Sequence
<220> FEATURE:
<223> OTHER INFORMATION: CD19 VH

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Glu Leu Phe Asp Tyr Trp Gly
            100                 105                 110

Gln Gly Thr Thr Val Thr Val Ser Ser
        115                 120

<210> SEQ ID NO 114
<211> LENGTH: 112
<212> TYPE: PRT
<213> ORGANISM: Artificial Sequence
<220> FEATURE:
<223> OTHER INFORMATION: CD19 VL

<400> SEQUENCE: 114

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
                20                  25                  30

Thr Gly Asn Thr Tyr Leu Asn Trp Tyr Leu Gln Lys Pro Gly Gln Ser
            35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Glu Pro Tyr Thr Phe Gly Gln Gly Thr Lys Leu Glu Ile Lys
            100                 105                 110

<210> SEQ ID NO 115
<211> LENGTH: 207
<212> TYPE: PRT
<213> ORGANISM: Homo sapiens
```

<400> SEQUENCE: 115

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 116
<211> LENGTH: 198
<212> TYPE: PRT
<213> ORGANISM: Macaca fascicularis

<400> SEQUENCE: 116

```
Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Val Tyr Tyr Trp Ser Lys
    130                 135                 140

Asn Arg Lys Ala Lys Ala Lys Pro Val Thr Arg Gly Ala Gly Ala Gly
145                 150                 155                 160
```

Gly Arg Gln Arg Gly Gln Asn Lys Glu Arg Pro Pro Val Pro Asn
            165                 170                 175

Pro Asp Tyr Glu Pro Ile Arg Lys Gly Gln Gln Asp Leu Tyr Ser Gly
            180                 185                 190

Leu Asn Gln Arg Arg Ile
        195

<210> SEQ ID NO 117
<211> LENGTH: 556
<212> TYPE: PRT
<213> ORGANISM: Homo sapiens

<400> SEQUENCE: 117

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
            165                 170                 175

Arg Asp Ser Leu Asn Gln Ser Leu Ser Gln Asp Leu Thr Met Ala Pro
        180                 185                 190

Gly Ser Thr Leu Trp Leu Ser Cys Gly Val Pro Pro Asp Ser Val Ser
    195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
        260                 265                 270

Glu Ile Thr Ala Arg Pro Val Leu Trp His Trp Leu Leu Arg Thr Gly
    275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val

```
                325                 330                 335
Thr Pro Pro Pro Gly Ser Gly Pro Gln Asn Gln Tyr Gly Asn Val Leu
            340                 345                 350
Ser Leu Pro Thr Pro Thr Ser Gly Leu Gly Arg Ala Gln Arg Trp Ala
            355                 360                 365
Ala Gly Leu Gly Gly Thr Ala Pro Ser Tyr Gly Asn Pro Ser Ser Asp
            370                 375                 380
Val Gln Ala Asp Gly Ala Leu Gly Ser Arg Ser Pro Pro Gly Val Gly
385                 390                 395                 400
Pro Glu Glu Glu Glu Gly Gly Tyr Glu Glu Pro Asp Ser Glu Glu
                405                 410                 415
Asp Ser Glu Phe Tyr Glu Asn Asp Ser Asn Leu Gly Gln Asp Gln Leu
            420                 425                 430
Ser Gln Asp Gly Ser Gly Tyr Glu Asn Pro Glu Asp Glu Pro Leu Gly
            435                 440                 445
Pro Glu Asp Glu Asp Ser Phe Ser Asn Ala Glu Ser Tyr Glu Asn Glu
450                 455                 460
Asp Glu Glu Leu Thr Gln Pro Val Ala Arg Thr Met Asp Phe Leu Ser
465                 470                 475                 480
Pro His Gly Ser Ala Trp Asp Pro Ser Arg Glu Ala Thr Ser Leu Gly
            485                 490                 495
Ser Gln Ser Tyr Glu Asp Met Arg Gly Ile Leu Tyr Ala Ala Pro Gln
            500                 505                 510
Leu Arg Ser Ile Arg Gly Gln Pro Gly Pro Asn His Glu Glu Asp Ala
            515                 520                 525
Asp Ser Tyr Glu Asn Met Asp Asn Pro Asp Gly Pro Asp Pro Ala Trp
            530                 535                 540
Gly Gly Gly Gly Arg Met Gly Thr Trp Ser Thr Arg
545                 550                 555

<210> SEQ ID NO 118
<211> LENGTH: 10
<212> TYPE: PRT
<213> ORGANISM: Artificial Sequence
<220> FEATURE:
<223> OTHER INFORMATION: linker

<400> SEQUENCE: 118

Gly Gly Gly Gly Ser Gly Gly Gly Gly Ser
1               5                   10

<210> SEQ ID NO 119
<211> LENGTH: 11
<212> TYPE: PRT
<213> ORGANISM: Artificial Sequence
<220> FEATURE:
<223> OTHER INFORMATION: linker

<400> SEQUENCE: 119

Asp Gly Gly Gly Gly Ser Gly Gly Gly Gly Ser
1               5                   10

<210> SEQ ID NO 120
<211> LENGTH: 5
<212> TYPE: PRT
<213> ORGANISM: Artificial Sequence
<220> FEATURE:
<223> OTHER INFORMATION: CD3 HVR-H1

<400> SEQUENCE: 120
```

```
Asn Tyr Tyr Ile His
1               5

<210> SEQ ID NO 121
<211> LENGTH: 17
<212> TYPE: PRT
<213> ORGANISM: Artificial Sequence
<220> FEATURE:
<223> OTHER INFORMATION: CD3 HVR-H2

<400> SEQUENCE: 121

Trp Ile Tyr Pro Gly Asp Gly Asn Thr Lys Tyr Asn Glu Lys Phe Lys
1               5                   10                  15

Gly

<210> SEQ ID NO 122
<211> LENGTH: 10
<212> TYPE: PRT
<213> ORGANISM: Artificial Sequence
<220> FEATURE:
<223> OTHER INFORMATION: CD3 HVR-H3

<400> SEQUENCE: 122

Asp Ser Tyr Ser Asn Tyr Tyr Phe Asp Tyr
1               5                   10

<210> SEQ ID NO 123
<211> LENGTH: 17
<212> TYPE: PRT
<213> ORGANISM: Artificial Sequence
<220> FEATURE:
<223> OTHER INFORMATION: CD3 HVR-L1

<400> SEQUENCE: 123

Lys Ser Ser Gln Ser Leu Leu Asn Ser Arg Thr Arg Lys Asn Tyr Leu
1               5                   10                  15

Ala

<210> SEQ ID NO 124
<211> LENGTH: 7
<212> TYPE: PRT
<213> ORGANISM: Artificial Sequence
<220> FEATURE:
<223> OTHER INFORMATION: CD3 HVR-L2

<400> SEQUENCE: 124

Trp Ala Ser Thr Arg Glu Ser
1               5

<210> SEQ ID NO 125
<211> LENGTH: 8
<212> TYPE: PRT
<213> ORGANISM: Artificial Sequence
<220> FEATURE:
<223> OTHER INFORMATION: CD3 HVR-L3

<400> SEQUENCE: 125

Thr Gln Ser Phe Ile Leu Arg Thr
1               5

<210> SEQ ID NO 126
<211> LENGTH: 119
<212> TYPE: PRT
<213> ORGANISM: Artificial Sequence
<220> FEATURE:
```

<223> OTHER INFORMATION: CD3 VH

<400> SEQUENCE: 126

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
            115

<210> SEQ ID NO 127
<211> LENGTH: 112
<212> TYPE: PRT
<213> ORGANISM: Artificial Sequence
<220> FEATURE:
<223> OTHER INFORMATION: CD3 VL

<400> SEQUENCE: 127

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 128
<211> LENGTH: 10
<212> TYPE: PRT
<213> ORGANISM: Artificial Sequence
<220> FEATURE:
<223> OTHER INFORMATION: CD20 HVR-H1

<400> SEQUENCE: 128

Gly Tyr Thr Phe Thr Ser Tyr Asn Met His
1               5                   10

<210> SEQ ID NO 129
<211> LENGTH: 17
<212> TYPE: PRT
<213> ORGANISM: Artificial Sequence
<220> FEATURE:
<223> OTHER INFORMATION: CD20 HVR-H2

<400> SEQUENCE: 129

Ala Ile Tyr Pro Gly Asn Gly Asp Thr Ser Tyr Asn Gln Lys Phe Lys
1               5                   10                  15

Gly

<210> SEQ ID NO 130
<211> LENGTH: 13
<212> TYPE: PRT
<213> ORGANISM: Artificial Sequence
<220> FEATURE:
<223> OTHER INFORMATION: CD20 HVR-H3

<400> SEQUENCE: 130

Val Val Tyr Tyr Ser Asn Ser Tyr Trp Tyr Phe Asp Val
1               5                   10

<210> SEQ ID NO 131
<211> LENGTH: 10
<212> TYPE: PRT
<213> ORGANISM: Artificial Sequence
<220> FEATURE:
<223> OTHER INFORMATION: CD20 HVR-L1

<400> SEQUENCE: 131

Arg Ala Ser Ser Ser Val Ser Tyr Met His
1               5                   10

<210> SEQ ID NO 132
<211> LENGTH: 7
<212> TYPE: PRT
<213> ORGANISM: Artificial Sequence
<220> FEATURE:
<223> OTHER INFORMATION: CD20 HVR-L2

<400> SEQUENCE: 132

Ala Pro Ser Asn Leu Ala Ser
1               5

<210> SEQ ID NO 133
<211> LENGTH: 9
<212> TYPE: PRT
<213> ORGANISM: Artificial Sequence
<220> FEATURE:
<223> OTHER INFORMATION: CD20 HVR-L3

<400> SEQUENCE: 133

Gln Gln Trp Ser Phe Asn Pro Pro Thr
1               5

<210> SEQ ID NO 134
<211> LENGTH: 122
<212> TYPE: PRT
<213> ORGANISM: Artificial Sequence
<220> FEATURE:
<223> OTHER INFORMATION: CD20 VH

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
            50                  55                  60

Lys Gly Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 135
<211> LENGTH: 107
<212> TYPE: PRT
<213> ORGANISM: Artificial Sequence
<220> FEATURE:
<223> OTHER INFORMATION: CD20 VL

<400> SEQUENCE: 135

Asp Ile Gln Met Thr Gln Ser Pro Ser Ser Leu Ser Ala Ser Val Gly
 1               5                   10                  15

Asp Arg Val Thr Ile Thr Cys Arg Ala Ser Ser Ser Val Ser Tyr Met
             20                  25                  30

His Trp Tyr Gln Gln Lys Pro Gly Lys Ala Pro Lys Pro Leu Ile Tyr
         35                  40                  45

Ala Pro Ser Asn Leu Ala Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Phe Asn Pro Pro Thr
                 85                  90                  95

Phe Gly Gln Gly Thr Lys Val Glu Ile Lys Arg
            100                 105

<210> SEQ ID NO 136
<211> LENGTH: 5
<212> TYPE: PRT
<213> ORGANISM: Mus musculus

<400> SEQUENCE: 136

Asp Thr Tyr Met His
 1               5

<210> SEQ ID NO 137
<211> LENGTH: 17
<212> TYPE: PRT
<213> ORGANISM: Mus musculus

<400> SEQUENCE: 137

Arg Ile Asp Pro Ala Asn Gly Asn Ser Lys Tyr Val Pro Lys Phe Gln
 1               5                   10                  15

Gly

<210> SEQ ID NO 138
<211> LENGTH: 12
<212> TYPE: PRT
<213> ORGANISM: Mus musculus

<400> SEQUENCE: 138

Phe Gly Tyr Tyr Val Ser Asp Tyr Ala Met Ala Tyr

```
1               5                   10
```

<210> SEQ ID NO 139
<211> LENGTH: 15
<212> TYPE: PRT
<213> ORGANISM: Mus musculus

<400> SEQUENCE: 139

```
Arg Ala Gly Glu Ser Val Asp Ile Phe Gly Val Gly Phe Leu His
1               5                   10                  15
```

<210> SEQ ID NO 140
<211> LENGTH: 7
<212> TYPE: PRT
<213> ORGANISM: Mus musculus

<400> SEQUENCE: 140

```
Arg Ala Ser Asn Arg Ala Thr
1               5
```

<210> SEQ ID NO 141
<211> LENGTH: 9
<212> TYPE: PRT
<213> ORGANISM: Mus musculus

<400> SEQUENCE: 141

```
Gln Gln Thr Asn Glu Asp Pro Tyr Thr
1               5
```

<210> SEQ ID NO 142
<211> LENGTH: 121
<212> TYPE: PRT
<213> ORGANISM: Artificial Sequence
<220> FEATURE:
<223> OTHER INFORMATION: CEA VH

<400> SEQUENCE: 142

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
        115                 120
```

<210> SEQ ID NO 143
<211> LENGTH: 111
<212> TYPE: PRT
<213> ORGANISM: Artificial Sequence
<220> FEATURE:
<223> OTHER INFORMATION: CEA VL

<400> SEQUENCE: 143

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys
            100                 105                 110

<210> SEQ ID NO 144
<211> LENGTH: 232
<212> TYPE: PRT
<213> ORGANISM: Artificial Sequence
<220> FEATURE:
<223> OTHER INFORMATION: CD3 VH-CL

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 145
<211> LENGTH: 449

```
<212> TYPE: PRT
<213> ORGANISM: Artificial Sequence
<220> FEATURE:
<223> OTHER INFORMATION: CEA VH-CH1(EE)-Fc (hole, P329G LALA)

<400> SEQUENCE: 145
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 |
| Ser | Val | Lys | Val | Ser | Cys | Lys | Ala | Ser | Gly | Phe | Asn | Ile | Lys | Asp | Thr |
| | | | 20 | | | | | 25 | | | | | 30 | |
| Tyr | Met | His | Trp | Val | Arg | Gln | Ala | Pro | Gly | Gln | Gly | Leu | Glu | Trp | Met |
| | | 35 | | | | | 40 | | | | | 45 | | |
| Gly | Arg | Ile | Asp | Pro | Ala | Asn | Gly | Asn | Ser | Lys | Tyr | Val | Pro | Lys | Phe |
| 50 | | | | | 55 | | | | | 60 | | | | |
| Gln | Gly | Arg | Val | Thr | Ile | Thr | Ala | Asp | Thr | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Pro | Phe | Gly | Tyr | Tyr | Val | Ser | Asp | Tyr | Ala | Met | Ala | Tyr | Trp | Gly |
| | | | 100 | | | | | 105 | | | | | 110 | | |
| Gln | Gly | Thr | Leu | Val | Thr | Val | Ser | Ser | Ala | Ser | Thr | Lys | Gly | Pro | Ser |
| | | | 115 | | | | | 120 | | | | | 125 | | |
| Val | Phe | Pro | Leu | Ala | Pro | Ser | Ser | Lys | Ser | Thr | Ser | Gly | Gly | Thr | Ala |
| 130 | | | | | 135 | | | | | 140 | | | | | |
| Ala | Leu | Gly | Cys | Leu | Val | Glu | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | | 195 | | | | | 200 | | | | | 205 | | |
| Lys | Pro | Ser | Asn | Thr | Lys | Val | Asp | Glu | Lys | Val | Glu | Pro | Lys | Ser | Cys |
| 210 | | | | | 215 | | | | | 220 | | | | | |
| Asp | Lys | Thr | His | Thr | Cys | Pro | Pro | Cys | Pro | Ala | Pro | Glu | Ala | Ala | Gly |
| 225 | | | | | 230 | | | | | 235 | | | | | 240 |
| Gly | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | | 275 | | | | | 280 | | | | | 285 | | |
| His | Asn | Ala | Lys | Thr | Lys | Pro | Arg | Glu | Glu | Gln | Tyr | Asn | Ser | Thr | Tyr |
| | | 290 | | | | | 295 | | | | | 300 | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Gly | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Cys | Thr | Leu | Pro | Pro | Ser | Arg | Asp | Glu | Leu | Thr | Lys | Asn | Gln | Val | Ser |
| | | 355 | | | | | 360 | | | | | 365 | | | |
| Leu | Ser | Cys | Ala | Val | Lys | Gly | Phe | Tyr | Pro | Ser | Asp | Ile | Ala | Val | Glu |
| 370 | | | | | 375 | | | | | 380 | | | | | |

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro

<210> SEQ ID NO 146
<211> LENGTH: 674
<212> TYPE: PRT
<213> ORGANISM: Artificial Sequence
<220> FEATURE:
<223> OTHER INFORMATION: CEA VH-CH1(EE)-CD3 VL-CH1-Fc (knob, P329G LALA)

<400> SEQUENCE: 146

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Gly Gly Gly Ser Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Gly Ser Ser Thr Gly Ala Val Thr Thr Ser Asn Tyr Ala Asn Trp
            260                 265                 270

Val Gln Glu Lys Pro Gly Gln Ala Phe Arg Gly Leu Ile Gly Gly Thr
        275                 280                 285

Asn Lys Arg Ala Pro Gly Thr Pro Ala Arg Phe Ser Gly Ser Leu Leu

```
                290                 295                 300
Gly Gly Lys Ala Ala Leu Thr Leu Ser Gly Ala Gln Pro Glu Asp Glu
305                 310                 315                 320

Ala Glu Tyr Tyr Cys Ala Leu Trp Tyr Ser Asn Leu Trp Val Phe Gly
                325                 330                 335

Gly Gly Thr Lys Leu Thr Val Leu Ser Ser Ala Ser Thr Lys Gly Pro
                340                 345                 350

Ser Val Phe Pro Leu Ala Pro Ser Ser Lys Ser Thr Ser Gly Gly Thr
            355                 360                 365

Ala Ala Leu Gly Cys Leu Val Lys Asp Tyr Phe Pro Glu Pro Val Thr
        370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
            420                 425                 430

His Lys Pro Ser Asn Thr Lys Val Asp Lys Val Glu Pro Lys Ser
        435                 440                 445

Cys Asp Lys Thr His Thr Cys Pro Pro Cys Pro Ala Pro Glu Ala Ala
        450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
        530                 535                 540

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
            580                 585                 590

Ser Leu Trp Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
        610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro

<210> SEQ ID NO 147
<211> LENGTH: 218
<212> TYPE: PRT
<213> ORGANISM: Artificial Sequence
<220> FEATURE:
```

<223> OTHER INFORMATION: CEA VL-CL(RK)

<400> SEQUENCE: 147

```
Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 148
<211> LENGTH: 449
<212> TYPE: PRT
<213> ORGANISM: Artificial Sequence
<220> FEATURE:
<223> OTHER INFORMATION: CD19 VH-CH1(EE)-Fc(hole, P329G LALA)

<400> SEQUENCE: 148

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
        115                 120                 125
```

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 149
<211> LENGTH: 674
<212> TYPE: PRT
<213> ORGANISM: Artificial Sequence
<220> FEATURE:
<223> OTHER INFORMATION: CD19 VH-CH1(EE)-CD3 VL-CH1-Fc(knob, P329G LALA)

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

```
Ile Met His Trp Val Arg Gln Ala Pro Gly Gln Gly Leu Glu Trp Met
            35                  40                  45
Gly Tyr Ile Asn Pro Tyr Asn Asp Gly Ser Lys Tyr Thr Glu Lys Phe
 50                  55                  60
Gln Gly Arg Val Thr Met Thr Ser Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Gly Thr Tyr Tyr Gly Pro Gln Leu Phe Asp Tyr Trp Gly
                100                 105                 110
Gln Gly Thr Thr Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
130                 135                 140
Ala Leu Gly Cys Leu Val Glu Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Glu Lys Val Glu Pro Lys Ser Cys
                210                 215                 220
Asp Gly Gly Gly Ser Gly Gly Gly Ser Gln Ala Val Val Thr
225                 230                 235                 240
Gln Glu Pro Ser Leu Thr Val Ser Pro Gly Gly Thr Val Thr Leu Thr
                245                 250                 255
Cys Gly Ser Ser Thr Gly Ala Val Thr Thr Ser Asn Tyr Ala Asn Trp
                260                 265                 270
Val Gln Glu Lys Pro Gly Gln Ala Phe Arg Gly Leu Ile Gly Gly Thr
                275                 280                 285
Asn Lys Arg Ala Pro Gly Thr Pro Ala Arg Phe Ser Gly Ser Leu Leu
                290                 295                 300
Gly Gly Lys Ala Ala Leu Thr Leu Ser Gly Ala Gln Pro Glu Asp Glu
305                 310                 315                 320
Ala Glu Tyr Tyr Cys Ala Leu Trp Tyr Ser Asn Leu Trp Val Phe Gly
                325                 330                 335
Gly Gly Thr Lys Leu Thr Val Leu Ser Ser Ala Ser Thr Lys Gly Pro
                340                 345                 350
Ser Val Phe Pro Leu Ala Pro Ser Ser Lys Ser Thr Ser Gly Gly Thr
                355                 360                 365
Ala Ala Leu Gly Cys Leu Val Lys Asp Tyr Phe Pro Glu Pro Val Thr
                370                 375                 380
Val Ser Trp Asn Ser Gly Ala Leu Thr Ser Gly Val His Thr Phe Pro
385                 390                 395                 400
Ala Val Leu Gln Ser Ser Gly Leu Tyr Ser Leu Ser Ser Val Val Thr
                405                 410                 415
Val Pro Ser Ser Ser Leu Gly Thr Gln Thr Tyr Ile Cys Asn Val Asn
                420                 425                 430
His Lys Pro Ser Asn Thr Lys Val Asp Lys Lys Val Glu Pro Lys Ser
                435                 440                 445
Cys Asp Lys Thr His Thr Cys Pro Pro Cys Pro Ala Pro Glu Ala Ala
```

```
                450                 455                 460
Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
            515                 520                 525

Tyr Arg Val Val Ser Val Leu Thr Val Leu His Gln Asp Trp Leu Asn
        530                 535                 540

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
                580                 585                 590

Ser Leu Trp Cys Leu Val Lys Gly Phe Tyr Pro Ser Asp Ile Ala Val
                595                 600                 605

Glu Trp Glu Ser Asn Gly Gln Pro Glu Asn Asn Tyr Lys Thr Thr Pro
            610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
                660                 665                 670

Ser Pro

<210> SEQ ID NO 150
<211> LENGTH: 219
<212> TYPE: PRT
<213> ORGANISM: Artificial Sequence
<220> FEATURE:
<223> OTHER INFORMATION: CD19 VL-CL(RK)

<400> SEQUENCE: 150

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Arg
            115                 120                 125

Lys Leu Lys Ser Gly Thr Ala Ser Val Val Cys Leu Leu Asn Asn Phe
    130                 135                 140
```

-continued

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

TREATMENT METHOD

CROSS REFERENCE TO RELATED APPLICATIONS

This application claims priority to European Patent Application No. EP 15198715.3, filed Dec. 9, 2015, European Patent Application No. EP 16172739.1, filed Jun. 2, 2016, and European Patent Application No. EP 16193151.4, filed Oct. 10, 2016, the disclosures of which are incorporated herein by reference in their entirety.

SEQUENCE LISTING

The present application contains a Sequence Listing which has been submitted in ASCII format via EFS-Web and is hereby incorporated by reference in its entirety. Said ASCII copy, created on Dec. 7, 2016, is named P33257 US_ST25.txt and is 155,210 bytes in size.

FIELD OF THE INVENTION

The present invention relates to methods of treating a disease, and methods for reduction of the formation of anti-drug antibodies (ADAs) in response to the administration of a therapeutic agent. The invention further relates to methods of treating a disease, particularly a B-cell proliferative disorder, and methods for reduction of adverse effects in response to the administration of a therapeutic agent, particularly a T-cell activating therapeutic agent.

BACKGROUND

The number of biotechnology-derived therapeutic agents available for use in clinical settings has dramatically increased in recent years, and includes recombinant human cytokines (e.g. α and β interferon, interleukin-2), cellular growth factors (e.g. GM-CSF), hormones (e.g. glucagon), neuromuscular antagonists (e.g. botulinum toxin), blood products (e.g. clotting factor VIII), recombinant receptors (e.g. etanercept) and monoclonal antibodies. Although therapeutic proteins are generally considered safe and non-toxic, antibodies against these therapeutic agents, known as anti-drug antibodies (ADAs), can develop during treatment.

ADAs have been observed in connection with various therapeutic agents, such as erythropoietin, factor VIII, insulin, immunotoxins and monoclonal antibodies (Schellekens and Casadevall, J Neurol (2004), 251 [Suppl 2]II/4-II/9; Mossoba et al., Clin Cancer Res (2011) 17(11): 3697-3705; Hsu et al., British Journal of Dermatology (2014) 170, 261-273). ADA formation is frequent for example in autoimmune patients treated with TNF blockers and impacts clinical outcome (Schaeverbecke et al., Rheumatology (2015) doi: 10.1093/rheumatology/kev277).

The development of ADAs may influence serum concentrations and function of therapeutic agents. The presence of ADAs may increase clearance of the therapeutic agent through formation of immune complexes between therapeutic agent and antibody (neutralizing, non-neutralizing or both), thus reducing the therapeutic agent's half-life. Furthermore, the activity and effectiveness of the therapeutic agent may be decreased through binding of antibody to the therapeutic agent. ADAs can also be associated with allergic or hypersensitivity reactions and other adverse events. Since these adverse events associated with immune responses can influence the safety and efficacy profile of therapeutics, identification and development of strategies to overcome or inhibit ADAs is of great interest.

Several protein engineering approaches have been investigated to reduce the immunogenicity of protein therapeutics, including for example masking or alteration of protein B cell epitopes or modification of protein T cell epitopes. However, clinical safety and success of these approaches has not been tested and will require a significant degree of time to evaluate. Therefore, there exists an immediate need to develop new interventions using FDA-approved reagents to prevent ADA responses.

Chemotherapy-based approaches aimed at host immune suppression have been reported (Mossoba et al., Clin Cancer Res (2011) 17(11): 3697-3705).

The anti-CD20 antibody rituximab has been used in combination with methotrexate and intravenous immune globulin to achieve tolerance to enzyme replacement therapy in a Morbus Pompe patient (Mendelsohn et al., NEJM (2009) 360:2, 194-195). However, in a clinical trial, host pretreatment with rituximab did not inhibit the human immune response against the immunotoxin LMB-1 (Hassan et al., Clin Cancer Res (2004) 10, 16-18).

B-cell proliferative disorders describe a heterogeneous group of malignancies that includes both leukemias and lymphomas. Lymphomas develop from lymphatic cells and include two main categories: Hodgkin lymphomas (HL) and the non-Hodgkin lymphomas (NHL). In the United States, lymphomas of B cell origin constitute approximately 80-85% of all non-Hodgkin lymphoma cases, and there is considerable heterogeneity within the B-cell subset, based upon genotypic and phenotypic expression patterns in the B-cell of origin. For example, B cell lymphoma subsets include the slow-growing indolent and incurable diseases, such as Follicular lymphoma (FL) or chronic lymphocytic leukemia (CLL), as well as the more aggressive subtypes, mantle cell lymphoma (MCL) and diffuse large B cell lymphoma (DLBCL).

Despite the availability of various agents for the treatment of B-cell proliferative disorders, there is an ongoing need for development of safe and effective therapies to prolong remission and improve cure rates in patients.

A strategy currently being investigated is the engagement of T cells against malignant B cells. In order to effectively engage T cells against malignant B cells, two recent approaches have been developed. These two approaches are: 1) the administration of T cells engineered ex vivo to recognize tumour cells (also known as chimeric antigen receptor-modified T cell therapy [CAR-T cells]) (Maude et al., N Engl J Med (2014) 371, 1507-1517); and, 2) the administration of agents that activate endogenous T cells, such as bispecific antibodies (Oak and Bartlett, Expert Opin Investig Drugs (2015) 24, 715-724).

An example of the first approach is reported in the study by Maude et al., in which 30 adult and pediatric patients were treated with autologous T cells transduced with a CD19-directed chimeric antigen receptor lentiviral vector (CTL019 CAR-T cells). The result was a sustained remission based upon a 6-month event-free survival rate of 67% and an overall survival rate of 78%. However, all patients had cytokine release syndrome (CRS) (associated with tumour burden), with 27% of patients having severe CRS. Central nervous system toxicities of unknown cause were also noted at high frequencies.

In contrast, the second approach, which involves activating endogenous T cells to recognize tumour targets, bypasses this hurdle of scalability, and can also provide competitive efficacy, safety data and potentially long term durations of response. In different CD20+ hematologic malignancies, this approach is best exemplified by blinatumomab, a CD19 CD3 targeting T cell bispecific molecule (Bargou et al., Science (2008) 321, 974-977) that was recently approved for patients with minimal residual disease-positive acute lymphocytic leukemia (ALL). This compound, which is composed of two single chain Fv fragments (the so called BiTE® format), directs the lysis of CD19+ cells by cytolytic T cells. The primary constraint of blinatumomab is its short half-life (approximately 2 hours), which necessitates continuous infusion via a pump over 4-8 weeks. Nonetheless, it has potent efficacy in patients with both relapsed/refractory Non-Hodgkin Lymphoma (r/r NHL) and ALL, with step-up dosing (SUD) required to mitigate severe cytokine release syndrome and CNS toxicities (Nagorsen and Baeuerle, Exp Cell Res (2011) 317, 1255-1260).

The CD20 CD3 targeting T cell bispecific molecule, CD20XCD3 bsAB, is another example of a next generation of B cell targeting antibody. CD20XCD3 bsAB is a T cell bispecific (TCB) antibody targeting CD20 expressed on B cells and CD3 epsilon chain (CD3e) present on T cells. The mechanism of action of CD20XCD3 bsAB comprises simultaneous binding to CD20+ B cells and CD3+ T cells, leading to T-cell activation and T-cell mediated killing of B cells. In the presence of CD20+B cells, whether circulating or tissue resident, pharmacologically active doses will trigger T-cell activation and associated cytokine release. CD20XCD3 bsAB has shown enhanced potency in nonclinical models over competitive T cell engaging agents and, having an IgG-based format, has a greatly improved half-life over blinatumomab.

Cytokine release is the result of activation of T cells. In a phase 1 study conducted by TeGenero (Suntharalingam et al., N Engl J Med (2006) 355, 1018-1028), all 6 healthy volunteers experienced near fatal, severe cytokine release syndrome (CRS) rapidly post-infusion of an inappropriately-dosed, T-cell stimulating super-agonist anti-CD28 monoclonal antibody. More recently, in the above-mentioned study by Maude et al. of CD19-targeting, chimeric antigen receptor T cell (CAR-T cell) treatment of patients with relapsed ALL, all 30 patients had cytokine release, which was categorized as severe in 27% of the patients. CRS is a common but severe complication of CAR-T cell therapy (reviewed in Xu and Tang, Cancer Letters (2014) 343, 172-178).

Severe CRS and CNS toxicity have also been frequently observed with the CD19-CD3 T cell bispecific agent, blinatumomab (Klinger et al., Blood. 2012; 119(26):6226-6233). In patients receiving blinatumomab in all clinical trials, neurological toxicities have occurred in approximately 50% of patients, and the types of toxicities observed are well-defined in the package insert.

It is not well understood if or how CNS toxicity is related to earlier cytokine release or T cell activation. Similar to blinatumomab, CNS AEs (ranging from delirium to global encephalopathy) were reported for 43% (13/30) of the patients with r/r ALL treated with CD19-targeting CAR-T cells (Maude et al., N Engl J Med (2014) 371, 1507-1517; Ghorashian et al., Br J Haematol (2015) 169, 463-478). Neurologic toxic effects typically occurred after symptoms of CRS had peaked and started to resolve; however no direct, unequivocal association with severe CRS was found. The authors proposed that the mechanism of neurotoxicity could involve direct CAR-T-cell-mediated toxicity or it could be cytokine-mediated. In contrast, an association between severe CRS and neurotoxicity (e.g., encephalopathy) has been suggested in another study of CD19-targeting CAR-T cell therapy (Davila et al., Sci Transl Med (2014) 6, 224ra25) and speculated to be due to general T cell activation, versus direct CAR-T-induced damage.

Cytokine release and/or CNS-related toxicities are particularly pronounced in T cell bispecific antibodies that link CD3+ cells to B cells, as compared to other T cell bispecific antibodies that link CD3+ cells to tissue-restricted (i.e., non-circulating) target cells.

There is thus a need for methods to reduce or prevent such adverse effects of these promising agents which have the potential to significantly contribute to the treatment of patients with B-cell proliferative disorders such as NHL and CLL.

SUMMARY OF THE INVENTION

The present invention is based on the surprising finding that (i) the formation of ADAs in response to administration of an immunogenic therapeutic agent to a subject can effectively and sustainably be prevented, and (ii) the cytokine release associated with administration of a therapeutic agent, particularly a T-cell activating therapeutic agent such as CD20XCD3 bsAB, to a subject can be significantly reduced, by pre-treatment of said subject with a Type II anti-CD20 antibody, such as obinutuzumab.

Obinutuzumab is a humanized glyco-engineered type II anti-CD20 mAb that binds with high-affinity to the CD20 antigen, inducing antibody-dependent cellular cytotoxicity (ADCC) and antibody-dependent cellular phagocytosis (ADCP), low complement-dependent cytotoxicity (CDC) activity, and high direct cell death induction. To date, the safety profile of obinutuzumab (including cytokine release) has been assessed and managed in hundreds of patients in ongoing obinutuzumab clinical trials.

Without wishing to be bound by theory, the use of obinutuzumab (GAZYVA®) pre-treatment (GPT) should aid in the rapid depletion of B cells, both in the peripheral blood and in secondary lymphoid organs, such that the risk of highly relevant adverse events (AEs) from strong systemic T cell activation by (T-cell activating) therapeutic agents (e.g. CRS) is reduced, while supporting exposure levels of therapeutic agents that are high enough from the start of dosing to mediate tumour cell elimination. In addition to supporting the safety profile of (T-cell activating) therapeutic agents such as CD20XCD3 bsAB, GPT should also help prevent the formation of anti-drug antibodies (ADAs) to therapeutic molecules.

For patients, GPT should translate into better drug exposure with an enhanced safety profile.

GPT should be more effective in accomplishing the above goals compared to other methods used, such as step up dosing (SUD). For example, a single dose of obinutuzumab should allow relapsed/refractory patients to receive the full therapeutic dose of T-cell activating therapeutic agent such as CD20XCD3 bsAB, once determined, without a time delay from step up dosing. In contrast thereto, it was recently reported that the blinatumomab dosing regimen for patients with r/r DLBCL in an ongoing Phase 2 trial incorporates a double step up approach (i.e., 9→28→112 µg/m²/day), thus, requiring 14 days to reach the maximum dose of 112 µg/m²/day (Viardot el at., Hematol Oncol (2015) 33, 242 (Abstract 285)). As shown in the Examples, following pretreatment with obinutuzumab, administration of CD20XCD3 bsAB to cynomolgus monkeys was tolerated up to a level that was ten times higher than that tolerated without GPT. Efficient peripheral blood B-cell depletion and anti-tumour activity along with strongly reduced cytokine release in the peripheral blood associated with the first CD20XCD3 bsAB injection was observed upon GPT.

Accordingly, in a first aspect the present invention provides a method for (i) reducing the formation of anti-drug antibodies (ADAs) against a therapeutic agent in a subject and/or (ii) reducing cytokine release associated with administration of a therapeutic agent, particularly a T-cell activating therapeutic agent, in a subject, comprising administration of a Type II anti-CD20 antibody to the subject prior to administration of the therapeutic agent. In one embodiment the period of time between the administration of the Type II anti-CD20 antibody and administration of the therapeutic agent is sufficient for reduction of the number of B-cells in the subject in response to the administration of the Type II anti-CD20 antibody.

In a further aspect, the invention provides a method of treating a disease in a subject, the method comprising a treatment regimen comprising (i) administration to the subject of a Type II anti-CD20 antibody, and consecutively after a period of time (ii) administration to the subject of a therapeutic agent, wherein the period of time between the administration of the Type II anti-CD20 antibody and the administration of the therapeutic agent is sufficient for reduction of the number of B-cells in the subject in response to the administration of the Type II anti-CD20 antibody.

In one embodiment, the treatment regimen effectively reduces the formation of anti-drug antibodies (ADAs) in the subject in response to the administration of the therapeutic agent as compared to a corresponding treatment regimen without the administration of the Type II anti-CD20 antibody.

In another embodiment, the treatment regimen effectively reduces cytokine release associated with the administration of the therapeutic agent in the subject as compared to a corresponding treatment regimen without the administration of the Type II anti-CD20 antibody. In such embodiment, the therapeutic agent preferably is a T cell activating therapeutic agent.

In a further aspect, the invention provides a Type II anti-CD20 antibody for use in a method for (i) reducing the formation of anti-drug antibodies (ADAs) against a therapeutic agent in a subject and/or (ii) reducing cytokine release associated with the administration a therapeutic agent, particularly a T-cell activating therapeutic agent, in a subject, comprising administration of the Type II anti-CD20 antibody to the subject prior to administration of the therapeutic agent.

In one embodiment, the period of time between the administration of the Type II anti-CD20 antibody and administration of the therapeutic agent is sufficient for reduction of the number of B-cells in the subject in response to the administration of the CD20 antibody.

In a further aspect, the invention provides a Type II anti-CD20 antibody for use in a method of treating a disease in a subject, the method comprising a treatment regimen comprising (i) administration to the subject of the Type II anti-CD20 antibody, and consecutively after a period of time (ii) administration to the subject of a therapeutic agent, wherein the period of time between the administration of the Type II anti-CD20 antibody and the administration of the therapeutic agent is sufficient for reduction of the number of B-cells in the subject in response to the administration of the Type II anti-CD20 antibody.

In one embodiment, the treatment regimen effectively reduces the formation of anti-drug antibodies (ADAs) against the therapeutic agent in the subject (in response to the administration of the therapeutic agent) as compared to a corresponding treatment regimen without the administration of the anti-CD20 antibody.

In another embodiment, the treatment regimen effectively reduces cytokine release associated with the administration of the therapeutic agent in the subject as compared to a corresponding treatment regimen without the administration of the Type II anti-CD20 antibody. In such embodiment, the therapeutic agent preferably is a T cell activating therapeutic agent.

In a further aspect, the invention provides the use of a Type II anti-CD20 antibody in the manufacture of a medicament for (i) reduction of the formation of anti-drug antibodies (ADAs) against a therapeutic agent in a subject and/or (ii) the reduction of cytokine release associated with administration of a therapeutic agent, particularly a T-cell activating therapeutic agent, in a subject, wherein the medicament is to be used in a treatment regimen comprising (i) administration to the subject of the Type II anti-CD20 antibody, and consecutively after a period of time (ii) administration to the subject of a therapeutic agent, wherein the period of time between the administration of the Type II anti-CD20 antibody and the administration of the therapeutic agent is sufficient for reduction of the number of B-cells in the subject in response to the administration of the Type II anti-CD20 antibody.

In one embodiment, the treatment regimen effectively reduces the formation of anti-drug antibodies (ADAs) against the therapeutic agent in the subject as compared to a corresponding treatment regimen without the administration of the anti-CD20 antibody.

In another embodiment, the treatment regimen effectively reduces cytokine release associated with administration of the therapeutic agent in the subject as compared to a corresponding treatment regimen without the administration of the Type II anti-CD20 antibody. In such embodiment, the therapeutic agent preferably is a T cell activating therapeutic agent.

In still a further aspect, the invention provides a kit for (i) the reduction of the formation of anti-drug antibodies (ADAs) against a therapeutic agent in a subject and/or (ii) the reduction of cytokine release associated with administration of a therapeutic agent, particularly a T-cell activating therapeutic agent, in a subject, comprising a package comprising a Type II anti-CD20 antibody composition and instructions for using the Type II anti-CD20 antibody composition in a treatment regimen comprising (i) administration to the subject of the Type II anti-CD20 antibody composition, and consecutively after a period of time (ii) administration to the subject of a therapeutic agent, wherein the period of time between the administration of the Type II anti-CD20 antibody composition and the administration of the therapeutic agent is sufficient for reduction of the number of B-cells in the subject in response to the administration of the Type II CD20 antibody.

In one embodiment, the treatment regimen effectively reduces the formation of anti-drug antibodies (ADAs) against the therapeutic agent in the subject as compared to a corresponding treatment regimen without the administration of the Type II anti-CD20 antibody composition.

In another embodiment, the treatment regimen effectively reduces cytokine release associated with administration of the therapeutic agent in the subject as compared to a corresponding treatment regimen without the administration of the Type II anti-CD20 antibody composition. In such embodiment, the therapeutic agent preferably is a T cell activating therapeutic agent.

In one embodiment, the kit further comprises a therapeutic agent composition.

The invention in a further aspect as provides a therapeutic agent for use in a method of treating a disease in a subject, the method comprising a treatment regimen comprising (i) administration to the subject of a Type II anti-CD20 antibody, and consecutively after a period of time (ii) administration to the subject of the therapeutic agent, wherein the period of time between the administration of the Type II anti-CD20 antibody and the administration of the therapeutic agent is sufficient for reduction of the number of B-cells in the subject in response to the administration of the CD20 antibody.

In one embodiment, the treatment regimen effectively reduces the formation of anti-drug antibodies (ADAs) in the subject in response to the administration of the therapeutic agent as compared to a corresponding treatment regimen without the administration of the Type II anti-CD20 antibody.

In another embodiment, the treatment regimen effectively reduces cytokine release associated with administration of the therapeutic agent in the subject as compared to a corresponding treatment regimen without the administration of the Type II anti-CD20 antibody. In such embodiment, the therapeutic agent preferably is a T cell activating therapeutic agent.

The invention in still a further aspect provides the use of a therapeutic agent in the manufacture of a medicament for treatment of a disease in a subject, wherein the treatment comprises a treatment regimen comprising (i) administration to the subject of a Type II anti-CD20 antibody, and consecutively after a period of time (ii) administration to the subject of the therapeutic agent, wherein the period of time between the administration of the Type II anti-CD20 antibody and the administration of the therapeutic agent is sufficient for reduction of the number of B-cells in the subject in response to the administration of the Type II anti-CD20 antibody.

In one embodiment, the treatment regimen effectively reduces the formation of anti-drug antibodies (ADAs) in the subject in response to the administration of the therapeutic agent as compared to a corresponding treatment regimen without the administration of the Type II anti-CD20 antibody.

In another embodiment, the treatment regimen effectively reduces cytokine release associated with administration of the therapeutic agent in the subject as compared to a corresponding treatment regimen without the administration of the Type II anti-CD20 antibody. In such embodiment, the therapeutic agent preferably is a T cell activating therapeutic agent.

The invention in a further aspect provides a kit for the treatment of a disease in a subject, comprising a package comprising a therapeutic agent composition and instructions for using the therapeutic agent composition in a treatment regimen comprising (i) administration to the subject of a Type II anti-CD20 antibody, and consecutively after a period of time (ii) administration to the subject of the therapeutic agent composition, wherein the period of time between the administration of the Type II anti-CD20 antibody and the administration of the therapeutic agent composition is sufficient for reduction of the number of B-cells in the subject in response to the administration of the Type II anti-CD20 antibody.

In one embodiment, the treatment regimen effectively reduces the formation of anti-drug antibodies (ADAs) against the therapeutic agent in the subject as compared to a corresponding treatment regimen without the administration of the Type II anti-CD20 antibody composition.

In another embodiment, the treatment regimen effectively reduces cytokine release associated with administration of the therapeutic agent in the subject as compared to a corresponding treatment regimen without the administration of the Type II anti-CD20 antibody composition. In such embodiment, the therapeutic agent preferably is a T cell activating therapeutic agent.

In one embodiment, the kit further comprises a Type II anti-CD20 antibody composition.

The methods, uses, Type II anti-CD20 antibodies, therapeutic agents and kits of the invention may incorporate, singly or in combination, any of the features described hereinbelow.

In one embodiment, the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

In a more specific embodiment, the Type II anti-CD20 antibody comprises the heavy chain variable region sequence of SEQ ID NO: 10 and the light chain variable region sequence of SEQ ID NO: 11.

In one embodiment, the Type II anti-CD20 antibody is an IgG antibody, particularly an $IgG_1$ antibody.

In one embodiment, the Type II anti-CD20 antibody is engineered to have an increased proportion of non-fucosylated oligosaccharides in the Fc region as compared to a non-engineered antibody. In one embodiment, at least about 40% of the N-linked oligosaccharides in the Fc region of the Type II anti-CD20 antibody are non-fucosylated.

In a particular embodiment the anti-CD20 antibody is obinutuzumab.

In some embodiments, in particular in relation aspects of the invention concerned with the reduction of the formation of anti-drug antibodies (ADAs) against a therapeutic agent in a subject, the therapeutic agent comprises a polypeptide.

In some embodiments, in particular in relation aspects of the invention concerned with the reduction of the formation of anti-drug antibodies (ADAs) against a therapeutic agent in a subject, the therapeutic agent comprises an antibody.

In one such embodiment, the antibody specifically binds to carcinoembryonic antigen (CEA). In one embodiment, the antibody comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19. In a further embodiment, the antibody comprises the heavy chain variable region sequence of SEQ ID NO: 20 and the light chain variable region sequence of SEQ ID NO: 21.

In another such embodiment, the antibody specifically binds to CD3, particularly CD3 epsilon. In one embodiment, the antibody comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37. In a further embodiment, the antibody comprises the heavy chain variable region sequence of SEQ ID NO: 38 and the light chain variable region sequence of SEQ ID NO: 39.

In some embodiments, in particular in relation aspects of the invention concerned with the reduction of the formation of anti-drug antibodies (ADAs) against a therapeutic agent in a subject, the therapeutic agent comprises a cytokine.

In one such embodiment, the cytokine is interleukin-2 (IL-2).

In another such embodiment, the cytokine is a mutant human IL-2 polypeptide comprising the amino acid substitutions F42A, Y45A and L72G (numbering relative to the human IL-2 sequence SEQ ID NO: 12).

In some embodiments, in particular in relation aspects of the invention concerned with the reduction of the formation of anti-drug antibodies (ADAs) against a therapeutic agent in a subject, the therapeutic agent comprises an immunoconjugate.

In one such embodiment, the immunoconjugate comprises (a) an antibody that specifically binds to CEA and comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19, and (b) a mutant human IL-2 polypeptide comprising the amino acid substitutions F42A, Y45A and L72G (numbering relative to the human IL-2 sequence SEQ ID NO: 12).

In a particular such embodiment, the therapeutic agent comprises cergutuzumab amunaleukin (CEA-IL2v).

In some embodiments, in particular in relation aspects of the invention concerned with the reduction of the formation of anti-drug antibodies (ADAs) against a therapeutic agent in a subject, the therapeutic agent comprises a bispecific antibody that specifically binds to CEA and to CD3.

In one such embodiment the therapeutic agent comprises a bispecific antibody comprising
(i) an antigen binding moiety that specifically binds to CD3 and comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37; and
(ii) an antigen binding moiety that specifically bind to CEA and comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19.

In a particular embodiment, the therapeutic agent comprises CEA TCB.

In some embodiments, in particular in relation aspects of the invention concerned with the reduction of cytokine release associated with the administration of a therapeutic agent in a subject, the therapeutic agent is a T cell activating therapeutic agent.

In one embodiment, the T-cell activating therapeutic agent comprises an antibody, particularly a multispecific (e.g. a bispecific) antibody.

In one embodiment, the antibody specifically binds to an activating T cell antigen.

In one embodiment, the antibody specifically binds to an antigen selected from the group of CD3, CD28, CD137 (also known as 4-1BB), CD40, CD226, OX40, GITR, CD27, HVEM, and CD127.

In one embodiment, the antibody specifically binds to CD3, particularly CDR.

In one embodiment, the antibody comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

In one embodiment, the antibody comprises the heavy chain variable region sequence of SEQ ID NO: 38 and the light chain variable region sequence of SEQ ID NO: 39.

In one embodiment, the antibody specifically binds to a B-cell antigen, particularly a malignant B-cell antigen.

In one embodiment, the antibody specifically binds to an antigen selected from the group consisting of CD20, CD19, CD22, ROR-1, CD37 and CD5, particularly to CD20 or CD19.

In one embodiment, the antibody specifically binds to CD20.

In one embodiment, the antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

In one embodiment, the antibody comprises the heavy chain variable region sequence of SEQ ID NO: 10 and the light chain variable region sequence of SEQ ID NO: 11.

In one embodiment, the antibody is a multispecific antibody, particularly a bispecific antibody.

In one embodiment, the multispecific antibody specifically binds to (i) an activating T cell antigen and (ii) a B cell antigen.

In one embodiment, the multispecific antibody specifically binds to (i) CD3 and (ii) an antigen selected from CD20 and CD19.

In one embodiment, the multispecific antibody specifically binds to CD3 and CD20.

In some embodiments, in particular in relation aspects of the invention concerned with the reduction of cytokine release associated with the administration of a therapeutic agent in a subject, the therapeutic agent comprises a bispecific antibody comprising
(i) an antigen binding moiety that specifically binds to CD3 and comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37; and
(ii) an antigen binding moiety that specifically binds to CD20 and comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

In a particular embodiment, the therapeutic agent comprises CD20XCD3 bsAB.

In some embodiments, in particular in relation aspects of the invention concerned with the reduction of cytokine release associated with the administration of a therapeutic agent in a subject, the therapeutic agent comprises a chimeric antigen receptor (CAR) or a T cell expressing a CAR, particularly a CAR that specifically binds to a B-cell antigen, more particularly a CAR that specifically binds to an antigen selected from the group of CD20, CD19, CD22, ROR-1, CD37 and CD5.

In some embodiments, in particular in relation aspects of the invention concerned with the reduction of cytokine release associated with the administration of a therapeutic agent in a subject, the disease is a B cell proliferative disorder, particularly a CD20-positive B-cell disorder. In one embodiment, the disease is selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM), and Hodgkin lymphoma (HL).

BRIEF DESCRIPTION OF THE DRAWINGS

(FIG. 6A, FIG. 6D) Illustration of the "1+1 CrossMab" molecule. (FIG. 6G, FIG. 6K) Illustration of the "1+1 IgG Crossfab" molecule with alternative order of Crossfab and Fab components ("inverted"). (FIG. 6H, FIG. 6L) Illustration of the "1+1 IgG Crossfab" molecule. (FIG. 6I, FIG. 6M) Illustration of the "2+1 IgG Crossfab" molecule with two CrossFabs. (FIG. 6J, FIG. 6N) Illustration of the "2+1 IgG Crossfab" molecule with two CrossFabs and alternative order of Crossfab and Fab components ("inverted"). (FIG. 6X, FIG. 6Z) Illustration of the "(Crossfab)$_2$-Fab" molecule. Black dot: optional modification in the Fc domain promoting heterodimerization. ++, --: amino acids of opposite charges optionally introduced in the CH1 and CL domains. Crossfab molecules are depicted as comprising an exchange of VH and VL regions, but may—in embodiments wherein no charge modifications are introduced in CH1 and CL domains—alternatively comprise an exchange of the CH1 and CL domains.

FIGS. 10A-10E. Cytokines released in peripheral blood of cynomolgus monkeys following dosing with CD20XCD3 bsAB and Gpt+CD20XCD3 bsAB treatments. (FIG. 10A) IFNγ, (FIG. 10B) IL-8, (FIG. 10C) TNFα, (FIG. 10D) IL-2, (FIG. 10E) IL-6.

(FIG. 12A) vehicle, (FIG. 12B) obinutuzumab 10 mg/kg, (FIG. 12C) CD20XCD3 bsAB 0.15 mg/kg, (FIG. 12D) CD20XCD3 bsAB 0.5 mg/kg, (FIG. 12E) vehicle+ vehicle, (FIG. 12F) obinutuzumab 10 mg/kg+CD20XCD3 bsAB 0.5 mg/kg, (FIG. 12G) CD20XCD3 bsAB 0.15 mg/kg+CD20XCD3 bsAB 0.5 mg/kg, (FIG. 12H) vehicle+ CD20XCD3 bsAB 0.5 mg/kg. Lung sections are immunohistochemically-stained with anti-CD3 antibody (dark); nuclei were counterstained with hematoxylin. Magnification 20×. Arrows point to increase in perivascular CD3 positive cells.

FIGS. 13A and 13B. Lung of humanized NOG mouse sacrificed 24 hours after single treatment with 0.5 mg/kg of CD20XCD3 bsAB. Margination and adhesion of T cells (arrows) to the endothelium in vessels. Few T cells have transmigrated to the perivascular space (asterisks). (FIG. 13A) 20× magnification, (FIG. 13B) 40× magnification.

DETAILED DESCRIPTION OF THE INVENTION

Definitions

Figure 1:
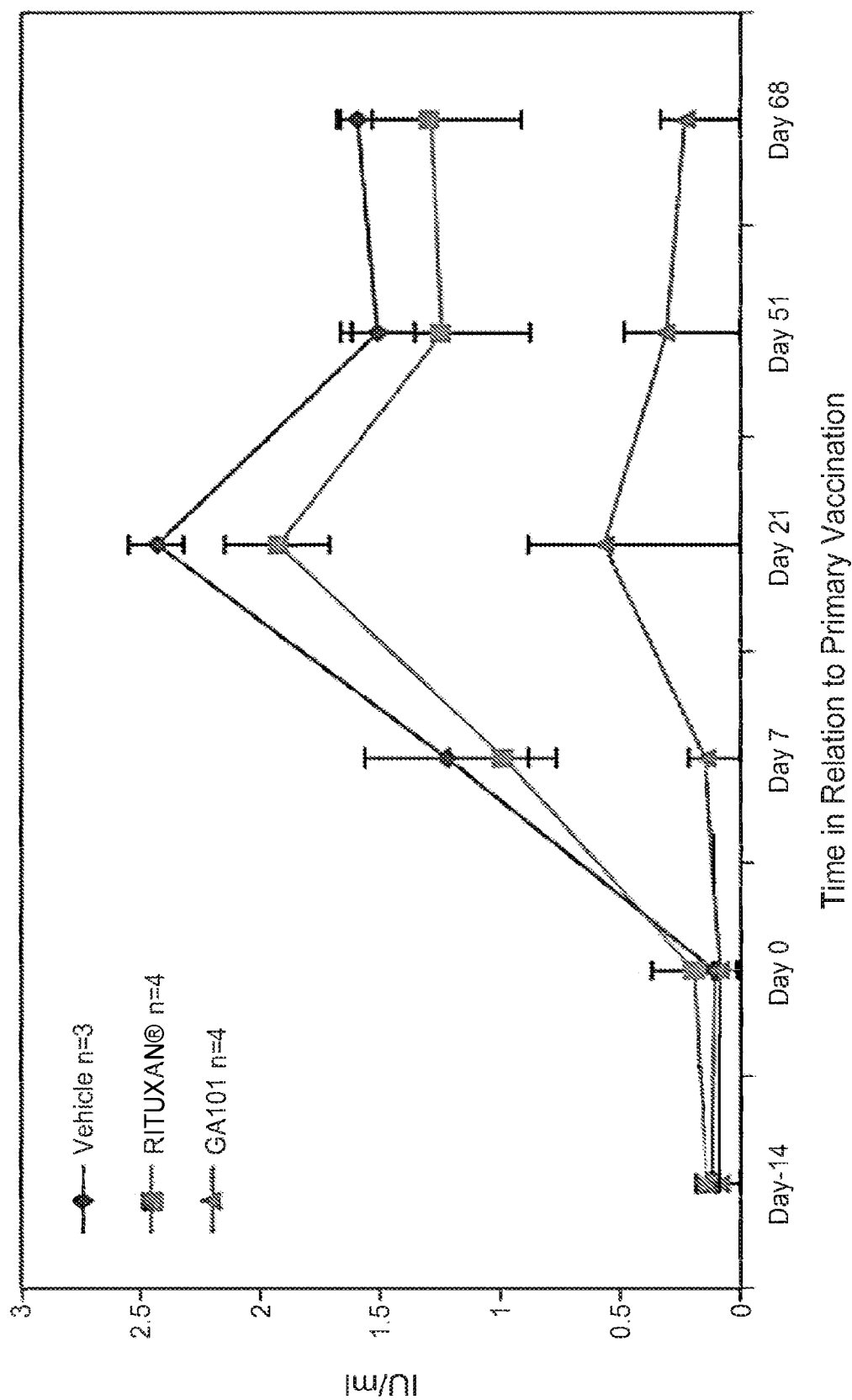
FIG. 1. Prior treatment with obinutuzumab but not rituximab or vehicle results in the attenuation of tetanus toxoid specific de novo IgG antibody responses in cynomolgus monkeys. RITUXAN® indicates rituximab and GA101 obinutuzumab, respectively.

Terms are used herein as generally used in the art, unless otherwise defined in the following.

CD20 (also known as B-lymphocyte antigen CD20, B-lymphocyte surface antigen B1, Leu-16, Bp35, BMS, and LFS; the human protein is characterized in UNIPROT® database entry P11836) is a hydrophobic transmembrane protein with a molecular weight of approximately 35 kD expressed on pre-B and mature B lymphocytes (Valentine, M. A. et al., J. Biol. Chem. 264 (1989) 11282-11287; Tedder, T. F., et al., Proc. Natl. Acad. Sci. U.S.A. 85 (1988) 208-212; Stamenkovic, I., et al., J. Exp. Med. 167 (1988) 1975-1980; Einfeld, D. A., et al., EMBO J. 7 (1988) 711-717; Tedder, T. F., et al., J. Immunol. 142 (1989) 2560-2568). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein.

The term "CD20" as used herein, refers to any native CD20 from any vertebrate source, including mammals such as primates (e.g. humans) and rodents (e.g., mice and rats), unless otherwise indicated. The term encompasses "full-length," unprocessed CD20 as well as any form of CD20 that results from processing in the cell. The term also encompasses naturally occurring variants of CD20, e.g., splice variants or allelic variants. In one embodiment, CD20 is human CD20. The amino acid sequence of an exemplary human CD20 is shown in SEQ ID NO: 1.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-CD20 antibody binds to an epitope of CD20 that is conserved among CD20 from different species.

By "Type II anti-CD20 antibody" is meant an anti-CD20 antibody having binding properties and biological activities of Type II anti-CD20 antibodies as described in Cragg et al., Blood 103 (2004) 2738-2743; Cragg et al., Blood 101 (2003) 1045-1052, Klein et al., mAbs 5 (2013), 22-33, and summarized in Table 1 below.

TABLE 1

| Properties of type I and type II anti-CD20 antibodies | |
|---|---|
| type I anti-CD20 antibodies | type II anti-CD20 antibodies |
| Bind class I CD20 epitope | Bind class II CD20 epitope |
| Localize CD20 to lipid rafts | Do not localize CD20 to lipid rafts |
| High CDC * | Low CDC * |
| ADCC activity * | ADCC activity * |
| Full binding capacity to B cells | Approx. half binding capacity to B cells |
| Weak homotypic aggregation | Homotypic aggregation |
| Low cell death induction | Strong cell death induction |

* if $IgG_1$ isotype

Examples of type II anti-CD20 antibodies include e.g. obinutuzumab (GA101), tositumumab (B1), humanized B-Ly1 antibody IgG1 (a chimeric humanized IgG1 antibody as disclosed in WO 2005/044859), 11B8 IgG1 (as disclosed in WO 2004/035607) and AT80 IgG1.

Examples of type I anti-CD20 antibodies include e.g. rituximab, ofatumumab, veltuzumab, ocaratuzumab, ocrelizumab, PRO131921, ublituximab, HI47 IgG3 (ECACC, hybridoma), 2C6 IgG1 (as disclosed in WO 2005/103081), 2F2 IgG1 (as disclosed in WO 2004/035607 and WO 2005/103081) and 2H7 IgG1 (as disclosed in WO 2004/056312).

The term "humanized B-Ly1 antibody" refers to humanized B-Ly1 antibody as disclosed in WO 2005/044859 and WO 2007/031875, which were obtained from the murine monoclonal anti-CD20 antibody B-Ly1 (variable region of the murine heavy chain (VH): SEQ ID NO: 2; variable region of the murine light chain (VL): SEQ ID NO: 3 (see Poppema, S. and Visser, L., Biotest Bulletin 3 (1987) 131-139) by chimerization with a human constant domain from IgG1 and following humanization (see WO 2005/044859 and WO 2007/031875). These "humanized B-Ly1 antibodies" are disclosed in detail in WO 2005/044859 and WO 2007/031875.

As used herein, the term "cytokine" refers to a molecule that mediates and/or regulates a biological or cellular function or process (e.g. immunity, inflammation, and hematopoiesis). The term "cytokine" as used herein includes "lymphokines," "chemokines," "monokines," and "interleukins". Examples of useful cytokines include, but are not limited to, GM-CSF, IL-1α, IL-1β, IL-2, IL-3, IL-4, IL-5, IL-6, IL-7, IL-8, IL-10, IL-12, IL-15, IFN-α, IFN-β, IFN-γ, MIP-1α, MIP-1β, TGF-β, TNF-α, and TNF-β. A particular cytokines is IL-2. The term "cytokine" as used herein is meant to also include cytokine variants comprising one or more amino acid mutations in the amino acid sequences of the corresponding wild-type cytokine, such as for example the IL-2 variants described in Sauve et al., Proc Natl Acad Sci USA 88, 4636-40 (1991); Hu et al., Blood 101, 4853-4861 (2003) and US Pat. Publ. No. 2003/0124678; Shanafelt et al., Nature Biotechnol 18, 1197-1202 (2000); Heaton et al., Cancer Res 53, 2597-602 (1993) and U.S. Pat. No. 5,229,109; US Pat. Publ. No. 2007/0036752; WO 2008/0034473; WO 2009/061853; or in WO 2012/107417.

The term "interleukin-2" or "IL-2" as used herein, refers to any native IL-2 from any vertebrate source, including mammals such as primates (e.g. humans) and rodents (e.g., mice and rats), unless otherwise indicated. The term encompasses unprocessed IL-2 as well as any form of IL-2 that results from processing in the cell. The term also encompasses naturally occurring variants of IL-2, e.g. splice variants or allelic variants. The amino acid sequence of an exemplary human IL-2 is shown in SEQ ID NO: 12. Unprocessed human IL-2 additionally comprises an N-terminal 20 amino acid signal peptide having the sequence of SEQ ID NO: 31, which is absent in the mature IL-2 molecule. The term "interleukin-2" as used herein is meant to also include IL-2 variants comprising one or more amino acid mutations in the amino acid sequences of the corresponding wild-type cytokine, such as for example the IL-2 variants described in Sauve et al., Proc Natl Acad Sci USA 88, 4636-40 (1991); Hu et al., Blood 101, 4853-4861 (2003) and US Pat. Publ. No. 2003/0124678; Shanafelt et al., Nature Biotechnol 18, 1197-1202 (2000); Heaton et al., Cancer Res 53, 2597-602 (1993) and U.S. Pat. No. 5,229, 109; US Pat. Publ. No. 2007/0036752; WO 2008/0034473; WO 2009/061853; or in WO 2012/107417.

The term "IL-2 mutant" or "mutant IL-2 polypeptide" as used herein is intended to encompass any mutant forms of various forms of the IL-2 molecule including full-length IL-2, truncated forms of IL-2 and forms where IL-2 is linked to another molecule such as by fusion or chemical conjugation. "Full-length" when used in reference to IL-2 is intended to mean the mature, natural length IL-2 molecule. For example, full-length human IL-2 refers to a molecule that has 133 amino acids (see e.g. SEQ ID NO: 12). The various forms of IL-2 mutants are characterized in having a at least one amino acid mutation affecting the interaction of IL-2 with CD25. This mutation may involve substitution, deletion, truncation or modification of the wild-type amino acid residue normally located at that position. Mutants obtained by amino acid substitution are preferred. Unless otherwise indicated, an IL-2 mutant may be referred to herein as an IL-2 mutant peptide sequence, an IL-2 mutant polypeptide, IL-2 mutant protein or IL-2 mutant analog. Designation of various forms of IL-2 is herein made with respect to the sequence shown in SEQ ID NO: 12. Various designations may be used herein to indicate the same mutation. For example a mutation from phenylalanine at position 42 to alanine can be indicated as 42A, A42, A42, F42A, or Phe42Ala.

As used herein, the term "release of cytokines" or "cytokine release" is synonymous with "cytokine storm" or "cytokine release syndrome" (abbreviated as "CRS"), and refers to an increase in the levels of cytokines, particularly tumor necrosis factor alpha (TNF-α), interferon gamma (IFN-γ), interleukin-6 (IL-6), interleukin-10 (IL-10), interleukin-2 (IL-2) and/or interleukin-8 (IL-8), in the blood of a subject during or shortly after (e.g. within 1 day of) administration of a therapeutic agent, resulting in adverse symptoms. Cytokine release is a type of infusion-related reaction (IRR), which are common adverse drug reactions to therapeutic agent and timely related to administration of the therapeutic agent. IRRs typically occur during or shortly after an administration of the therapeutic agent, i.e. typically within 24 hours after infusion, predominantly at the first infusion. In some instances, e.g. after the administration of CAR-T cells, CRS can also occur only later, e.g. several days after administration upon expansion of the CAR-T cells. The incidence and severity typically decrease with subsequent infusions. Symptoms may range from symptomatic discomfort to fatal events, and may include fever, chills, dizziness, hypertension, hypotension, dyspnea, restlessness, sweating, flushing, skin rash, tachycardia, tachypnoea, headache, tumour pain, nausea, vomiting and/or organ failure.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to CD25 or to an Fc receptor. Amino acid sequence deletions and insertions include amino- and/or carboxy-terminal deletions and insertions of amino acids. Particular amino acid mutations are amino acid substitutions. For the purpose of altering e.g. the binding characteristics of an IL-2 polypeptide or an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc region to glycine can be indicated as 329G, G329, $G_{329}$, P329G, or Pro329Gly.

The term "CD25" or "α-subunit of the IL-2 receptor" as used herein, refers to any native CD25 from any vertebrate source, including mammals such as primates (e.g. humans) and rodents (e.g., mice and rats), unless otherwise indicated. The term encompasses "full-length", unprocessed CD25 as well as any form of CD25 that results from processing in the cell. The term also encompasses naturally occurring variants of CD25, e.g. splice variants or allelic variants. In certain embodiments CD25 is human CD25. The amino acid sequence of human CD25 is shown in UNIPROT® (www.uniprot.org) accession no. P01589, or NCBI (www.ncbi.nlm.nih.gov/) RefSeq NP_000408.

The term "high-affinity IL-2 receptor" as used herein refers to the heterotrimeric form of the IL-2 receptor, consisting of the receptor γ-subunit (also known as common cytokine receptor γ-subunit, $\gamma_c$, or CD132), the receptor β-subunit (also known as CD122 or p70) and the receptor α-subunit (also known as CD25 or p55). The term "intermediate-affinity IL-2 receptor" by contrast refers to the IL-2 receptor including only the γ-subunit and the β-subunit, without the α-subunit (for a review see e.g. Olejniczak and Kasprzak, Med Sci Monit 14, RA179-189 (2008)).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., receptor and a ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art. A particular method for measuring affinity is Surface Plasmon Resonance (SPR).

"Reduction" (and grammatical variations thereof such as "reduce" or "reducing"), for example reduction of the number of B cells or the formation of ADAs or cytokine release, refers to a decrease in the respective quantity, as measured by appropriate methods known in the art. For clarity the term includes also reduction to zero (or below the detection limit of the analytical method), i.e. complete abolishment or elimination. Conversely, "increased" refers to an increase in the respective quantity.

By "regulatory T cell" or "$T_{reg}$ cell" is meant a specialized type of CD4$^+$ T cell that can suppress the responses of other T cells. $T_{reg}$ cells are characterized by expression of the α-subunit of the IL-2 receptor (CD25) and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors. $T_{reg}$ cells require IL-2 for their function and development and induction of their suppressive characteristics.

As used herein, the term "antigen binding moiety" refers to a polypeptide molecule that specifically binds to an antigenic determinant. In one embodiment, an antigen binding moiety is able to direct the entity to which it is attached (e.g. a cytokine or a second antigen binding moiety) to a target site, for example to a specific type of tumor cell or tumor stroma bearing the antigenic determinant. Antigen binding moieties include antibodies and fragments thereof as further defined herein. Preferred antigen binding moieties include an antigen binding domain of an antibody, comprising an antibody heavy chain variable region and an antibody light chain variable region. In certain embodiments, the antigen binding moieties may include antibody constant regions as further defined herein and known in the art. Useful heavy chain constant regions include any of the five isotypes: α, δ, ε, γ, or μ. Useful light chain constant regions include any of the two isotypes: κ and λ.

By "specifically binds" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance technique (analyzed on a BIACORE® instrument) (Liljeblad et al., Glyco J 17, 323-329 (2000)), and traditional binding assays (Heeley, Endocr Res 28, 217-229 (2002)).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, free in blood serum, and/or in the extracellular matrix (ECM).

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

As used herein, the term "effector moiety" refers to a polypeptide, e.g., a protein or glycoprotein, that influences cellular activity, for example, through signal transduction or other cellular pathways. Accordingly, the effector moiety can be associated with receptor-mediated signaling that transmits a signal from outside the cell membrane to modulate a response in a cell bearing one or more receptors for the effector moiety. In one embodiment, an effector moiety can elicit a cytotoxic response in cells bearing one or more receptors for the effector moiety. In another embodiment, an effector moiety can elicit a proliferative response in cells bearing one or more receptors for the effector moiety. In another embodiment, an effector moiety can elicit differentiation in cells bearing receptors for the effector moiety. In another embodiment, an effector moiety can alter expression (i.e. upregulate or downregulate) of an endogenous cellular protein in cells bearing receptors for the effector moiety. Non-limiting examples of effector moieties include cytokines, growth factors, hormones, enzymes, substrates, and cofactors. An effector moiety can be associated with an antigen binding moiety such as an antibody in a variety of configurations to form an immunoconjugate.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen binding activity.

The terms "full length antibody," "intact antibody," and "whole antibody" are used herein interchangeably to refer to an antibody having a structure substantially similar to a native antibody structure or having heavy chains that contain an Fc region as defined herein.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and multispecific antibodies formed from antibody fragments. The term "antibody fragment" as used herein also encompasses single-domain antibodies.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five classes, called α (IgA), δ (IgD), ε(IgE), γ (IgG), or μ (IgM), some of which may be further divided into subclasses, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (k), based on the amino acid sequence of its constant domain. An immunoglobulin essentially consists of two Fab molecules and an Fc domain, linked via the immunoglobulin hinge region.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen binding specificity.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));
  (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
  (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting heterodimerization" is a manipulation of the peptide backbone or the post-translational modifications of a polypeptide, e.g. an immunoglobulin heavy chain, that reduces or prevents the association of the polypeptide with an identical polypeptide to form a homodimer. A modification promoting heterodimerization as used herein particularly includes separate modifications made to each of two polypeptides desired to form a dimer, wherein the modifications are complementary to each other so as to promote association of the two polypeptides. For example, a modification promoting heterodimerization may alter the structure or charge of one or both of the polypeptides desired to form a dimer so as to make their association sterically or electrostatically favorable, respectively. Heterodimerization occurs between two non-identical polypeptides, such as two immunoglobulin heavy chains wherein further immunoconjugate components fused to each of the heavy chains (e.g. IL-2 polypeptide) are not the same. In the immunoconjugates useful in the present invention, the modification promoting heterodimerization is in the heavy chain(s), specifically in the Fc domain, of an immunoglobulin molecule. In some embodiments the modification promoting heterodimerziation comprises an amino acid mutation, specifically an amino acid substitution. In a particular embodiment, the modification promoting heterodimerization comprises a separate amino acid mutation, specifically an amino acid substitution, in each of the two immunoglobulin heavy chains.

Similarly, a "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89).

The term "effector functions" when used in reference to antibodies refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the term "effector cells" refers to a population of lymphocytes that display effector moiety receptors, e.g. cytokine receptors, and/or Fc receptors on their surface through which they bind an effector moiety, e.g. a cytokine, and/or an Fc region of an antibody and contribute to the destruction of target cells, e.g. tumor cells. Effector cells may for example mediate cytotoxic or phagocytic effects. Effector cells include, but are not limited to, effector T cells such as CD8$^+$ cytotoxic T cells, CD4$^+$ helper T cells, γδ T cells, NK cells, lymphokine-activated killer (LAK) cells and macrophages/monocytes.

As used herein, the terms "engineer, engineered, engineering," are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. "Engineering", particularly with the prefix "glyco-", as well as the term "glycosylation engineering" includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity. Glycosylation engineering can be used to obtain a "host cell having increased GnTIII activity" (e.g. a host cell that has been manipulated to express increased levels of one or more polypeptides having β(1,4)-N-acetylglucosaminyltransferase III (GnTIII) activity), a "host cell having increased ManII activity" (e.g. a host cell that has been manipulated to express increased levels of one or more polypeptides having α-mannosidase II (ManII) activity), or a "host cell having decreased α(1,6) fucosyltransferase activity" (e.g. a host cell that has been manipulated to express decreased levels of α(1,6) fucosyltransferase).

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate proteins used for the present invention. In one embodiment, the host cell is engineered to allow the production of an antibody with modified oligosaccharides. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term "polypeptide having GnTIII activity" refers to polypeptides that are able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependency in a given activity as compared to the GnTIII (i.e. the candidate polypeptide will exhibit greater activity or not more than about 25-fold less and, preferably, not more than about ten-fold less activity, and most preferably, not more than about three-fold less activity relative to the GnTIII). In certain embodiments the polypeptide having GnTIII activity is a fusion polypeptide comprising the catalytic domain of GnTIII and the Golgi localization domain of a heterologous Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference.

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the term "polypeptide having ManII activity" refers to polypeptides that are able to catalyze the hydrolysis of the terminal 1,3- and 1,6-linked α-D-mannose residues in the branched $GlcNAcMan_5GlcNAc_2$ mannose intermediate of N-linked oligosaccharides. This includes polypeptides exhibiting enzymatic activity similar to, but not necessarily identical to, an activity of Golgi α-mannosidase II, also known as mannosyl oligosaccharide 1,3-1,6-α-mannosidase II (EC 3.2.1.114), according to the Nomenclature Committee of the International Union of Biochemistry and Molecular Biology (NC-IUBMB).

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g. to express the glycosyltransferase, GnTIII, or other glycosyltransferases) by the methods described herein, is relative to the ADCC mediated by the same antibody produced by the same type of non-engineered host cells.

By "antibody having increased/reduced antibody dependent cell-mediated cytotoxicity (ADCC)" is meant an antibody having increased/reduced ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
    i) the PBMCs are isolated using standard density centrifugation procedures and are suspended at $5 \times 10^6$ cells/ml in RPMI cell culture medium;
    ii) the target cells are grown by standard tissue culture methods, harvested from the exponential growth phase with a viability higher than 90%, washed in RPMI cell culture medium, labeled with 100 microCuries of $^{51}Cr$, washed twice with cell culture medium, and resuspended in cell culture medium at a density of $10^5$ cells/ml;
    iii) 100 microliters of the final target cell suspension above are transferred to each well of a 96-well microtiter plate;
    iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
    v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
    vi) for the spontaneous release (SR) controls, 3 additional wells in the plate containing the labeled target cells, receive 50 microliters of RPMI cell culture medium instead of the antibody solution (point iv above);
    vii) the 96-well microtiter plate is then centrifuged at 50×g for 1 minute and incubated for 1 hour at 4° C.;
    viii) 50 microliters of the PBMC suspension (point i above) are added to each well to yield an effector: target cell ratio of 25:1 and the plates are placed in an incubator under 5% $CO_2$ atmosphere at 37° C. for 4 hours;
    ix) the cell-free supernatant from each well is harvested and the experimentally released radioactivity (ER) is quantified using a gamma counter;
    x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased/reduced ADCC" is defined as either an increase/reduction in the maximum percentage of specific lysis observed within the antibody concentration range tested above, and/or a reduction/increase in the concentration of antibody required to achieve one half of the maximum percentage of specific lysis observed within the antibody concentration range tested above. The increase/reduction in ADCC is relative to the ADCC, measured with the above assay, mediated by the same antibody, produced by the same type of host cells, using the same standard production, purification, formulation and storage methods, which are known to those skilled in the art, but that has not been engineered.

As used herein, the term "immunoconjugate" refers to a polypeptide molecule that includes at least one effector moiety, such as a cytokine, and an antigen binding moiety, such as an antibody. In certain embodiments, the immunoconjugate comprises not more than one effector moiety. Particular immunoconjugates useful in the invention essentially consist of one effector moiety and an antibody joined by one or more peptide linkers. Particular immunoconjugates according to the invention are fusion proteins, i.e. the components of the immunconjugate are joined by peptide bonds.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the terms "first", "second", "third" etc. with respect to antigen binding moieties etc., are used for convenience of distinguishing when there is more than one of each type of moiety. Use of these terms is not intended to confer a specific order or orientation unless explicitly so stated.

The terms "multispecific" and "bispecific" mean that the antigen binding molecule is able to specifically bind to at least two distinct antigenic determinants. Typically, a bispecific antigen binding molecule comprises two antigen binding sites, each of which is specific for a different antigenic determinant. In certain embodiments a bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

A "T cell activating therapeutic agent" as used herein refers to a therapeutic agent capable of inducing T cell activation in a subject, particularly a therapeutic agent designed for inducing T-cell activation in a subject. Examples of T cell activating therapeutic agents include bispecific antibodies that specifically bind an activating T cell antigen, such as CD3, and a target cell antigen, such as CD20 or CD19. Further examples include chimeric antigen receptors (CARs) which comprise a T cell activating domain and an antigen binding moiety that specifically binds to a target cell antigen, such as CD20 or CD19.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules and T cell activating therapeutic agents used in the present invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma.

A "B-cell antigen" as used herein refers to an antigenic determinant presented on the surface of a B lymphocyte, particularly a malignant B lymphocyte (in that case the antigen also being referred to as "malignant B-cell antigen").

A "T-cell antigen" as used herein refers to an antigenic determinant presented on the surface of a T lymphocyte, particularly a cytotoxic T lymphocyte.

A "Fab molecule" refers to a protein consisting of the VH and CH1 domain of the heavy chain (the "Fab heavy chain") and the VL and CL domain of the light chain (the "Fab light chain") of an immunoglobulin.

By "chimeric antigen receptor" or "CAR" is meant a genetically engineered receptor protein comprising an antigen binding moiety, e.g. a single-chain variable fragment (scFv) of a targeting antibody, a transmembrane domain, an intracellular T-cell activating signaling domain (e.g. the CD3 zeta chain of the T-cell receptor) and optionally one or more intracellular co-stimulatory domains (e.g. of CD28, CD27, CD137 (4-1BB), Ox40). CARs mediate antigen recognition, T cell activation, and—in the case of second-generation CARs—costimulation to augment T cell functionality and persistence. For a review see e.g. Jackson et al., Nat Rev Clin Oncol (2016) 13, 370-383.

By "B cell proliferative disorder" is meant a disease wherein the number of B cells in a patient is increased as compared to the number of B cells in a healthy subject, and particularly wherein the increase in the number of B cells is the cause or hallmark of the disease. A "CD20-positive B cell proliferative disorder" is a B cell proliferative disorder wherein B-cells, particularly malignant B-cells (in addition to normal B-cells), express CD20.

Exemplary B cell proliferation disorders include Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), as well as some types of Multiple myeloma (MM) and Hodgkin lymphoma (HL).

By "fused" is meant that the components (e.g. a Fab molecule and an Fc domain subunit) are linked by peptide bonds, either directly or via one or more peptide linkers.

An "anti-drug antibody" or "ADA" refers to an antibody that binds to a therapeutic agent and may influence serum concentrations and function of the therapeutic agent in a subject. The presence of ADAs may increase clearance of the therapeutic agent through formation of immune complexes between therapeutic agent and antibody (neutralizing, non-neutralizing or both), thus reducing the therapeutic agent's half-life. Furthermore, the activity and effectiveness of the therapeutic agent may be decreased through binding of antibody to the therapeutic agent (particularly in the case of neutralizing ADAs). ADAs can also be associated with allergic or hypersensitivity reactions and other adverse events.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

By "therapeutic agent" is meant an active ingredient, e.g. of a pharmaceutical composition, that is administered to a subject in an attempt to alter the natural course of a disease in the subject being treated, and can be performed either for prophylaxis or during the course of clinical pathology. An "immunotherapeutic agent" refers to a therapeutic agent that is administered to a subject in an attempt to restore or enhance the subject's immune response, e.g. to a tumor.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Preferably, the individual or subject is a human.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, methods of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

"CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3c). The amino acid sequence of human CD3c is shown in UNIPROT® (www.uniprot.org) accession no. P07766 (version 144), or NCBI (www.ncbi.nlm.nih.gov/) RefSeq NP_000724.1. See also SEQ ID NO: 115. The amino acid sequence of cynomolgus [*Macaca fascicularis*] CD3c is shown in NCBI GENBANK® no. BAB71849.1. See also SEQ ID NO: 116.

"CD19" refers to B-lymphocyte antigen CD19, also known as B-lymphocyte surface antigen B4 or T-cell surface antigen Leu-12 and includes any native CD19 from any vertebrate source, including mammals such as primates (e.g. humans) and rodents (e.g., mice and rats), unless otherwise indicated. The term encompasses "full-length," unprocessed CD19 as well as any form of CD19 that results from processing in the cell. The term also encompasses naturally occurring variants of CD19, e.g., splice variants or allelic variants. In one embodiment, CD19 is human CD19. The amino acid sequence of an exemplary human CD19 is shown in UNIPROT® (www.uniprot.org) accession no. P15391 (version 174), or NCBI (www.ncbi.nlm.nih.gov/) RefSeq NP_001770.5, and SEQ ID NO: 117.

"Carcinoembryonic antigen" or "CEA" (also known as Carcinoembryonic antigen-related cell adhesion molecule 5 (CEACAM5)) refers to any native CEA from any vertebrate source, including mammals such as primates (e.g. humans), non-human primates (e.g. cynomolgus monkeys) and rodents (e.g. mice and rats), unless otherwise indicated. The term encompasses "full-length," unprocessed CEA as well as any form of CEA that results from processing in the cell. The term also encompasses naturally occurring variants of CEA, e.g., splice variants or allelic variants. In one embodiment, CEA is human CEA. The amino acid sequence of human CEA is shown in UNIPROT® (www.uniprot.org) accession no. P06731, or NCBI (www.ncbi.nlm.nih.gov/) RefSeq NP_004354.2.

"Fibroblast activation protein" or "FAP" (also known as seprase) refers to any native FAP from any vertebrate source, including mammals such as primates (e.g. humans), non-human primates (e.g. cynomolgus monkeys) and rodents (e.g. mice and rats), unless otherwise indicated. The term encompasses "full-length," unprocessed FAP as well as any form of FAP that results from processing in the cell. The term also encompasses naturally occurring variants of FAP, e.g., splice variants or allelic variants. In one embodiment, FAP is human FAP. The amino acid sequence of human FAP is shown in UNIPROT® (www.uniprot.org) accession no. Q12884, or NCBI (www.ncbi.nlm.nih.gov/) RefSeq NP_004451.2.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

Type II Anti-CD20 Antibodies

The CD20 molecule (also called human B-lymphocyte-restricted differentiation antigen or Bp35) is a hydrophobic transmembrane protein expressed on the surface of malignant and non-malignant pre-B and mature B lymphocytes that has been described extensively (Valentine, M. A., et al., J. Biol. Chem. 264 (1989) 11282-11287; and Einfeld, D. A., et al., EMBO J. 7 (1988) 711-717; Tedder, T. F., et al., Proc. Natl. Acad. Sci. U.S.A. 85 (1988) 208-212; Stamenkovic, I., et al., J. Exp. Med. 167 (1988) 1975-1980; Tedder, T. F., et al., J. Immunol. 142 (1989) 2560-2568).

CD20 is highly expressed by over 90% of B cell non-Hodgkin's lymphomas (NHL) (Anderson, K. C., et al., Blood 63 (1984) 1424-1433) but is not found on hematopoietic stem cells, pro-B cells, normal plasma cells, or other normal tissues (Tedder, T. F., et al., J, Immunol. 135 (1985) 973-979).

There exist two different types of anti-CD20 antibodies differing significantly in their mode of CD20 binding and biological activities (Cragg, M. S., et al., Blood 103 (2004) 2738-2743; and Cragg, M. S., et al., Blood 101 (2003) 1045-1052). Type I anti-CD20 antibodies primarily utilize complement to kill target cells, while Type II antibodies primarily operate through direct induction of cell death.

Type I and Type II anti-CD20 antibodies and their characteristics are reviewed e.g. in Klein et al., mAbs 5 (2013), 22-33. Type II anti-CD20 antibodies do not localize CD20 to lipid rafts, show low CDC activity, show only about half the binding capacity to B cells as compared to Type I anti-CD20 antibodies, and induce homotypic aggregation and direct cell death. In contrast thereto, Type I antibodies localize CD20 to lipid rafts, show high CDC activity, full binding capacity to B cells, and only weak induction of homotypic aggregation and direct cell death.

Obinutuzumab and tositumomab (CAS number 192391-48) are examples of Type II anti-CD20 antibodies, while rituximab, ofatumumab, veltuzumab, ocaratuzumab, ocrelizumab, PRO131921 and ublituximab are examples of Type I anti-CD20 antibodies.

According to the invention, the anti-CD20 antibody is a Type II anti-CD20 antibody. In one embodiment according to the present invention, the Type II anti-CD20 antibody is capable of reducing the number of B cells in a subject. In one embodiment the Type II anti-CD20 antibody is an IgG antibody, particularly an IgG1 antibody. In one embodiment, the Type II anti-CD20 antibody is a full-length antibody. In one embodiment, the Type II anti-CD20 antibody comprises an Fc region, particularly an IgG Fc region or, more particularly, an IgG1 Fc region. In one embodiment the Type II anti-CD20 antibody is a humanized B-Ly1 antibody. Particularly, the Type II anti-CD20 antibody is a humanized, IgG-class Type II anti-CD20 antibody, having the binding specificity of the murine B-Ly1 antibody (Poppema and Visser, Biotest Bulletin 3, 131-139 (1987); SEQ ID NOs 2 and 3).

In one embodiment, the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9. Particularly, the heavy chain variable region framework regions (FRs) FR1, FR2, and FR3 of said Type II anti-CD20 antibody are human FR sequences encoded by the VH1_10 human germ-line sequence, the heavy chain variable region FR4 of said anti-CD20 antibody is a human FR sequence encoded by the JH4 human germ-line sequence, the light chain variable region FRs FR1, FR2, and FR3 of said Type II anti-CD20 antibody are human FR sequences encoded by the VK_2_40 human germ-line sequence, and the light chain variable region FR4 of said anti-CD20 antibody is a human FR sequence encoded by the JK4 human germ-line sequence. In one embodiment, the Type II anti-CD20 antibody comprises the heavy chain variable region sequence of SEQ ID NO: 10 and the light chain variable region sequence of SEQ ID NO: 11.

In a particular embodiment, the Type II anti-CD20 antibody is obinutuzumab (recommended INN, WHO Drug Information, Vol. 26, No. 4, 2012, p. 453). As used herein, obinutuzumab is synonymous for GA101. The tradename is GAZYVA® or GAZYVARO®. This replaces all previous versions (e.g. Vol. 25, No. 1, 2011, p.'75-'76), and is formerly known as afutuzumab (recommended INN, WHO Drug Information, Vol. 23, No. 2, 2009, p. 176; Vol. 22, No. 2, 2008, p. 124). In one embodiment, the Type II anti-CD20 antibody is tositumomab.

The Type II anti-CD20 antibody useful in the present invention may be engineered to have increased effector function, as compared to a corresponding non-engineered antibody. In one embodiment the antibody engineered to have increased effector function has at least 2-fold, at least 10-fold or even at least 100-fold increased effector function, compared to a corresponding non-engineered antibody. The increased effector function can include, but is not limited to, one or more of the following: increased Fc receptor binding, increased C1q binding and complement dependent cytotoxicity (CDC), increased antibody-dependent cell-mediated cytotoxicity (ADCC), increased antibody-dependent cellular phagocytosis (ADCP), increased cytokine secretion, increased immune complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming.

In one embodiment the increased effector function one or more selected from the group of increased Fc receptor binding, increased CDC, increased ADCC, increased ADCP, and increased cytokine secretion. In one embodiment the increased effector function is increased binding to an activating Fc receptor. In one such embodiment the binding affinity to the activating Fc receptor is increased at least 2-fold, particularly at least 10-fold, compared to the binding affinity of a corresponding non-engineered antibody. In a specific embodiment the activating Fc receptor is selected from the group of FcγRIIIa, FcγRI, and FcγRIIa. In one embodiment the activating Fc receptor is FcγRIIIa, particularly human FcγRIIIa. In another embodiment the increased effector function is increased ADCC. In one such embodiment the ADCC is increased at least 10-fold, particularly at least 100-fold, compared to the ADCC mediated by a corresponding non-engineered antibody. In yet another embodiment the increased effector function is increased binding to an activating Fc receptor and increased ADCC.

Increased effector function can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821, 337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998). Binding to Fc receptors can be easily determined e.g. by ELISA, or by Surface Plasmon Resonance (SPR) using standard instrumentation such as a BIACORE® instrument (GE Healthcare), and Fc receptors such as may be obtained by recombinant expression. According to a particular embodiment, binding affinity to an activating Fc receptor is measured by surface plasmon resonance using a BIACORE® T100 machine (GE Healthcare) at 25° C. Alternatively, binding affinity of antibodies for Fc receptors may be evaluated using cell lines known to express particular Fc receptors, such as NK cells expressing FcγIIIa receptor. C1q binding assays may also be carried out to determine whether the antibody is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Increased effector function may result e.g. from glycoengineering of the Fc region or the introduction of amino acid mutations in the Fc region of the antibody. In one embodiment the anti-CD20 antibody is engineered by introduction of one or more amino acid mutations in the Fc region. In a specific embodiment the amino acid mutations are amino acid substitutions. In an even more specific embodiment the amino acid substitutions are at positions 298, 333, and/or 334 of the Fc region (EU numbering of residues). Further suitable amino acid mutations are described e.g. in Shields et al., J Biol Chem 9(2), 6591-6604 (2001); U.S. Pat. No. 6,737,056; WO 2004/063351 and WO 2004/099249. Mutant Fc regions can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

In another embodiment the Type II anti-CD20 antibody is engineered by modification of the glycosylation in the Fc region. In a specific embodiment the Type II anti-CD20 antibody is engineered to have an increased proportion of non-fucosylated oligosaccharides in the Fc region as compared to a non-engineered antibody. An increased proportion of non-fucosylated oligosaccharides in the Fc region of an antibody results in the antibody having increased effector function, in particular increased ADCC.

In a more specific embodiment, at least about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 40%, of the N-linked oligosaccharides in the Fc region of the Type II anti-CD20 antibody are non-fucosylated. In one embodiment, between about 40% and about 80% of the N-linked oligosaccharides in the Fc region of the Type II anti-CD20 antibody are non-fucosylated. In one embodiment, between about 40% and about 60% of the N-linked oligosaccharides in the Fc region of the Type II anti-CD20 antibody are non-fucosylated. The non-fucosylated oligosaccharides may be of the hybrid or complex type.

In another specific embodiment the Type II anti-CD20 antibody is engineered to have an increased proportion of bisected oligosaccharides in the Fc region as compared to a non-engineered antibody. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 40%, of the N-linked oligosaccharides in the Fc region of the Type II anti-CD20 antibody are bisected. In one embodiment, between about 40% and about 80% of the N-linked oligosaccharides in the Fc region of the anti-CD20 antibody are bisected. In one embodiment, between about 40% and about 60% of the N-linked oligosaccharides in the Fc region of the Type II anti-CD20 antibody are bisected. The bisected oligosaccharides may be of the hybrid or complex type.

In yet another specific embodiment the anti-CD20 antibody is engineered to have an increased proportion of bisected, non-fucosylated oligosaccharides in the Fc region, as compared to a non-engineered antibody. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 15%, more preferably at least about 25%, of the N-linked oligosaccharides in the Fc region of the anti-CD20 antibody are bisected, non-fucosylated. The bisected, non-fucosylated oligosaccharides may be of the hybrid or complex type.

The oligosaccharide structures in the antibody Fc region can be analysed by methods well known in the art, e.g. by MALDI TOF mass spectrometry as described in Umana et al., Nat Biotechnol 17, 176-180 (1999) or Ferrara et al., Biotechn Bioeng 93, 851-861 (2006). The percentage of non-fucosylated oligosaccharides is the amount of oligosaccharides lacking fucose residues, relative to all oligosaccharides attached to Asn 297 (e. g. complex, hybrid and high mannose structures) and identified in an N-glycosidase F treated sample by MALDI TOF MS. Asn 297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. The percentage of bisected, or bisected non-fucosylated, oligosaccharides is determined analogously.

In one embodiment the Type II anti-CD20 antibody is engineered to have modified glycosylation in the Fc region, as compared to a non-engineered antibody, by producing the antibody in a host cell having altered activity of one or more glycosyltransferase. Glycosyltransferases include β(1,4)-N-acetylglucosaminyltransferase III (GnTIII), β(1,4)-galactosyltransferase (GalT), 13(1,2)-N-acetylglucosaminyltransferase I (GnTI), β(1,2)-N-acetylglucosaminyltransferase II (GnTII) and α(1,6)-fucosyltransferase. In a specific embodiment the Type II anti-CD20 antibody is engineered to have an increased proportion of non-fucosylated oligosaccharides in the Fc region, as compared to a non-engineered antibody, by producing the antibody in a host cell having increased β(1,4)-N-acetylglucosaminyltransferase III (GnTIII) activity. In an even more specific embodiment the host cell additionally has increased α-mannosidase II (ManII) activity. The glycoengineering methodology that can be used for engineering antibodies useful for the present invention has been described in greater detail in Umana et al., Nat Biotechnol 17, 176-180 (1999); Ferrara et al., Biotechn Bioeng 93, 851-861 (2006); WO 99/54342 (U.S. Pat. No. 6,602,684; EP 1071700); WO 2004/065540 (U.S. Pat. Appl. Publ. No. 2004/0241817; EP 1587921), WO 03/011878 (U.S. Pat. Appl. Publ. No. 2003/0175884), the entire content of each of which is incorporated herein by reference in its entirety. Antibodies glycoengineered using this methodology are referred to as GlycoMabs herein.

Generally, any type of cultured cell line, including the cell lines discussed herein, can be used to generate cell lines for the production of anti-TNC A2 antibodies with altered glycosylation pattern. Particular cell lines include CHO cells, BHK cells, NS0 cells, SP2/0 cells, YO myeloma cells, P3X63 mouse myeloma cells, PER cells, PER.C6 cells or hybridoma cells, and other mammalian cells. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. In a specific embodiment, the polypeptide having GnTIII activity is a fusion polypeptide comprising the catalytic domain of GnTIII and the Golgi localization domain of a heterologous Golgi resident polypeptide. Particularly, said Golgi localization domain is the Golgi localization domain of mannosidase II. Methods for generating such fusion polypeptides and using them to produce antibodies with increased effector functions are disclosed in Ferrara et al., Biotechn Bioeng 93, 851-861 (2006) and WO2004/065540, the entire contents of which are expressly incorporated herein by reference.

The host cells which contain the coding sequence of an antibody useful for the invention and/or the coding sequence of polypeptides having glycosyltransferase activity, and which express the biologically active gene products may be identified e.g. by DNA-DNA or DNA-RNA hybridization; the presence or absence of "marker" gene functions; assessing the level of transcription as measured by the expression of the respective mRNA transcripts in the host cell; or detection of the gene product as measured by immunoassay or by its biological activity—methods which are well known in the art. GnTIII or Man II activity can be detected e.g. by employing a lectin which binds to biosynthetis products of GnTIII or ManII, respectively. An example for such a lectin is the E4-PHA lectin which binds preferentially to oligosaccharides containing bisecting GlcNAc. Biosynthesis products (i.e. specific oligosaccharide structures) of polypeptides having GnTIII or ManII activity can also be detected by mass spectrometric analysis of oligosaccharides released from glycoproteins produced by cells expressing said polypeptides. Alternatively, a functional assay which measures the increased effector function, e.g. increased Fc receptor binding, mediated by antibodies produced by the cells engineered with the polypeptide having GnTIII or ManII activity may be used.

In another embodiment the anti-CD20 antibody is engineered to have an increased proportion of non-fucosylated oligosaccharides in the Fc region, as compared to a non-engineered antibody, by producing the antibody in a host cell having decreased α(1,6)-fucosyltransferase activity. A host cell having decreased α(1,6)-fucosyltransferase activity may be a cell in which the α(1,6)-fucosyltransferase gene has been disrupted or otherwise deactivated, e.g. knocked out (see Yamane-Ohnuki et al., Biotech Bioeng 87, 614 (2004); Kanda et al., Biotechnol Bioeng, 94(4), 680-688 (2006); Niwa et al., J Immunol Methods 306, 151-160 (2006)).

Other examples of cell lines capable of producing defucosylated antibodies include Lec13 CHO cells deficient in protein fucosylation (Ripka et al., Arch Biochem Biophys 249, 533-545 (1986); US Pat. Appl. No. US 2003/0157108; and WO 2004/056312, especially at Example 11). The antibodies useful in the present invention can alternatively be glycoengineered to have reduced fucose residues in the Fc region according to the techniques disclosed in EP 1 176 195 A1, WO 03/084570, WO 03/085119 and U.S. Pat. Appl. Pub. Nos. 2003/0115614, 2004/093621, 2004/110282, 2004/110704, 2004/132140, U.S. Pat. No. 6,946,292 (Kyowa), e.g. by reducing or abolishing the activity of a GDP-fucose transporter protein in the host cells used for antibody production.

Glycoengineered antibodies useful in the invention may also be produced in expression systems that produce modified glycoproteins, such as those taught in WO 03/056914 (GlycoFi, Inc.) or in WO 2004/057002 and WO 2004/024927 (Greenovation).

Therapeutic Agents

The present invention is useful in connection with various therapeutic agents, particularly with therapeutic agents that are immunogenic in the subject (i.e. have the ability of inducing an immune response in the subject) and/or that activate T-cells in the subject. Such therapeutic agents include, for example, recombinant proteins.

In one embodiment, the therapeutic agent induces the formation of ADAs in a subject when administered to the subject in a treatment regimen without the administration of a Type II anti-CD20 antibody. In one embodiment, the therapeutic agent induces cytokine release in a subject when administered to the subject in a treatment regimen without the administration of a Type II anti-CD20 antibody. In one embodiment, the therapeutic agent induces formation of ADAs and cytokine release in a subject when administered to the subject in a treatment regimen without the administration of a Type II anti-CD20 antibody.

In one embodiment, the therapeutic agent is a biologic agent. In one embodiment, the therapeutic agent comprises a polypeptide, particularly a recombinant polypeptide. In one embodiment, the therapeutic agent comprises a polypeptide that does not naturally occur in the subject and/or is immunogenic in the subject. In one embodiment, the therapeutic agent is to be systemically administered. In one embodiment, the therapeutic agent is to be administered by infusion, particularly intravenous infusion.

In one embodiment, the therapeutic agent comprises an antigen binding polypeptide. In one embodiment, the therapeutic agent comprises a polypeptide selected from the group of an antibody, an antibody fragment, an Fc domain, and an immunoconjugate. In one embodiment, the therapeutic agent comprises a polypeptide selected from the group of an antibody, an antibody fragment, an antigen receptor or an antigen-binding fragment thereof, and a receptor ligand or a receptor-binding fragment thereof. In one embodiment, the therapeutic agent comprises an antibody. In one embodiment, the antibody is a monoclonal antibody. In one embodiment, the antibody is a polyclonal antibody. In one embodiment the antibody is a human antibody. In one embodiment, the antibody is humanized antibody. In one embodiment the antibody is a chimeric antibody. In one embodiment the antibody is full-length antibody. In one embodiment the antibody is an IgG-class antibody, particularly an IgG1 subclass antibody. In one embodiment, the antibody is a recombinant antibody.

In certain embodiments, the therapeutic agent comprises an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Plückthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. In one embodiment, the antibody fragment is a Fab fragment or a scFv fragment.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., *Proc. Natl. Acad. Sci. USA* 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

In certain embodiments, the therapeutic agent comprises a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, the therapeutic agent comprises a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, the therapeutic agent comprises a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOuSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., J. Immunol., 147:86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies comprised in the therapeutic agent may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

In certain embodiments, the therapeutic agent comprises a multispecific antibody, e.g. a bispecific antibody. Multispecific antibodies are monoclonal antibodies that have binding specificities for at least two different sites. In certain embodiments, the binding specificities are for different antigens. In certain embodiments, the binding specificities are for different epitopes on the same antigen. Bispecific antibodies may also be used to localize cytotoxic agents to cells which express an antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to two different antigens (see, US 2008/0069820, for example).

"Crossmab" antibodies are also included herein (see e.g. WO2009080251, WO2009080252, WO2009080253, WO2009080254).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain (VH) and a variable light chain (VL) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell. As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

Antibodies with more than two valencies are contemplated. For example, trispecific antibodies can be prepared. Tuft et al. *J. Immunol.* 147: 60 (1991).

In certain embodiments, an antibody comprised in the therapeutic agent may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The therapeutic agent may also comprise an antibody conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, the therapeutic agent comprises an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, the therapeutic agent comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, the therapeutic agent comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-4-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

In some embodiments, the therapeutic agent may comprise an monoclonal antibody such as, but not limited to, alemtuzumab (LEMTRADA®), bevacizumab (AVASTIN®), cetuximab (ERBITUX®), panitumumab (VECTIBIX®), pertuzumab (OMNITARG®, 2C4), trastuzumab (HERCEPTIN®), tositumomab (Bexxar®), abciximab (REOPRO®), adalimumab (HUMIRA®), apolizumab, aselizumab, atlizumab, bapineuzumab, basiliximab (SIMULECT®), bavituximab, belimumab (BENLYSTA®) briankinumab, canakinumab (ILARIS®), cedelizumab, certolizumab pegol (CIMZIA®), cidfusituzumab, cidtuzumab, cixutumumab, clazakizumab, crenezumab, daclizumab (ZENAPAX®), dalotuzumab, denosumab (PROLIA®, XGEVA®), eculizumab (SOLIRIS®), efalizumab, epratuzumab, erlizumab, felvizumab, fontolizumab, golimumab (SIMPONI®), ipilimumab, imgatuzumab, infliximab (REMICADE®), labetuzumab, lebrikizumab, lexatumumab, lintuzumab, lucatumumab, lulizumab pegol, lumretuzumab, mapatumumab, matuzumab, mepolizumab, mogamulizumab, motavizumab, motovizumab, muronomab, natalizumab (TYSABRI®), necitumumab (PORTRAZZA®), nimotuzumab (THERACIM®), nolovizumab, numavizumab, olokizumab, omalizumab (XOLAIR®), onartuzumab (also known as MetMAb), palivizumab (SYNAGIS®), pascolizumab, pecfusituzumab, pectuzumab, pembrolizumab (KEYTRUDA®), pexelizumab, priliximab, ralivizumab, ranibizumab (LUCENTIS®) reslivizumab, reslizumab, resyvizumab, robatumumab, rontalizumab, rovelizumab, ruplizumab, sarilumab, secukinumab, seribantumab, sifalimumab, sibrotuzumab, siltuximab (SYLVANT®) siplizumab, sontuzumab, tadocizumab, talizumab, tefibazumab, tocilizumab (ACTEMRA®), toralizumab, tucusituzumab, umavizumab, urtoxazumab, ustekinumab (STELARA®), vedolizumab (ENTYVIO®), visilizumab, zanolimumab, zalutumumab.

In one embodiment, the therapeutic agent comprises an antibody indicated for the treatment of cancer. In one embodiment, the therapeutic agent comprises an antibody indicated for the treatment of an autoimmune disease. In one embodiment, the therapeutic agent is an immunotherapeutic agent. In one embodiment the therapeutic agent is indicated for the treatment of cancer. In some embodiments, in particular in relation aspects of the invention concerned with the reduction of cytokine release associated with the administration of a therapeutic agent in a subject, the cancer is a B-cell proliferative disorder. In one embodiment, the cancer is a CD20-positive B-cell proliferative disorder. In one embodiment, the cancer is selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM), and Hodgkin lymphoma (HL). In one embodiment, the therapeutic agent is an immunotherapeutic agent.

In one embodiment, the therapeutic agent is an immunosuppressive agent. In one embodiment, the therapeutic agent is indicated for the treatment of an autoimmune disease.

Without wishing to be bound to theory, it is thought that enhancing T cell stimulation, by promoting an activating co-stimulatory molecule or by inhibiting a negative co-stimulatory molecule, may promote tumor cell death thereby treating or delaying progression of cancer. In some embodiments, the therapeutic agent may comprise an agonist directed against an activating co-stimulatory molecule. In some embodiments, an activating co-stimulatory molecule may include CD40. CD226. CD28, OX40. GITR, CD137, CD27, HVEM, or CD127. In some embodiments, the agonist directed against an activating co-stimulatory molecule is an agonist antibody that binds to CD40, CD226. CD28.OX40, GITR. CD137, CD27, HVEM, or CD127. In some embodiments, the therapeutic agent may comprise an antibody targeting GITR. In some embodiments, the antibody targeting GITR is TRX518. In some the therapeutic agent may comprise an antagonist directed against an inhibitory co-stimulatory molecule. In some embodiments, an inhibitory co-stimulatory molecule may include CTLA-4 (also known as CD152), PD-1, TIM-3, BTLA, VISTA. LAG-3. B7-H3, B7-H4, IDO, TIGIT, MICA/B. or arginase. In some embodiments, the antagonist directed against an inhibitory co-stimulatory molecule is an antagonist antibody that binds to CTLA-4, PD-1 TIM-3, BTLA, VISTA, LAG-3, B7-H3, B7-H4, IDO, TIGIT, MICA/B. or arginase.

In some embodiments, the therapeutic agent may comprise an anti-PD-1 antibody. In one embodiment the anti-PD-1 antibody is selected from the group consisting of MDX-1106 (nivolumab), MK-3475 (pembrolizumab, formerly known as lambrolizumab), CT-01 (pidilizumab). MDX-1106, also known as MDX-1106-04, ONO-4538, BMS-936558, or nivolumab, is an anti-PD-1 antibody described in WO2006/121168. MK-3475, also known as pembrolizumab or (formerly) lambrolizumab, is an anti-PD-1 antibody described in WO2009/114335. CT-011, also known as hBAT, hBAT-1 or pidilizumab, is an anti-PD-1 antibody described in WO2009/101 611.

In some embodiments, the therapeutic agent may comprise an immunoadhesin (e.g., an immunoadhesin comprising an extracellular or PD-1 binding portion of PD-L1 or PD-L2 fused to a constant region (e.g., an Fc region of an immunoglobulin sequence)). In one embodiment, the therapeutic agent may comprise AMP-224, also known as B7-DCIg (a PD-L2-Fc fusion soluble receptor described in WO2010/027827 and WO2011/066342).

In some embodiments, the therapeutic agent may comprise an anti-PD-L1 antibody. In one embodiment the anti-PD-L1 antibody is selected from the group consisting of YW243.55.S70. MPDL3280A. MDX-1105, and MEDI4736. Antibody YW243.55.S70 is an anti-PD-L1 antibody described in WO 2010/077634. MDX-1105, also known as BMS-936559, is an anti-PD-L1 antibody described in WO2007/005874. MEDI4736 is an anti-PD-L1 monoclonal antibody described in WO2011/066389 and US2013/034559. In one embodiment, the anti-PD-L1 antibody is atezolizumab.

In some embodiments, the therapeutic agent may comprise an antagonist directed against CTLA-4 (also known as CD152) for example, a blocking antibody. In some embodiments, the therapeutic agent may comprise ipilimumab (also known as MDX-010, MDX-101, or YERVOY®). In some embodiments, the therapeutic agent may comprise tremelimumab (also known as ticilimumab or CP-675,206). In some embodiments, the therapeutic agent may comprise an antagonist directed against B7-H3 (also known as CD276), for example, a blocking antibody. In some embodiments, the therapeutic agent may comprise MGA271. In some embodiments, the therapeutic agent may comprise an antagonist directed against a TGF beta, for example, metelimumab (also known as CAT-192), fresolimumab (also known as GC1008), or LY2157299.

In some embodiments, the therapeutic agent may comprise an agonist directed against CD137 (also known as TNFRSF9, 4-1BB, or ILA), for example, an activating antibody. In some embodiments, the therapeutic agent may comprise urelumab (also known as BMS-663513). In some embodiments, the therapeutic agent may comprise ligand of CD137 (also known as TNFRSF9, 4-1BB, or ILA), such as 4-1BBL. In some embodiments, the therapeutic agent may comprise an agonist directed against CD40, for example, an activating antibody. In some embodiments, the therapeutic agent may comprise CP-870893. In some embodiments, the therapeutic agent may comprise an agonist directed against OX40 (also known as CD134), for example, an activating antibody. In some embodiments, the therapeutic agent may comprise an anti-OX40 antibody (e.g., AgonOX). In some embodiments, the therapeutic agent may comprise a ligand of OX40, such as OX40L. In some embodiments, the therapeutic agent may comprise an agonist directed against CD27, for example, an activating antibody. In some embodiments, the therapeutic agent may comprise CDX-1127.

In some embodiments, the therapeutic agent may comprise a T cell (e.g., a cytotoxic T cell or CTL) expressing a chimeric antigen receptor (CAR). In some embodiments, the therapeutic agent may comprise a T cell comprising a dominant-negative TGF beta receptor, e.g, a dominant-negative TGF beta type II receptor.

In some embodiments, the therapeutic agent may comprise an antibody-drug conjugate. In some embodiments, the antibody-drug conjugate comprises mertansine or monomethyl auristatin E (MMAE). In some embodiments, the therapeutic agent may comprise an anti-NaPi2b antibody-MMAE conjugate (also known as DNIB0600A or RG7599). In some embodiments, the therapeutic agent may comprise trastuzumab emtansine (also known as T-DM1, ado-trastuzumab emtansine, or KADCYLA®). In some embodiments, the therapeutic agent may comprise DMUC5754A. In some embodiments, the therapeutic agent may comprise an antibody-drug conjugate targeting the endothelin B receptor (EDNBR), for example, an antibody directed against EDNBR conjugated with MMAE (also known as DEDN6526A). In some embodiments, the therapeutic agent may comprise gemtuzumab ozogamicin (MYLOTARG®). In some embodiments, the therapeutic agent may comprise inotuzumab ozogamicin. In some embodiments, the therapeutic agent may comprise bivatuzumab mertansine. In some embodiments, the therapeutic agent may comprise cantuzumab mertansine. In some embodiments, the therapeutic agent may comprise cantuzumab ravtansine. In some embodiments, the therapeutic agent may comprise brentuximab vedotin (ADECTRIS®). In some embodiments, the therapeutic agent may comprise pinatuzumab vedotin. In some embodiments, the therapeutic agent may comprise polatuzumab vedotin In some embodiments, the therapeutic agent may comprise glembatumumab vedotin. In some embodiments, the therapeutic agent may comprise lorvotuzumab mertansine. In some embodiments, the therapeutic agent may comprise tacatuzumab tetraxetan. In some embodiments, the therapeutic agent may comprise vandortuzumab vedotin (DSTP3086S). In some embodiments, the therapeutic agent may comprise ibritumomab tiuxetan (ZEVALIN®)

In some embodiments, the therapeutic agent may comprise an antibody directed against angiopoietin 2 (also known as Ang2). In some embodiments, the therapeutic agent may comprise MEDI3617.

In some embodiments, the therapeutic agent may comprise an antibody targeting CSF-1R (also known as M-CSFR or CD115). In some embodiments, the therapeutic agent may comprise IMC-CS4 (LY3022855)). In some embodiments, the therapeutic agent may comprise emactuzumab.

In some embodiment, the therapeutic agent may comprise a cytokine. In some embodiments, the therapeutic agent may comprise an interferon, for example interferon alpha or interferon gamma. In some embodiments the therapeutic agent may comprise Roferon-A (also known as recombinant Interferon alpha-2a). In some embodiments, the therapeutic agent may comprise GM-CSF (also known as recombinant human granulocyte macrophage colony stimulating factor, rhu GM-CSF, sargramostim, or LEUKIN E®). In some embodiments, the therapeutic agent may comprise aldesleukin (PROLEUKIN®). In some embodiments, the therapeutic agent may comprise IL-12. In some embodiments, the therapeutic agent may comprise IL-10.

In some embodiments, the therapeutic agent may comprise an IL-2 fusion protein. In some embodiments, the therapeutic agent may comprise tucotuzumab celmoleukin. In some embodiments, the therapeutic agent may comprise darleukin. In some embodiments, the therapeutic agent may comprise teleukin.

In some embodiments, the therapeutic agent may comprise an IL-10 fusion protein. In some embodiments, the therapeutic agent may comprise dekavil. In some embodiments, the therapeutic agent may comprise a TNF fusion protein. In some embodiments, the therapeutic agent may comprise fibromun.

In some embodiments, the therapeutic agent may comprise a bispecific antibody. In some embodiments, the therapeutic agent may comprise a bispecific antibody, such as, but not limited to, duligotuzumab, MM-11, MM141, TF2, ABT-981, ABT-122, LY3164530, SAR156597, GSK2434735, ozoralizumab, ALX-0761, ALX-0061, ALX-0141, ACE910.

In some embodiments, the therapeutic agent may comprise a bispecific antibody capable of binding to a T cell and a target cell, e.g. a tumor cell. In some embodiment, the therapeutic agent may comprise a bispecific antibody that specifically binds to CD3 on a T cell and to a target cell antigen. In some embodiment, the therapeutic agent may comprise a bispecific T cell engager (BiTE®). In some embodiments, the therapeutic agent may comprise a bispecific antibody directed against CD3 and CD19. In one embodiment, the bispecific antibody is blinatumomab (BLINCYTO®). In one embodiment, the bispecific antibody is AFM11. In some embodiments, the therapeutic agent may comprise a bispecific antibody directed against CD3 and EpCAM. In one embodiment, the bispecific antibody is catumaxomab (REVOMAB®). In one embodiment, the bispecific antibody is solitomab (AMG 110, MT110). In some embodiments, the therapeutic agent may comprise a bispecific antibody directed against CD3 and Her2. In one embodiment, the bispecific antibody is ertumaxomab. In some embodiments, the therapeutic agent may comprise a bispecific antibody directed against CD3 and PSMA. In one embodiment, the bispecific antibody is BAY2010112 (AMG212. MT112). In some embodiments, the therapeutic agent may comprise a bispecific antibody directed against CD3 and CEA. In one embodiment, the bispecific antibody is MED1565 (AMG211, MT111). In some embodiments, the therapeutic agent may comprise a bispecific antibody directed against CD3 and CD33. In one embodiment, the bispecific antibody is AMG330. In some embodiments, the therapeutic agent may comprise a bispecific antibody directed against CD3 and CD123. In one embodiment, the bispecific antibody is MGD006. In one embodiment, the bispecific antibody is XmAb®14045. In some embodiments, the therapeutic agent may comprise a bispecific antibody directed against CD3 and CD38. In some embodiments, the therapeutic agent may comprise a bispecific antibody directed against CD3 and gpA33. In one embodiment, the bispecific antibody is MGD007. In some embodiments, the therapeutic agent may comprise a bispecific antibody directed against CD3 and CD20. In one embodiment, the bispecific antibody is XmAb®13676. In one embodiment, the bispecific antibody is REGN1979. In one embodiment, the bispecific antibody is FBTA05 (Lymphomun).

In some embodiments, the therapeutic agent may comprise a bispecific antibody directed against CD30 and CD16A. In one embodiment, the bispecific antibody is AFM13. In some embodiments, the therapeutic agent may comprise a bispecific antibody directed against DR5 and FAP. In some embodiments, the therapeutic agent may comprise a bispecific antibody directed against Ang2 and VEGF. In one embodiment, the bispecific antibody is vanucizumab.

In some embodiments, the therapeutic agent may comprise an Fc domain. In some embodiments, the therapeutic agent may comprise a fusion protein comprising an Fc domain.

In some embodiments, the therapeutic agent may comprise a recombinant receptor or a fragment thereof. In some embodiments, the receptor is a T cell receptor. In some embodiments, the receptor is a TNF receptor. In some embodiments, the therapeutic agent may comprise etanercept (ENBREL®). In some embodiments, the receptor is a VEGF receptor. In some embodiments, the therapeutic agent may comprise ziv-aflibercept (ZALTRAP®). In some embodiments, the therapeutic agent may comprise aflibercept (EYLEA®). In some embodiments, the receptor is an IL-1 receptor. In some embodiments, the therapeutic agent may comprise rilonacept (ARCALYST®). In some embodiments, the therapeutic agent may comprise IMCgp100. In some embodiments, the therapeutic agent may comprise a chimeric antigen receptor (CAR). In some embodiments, the therapeutic agent may comprise a Factor IX-Fc fusion protein. In some embodiments, the therapeutic agent may comprise a Factor VIII-Fc fusion protein. In some embodiments, the therapeutic agent may comprise a CTLA-4-Fc fusion protein, such as e.g. belatacept, abatacept (ORENCIA®). In one embodiment, the therapeutic agent may comprise romiplostin.

In some embodiments, the therapeutic agent may comprise a recombinant receptor ligand, such as a TNF receptor ligand.

In some embodiments, the therapeutic agent may comprise a generic, biosimilar or non-comparable biologic version of an agent, e.g. an antibody, named herein.

In one embodiment, the therapeutic agent does not comprise obinutuzumab.

T Cell Activating Therapeutic Agents

The following describes in further detail T cell activating therapeutic agents for which the invention may be useful, in particular aspects of the invention concerned with the reduction of cytokine release associated with the administration of a therapeutic agent in a subject.

In some embodiments, the therapeutic agent comprises an antibody that specifically binds to an activating T cell antigen. In one embodiment, the therapeutic agent may comprise an antibody that specifically binds to an antigen selected from the group of CD3, CD28, CD137 (also known as 4-1BB), CD40, CD226, OX40, GITR, CD27, HVEM, and CD127.

In one embodiment, the therapeutic agent comprises an antibody that specifically binds to CD3, particularly CD3E.

In one embodiment, the therapeutic agent comprises an antibody that is or can compete for binding with antibody H2C (PCT publication no. WO2008/119567), antibody V9 (Rodrigues et al., Int J Cancer Suppl 7, 45-50 (1992) and U.S. Pat. No. 6,054,297), antibody FN18 (Nooij et al., Eur J Immunol 19, 981-984 (1986)), antibody SP34 (Pessano et al., EMBO J 4, 337-340 (1985)), antibody OKT3 (Kung et al., Science 206, 347-349 (1979)), antibody WT31 (Spits et al., J Immunol 135, 1922 (1985)), antibody UCHT1 (Burns et al., J Immunol 129, 1451-1457 (1982)), antibody 7D6 (Coulie et al., Eur J Immunol 21, 1703-1709 (1991)) or antibody Leu-4. In some embodiments, the therapeutic agent may also comprise an antibody that specifically binds to CD3 as described in WO 2005/040220, WO 2005/118635, WO 2007/042261, WO 2008/119567, WO 2008/119565, WO 2012/162067, WO 2013/158856, WO 2013/188693, WO 2013/186613, WO 2014/110601, WO 2014/145806, WO 2014/191113, WO 2014/047231, WO 2015/095392, WO 2015/181098, WO 2015/001085, WO 2015/104346, WO 2015/172800, WO 2016/020444, or WO 2016/014974.

In one embodiment, the therapeutic agent may comprise an antibody that specifically binds to a B-cell antigen, particularly a malignant B-cell antigen. In one embodiment, the therapeutic agent may comprise an antibody that specifically binds to an antigen selected from the group consisting of CD20, CD19, CD22, ROR-1, CD37 and CD5, particularly to CD20 or CD19.

In some embodiments, the therapeutic agent may comprise an antibody selected from rituximab, ocrelizumab, ofatumumab, ocaratuzumab, veltuzumab, and ublituximab.

In some embodiments, the therapeutic agent may comprise a multispecific antibody, particularly a bispecific antibody. In some embodiments, the therapeutic agent may comprise a bispecific antibody capable of binding to a T cell and a target cell, e.g. a tumor cell. In some embodiments, the target cell is a B-cell, particularly a malignant B-cell. In some embodiments, the therapeutic agent may comprise a bispecific antibody that specifically binds to (i) an activating T cell antigen and (ii) a B cell antigen. In some embodiments, the therapeutic agent may comprise a bispecific antibody that specifically binds to CD3 on a T cell and to a target cell antigen. In some embodiments, the target cell antigen is a B-cell antigen, particularly a malignant B-cell antigen. In some embodiments, the therapeutic agent may comprise a bispecific T cell engager (BiTE®).

In some embodiments, the therapeutic agent may comprise a bispecific antibody directed against CD3 and CD20. In one embodiment, the bispecific antibody is XmAb®13676. In one embodiment, the bispecific antibody is REGN1979. In one embodiment, the bispecific antibody is FBTA05 (Lymphomun).

In some embodiments, the therapeutic agent may comprise a bispecific antibody directed against CD3 and CD19. In one embodiment, the bispecific antibody is blinatumomab (BLINCYTO®). In one embodiment, the bispecific antibody is AFM11. In one embodiment, the bispecific antibody is MGD011 (JNJ-64052781).

In some embodiments, the therapeutic agent may comprise a bispecific antibody directed against CD3 and CD38. In one embodiment, the bispecific antibody is XmAb®13551, XmAb®15426, or XmAb®14702.

In some embodiments, the therapeutic agent may comprise a bispecific antibody directed against CD3 and BCMA. In one embodiment, the bispecific antibody is BI836909.

In some embodiments, the therapeutic agent may comprise a bispecific antibody directed against CD3 and CD33. In one embodiment, the bispecific antibody is AMG330.

In some embodiments, the therapeutic agent may comprise a bispecific antibody directed against CD3 and CD123. In one embodiment, the bispecific antibody is MGD006. In one embodiment, the bispecific antibody is XmAb®14045. In one embodiment, the bispecific antibody is JNJ-63709178.

In some embodiments, the therapeutic agent may comprise a recombinant receptor or a fragment thereof. In some embodiments, the receptor is a T cell receptor (TCR). In some embodiments, the therapeutic agent may comprise a chimeric antigen receptor (CAR).

In some embodiments, the therapeutic agent may comprise a T cell (e.g., a cytotoxic T cell or CTL) expressing a chimeric antigen receptor (CAR). In some embodiments, the therapeutic agent may comprise a T cell expressing a recombinant T cell receptor (TCR).

In one embodiment, the therapeutic agent may comprise a CAR that specifically binds to a B-cell antigen, particularly a malignant B-cell antigen. In one embodiment, the therapeutic agent may comprise a CAR that specifically binds to an antigen selected from the group consisting of CD20, CD19, CD22, ROR-1, CD37 and CD5, particularly to CD20 or CD19.

In some embodiments, the therapeutic agent may comprise a CAR directed to CD19, or a T cell expressing a CAR directed to CD19. In some embodiments, the therapeutic agent may comprise KTE-C19, CTL019, JCAR-014, JCAR-015, JCAR-017, BPX-401, UCART19, In some embodiments, the therapeutic agent may comprise a CAR directed to CD22, or a T cell expressing a CAR directed to CD22. In some embodiments, the therapeutic agent may comprise JCAR-018 or UCART22.

In some embodiments, the therapeutic agent may comprise an agonist directed against an T cell activating co-stimulatory molecule. In some embodiments, a T cell activating co-stimulatory molecule may include CD40, CD226, CD28, OX40, GITR, CD137, CD27, HVEM, or CD127. In some embodiments, the agonist directed against a T cell activating co-stimulatory molecule is an agonist antibody that binds to CD40, CD226, CD28, OX40, GITR, CD137, CD27, HVEM, or CD127. In some embodiments, the therapeutic agent may comprise an antibody targeting GITR. In some embodiments, the antibody targeting GITR is TRX518.

In some embodiments, the therapeutic agent may comprise an agonist directed against CD137 (also known as TNFRSF9, 4-1BB, or ILA), for example, an activating antibody. In some embodiments, the therapeutic agent may comprise urelumab (also known as BMS-663513). In some embodiments, the therapeutic agent may comprise ligand of CD137 (also known as TNFRSF9, 4-1BB, or ILA), such as 4-1BBL. In some embodiments, the therapeutic agent may comprise an agonist directed against CD40, for example, an activating antibody. In some embodiments, the therapeutic agent may comprise CP-870893. In some embodiments, the therapeutic agent may comprise an agonist directed against OX40 (also known as CD134), for example, an activating antibody. In some embodiments, the therapeutic agent may comprise an anti-OX40 antibody (e.g., AgonOX). In some embodiments, the therapeutic agent may comprise a ligand of OX40, such as OX40L. In some embodiments, the therapeutic agent may comprise an agonist directed against CD27, for example, an activating antibody. In some embodiments, the therapeutic agent may comprise CDX-1127.

Particular Therapeutic Agents (i) Reduction of the Formation of Anti-Drug Antibodies (ADAs)

The therapeutic agents described in the following are particularly useful in the invention, in particular in relation aspects of the invention concerned with the reduction of the formation of anti-drug antibodies (ADAs) against a therapeutic agent in a subject.

In some embodiments, the therapeutic agent comprises an antibody that specifically binds to carcinoembryonic antigen (CEA).

In one embodiment, the antibody that specifically binds to CEA comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19. In a further embodiment, the antibody that specifically binds CEA comprises a heavy chain variable region sequence that is at least 80%, 85%, 90%, 95%, 96%, 97%, 98%, or 99% identical to of SEQ ID NO: 20 and a light chain variable region sequence that is at least 80%, 85%, 90%, 95%, 96%, 97%, 98%, or 99% identical to the sequence of SEQ ID NO: 21. In a further embodiment, the antibody that specifically binds CEA comprises the heavy chain variable region sequence of SEQ ID NO: 20 and the light chain variable region sequence of SEQ ID NO: 21.

In one embodiment, the antibody that specifically binds to CEA comprises a heavy chain variable region comprising the heavy chain CDR (HCDR) 1 of SEQ ID NO: 136, the HCDR2 of SEQ ID NO: 137, and the HCDR3 of SEQ ID NO: 138; and a light chain variable region comprising the light chain CDR (LCDR) 1 of SEQ ID NO: 139, the LCDR2 of SEQ ID NO: 140 and the LCDR3 of SEQ ID NO: 141. In a further embodiment, the antibody that specifically binds CEA comprises a heavy chain variable region sequence that is at least 80%, 85%, 90%, 95%, 96%, 97%, 98%, or 99% identical to of SEQ ID NO: 142 and a light chain variable region sequence that is at least 80%, 85%, 90%, 95%, 96%, 97%, 98%, or 99% identical to the sequence of SEQ ID NO: 143. In a further embodiment, the antibody that specifically binds CEA comprises the heavy chain variable region sequence of SEQ ID NO: 142 and the light chain variable region sequence of SEQ ID NO: 143.

In one embodiment, the antibody that specifically binds to CEA is a full-length antibody. In one embodiment, the antibody that specifically binds to CEA is an antibody of the human IgG class, particularly an antibody of the human IgG$_1$ class. In one embodiment, the antibody that specifically binds to CEA is an antibody fragment, particularly a Fab molecule or a scFv molecule, more particularly a Fab molecule. In one embodiment, the antibody that specifically binds to CEA is a humanized antibody.

In some embodiments, the therapeutic agent comprises an antibody that specifically binds to fibroblast activation protein (FAP). In one embodiment, the antibody that specifically binds FAP comprises a heavy chain variable region sequence that is at least 80%, 85%, 90%, 95%, 96%, 97%, 98%, or 99% identical to of SEQ ID NO: 25 and a light chain variable region sequence that is at least 80%, 85%, 90%, 95%, 96%, 97%, 98%, or 99% identical to the sequence of SEQ ID NO: 26. In a further embodiment, the antibody that specifically binds FAP comprises the heavy chain variable region sequence of SEQ ID NO: 25 and the light chain variable region sequence of SEQ ID NO: 26.

In one embodiment, the antibody that specifically binds to FAP is a full-length antibody. In one embodiment, the antibody that specifically binds to FAP is an antibody of the human IgG class, particularly an antibody of the human IgG$_1$ class. In one embodiment, the antibody that specifically binds to FAP is an antibody fragment, particularly a Fab molecule or a scFv molecule, more particularly a Fab molecule. In one embodiment, the antibody that specifically binds to FAP is a human antibody.

In some embodiments, the therapeutic agent comprises an antibody that specifically binds to CD3, particularly CD3 epsilon. In one embodiment, the antibody that specifically binds to CD3 comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37. In a further embodiment, the antibody that specifically binds CD3 comprises a heavy chain variable region sequence that is at least 80%, 85%, 90%, 95%, 96%, 97%, 98%, or 99% identical to of SEQ ID NO: 38 and a light chain variable region sequence that is at least 80%, 85%, 90%, 95%, 96%, 97%, 98%, or 99% identical to the sequence of SEQ ID NO: 39. In a further embodiment, the antibody that specifically binds CD3 comprises the heavy chain variable region sequence of SEQ ID NO: 38 and the light chain variable region sequence of SEQ ID NO: 39.

In one embodiment, the antibody that specifically binds to CD3 is a full-length antibody. In one embodiment, the antibody that specifically binds to CD3 is an antibody of the human IgG class, particularly an antibody of the human IgG$_1$ class. In one embodiment, the antibody that specifically binds to CD3 is an antibody fragment, particularly a Fab molecule or a scFv molecule, more particularly a Fab molecule. In a particular embodiment, the antibody that specifically binds to CD3 is a crossover Fab molecule wherein the variable domains or the constant domains of the Fab heavy and light chain are exchanged (i.e. replaced by each other). In one embodiment, the antibody that specifically binds to CD3 is a humanized antibody.

In some embodiments, the therapeutic agent comprises a cytokine. In one embodiment the cytokine is selected from the group consisting of, GM-CSF, IL-1α, IL-1β, IL-2, IL-3, IL-4, IL-5, IL-6, IL-7, IL-8, IL-10, IL-12, IL-15, IFN-α, IFN-βP, IFN-γ, MIP-1α, MIP-1β, TGF-β, TNF-α, and TNF-β. In one embodiment, the cytokine is IL-2, particularly human IL-2. The sequence of wild-type human IL-2 is shown in SEQ ID NO: 12.

In one embodiment, the therapeutic agent comprises a mutant IL-2 polypeptide having reduced binding affinity to the α-subunit of the IL-2 receptor as compared to wild-type IL-2. Together with the β- and γ-subunits (also known as CD122 and CD132, respectively), the α-subunit (also known as CD25) forms the heterotrimeric high-affinity IL-2 receptor, while the dimeric receptor consisting only of the β- and γ-subunits is termed the intermediate-affinity IL-2 receptor. A mutant IL-2 polypeptide with reduced binding to the α-subunit of the IL-2 receptor has a reduced ability to induce IL-2 signaling in regulatory T (T) cells, induces less activation-induced cell death (AICD) in T cells, and has a reduced toxicity profile in vivo, compared to a wild-type IL-2 polypeptide (see e.g. WO 2012/107417, incorporated herein by reference in its entirety).

In a more specific embodiment, the mutant IL-2 polypeptide comprises three amino acid substitutions at the positions corresponding to residue 42, 45 and 72 of human IL-2. In an even more specific embodiment, the mutant IL-2 polypeptide is a human IL-2 polypeptide comprising the amino acid substitutions F42A, Y45A and L72G (numbering relative to the human IL-2 sequence SEQ ID NO: 12). In one embodiment the mutant IL-2 polypeptide additionally comprises an amino acid mutation at a position corresponding to position 3 of human IL-2, which eliminates the O-glycosylation site of IL-2. In one embodiment said amino acid mutation which eliminates the O-glycosylation site of IL-2 at a position corresponding to residue 3 of human IL-2 is an amino acid substitution selected from the group of T3A, T3G, T3Q, T3E, T3N, T3D, T3R, T3K, and T3P. Particularly, said additional amino acid mutation is an amino acid substitution replacing a threonine residue by an alanine residue. A particular mutant IL-2 polypeptide useful in the invention comprises four amino acid substitutions at positions corresponding to residues 3, 42, 45 and 72 of human IL-2. Specific amino acid substitutions are T3A, F42A, Y45A and L72G. This mutant IL-2 polypeptide exhibits no detectable binding to CD25, reduced ability to induce apoptosis in T cells, reduced ability to induce IL-2 signaling in T$_{reg}$ cells, and a reduced toxicity profile in vivo (see e.g. WO 2012/107417, incorporated herein by reference in its entirety). However, it retains ability to activate IL-2 signaling in effector cells, to induce proliferation of effector cells, and to generate IFN-γ as a secondary cytokine by NK cells.

The IL-2 or mutant IL-2 polypeptide according to any of the above embodiments may comprise additional mutations that provide further advantages such as increased expression or stability. For example, the cysteine at position 125 may be replaced with a neutral amino acid such as serine, alanine, threonine or valine, yielding C125S IL-2, C125A IL-2, C125T IL-2 or C125V IL-2 respectively, as described in U.S. Pat. No. 4,518,584. As described therein, one may also delete the N-terminal alanine residue of IL-2 yielding such mutants as des-A1 C125S or des-A1 C125A. Alternatively or conjunctively, the IL-2 mutant may include a mutation whereby methionine normally occurring at position 104 of wild-type human IL-2 is replaced by a neutral amino acid such as alanine (see U.S. Pat. No. 5,206,344). The resulting mutants, e. g., des-A1 M104A IL-2, des-A1 M104A C125S IL-2, M104A IL-2, M104A C125A IL-2, des-A1 M104A C125A IL-2, or M104A C125S IL-2 (these and other mutants may be found in U.S. Pat. No. 5,116,943 and in Weiger et al., Eur J Biochem 180, 295-300 (1989)) may be used in conjunction with the particular IL-2 mutations described herein.

Thus, in certain embodiments the IL-2 or mutant IL-2 polypeptide comprises an additional amino acid mutation at a position corresponding to residue 125 of human IL-2. In one embodiment said additional amino acid mutation is the amino acid substitution C125A.

In certain embodiments the mutant IL-2 polypeptide is essentially a full-length IL-2 molecule, particularly a human full-length IL-2 molecule. In one embodiment, the mutant IL-2 polypeptide comprises a polypeptide sequence that is at least 80%, at least 85%, or at least 90% identical to the sequence of SEQ ID NO: 12.

In a specific embodiment the mutant IL-2 polypeptide comprises the polypeptide sequence of SEQ ID NO: 13.

In some embodiments, the therapeutic agent comprises an immunoconjugate. Particular immunoconjugates are described in WO 2012/107417 and WO 2012/146628 (each incorporated herein by reference in its entirety).

In one embodiment, the immunoconjugate comprises an antibody that specifically binds to CEA as described herein, and a mutant IL-2 polypeptide as described herein. In one embodiment, the antibody is a full-length antibody.

In one embodiment the therapeutic agent comprises an immunoconjugate comprising
  (i) an antibody of the human IgG$_1$ subclass that specifically binds to CEA and comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19; and
  (ii) a mutant human IL-2 polypeptide comprising the amino acid substitutions F42A, Y45A and L72G (numbering relative to the human IL-2 sequence SEQ ID NO: 12).

In one embodiment, the immunoconjugate comprises an antibody that specifically binds to FAP as described herein, and a mutant IL-2 polypeptide as described herein. In one embodiment, the antibody is a full-length antibody.

In one embodiment the therapeutic agent comprises an immunoconjugate comprising
  (i) an antibody of the human $IgG_1$ subclass that specifically binds to FAP and comprises the heavy chain variable region of SEQ ID NO: 25; and the light chain variable region of SEQ ID NO: 26; and
  (ii) a mutant human IL-2 polypeptide comprising the amino acid substitutions F42A, Y45A and L72G (numbering relative to the human IL-2 sequence SEQ ID NO: 12).

In one embodiment, the immunoconjugate comprises no more than one mutant IL-2 polypeptide. In one embodiment, the mutant IL-2 polypeptide is fused to the carboxy-terminal amino acid of one of the antibody heavy chains, optionally through a linker peptide. Suitable, non-immunogenic linker peptides include, for example, $(G_4S)_n$, $(SG_4)_n$ or $G_4(SG_4)_n$ linker peptides, wherein n is generally a number between 1 and 10, typically between 2 and 4. In one embodiment, the linker peptide is $(G_4S)_3$.

In one embodiment, the immunoconjugate comprises a polypeptide comprising a sequence that is at least 80%, 85%, 90%, 95%, 96%, 97%, 98%, or 99% identical to the sequence of SEQ ID NO: 22, a polypeptide comprising a sequence that is at least 80%, 85%, 90%, 95%, 96%, 97%, 98%, or 99% identical to the sequence of SEQ ID NO: 23, and a polypeptide comprising a sequence that is at least 80%, 85%, 90%, 95%, 96%, 97%, 98%, or 99% identical to the sequence of SEQ ID NO: 24.

In one embodiment, the immunoconjugate comprises a polypeptide comprising the sequence of SEQ ID NO: 22, a polypeptide comprising the sequence of SEQ ID NO: 23, and a polypeptide comprising the sequence of SEQ ID NO: 24.

In one embodiment, the immunoconjugate is cergutuzumab amunaleukin (see WHO Drug Information (International Nonproprietary Names for Pharmaceutical Substances), Recommended INN: List 75, 2016, pre-publication copy" (incorporated herein by reference in its entirety).

In one embodiment, the immunoconjugate comprises a polypeptide comprising a sequence that is at least 80%, 85%, 90%, 95%, 96%, 97%, 98%, or 99% identical to the sequence of SEQ ID NO: 27, a polypeptide comprising a sequence that is at least 80%, 85%, 90%, 95%, 96%, 97%, 98%, or 99% identical to the sequence of SEQ ID NO: 28, and a polypeptide comprising a sequence that is at least 80%, 85%, 90%, 95%, 96%, 97%, 98%, or 99% identical to the sequence of SEQ ID NO: 29.

In one embodiment, the immunoconjugate comprises a polypeptide comprising the sequence of SEQ ID NO: 27, a polypeptide comprising the sequence of SEQ ID NO: 28, and a polypeptide comprising the sequence of SEQ ID NO: 29.

In one embodiment, the therapeutic agent comprises a bispecific antibody. Particular bispecific antibodies are described in PCT publication nos. WO 2013/026833 and WO 2014/131712 and in PCT application no. PCT/EP2016/073171 (each incorporated herein by reference in its entirety).

In one embodiment, the bispecific antibody comprises an antibody that specifically binds to CEA as described herein, and an antibody that specifically binds to CD3 as described herein. In one embodiment, the bispecific antibody comprises a first antibody that specifically binds to CD3 as described herein, and a second and a third antibody that specifically bind to CEA as described herein. In one embodiment, the first antibody is a crossover Fab molecule as described herein, and the second and the first antibody are each a conventional Fab molecule. In one embodiment, the bispecific antibody further comprises an Fc domain as described herein. The bispecific antibody may have the antibody formats described herein and may comprise the antigen binding moieties described herein. The bispecific antibody may comprise modifications in the Fc region and/or the antigen binding moieties as described herein.

In one embodiment the therapeutic agent comprises a bispecific antibody comprising
  (i) a first antigen binding moiety that specifically binds to CD3, comprising a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37, wherein the first antigen binding moiety is a crossover Fab molecule wherein either the variable or the constant regions, particularly the constant regions, of the Fab light chain and the Fab heavy chain are exchanged;
  (ii) a second and a third antigen binding moiety that specifically bind to CEA, comprising a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19, wherein the second and third antigen binding moiety are each a Fab molecule, particularly a conventional Fab molecule;
  (iii) an Fc domain composed of a first and a second subunit capable of stable association, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In one embodiment, the first antigen binding moiety that specifically binds to CD3, comprises the heavy chain variable region of SEQ ID NO: 38, and the light chain variable region of SEQ ID NO: 39. In one embodiment, the second and third antigen binding moieties that specifically bind to CEA comprise the heavy chain variable region of SEQ ID NO: 20, and the light chain variable region of SEQ ID NO: 21.

In one embodiment, the antigen binding moieties and the Fc region are fused to each other by peptide linkers, particularly by peptide linkers as in SEQ ID NO: 42 and SEQ ID NO: 43. In one embodiment, the bispecific antibody comprises a polypeptide comprising a sequence that is at least 80%, 85%, 90%, 95%, 96%, 97%, 98%, or 99% identical to the sequence of SEQ ID NO: 40, a polypeptide comprising a sequence that is at least 80%, 85%, 90%, 95%, 96%, 97%, 98%, or 99% identical to the sequence of SEQ ID NO: 41, a polypeptide comprising a sequence that is at least 80%, 85%, 90%, 95%, 96%, 97%, 98%, or 99% identical to the sequence of SEQ ID NO: 42, and a polypeptide comprising a sequence that is at least 80%, 85%, 90%, 95%, 96%, 97%, 98%, or 99% identical to the sequence of SEQ ID NO: 43.

In one embodiment, the bispecific antibody comprises a polypeptide comprising the sequence of SEQ ID NO: 40, a polypeptide comprising the sequence of SEQ ID NO: 41, a polypeptide comprising the sequence of SEQ ID NO: 42, and a polypeptide comprising the sequence of SEQ ID NO: 43. (CEA TCB)

In one embodiment the therapeutic antibody comprises a bispecific antibody comprising (i) a first antigen binding moiety that specifically binds to CD3, comprising a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37, wherein the first antigen binding moiety is a crossover Fab molecule wherein either the variable or the constant regions, particularly the variable regions, of the Fab light chain and the Fab heavy chain are exchanged;

(ii) a second and a third antigen binding moiety that specifically bind to CEA, comprising a heavy chain variable region comprising the heavy chain CDR (HCDR) 1 of SEQ ID NO: 136, the HCDR2 of SEQ ID NO: 137, and the HCDR3 of SEQ ID NO: 138; and a light chain variable region comprising the light chain CDR (LCDR) 1 of SEQ ID NO: 139, the LCDR2 of SEQ ID NO: 140 and the LCDR3 of SEQ ID NO: 141, wherein the second and third antigen binding moiety are each a Fab molecule, particularly a conventional Fab molecule;

(iii) an Fc domain composed of a first and a second subunit capable of stable association, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In one embodiment, the first antigen binding moiety that specifically binds to CD3, comprises the heavy chain variable region of SEQ ID NO: 38, and the light chain variable region of SEQ ID NO: 39. In one embodiment, the second and third antigen binding moiety that specifically bind to CEA comprise the heavy chain variable region of SEQ ID NO: 142, and the light chain variable region of SEQ ID NO: 143.

In one embodiment, the antigen binding moieties and the Fc region are fused to each other by peptide linkers, particularly by peptide linkers as in SEQ ID NO: 145 and SEQ ID NO: 146.

In one embodiment, in the constant domain CL of the second and the third Fab molecule under (ii) the amino acid at position 124 is substituted by lysine (K) (numbering according to Kabat) and the amino acid at position 123 is substituted by lysine (K) or arginine (R), particularly by arginine (R) (numbering according to Kabat), and in the constant domain CH1 of the second and the third Fab molecule under (ii) the amino acid at position 147 is substituted by glutamic acid (E) (numbering according to Kabat EU index) and the amino acid at position 213 is substituted by glutamic acid (E) (numbering according to Kabat EU index).

In one embodiment, the bispecific antibody comprises a polypeptide comprising a sequence that is at least 80%, 85%, 90%, 95%, 96%, 97%, 98%, or 99% identical to the sequence of SEQ ID NO: 144, a polypeptide comprising a sequence that is at least 80%, 85%, 90%, 95%, 96%, 97%, 98%, or 99% identical to the sequence of SEQ ID NO: 145, a polypeptide comprising a sequence that is at least 80%, 85%, 90%, 95%, 96%, 97%, 98%, or 99% identical to the sequence of SEQ ID NO: 146, and a polypeptide comprising a sequence that is at least 80%, 85%, 90%, 95%, 96%, 97%, 98%, or 99% identical to the sequence of SEQ ID NO: 147.

In one embodiment, the bispecific antibody comprises a polypeptide comprising the sequence of SEQ ID NO: 144, a polypeptide comprising the sequence of SEQ ID NO: 145, a polypeptide comprising the sequence of SEQ ID NO: 146, and a polypeptide comprising the sequence of SEQ ID NO: 147.

(ii) Reduction of Cytokine Release

The therapeutic agents described in the following are particularly useful in the invention, in particular in relation aspects of the invention concerned with the reduction of cytokine release associated with the administration of a therapeutic agent in a subject.

The aspects of the invention concerned with the reduction of cytokine release associated with the administration of a therapeutic agent in a subject are particularly useful in connection with therapeutic agents that are activating T-cells in the subject (T cell activating therapeutic agents), i.e. have the ability of inducing T-cell activation in the subject. Such therapeutic agents include, for example, antibodies directed to T-cell antigens (particularly activating T-cell antigens), or T-cells modified with chimeric antigen receptors (CAR) or recombinant T-cell receptors (TCR).

The aspects of the invention concerned with the reduction of cytokine release associated with the administration of a therapeutic agent in a subject are particularly useful in connection with B-cell targeted T-cell activating therapeutic agents.

In some embodiments, the therapeutic agent comprises an antibody that specifically binds to CD3, particularly CD3 epsilon.

In one embodiment, the antibody that specifically binds to CD3 comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37. In a further embodiment, the antibody that specifically binds CD3 comprises a heavy chain variable region sequence that is at least 80%, 85%, 90%, 95%, 96%, 97%, 98%, or 99% identical to of SEQ ID NO: 38 and a light chain variable region sequence that is at least 80%, 85%, 90%, 95%, 96%, 97%, 98%, or 99% identical to the sequence of SEQ ID NO: 39. In a further embodiment, the antibody that specifically binds CD3 comprises the heavy chain variable region sequence of SEQ ID NO: 38 and the light chain variable region sequence of SEQ ID NO: 39.

In one embodiment, the antibody that specifically binds to CD3 comprises a heavy chain variable region comprising the heavy chain HVR 1 (H1-HVR) of SEQ ID NO: 120, the H2-HVR of SEQ ID NO: 121, and the H3-HVR of SEQ ID NO: 122; and a light chain variable region comprising the light chain HVR 1 (L1-HVR) of SEQ ID NO: 123, the L2-HVR of SEQ ID NO: 124 and the L3-HVR of SEQ ID NO: 125. In a further embodiment, the antibody that specifically binds CD3 comprises a heavy chain variable region sequence that is at least 80%, 85%, 90%, 95%, 96%, 97%, 98%, or 99% identical to of SEQ ID NO: 126 and a light chain variable region sequence that is at least 80%, 85%, 90%, 95%, 96%, 97%, 98%, or 99% identical to the sequence of SEQ ID NO: 127. In a further embodiment, the antibody that specifically binds CD3 comprises the heavy chain variable region sequence of SEQ ID NO: 126 and the light chain variable region sequence of SEQ ID NO: 127.

In one embodiment, the antibody that specifically binds to CD3 is a full-length antibody. In one embodiment, the antibody that specifically binds to CD3 is an antibody of the human IgG class, particularly an antibody of the human IgG$_1$ class. In one embodiment, the antibody that specifically binds to CD3 is an antibody fragment, particularly a Fab molecule or a scFv molecule, more particularly a Fab molecule. In a particular embodiment, the antibody that specifically binds to CD3 is a crossover Fab molecule wherein the variable domains or the constant domains of the Fab heavy and light chain are exchanged (i.e. replaced by each other). In one embodiment, the antibody that specifically binds to CD3 is a humanized antibody.

In one embodiment, the therapeutic agent comprises a multispecific antibody, particularly a bispecific antibody. In one embodiment, the multispecific antibody specifically binds to (i) an activating T cell antigen and (ii) a B cell antigen. Particular bispecific antibodies are described in PCT publication no. WO 2016/020309 and PCT application no. PCT/EP2016/073041, as well as PCT publication no. WO 2015/095392 (each incorporated herein by reference in its entirety).

In one embodiment, the bispecific antibody specifically binds to CD3 and CD20. In one embodiment, the bispecific antibody comprises an antigen binding moiety that specifically binds to CD20, and an antigen binding moiety that specifically binds to CD3. In one embodiment, the bispecific antibody comprises a first antigen binding moiety that specifically binds to CD3, and a second and a third antigen binding moiety that specifically bind to CD20. In one embodiment, the first antigen binding moiety is a crossover Fab molecule, and the second and the first antigen binding moiety are each a conventional Fab molecule. In one embodiment, the bispecific antibody further comprises an Fc domain. The bispecific antibody may have the antibody formats described herein and may comprise the antigen binding moieties described herein. The bispecific antibody may comprise modifications in the Fc region and/or the antigen binding moieties as described herein.

In one embodiment, the therapeutic agent comprises a bispecific antibody comprising
(i) an antigen binding moiety that specifically binds to CD3 and comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37; and
(ii) an antigen binding moiety that specifically binds to CD20 and comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

In one embodiment, the therapeutic agent comprises a bispecific antibody comprising
(i) an antigen binding moiety that specifically binds to CD3 and comprises a heavy chain variable region of SEQ ID NO: 38; and a light chain variable region of SEQ ID NO: 39; and
(ii) an antigen binding moiety that specifically binds to CD20 and comprises a heavy chain variable region of SEQ ID NO: 10; and a light chain variable region of SEQ ID NO: 11.

In a particular embodiment, the therapeutic agent comprises a bispecific antibody comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association;
wherein
(i) the first antigen is CD20 and the second antigen is CD3, particularly CD3 epsilon;
(ii) the first Fab molecule under a) and the third Fab molecule under c) each comprise the heavy chain complementarity determining region (CDR) 1 of SEQ ID NO: 4, the heavy chain CDR 2 of SEQ ID NO: 5, the heavy chain CDR 3 of SEQ ID NO: 6, the light chain CDR 1 of SEQ ID NO: 7, the light chain CDR 2 of SEQ ID NO: 8 and the light chain CDR 3 of SEQ ID NO: 9, and the second Fab molecule under b) comprises the heavy chain CDR 1 of SEQ ID NO: 32, the heavy chain CDR 2 of SEQ ID NO: 33, the heavy chain CDR 3 of SEQ ID NO: 34, the light chain CDR 1 of SEQ ID NO: 35, the light chain CDR 2 of SEQ ID NO: 36 and the light chain CDR 3 of SEQ ID NO: 37;
(iii) in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R), particularly by arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index); and
(iv) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d).

In one embodiment, the first Fab molecule under a) and the third Fab molecule under c) each comprise a heavy chain variable region that is at least 95%, 96%, 97%, 98%, or 99% identical to the sequence of SEQ ID NO: 10, and a light chain variable region that is at least 95%, 96%, 97%, 98%, or 99% identical to the sequence of SEQ ID NO: 11.

In one embodiment, the first Fab molecule under a) and the third Fab molecule under c) each comprise the heavy chain variable region sequence of SEQ ID NO: 10, and the light chain variable region sequence of SEQ ID NO: 11.

In one embodiment, the second Fab molecule under b) comprises a heavy chain variable region that is at least 95%, 96%, 97%, 98%, or 99% identical to the sequence of SEQ ID NO: 38, and a light chain variable region that is at least 95%, 96%, 97%, 98%, or 99% identical to the sequence of SEQ ID NO: 39.

In still a further embodiment, the second Fab molecule under b) comprises the heavy chain variable region sequence of SEQ ID NO: 38, and the light chain variable region sequence of SEQ ID NO: 39.

In a particular embodiment, the bispecific antibody comprises a polypeptide that is at least 95%, 96%, 97%, 98%, or 99% identical to the sequence of SEQ ID NO: 44, a polypeptide that is at least 95%, 96%, 97%, 98%, or 99% identical to the sequence of SEQ ID NO: 45, a polypeptide that is at least 95%, 96%, 97%, 98%, or 99% identical to the sequence of SEQ ID NO: 46, and a polypeptide that is at least 95%, 96%, 97%, 98%, or 99% identical to the sequence of SEQ ID NO: 47. In a further particular embodiment, the bispecific antibody comprises a polypeptide sequence of SEQ ID NO: 44, a polypeptide sequence of SEQ ID NO: 45, a polypeptide sequence of SEQ ID NO: 46 and a polypeptide sequence of SEQ ID NO: 47. (CD20XCD3 bsAB)

In one embodiment, the therapeutic agent comprises a bispecific antibody comprising
(i) an antigen binding moiety that specifically binds to CD3 and comprises a heavy chain variable region comprising the heavy chain HVR 1 (H1-HVR) of SEQ ID NO: 120, the H2-HVR of SEQ ID NO: 121, and the H3-HVR of SEQ ID NO: 122; and a light chain variable region comprising the light chain HVR 1 (L1-HVR) of SEQ ID NO: 123, the L2-HVR of SEQ ID NO: 124 and the L3-HVR of SEQ ID NO: 125; and
(ii) an antigen binding moiety that specifically binds to CD20 and comprises a heavy chain variable region comprising the heavy chain HVR 1 (H1-HVR) of SEQ ID NO: 128, the H2-HVR of SEQ ID NO: 129, and the H3-HVR of SEQ ID NO: 130; and a light chain variable region comprising the light chain HVR 1 (L1-HVR) of SEQ ID NO: 131, the L2-HVR of SEQ ID NO: 132 and the L3-HVR of SEQ ID NO: 133.

In one embodiment, the therapeutic agent comprises a bispecific antibody comprising
(i) an antigen binding moiety that specifically binds to CD3 and comprises a heavy chain variable region of SEQ ID NO: 126; and a light chain variable region of SEQ ID NO: 127; and
(ii) an antigen binding moiety that specifically binds to CD20 and comprises a heavy chain variable region of SEQ ID NO: 134; and a light chain variable region of SEQ ID NO: 135.

In one embodiment, the bispecific antibody comprises an antigen binding moiety that specifically binds to CD19, and an antigen binding moiety that specifically binds to CD3. In one embodiment, the bispecific antibody comprises a first antigen binding moiety that specifically binds to CD3, and a second and a third antigen binding moiety that specifically bind to CD19. In one embodiment, the first antigen binding moiety is a crossover Fab molecule, and the second and the first antigen binding moiety are each a conventional Fab molecule. In one embodiment, the bispecific antibody further comprises an Fc domain. The bispecific antibody may comprise modifications in the Fc region and/or the antigen binding moieties as described herein.

In one embodiment, the therapeutic agent comprises a bispecific antibody comprising
(i) an antigen binding moiety that specifically binds to CD3 and comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37; and
(ii) an antigen binding moiety that specifically binds to CD19 and comprises a heavy chain variable region comprising the heavy chain CDR (HCDR) 1 of SEQ ID NO: 48, the HCDR2 of SEQ ID NO: 49, and the HCDR3 of SEQ ID NO: 50; and a light chain variable region comprising the light chain CDR (LCDR) 1 of SEQ ID NO: 51, the LCDR2 of SEQ ID NO: 52 and the LCDR3 of SEQ ID NO: 53.

In one embodiment, the therapeutic agent comprises a bispecific antibody comprising
(i) an antigen binding moiety that specifically binds to CD3 and comprises a heavy chain variable region of SEQ ID NO: 38; and a light chain variable region of SEQ ID NO: 39; and
(ii) an antigen binding moiety that specifically binds to CD19 and comprises a heavy chain variable region of SEQ ID NO: 54; and a light chain variable region of SEQ ID NO: 55.

In a particular embodiment, the therapeutic agent comprises a bispecific antibody comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association; wherein
(i) the first antigen is CD19 and the second antigen is CD3, particularly CD3 epsilon;
(ii) the first Fab molecule under a) and the third Fab molecule under c) each comprise the heavy chain complementarity determining region (CDR) 1 of SEQ ID NO: 48, the heavy chain CDR 2 of SEQ ID NO: 49, the heavy chain CDR 3 of SEQ ID NO: 50, the light chain CDR 1 of SEQ ID NO: 51, the light chain CDR 2 of SEQ ID NO: 52 and the light chain CDR 3 of SEQ ID NO: 53, and the second Fab molecule under b) comprises the heavy chain CDR 1 of SEQ ID NO: 32, the heavy chain CDR 2 of SEQ ID NO: 33, the heavy chain CDR 3 of SEQ ID NO: 34, the light chain CDR 1 of SEQ ID NO: 35, the light chain CDR 2 of SEQ ID NO: 36 and the light chain CDR 3 of SEQ ID NO: 37;
(iii) in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R), particularly by arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index); and
(iv) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d).

In one embodiment, the first Fab molecule under a) and the third Fab molecule under c) each comprise a heavy chain variable region that is at least 95%, 96%, 97%, 98%, or 99% identical to the sequence of SEQ ID NO: 54, and a light chain variable region that is at least 95%, 96%, 97%, 98%, or 99% identical to the sequence of SEQ ID NO: 55.

In one embodiment, the first Fab molecule under a) and the third Fab molecule under c) each comprise the heavy chain variable region sequence of SEQ ID NO: 54, and the light chain variable region sequence of SEQ ID NO: 55.

In one embodiment, the second Fab molecule under b) comprises a heavy chain variable region that is at least 95%, 96%, 97%, 98%, or 99% identical to the sequence of SEQ ID NO: 38, and a light chain variable region that is at least 95%, 96%, 97%, 98%, or 99% identical to the sequence of SEQ ID NO: 39.

In still a further embodiment, the second Fab molecule under b) comprises the heavy chain variable region sequence of SEQ ID NO: 38, and the light chain variable region sequence of SEQ ID NO: 39.

In a particular embodiment, the bispecific antibody comprises a polypeptide that is at least 95%, 96%, 97%, 98%, or 99% identical to the sequence of SEQ ID NO: 47, a polypeptide that is at least 95%, 96%, 97%, 98%, or 99% identical to the sequence of SEQ ID NO: 56, a polypeptide that is at least 95%, 96%, 97%, 98%, or 99% identical to the sequence of SEQ ID NO: 57, and a polypeptide that is at least 95%, 96%, 97%, 98%, or 99% identical to the sequence of SEQ ID NO: 58. In a further particular embodiment, the bispecific antibody comprises a polypeptide sequence of SEQ ID NO: 47, a polypeptide sequence of SEQ ID NO: 56, a polypeptide sequence of SEQ ID NO: 57 and a polypeptide sequence of SEQ ID NO: 58.

In one embodiment, the therapeutic agent comprises a bispecific antibody comprising
(i) an antigen binding moiety that specifically binds to CD3 and comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37; and
(ii) an antigen binding moiety that specifically binds to CD19 and comprises a heavy chain variable region comprising the heavy chain CDR (HCDR) 1 of SEQ ID NO: 59, the HCDR2 of SEQ ID NO: 60, and the HCDR3 of SEQ ID NO: 61; and a light chain variable region comprising the light chain CDR (LCDR) 1 of SEQ ID NO: 62, the LCDR2 of SEQ ID NO: 63 and the LCDR3 of SEQ ID NO: 64.

In one embodiment, the therapeutic agent comprises a bispecific antibody comprising
(i) an antigen binding moiety that specifically binds to CD3 and comprises a heavy chain variable region of SEQ ID NO: 38; and a light chain variable region of SEQ ID NO: 39; and
(ii) an antigen binding moiety that specifically binds to CD19 and comprises a heavy chain variable region of SEQ ID NO: 65; and a light chain variable region of SEQ ID NO: 66.

In a particular embodiment, the therapeutic agent comprises a bispecific antibody comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association;

wherein
(i) the first antigen is CD19 and the second antigen is CD3, particularly CD3 epsilon;
(ii) the first Fab molecule under a) and the third Fab molecule under c) each comprise the heavy chain complementarity determining region (CDR) 1 of SEQ ID NO: 59, the heavy chain CDR 2 of SEQ ID NO: 60, the heavy chain CDR 3 of SEQ ID NO: 61, the light chain CDR 1 of SEQ ID NO: 62, the light chain CDR 2 of SEQ ID NO: 63 and the light chain CDR 3 of SEQ ID NO: 64, and the second Fab molecule under b) comprises the heavy chain CDR 1 of SEQ ID NO: 32, the heavy chain CDR 2 of SEQ ID NO: 33, the heavy chain CDR 3 of SEQ ID NO: 34, the light chain CDR 1 of SEQ ID NO: 35, the light chain CDR 2 of SEQ ID NO: 36 and the light chain CDR 3 of SEQ ID NO: 37;
(iii) in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R), particularly by arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index); and
(iv) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d).

In one embodiment, the first Fab molecule under a) and the third Fab molecule under c) each comprise a heavy chain variable region that is at least 95%, 96%, 97%, 98%, or 99% identical to the sequence of SEQ ID NO: 65, and a light chain variable region that is at least 95%, 96%, 97%, 98%, or 99% identical to the sequence of SEQ ID NO: 66.

In one embodiment, the first Fab molecule under a) and the third Fab molecule under c) each comprise the heavy chain variable region sequence of SEQ ID NO: 65, and the light chain variable region sequence of SEQ ID NO: 66.

In one embodiment, the second Fab molecule under b) comprises a heavy chain variable region that is at least 95%, 96%, 97%, 98%, or 99% identical to the sequence of SEQ ID NO: 38, and a light chain variable region that is at least 95%, 96%, 97%, 98%, or 99% identical to the sequence of SEQ ID NO: 39.

In still a further embodiment, the second Fab molecule under b) comprises the heavy chain variable region sequence of SEQ ID NO: 38, and the light chain variable region sequence of SEQ ID NO: 39.

In a particular embodiment, the bispecific antibody comprises a polypeptide that is at least 95%, 96%, 97%, 98%, or 99% identical to the sequence of SEQ ID NO: 47, a polypeptide that is at least 95%, 96%, 97%, 98%, or 99% identical to the sequence of SEQ ID NO: 148, a polypeptide that is at least 95%, 96%, 97%, 98%, or 99% identical to the sequence of SEQ ID NO: 149, and a polypeptide that is at least 95%, 96%, 97%, 98%, or 99% identical to the sequence of SEQ ID NO: 150. In a further particular embodiment, the bispecific antibody comprises a polypeptide sequence of SEQ ID NO: 47, a polypeptide sequence of SEQ ID NO: 148, a polypeptide sequence of SEQ ID NO: 149 and a polypeptide sequence of SEQ ID NO: 150.

Antibody Formats

The components of an antibody comprised in the therapeutic agent, particularly a multispecific antibody, can be fused to each other in a variety of configurations. Exemplary configurations are depicted in FIG. 6.

In particular embodiments, the antigen binding moieties comprised in the antibody are Fab molecules. In such embodiments, the first, second, third etc. antigen binding moiety may be referred to herein as first, second, third etc. Fab molecule, respectively. Furthermore, in particular embodiments, the antibody comprises an Fc domain composed of a first and a second subunit capable of stable association.

In some embodiments, the second Fab molecule is fused at the C-terminus of the Fab heavy chain to the N-terminus of the first or the second subunit of the Fc domain.

In one such embodiment, the first Fab molecule is fused at the C-terminus of the Fab heavy chain to the N-terminus of the Fab heavy chain of the second Fab molecule. In a specific such embodiment, the antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIGS. 6G and 6K. Optionally, the Fab light chain of the first Fab molecule and the Fab light chain of the second Fab molecule may additionally be fused to each other.

Figure 6C:
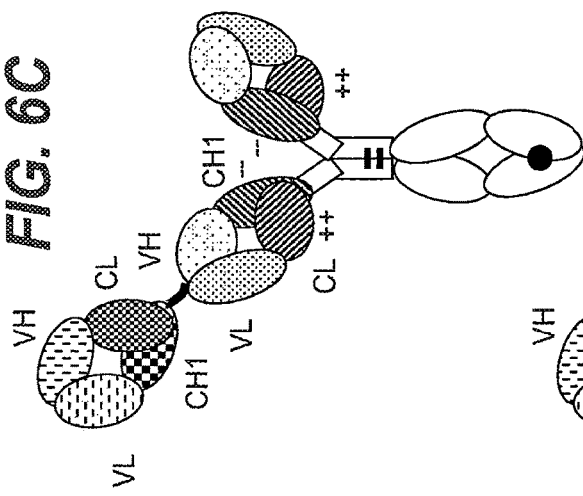
(FIG. 6C, FIG. 6F) Illustration of the "2+1 IgG Crossfab" molecule.
Figure 6F:
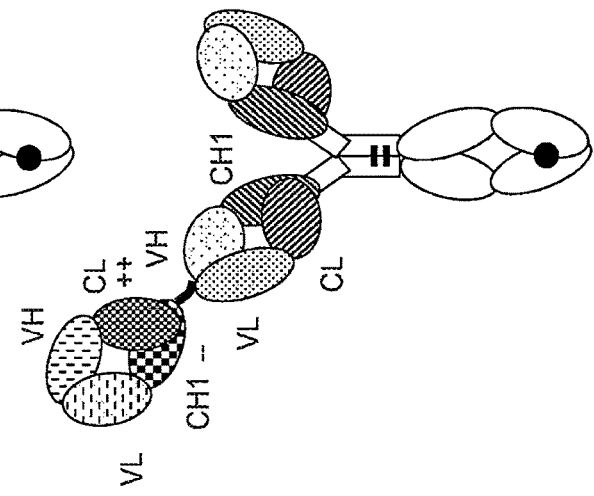
Figure 6B:
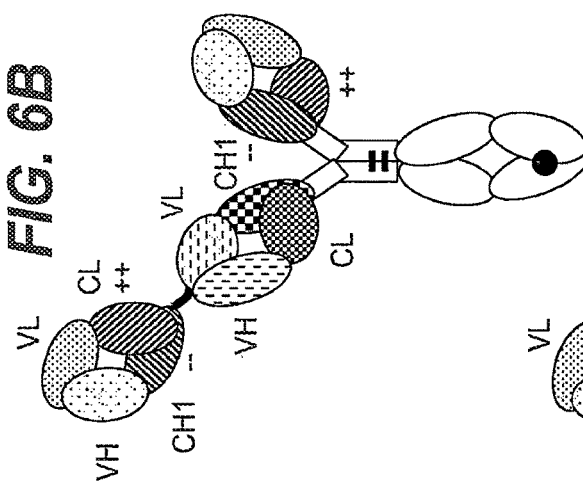
(FIG. 6B, FIG. 6E) Illustration of the "2+1 IgG Crossfab" molecule with alternative order of Crossfab and Fab components ("inverted").
Figure 6E:
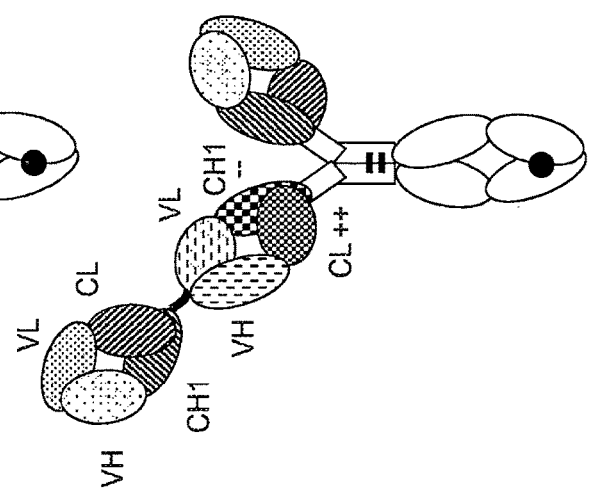
Figure 6A:
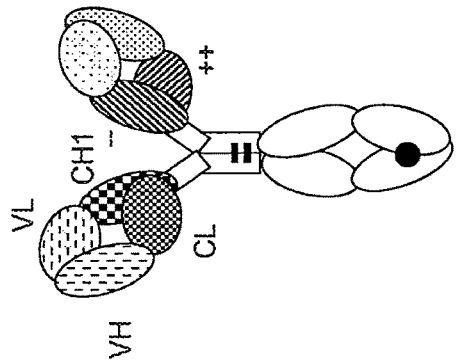
FIGS. 6A-6Z. Exemplary configurations of the T cell activating bispecific antigen binding molecules (TCBs) useful in the invention.
Figure 6D:
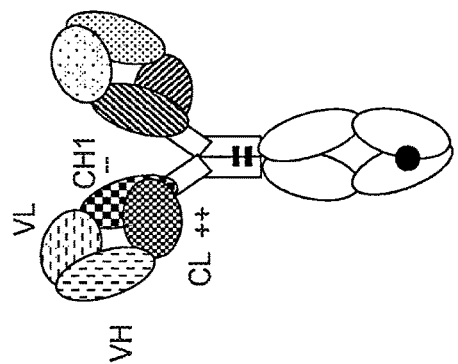

In another such embodiment, the first Fab molecule is fused at the C-terminus of the Fab heavy chain to the N-terminus of the first or second subunit of the Fc domain. In a specific such embodiment, the antibody essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIGS. 6A and 6D. The first and the second Fab molecule may be fused to the Fc domain directly or through a peptide linker. In a particular embodiment the first and the second Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain.

In other embodiments, the first Fab molecule is fused at the C-terminus of the Fab heavy chain to the N-terminus of the first or second subunit of the Fc domain.

In one such embodiment, the second Fab molecule is fused at the C-terminus of the Fab heavy chain to the N-terminus of the Fab heavy chain of the first Fab molecule. In a specific such embodiment, the antibody essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIGS. 6H and 6L. Optionally, the Fab light chain of the first Fab molecule and the Fab light chain of the second Fab molecule may additionally be fused to each other.

The Fab molecules may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=, 1, 2 or 3) or (x=4, n=2, 3, 4 or 5 and m=0, 1, 2 or 3), in one embodiment x=4 and n=2 or 3, in a further embodiment x=4 and n=2. In one embodiment said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 118 and 119). Another suitable such linker comprises the sequence $(G_4S)_4$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

An antibody with a single antigen binding moiety (such as a Fab molecule) capable of specific binding to a target cell antigen (for example as shown in FIG. 6A, D, G, H, K, L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have an antibody comprising two or more antigen binding moieties (such as Fab molecules) specific for a target cell antigen (see examples shown in FIG. 6B, 6C, 6E, 6F, 6I, 6J, 6M or 6N), for example to optimize targeting to the target site or to allow crosslinking of target cell antigens.

Accordingly, in particular embodiments, the antibody further comprises a third Fab molecule which specifically binds to the first antigen. The first antigen preferably is the target cell antigen. In one embodiment, the third Fab molecule is a conventional Fab molecule. In one embodiment, the third Fab molecule is identical to the first Fab molecule (i.e. the first and the third Fab molecule comprise the same heavy and light chain amino acid sequences and have the same arrangement of domains (i.e. conventional or crossover)). In a particular embodiment, the second Fab molecule specifically binds to an activating T cell antigen, particularly CD3, and the first and third Fab molecule specifically bind to a target cell antigen.

In alternative embodiments, the antibody further comprises a third Fab molecule which specifically binds to the second antigen. In these embodiments, the second antigen preferably is the target cell antigen. In one such embodiment, the third Fab molecule is a crossover Fab molecule (a Fab molecule wherein the variable domains VH and VL or the constant domains CL and CH1 of the Fab heavy and light chains are exchanged/replaced by each other). In one such embodiment, the third Fab molecule is identical to the second Fab molecule (i.e. the second and the third Fab molecule comprise the same heavy and light chain amino acid sequences and have the same arrangement of domains (i.e. conventional or crossover)). In one such embodiment, the first Fab molecule specifically binds to an activating T cell antigen, particularly CD3, and the second and third Fab molecule specifically bind to a target cell antigen.

In one embodiment, the third Fab molecule is fused at the C-terminus of the Fab heavy chain to the N-terminus of the first or second subunit of the Fc domain.

In a particular embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In a specific such embodiment, the antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 6B and 6E (particular embodiments, wherein the third Fab molecule is a conventional Fab molecule and preferably identical to the first Fab molecule), and FIGS. 6 and 6M (alternative embodiments, wherein the third Fab molecule is a crossover Fab molecule and preferably identical to the second Fab molecule). The second and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In another embodiment, the first and the third Fab molecule are each fused at the C-terminus of the Fab heavy chain to the N-terminus of one of the subunits of the Fc domain, and the second Fab molecule is fused at the C-terminus of the Fab heavy chain to the N-terminus of the Fab heavy chain of the first Fab molecule. In a specific such embodiment, the antibody essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 6C and 6F (particular embodiments, wherein the third Fab molecule is a conventional Fab molecule and preferably identical to the first Fab molecule) and in FIGS. 6J and 6N (alternative embodiments, wherein the third Fab molecule is a crossover Fab molecule and preferably identical to the second Fab molecule). The first and the third Fab molecule may be fused to the Fc domain directly or through a peptide linker. In a particular embodiment the first and the third Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In configurations of the antibody wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG$_4$ subclass immunoglobulin. In a further particular embodiment the immunoglobulin is a human immunoglobulin. In other embodiments the immunoglobulin is a chimeric immunoglobulin or a humanized immunoglobulin.

In some of the antibodies, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the antibodies.

In certain embodiments the antibody comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit (VL$_{(2)}$-CH1$_{(2)}$-CH2-CH3(-CH4)), and a polypeptide wherein the Fab heavy chain of the first Fab molecule shares a carboxy-terminal peptide bond with an Fc domain subunit (VH$_{(1)}$-CH1$_{(1)}$-CH2-CH3(-CH4)). In some embodiments the antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In certain embodiments the polypeptides are covalently linked, e.g., by a disulfide bond.

In certain embodiments the antibody comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit (VH$_{(2)}$-CL$_{(2)}$-CH2-CH3(-CH4)), and a polypeptide wherein the Fab heavy chain of the first Fab molecule shares a carboxy-terminal peptide bond with an Fc domain subunit (VH$_{(1)}$-CH1$_{(1)}$-CH2-CH3(-CH4)). In some embodiments the antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In certain embodiments the polypeptides are covalently linked, e.g., by a disulfide bond.

In some embodiments, the antibody comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with an Fc domain subunit (VL$_{(2)}$-CH1$_{(2)}$-VH$_{(1)}$-CH1$_{(1)}$-CH2-CH3(-CH4)). In other embodiments, the antibody comprises a polypeptide wherein the Fab heavy chain of the first Fab molecule shares a carboxy-terminal peptide bond with the Fab light chain variable region of the second Fab molecule which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit (VH$_{(1)}$-CH1$_{(1)}$-VL$_{(2)}$-CH1$_{(2)}$-CH2-CH3(-CH4)).

In some of these embodiments the antibody further comprises a crossover Fab light chain polypeptide of the second Fab molecule, wherein the Fab heavy chain variable region of the second Fab molecule shares a carboxy-terminal peptide bond with the Fab light chain constant region of the second Fab molecule (VH$_{(2)}$-CL$_{(2)}$), and the Fab light chain polypeptide of the first Fab molecule (VL$_{(1)}$-CL$_{(1)}$). In others of these embodiments the antibody further comprises a polypeptide wherein the Fab heavy chain variable region of the second Fab molecule shares a carboxy-terminal peptide bond with the Fab light chain constant region of the second Fab molecule which in turn shares a carboxy-terminal peptide bond with the Fab light chain polypeptide of the first Fab molecule (VH$_{(2)}$-CL$_{(2)}$-VL$_{(1)}$-CL$_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL$_{(1)}$-CL$_{(1)}$-VH$_{(2)}$-CL$_{(2)}$), as appropriate.

The antibody according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit (VH$_{(3)}$-CH1$_{(3)}$-CH2-CH3(-CH4)) and the Fab light chain polypeptide of a third Fab molecule (VL$_{(3)}$-CL$_{(3)}$). In certain embodiments the polypeptides are covalently linked, e.g., by a disulfide bond.

In some embodiments, the antibody comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with an Fc domain subunit (VH$_{(2)}$-CL$_{(2)}$-VH$_{(1)}$-CH1$_{(1)}$-CH2-CH3(-CH4)). In other embodiments, the antibody comprises a polypeptide wherein the Fab heavy chain of the first Fab molecule shares a carboxy-terminal peptide bond with the Fab heavy chain variable region of the second Fab molecule which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit (VH$_{(1)}$-CH1$_{(1)}$-VH$_{(2)}$-CL$_{(2)}$-CH2-CH3(-CH4)).

In some of these embodiments the antibody further comprises a crossover Fab light chain polypeptide of the second Fab molecule, wherein the Fab light chain variable region of the second Fab molecule shares a carboxy-terminal peptide bond with the Fab heavy chain constant region of the second Fab molecule (VL$_{(2)}$-CH1$_{(2)}$), and the Fab light chain polypeptide of the first Fab molecule (VL$_{(1)}$-CL$_{(1)}$). In others of these embodiments the antibody further comprises a polypeptide wherein the Fab light chain variable region of the second Fab molecule shares a carboxy-terminal peptide bond with the Fab heavy chain constant region of the second Fab molecule which in turn shares a carboxy-terminal peptide bond with the Fab light chain polypeptide of the first Fab molecule (VL$_{(2)}$-CH1$_{(2)}$-VL$_{(1)}$-CL$_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL$_{(1)}$-CL$_{(1)}$-VH$_{(2)}$-CL$_{(2)}$), as appropriate.

The antibody according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit (VH$_{(3)}$-CH1$_{(3)}$-CH2-CH3(-CH4)) and the Fab light chain polypeptide of a third Fab molecule (VL$_{(3)}$-CL$_{(3)}$). In certain embodiments the polypeptides are covalently linked, e.g., by a disulfide bond.

Figure 6O:
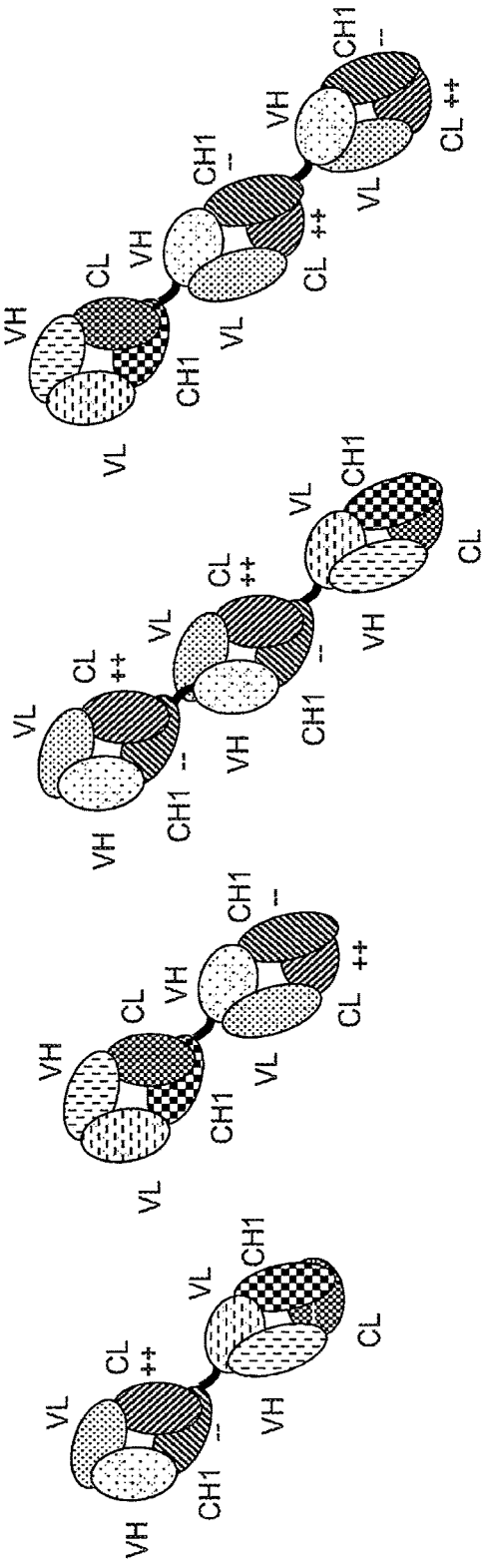
(FIG. 6O, FIG. 6S) Illustration of the "Fab-Crossfab" molecule.
Figure 6P:
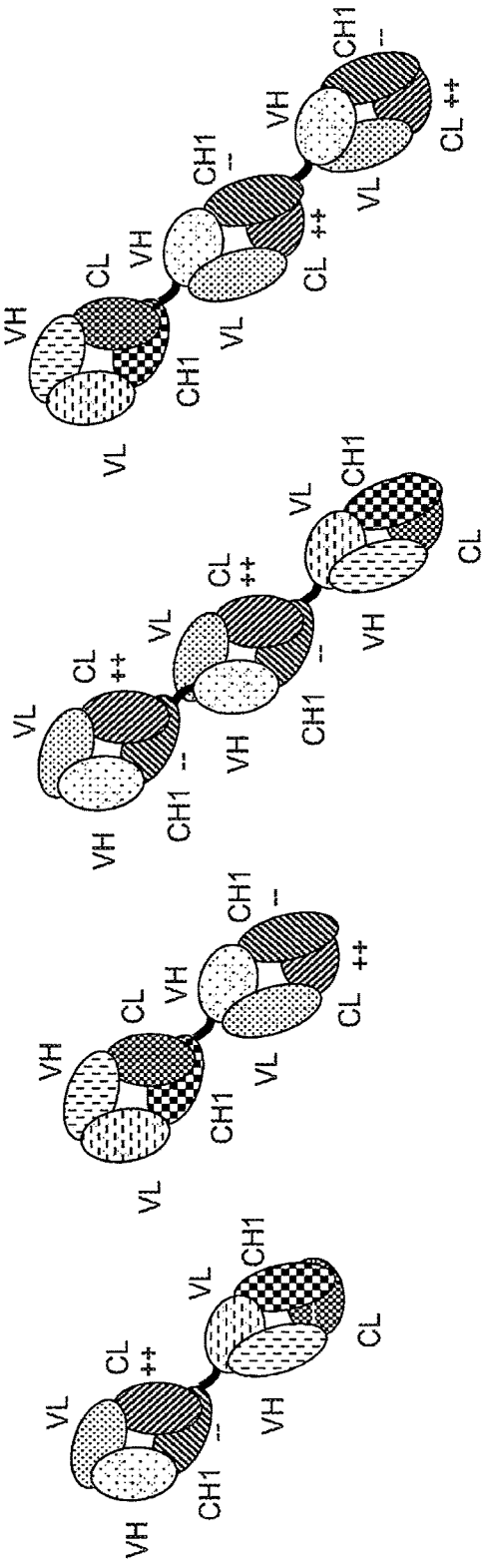
(FIG. 6P, FIG. 6T) Illustration of the "Crossfab-Fab" molecule.
Figure 6Q:
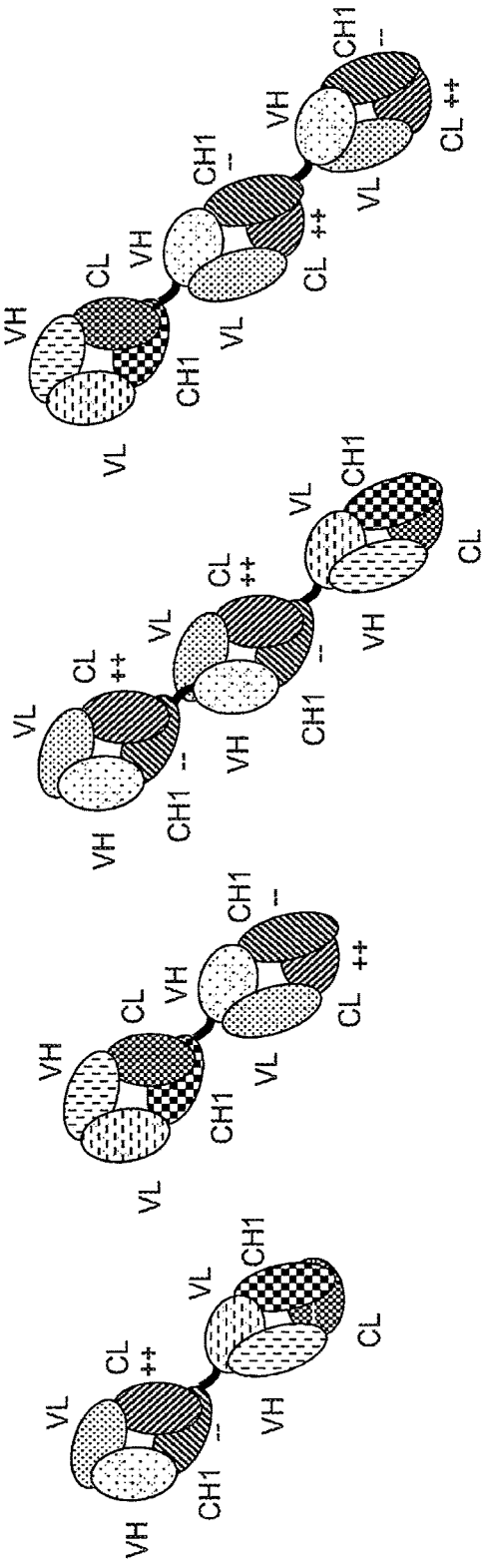
(FIG. 6Q, FIG. 6U) Illustration of the "(Fab)$_2$-Crossfab" molecule.
Figure 6R:
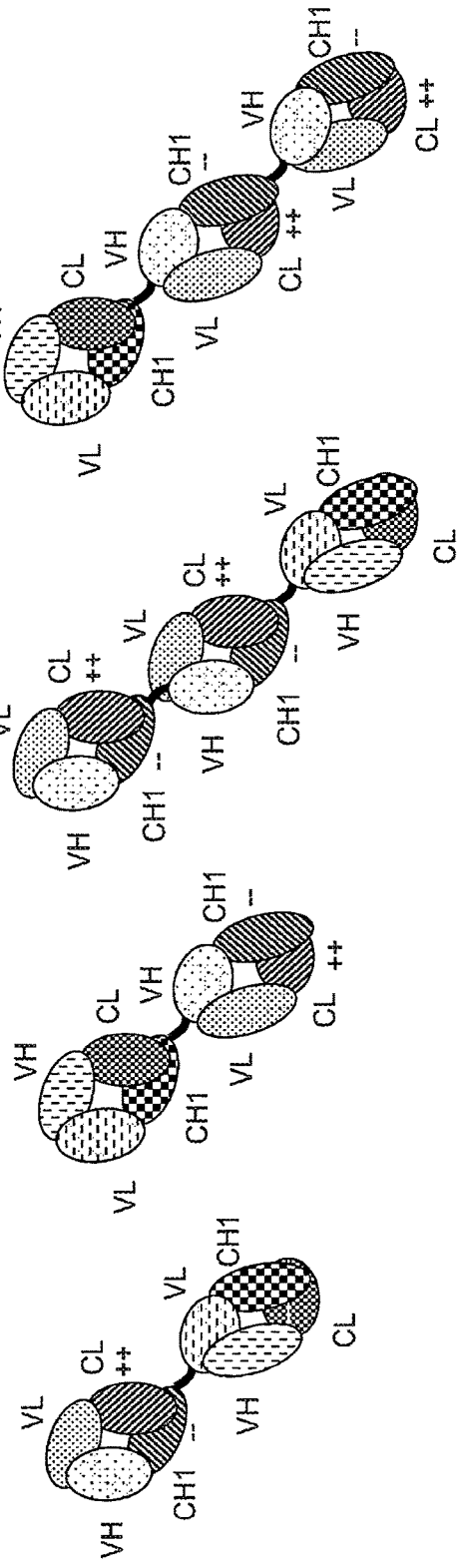
(FIG. 6R, FIG. 6V) Illustration of the "Crossfab-(Fab)$_2$" molecule.
Figure 6S:
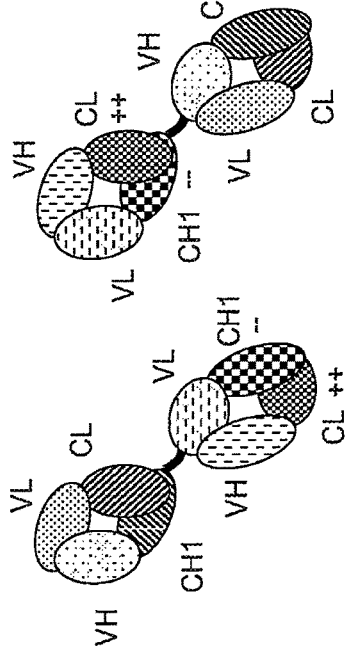

In some embodiments, the first Fab molecule is fused at the C-terminus of the Fab heavy chain to the N-terminus of the Fab heavy chain of the second Fab molecule. In certain such embodiments, the antibody does not comprise an Fc domain. In certain embodiments, the antibody essentially consists of the first and the second Fab molecule, and optionally one or more peptide linkers, wherein the first Fab molecule is fused at the C-terminus of the Fab heavy chain to the N-terminus of the Fab heavy chain of the second Fab molecule. Such a configuration is schematically depicted in FIGS. 6O and 6S.

Figure 6T:
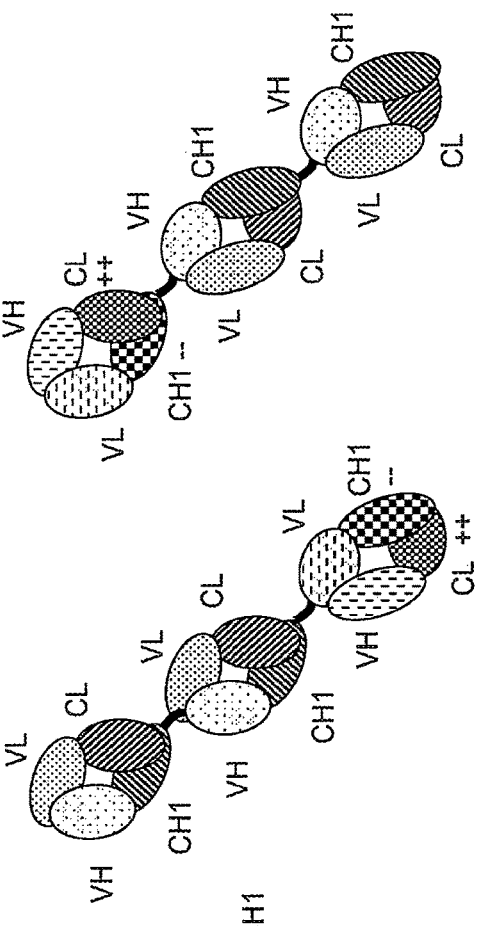

In other embodiments, the second Fab molecule is fused at the C-terminus of the Fab heavy chain to the N-terminus of the Fab heavy chain of the first Fab molecule. In certain such embodiments, the antibody does not comprise an Fc domain. In certain embodiments, the antibody essentially consists of the first and the second Fab molecule, and optionally one or more peptide linkers, wherein the second Fab molecule is fused at the C-terminus of the Fab heavy chain to the N-terminus of the Fab heavy chain of the first Fab molecule. Such a configuration is schematically depicted in FIGS. 6P and 6T.

Figure 6U:
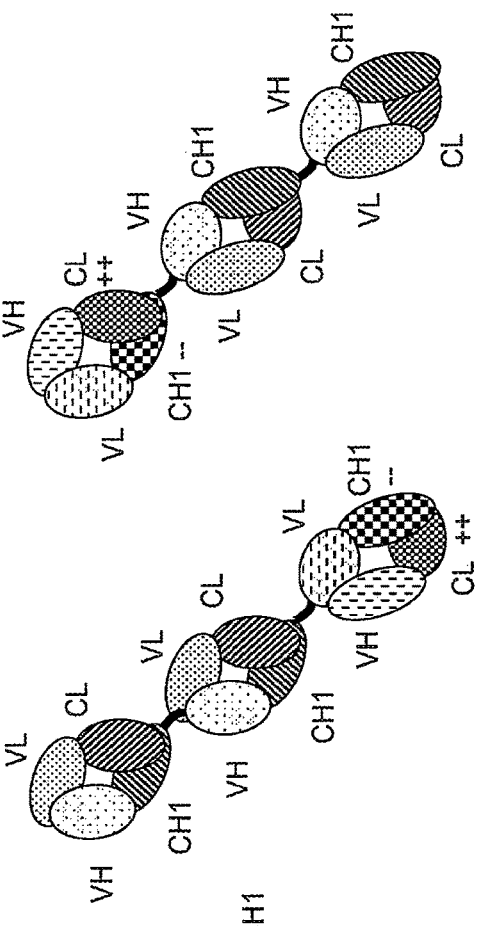

In some embodiments, the first Fab molecule is fused at the C-terminus of the Fab heavy chain to the N-terminus of the Fab heavy chain of the second Fab molecule, and the antibody further comprises a third Fab molecule, wherein said third Fab molecule is fused at the C-terminus of the Fab heavy chain to the N-terminus of the Fab heavy chain of the first Fab molecule. In particular such embodiments, said third Fab molecule is a conventional Fab molecule. In other such embodiments, said third Fab molecule is a crossover Fab molecule as described herein, i.e. a Fab molecule wherein the variable domains VH and VL or the constant domains CL and CH1 of the Fab heavy and light chains are exchanged/replaced by each other. In certain such embodiments, the antibody essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the C-terminus of the Fab heavy chain to the N-terminus of the Fab heavy chain of the first Fab molecule. Such a configuration is schematically depicted in FIGS. 6Q and 6U (particular embodiments, wherein the third Fab molecule is a conventional Fab molecule and preferably identical to the first Fab molecule).

Figure 6V:
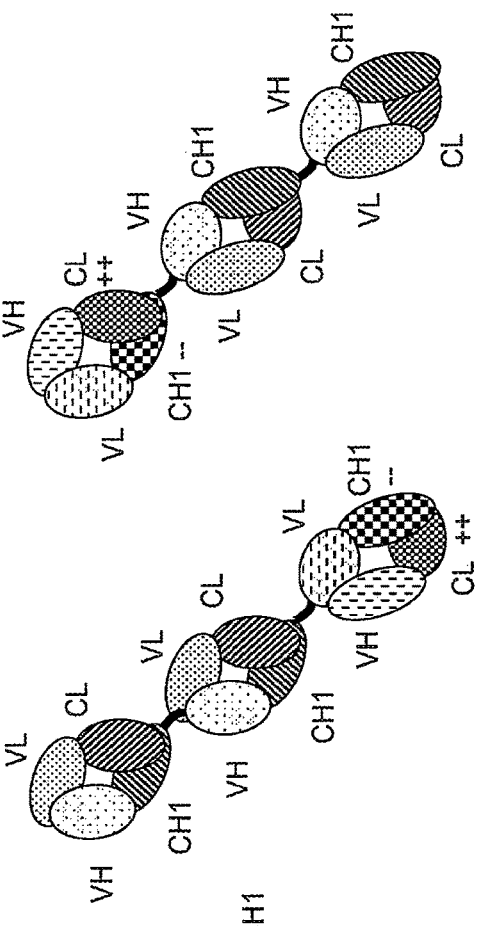
Figure 6W:
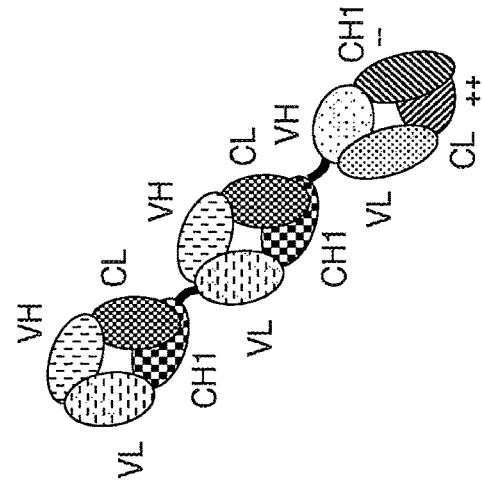
(FIG. 6W, FIG. 6Y) Illustration of the "Fab-(Crossfab)$_2$" molecule.
Figure 6X:
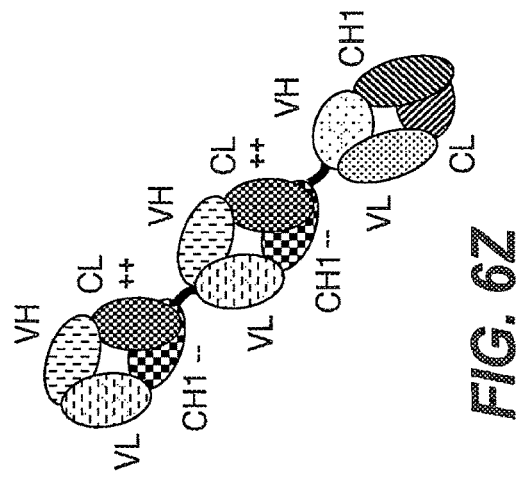
Figure 6Y:
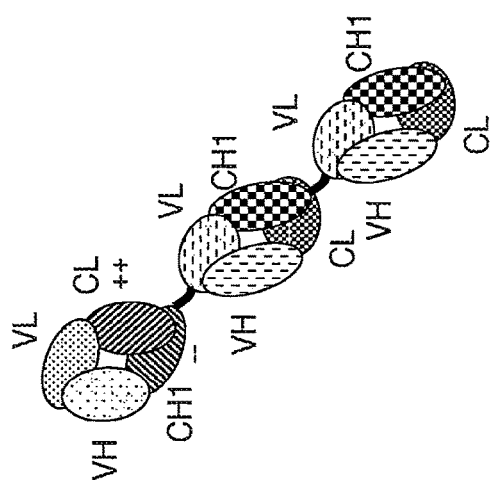

In some embodiments, the first Fab molecule is fused at the C-terminus of the Fab heavy chain to the N-terminus of the Fab heavy chain of the second Fab molecule, and the antibody further comprises a third Fab molecule, wherein said third Fab molecule is fused at the N-terminus of the Fab heavy chain to the C-terminus of the Fab heavy chain of the second Fab molecule. In particular such embodiments, said third Fab molecule is a crossover Fab molecule as described herein, i.e. a Fab molecule wherein the variable domains VH and VL or the constant domains CH1 and CL of the Fab heavy and light chains are exchanged/replaced by each other. In other such embodiments, said third Fab molecule is a conventional Fab molecule. In certain such embodiments, the antibody essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the N-terminus of the Fab heavy chain to the C-terminus of the Fab heavy chain of the second Fab molecule. Such a configuration is schematically depicted in FIGS. 6W and 6Y (particular embodiments, wherein the third Fab molecule is a crossover Fab molecule and preferably identical to the second Fab molecule).

In some embodiments, the second Fab molecule is fused at the C-terminus of the Fab heavy chain to the N-terminus of the Fab heavy chain of the first Fab molecule, and the antibody further comprises a third Fab molecule, wherein said third Fab molecule is fused at the N-terminus of the Fab heavy chain to the C-terminus of the Fab heavy chain of the first Fab molecule. In particular such embodiments, said third Fab molecule is a conventional Fab molecule. In other such embodiments, said third Fab molecule is a crossover Fab molecule as described herein, i.e. a Fab molecule wherein the variable domains VH and VL or the constant domains CH1 and CL of the Fab heavy and light chains are exchanged/replaced by each other. In certain such embodiments, the antibody essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the N-terminus of the Fab heavy chain to the C-terminus of the Fab heavy chain of the first Fab molecule. Such a configuration is schematically depicted in FIGS. 6R and 6V (particular embodiments, wherein the third Fab molecule is a conventional Fab molecule and preferably identical to the first Fab molecule).

Figure 6Z:
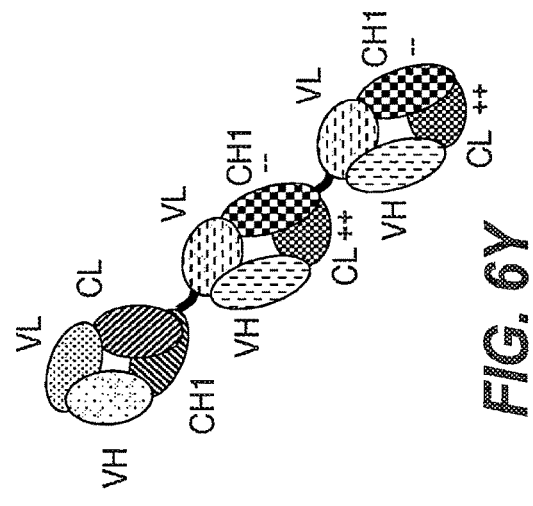

In some embodiments, the second Fab molecule is fused at the C-terminus of the Fab heavy chain to the N-terminus of the Fab heavy chain of the first Fab molecule, and the antibody further comprises a third Fab molecule, wherein said third Fab molecule is fused at the C-terminus of the Fab heavy chain to the N-terminus of the Fab heavy chain of the second Fab molecule. In particular such embodiments, said third Fab molecule is a crossover Fab molecule as described herein, i.e. a Fab molecule wherein the variable domains VH and VL or the constant domains CH1 and CL of the Fab heavy and light chains are exchanged/replaced by each other. In other such embodiments, said third Fab molecule is a conventional Fab molecule. In certain such embodiments, the antibody essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the C-terminus of the Fab heavy chain to the N-terminus of the Fab heavy chain of the second Fab molecule. Such a configuration is schematically depicted in FIGS. 6X and 6Z (particular embodiments, wherein the third Fab molecule is a crossover Fab molecule and preferably identical to the first Fab molecule).

In certain embodiments the antibody comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the antibody comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the antibody comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(2)}$-$CL_{(2)}$-$VH_{(1)}$-$CH1_{(1)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$).

In certain embodiments the antibody comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(3)}$-$CH1_{(3)}$-$VH_{(1)}$-$CH1_{(1)}$-$VL_{(2)}$-$CH1_{(2)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region) ($VH_{(3)}$-$CH1_{(3)}$-$VH_{(1)}$-$CH1_{(1)}$-$VH_{(2)}$-$CL_{(2)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule ($VL_{(2)}$-$CH1_{(2)}$-$VH_{(1)}$-$CH1_{(1)}$-$VH_{(3)}$-$CH1_{(3)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with the Fab heavy chain of a third Fab molecule ($VH_{(2)}$-$CL_{(2)}$-$VH_{(1)}$-$CH1_{(1)}$-$VH_{(3)}$-$CH1_{(3)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises the Fab light chain polypeptide of a third Fab molecule ($VL_{(3)}$-$CL_{(3)}$).

In certain embodiments the antibody comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$-$VL_{(3)}$-$CH1_{(3)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the antibody comprises a polypeptide wherein the Fab heavy chain of the first Fab molecule shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) ($VH_{(1)}$-$CH1_{(1)}$-$VH_{(2)}$-$CL_{(2)}$-$VH_{(3)}$-$CL_{(3)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In certain embodiments the antibody comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(3)}$-$CH1_{(3)}$-$VL_{(2)}$-$CH1_{(2)}$-$VH_{(1)}$-$CH1_{(1)}$). In some embodiments the antibody further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the antibody further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the antibody comprises a polypeptide wherein the Fab heavy chain variable region of a third Fab molecule shares a carboxy-terminal peptide bond with the Fab light chain constant region of a third Fab molecule (i.e. the third Fab molecule comprises a crossover Fab heavy chain, wherein the heavy chain constant region is replaced by a light chain constant region), which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(3)}$-$CL_{(3)}$-$VH_{(2)}$-$CL_{(2)}$-$VH_{(1)}$-$CH1_{(1)}$). In some embodiments the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the antibody further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

According to any of the above embodiments, components of the antibody (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally an integer from 1 to 10, typically from 2 to 4.

Fc Domain

An antibody, e.g. a bispecific antibody or an immunoconjugate, comprised in the therapeutic agent may comprise an Fc domain which consists of a pair of polypeptide chains comprising heavy chain domains of an antibody molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

In one embodiment, the Fc domain is an IgG Fc domain. In a particular embodiment the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment the Fc domain is human. An exemplary sequence of a human $IgG_1$ Fc region is given in SEQ ID NO: 30.

(i) Fc Domain Modifications Promoting Heterodimerization

Antibodies, particularly bispecific antibodies or immunoconjugates, comprised in the therapeutic agent may comprise different components (e.g. antigen binding domains, cytokines) fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of such antibodies in recombinant production, it will thus be advantageous to introduce in the Fc domain of the antibody a modification promoting the association of the desired polypeptides.

Accordingly, in particular embodiments the Fc domain comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed). These different approaches for improved heavy chain heterodimerization are contemplated as different alternatives in combination with heavy-light chain modifications (e.g. variable or constant region exchange/replacement in Fab arms, or introduction of substitutions of charged amino acids with opposite charges in the CH1/CL interface) which reduce light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain (the "knobs" subunit) the threonine residue at position 366 is replaced with a tryptophan residue (T366W), and in the CH3 domain of the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises amino acid substitutions S354C and T366W, and the second subunit of the Fc domain comprises amino acid substitutions Y349C, T366S, L368A and Y407V (numbering according to Kabat EU index).

In a particular embodiment the mutant IL-2 polypeptide in the immunoconjugate described herein, or the CD3 antigen binding moiety in the bispecific antibody described herein, is fused to the first subunit of the Fc domain (comprising the "knob" modification). Without wishing to be bound by theory, fusion of the IL-2 polypeptide or CD3 antigen binding moiety to the knob-containing subunit of the Fc domain will (further) minimize the generation of immunoconjugates comprising two IL-2 polypeptides or bispecific antibodies comprising two CD3 antigen binding moieties, respectively (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1870459 A1, is used alternatively. This approach is based on the introduction of charged amino acids with opposite charges at specific amino acid positions in the CH3/CH3 domain interface between the two subunits of the Fc domain. One preferred embodiment are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment the antibody comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment the antibody comprises amino acid mutations S354C, T366W in the CH3 domain of the first subunit of the Fc domain and amino acid mutations Y349C, T366S, L368A, Y407V in the CH3 domain of the second subunit of the Fc domain, or the antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment the heterodimerization approach described in WO 2013/157953 is used alternatively. In one embodiment a first CH3 domain comprises amino acid mutation T366K and a second CH3 domain comprises amino acid mutation L351D (numberings according to Kabat EU index). In a further embodiment the first CH3 domain comprises further amino acid mutation L351K. In a further embodiment the second CH3 domain comprises further an amino acid mutation selected from Y349E, Y349D and L368E (preferably L368E) (numberings according to Kabat EU index).

In one embodiment the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, S400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405, F405M, F405T, F405S, F405V or F405W, e) N390R, N390K or N390D, f) K392V, K392M, K392R, K392L, K392F or K392E (numberings according to Kabat EU index). In a further embodiment a first CH3 domain comprises amino acid mutations L351Y, Y407A and a second CH3 domain comprises amino acid mutations T366V, K409F. In a further embodiment a first CH3 domain comprises amino acid mutation Y407A and a second CH3 domain comprises amino acid mutations T366A, K409F. In a further embodiment the second CH3 domain further comprises amino acid mutations K392E, T411E, D399R and S400R (numberings according to Kabat EU index).

In one embodiment the heterodimerization approach described in WO 2011/143545 is used alternatively, e.g. with the amino acid modification at a position selected from the group consisting of 368 and 409 (numbering according to Kabat EU index).

In one embodiment the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment a first CH3 domain comprises amino acid mutation T366Y and a second CH3 domain comprises amino acid mutation Y407T (numberings according to Kabat EU index).

In one embodiment the antibody or its Fc domain is of IgG$_2$ subclass and the heterodimerization approach described in WO 2010/129304 is used alternatively.

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment the heterodimerization approach described in WO 2007/147901 is used alternatively. In one embodiment a first CH3 domain comprises amino acid mutations K253E, D282K, and K322D and a second CH3 domain comprises amino acid mutations D239K, E240K, and K292D (numberings according to Kabat EU index).

In still another embodiment the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

(ii) Fc Domain Modifications Reducing Fc Receptor Binding and/or Effector Function The Fc domain confers to an antibody, such as a bispecific antibody or immunoconjugate, favorable pharmacokinetic properties, including a long serum half-life which contributes to good accumulation in the target tissue and a favorable tissue-blood distribution ratio. At the same time it may, however, lead to undesirable targeting of the antibody to cells expressing Fc receptors rather than to the preferred antigen-bearing cells. Moreover, the co-activation of Fc receptor signaling pathways may lead to cytokine release which, in combination with other immunostimulatory properties the antibody may have and the long half-life of the antibody, results in excessive activation of cytokine receptors and severe side effects upon systemic administration.

Accordingly, in particular embodiments, the Fc domain of the antibody, particularly bispecific antibody or immunoconjugate, comprised in the therapeutic agent exhibits reduced binding affinity to an Fc receptor and/or reduced effector function, as compared to a native IgG$_1$ Fc domain. In one such embodiment the Fc domain (or the molecule, e.g. antibody, comprising said Fc domain) exhibits less than 50%, preferably less than 20%, more preferably less than 10% and most preferably less than 5% of the binding affinity to an Fc receptor, as compared to a native IgG$_1$ Fc domain (or a corresponding molecule comprising a native IgG$_1$ Fc domain), and/or less than 50%, preferably less than 20%, more preferably less than 10% and most preferably less than 5% of the effector function, as compared to a native IgG$_1$ Fc domain domain (or a corresponding molecule comprising a native IgG$_1$ Fc domain). In one embodiment, the Fc domain (or the molecule, e.g. antibody, comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain exhibits substantially similar binding affinity to neonatal Fc receptor (FcRn), as compared to a native IgG$_1$ Fc domain domain. Substantially similar binding to FcRn is achieved when the Fc domain (or the molecule, e.g. antibody, comprising said Fc domain) exhibits greater than about 70%, particularly greater than about 80%, more particularly greater than about 90% of the binding affinity of a native IgG$_1$ Fc domain (or the corresponding molecule comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the molecule, e.g. antibody, comprising an engineered Fc domain exhibits less than 20%, particularly less than 10%, more particularly less than 5% of the binding affinity to an Fc receptor as compared to a corresponding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the molecule, e.g. antibody, comprising said Fc domain) exhibits greater than about 70% of the binding affinity of a non-engineered form of the Fc domain (or a corresponding molecule comprising said non-engineered form of the Fc domain) to FcRn. The Fc domain, or molecule (e.g. antibody) comprising said Fc domain, may exhibit greater than about 80% and even greater than about 90% of such affinity. In certain embodiments the Fc domain is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a corresponding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329 (numberings according to Kabat EU index). In a more specific embodiment the Fc domain comprises an amino acid substitution at a position selected from the group of L234, L235 and P329 (numberings according to Kabat EU index). In some embodiments the Fc domain comprises the amino acid substitutions L234A and L235A (numberings according to Kabat EU index). In one such embodiment, the Fc domain is an $IgG_1$ Fc domain, particularly a human $IgG_1$ Fc domain. In one embodiment the Fc domain comprises an amino acid substitution at position P329. In a more specific embodiment the amino acid substitution is P329A or P329G, particularly P329G (numberings according to Kabat EU index). In one embodiment the Fc domain comprises an amino acid substitution at position P329 and a further amino acid substitution at a position selected from E233, L234, L235, N297 and P331 (numberings according to Kabat EU index). In a more specific embodiment the further amino acid substitution is E233P, L234A, L235A, L235E, N297A, N297D or P331S. In particular embodiments the Fc domain comprises amino acid substitutions at positions P329, L234 and L235 (numberings according to Kabat EU index). In more particular embodiments the Fc domain comprises the amino acid mutations L234A, L235A and P329G ("P329G LALA"). In one such embodiment, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

$IgG_4$ antibodies exhibit reduced binding affinity to Fc receptors and reduced effector functions as compared to $IgG_1$ antibodies. Hence, in some embodiments the Fc domain is an $IgG_4$ Fc domain, particularly a human $IgG_4$ Fc domain. In one embodiment the $IgG_4$ Fc domain comprises amino acid substitutions at position S228, specifically the amino acid substitution S228P (numberings according to Kabat EU index). To further reduce its binding affinity to an Fc receptor and/or its effector function, in one embodiment the $IgG_4$ Fc domain comprises an amino acid substitution at position L235, specifically the amino acid substitution L235E (numberings according to Kabat EU index). In another embodiment, the $IgG_4$ Fc domain comprises an amino acid substitution at position P329, specifically the amino acid substitution P329G (numberings according to Kabat EU index). In a particular embodiment, the $IgG_4$ Fc domain comprises amino acid substitutions at positions S228, L235 and P329, specifically amino acid substitutions S228P, L235E and P329G (numberings according to Kabat EU index). Such $IgG_4$ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A and optionally P329G. or a human $IgG_4$ Fc domain comprising the amino acid substitutions S228P, L235E and optionally P329G (numberings according to Kabat EU index).

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D) or glycine (N297G) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIACORE® instrument (GE Healthcare), and Fc receptors such as may be obtained by recombinant expression. Alternatively, binding affinity of Fc domains or molecules comprising an Fc domain for Fc receptors may be evaluated using cell lines known to express particular Fc receptors, such as human NK cells expressing FcγIIIa receptor.

Effector function of an Fc domain, or a molecule (e.g. an antibody) comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656(1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or molecule (e.g. antibody) comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103,2738-2743 (2004)).

Antigen Binding Moieties

The antibody comprised in the therapeutic agent may be bispecific, i.e. it comprises at least two antigen binding moieties capable of specific binding to two distinct antigenic determinants. According to particular embodiments, the antigen binding moieties are Fab molecules (i.e. antigen binding domains composed of a heavy and a light chain, each comprising a variable and a constant domain). In one embodiment said Fab molecules are human. In another embodiment said Fab molecules are humanized. In yet another embodiment said Fab molecules comprise human heavy and light chain constant domains.

In some embodiments, at least one of the antigen binding moieties is a crossover Fab molecule. Such modification reduces mispairing of heavy and light chains from different Fab molecules, thereby improving the yield and purity of the antibody in recombinant production. In a particular crossover Fab molecule useful for the antibody, the variable domains of the Fab light chain and the Fab heavy chain (VL and VH, respectively) are exchanged. Even with this domain exchange, however, the preparation of the antibody may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired antibody, charged amino acids with opposite charges may be introduced at specific amino acid positions in the CH and CL domains of either the Fab molecule(s) specifically binding to a target cell antigen, or the Fab molecule specifically binding to an activating T cell antigen. Charge modifications are made either in the conventional Fab molecule(s) comprised in the antibody (such as shown e.g. in FIGS. 6 A-C, G-J), or in the VH/VL crossover Fab molecule(s) comprised in the antibody (such as shown e.g. in FIG. 6 D-F, K-N) (but not in both). In particular embodiments, the charge modifications are made in the conventional Fab molecule(s) comprised in the antibody (which in particular embodiments specifically bind(s) to the target cell antigen).

In a particular embodiment according to the invention, the antibody is capable of simultaneous binding to a target cell antigen, particularly a tumor cell antigen, and an activating T cell antigen, particularly CD3. In one embodiment, the antibody is capable of crosslinking a T cell and a target cell by simultaneous binding to a target cell antigen and an activating T cell antigen. In an even more particular embodiment, such simultaneous binding results in lysis of the target cell, particularly a tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the antibody to the activating T cell antigen, particularly CD3, without simultaneous binding to the target cell antigen does not result in T cell activation.

In one embodiment, the antibody is capable of re-directing cytotoxic activity of a T cell to a target cell. In a particular embodiment, said re-direction is independent of MHC-mediated peptide antigen presentation by the target cell and and/or specificity of the T cell.

Particularly, a T cell according to any of the embodiments of the invention is a cytotoxic T cell. In some embodiments the T cell is a CD4+ or a CD8+ T cell, particularly a CD8+ T cell.

(i) Activating T Cell Antigen Binding Moiety

In some embodiments, an antibody comprised in the therapeutic agent, particularly a bispecific antibody, comprises at least one antigen binding moiety, particularly a Fab molecule, which specifically binds to an activating T cell antigen (also referred to herein as an "activating T cell antigen binding moiety, or activating T cell antigen binding Fab molecule"). In a particular embodiment, the antibody comprises not more than one antigen binding moiety capable of specific binding to an activating T cell antigen. In one embodiment, the antibody provides monovalent binding to the activating T cell antigen.

In particular embodiments, the antigen binding moiety which specifically binds an activating T cell antigen is a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) which specifically binds a target cell antigen is preferably a conventional Fab molecule. In embodiments where there is more than one antigen binding moiety, particularly Fab molecule, which specifically binds to a target cell antigen comprised in the antibody, the antigen binding moiety which specifically binds to an activating T cell antigen preferably is a crossover Fab molecule and the antigen binding moieties which specifically bind to a target cell antigen are conventional Fab molecules.

In alternative embodiments, the antigen binding moiety which specifically binds an activating T cell antigen is a conventional Fab molecule. In such embodiments, the antigen binding moiety(ies) which specifically binds a target cell antigen is a crossover Fab molecule as described herein, i.e. a Fab molecule wherein the variable domains VH and VL or the constant domains CH1 and CL of the Fab heavy and light chains are exchanged/replaced by each other.

In one embodiment, the activating T cell antigen is selected from the group consisting of CD3, CD28, CD137 (also known as 4-1BB), CD40, CD226, OX40, GITR, CD27, HVEM, and CD127.

In a particular embodiment, the activating T cell antigen is CD3, particularly human CD3 (SEQ ID NO: 115) or cynomolgus CD3 (SEQ ID NO: 116), most particularly human CD3. In a particular embodiment the activating T cell antigen binding moiety is cross-reactive for (i.e. specifically binds to) human and cynomolgus CD3. In some embodiments, the activating T cell antigen is the epsilon subunit of CD3 (CD3 epsilon).

In some embodiments, the activating T cell antigen binding moiety specifically binds to CD3, particularly CD3 epsilon, and comprises at least one heavy chain complementarity determining region (CDR) selected from the group consisting of SEQ ID NO: 32, SEQ ID NO: 33 and SEQ ID NO: 34 and at least one light chain CDR selected from the group of SEQ ID NO: 35, SEQ ID NO: 36, SEQ ID NO: 37.

In one embodiment the CD3 binding antigen binding moiety, particularly Fab molecule, comprises a heavy chain variable region comprising the heavy chain CDR1 of SEQ ID NO: 32, the heavy chain CDR2 of SEQ ID NO: 33, the heavy chain CDR3 of SEQ ID NO: 34, and a light chain variable region comprising the light chain CDR1 of SEQ ID NO: 35, the light chain CDR2 of SEQ ID NO: 36, and the light chain CDR3 of SEQ ID NO: 37.

In one embodiment the CD3 binding antigen binding moiety, particularly Fab molecule, comprises a heavy chain variable region sequence that is at least about 95%, 96%, 97%, 98%, 99% or 100% identical to SEQ ID NO: 38 and a light chain variable region sequence that is at least about 95%, 96%, 97%, 98%, 99% or 100% identical to SEQ ID NO: 39.

In one embodiment the CD3 binding antigen binding moiety, particularly Fab molecule, comprises a heavy chain variable region comprising the amino acid sequence of SEQ ID NO: 38 and a light chain variable region comprising the amino acid sequence of SEQ ID NO: 39.

In one embodiment the CD3 binding antigen binding moiety, particularly Fab molecule, comprises the heavy chain variable region sequence of SEQ ID NO: 38 and the light chain variable region sequence of SEQ ID NO: 39.

In some embodiments, the activating T cell antigen binding moiety specifically binds to CD3, particularly CD3 epsilon, and comprises at least one heavy chain HVR selected from the group consisting of SEQ ID NO: 120, SEQ ID NO: 121 and SEQ ID NO: 122 and at least one light chain HVR selected from the group of SEQ ID NO: 123, SEQ ID NO: 124, SEQ ID NO: 125.

In one embodiment the CD3 binding antigen binding moiety, particularly Fab molecule, comprises a heavy chain variable region comprising the heavy chain HVR 1 (H1-HVR) of SEQ ID NO: 120, the H2-HVR of SEQ ID NO: 121, and the H3-HVR of SEQ ID NO: 122; and a light chain variable region comprising the light chain HVR 1 (L1-HVR) of SEQ ID NO: 123, the L2-HVR of SEQ ID NO: 124 and the L3-HVR of SEQ ID NO: 125.

In one embodiment the CD3 binding antigen binding moiety, particularly Fab molecule, comprises a heavy chain variable region sequence that is at least about 95%, 96%, 97%, 98%, 99% or 100% identical to SEQ ID NO: 126 and a light chain variable region sequence that is at least about 95%, 96%, 97%, 98%, 99% or 100% identical to SEQ ID NO: 127.

In one embodiment the CD3 binding antigen binding moiety, particularly Fab molecule, comprises a heavy chain variable region comprising the amino acid sequence of SEQ ID NO: 126 and a light chain variable region comprising the amino acid sequence of SEQ ID NO: 127.

In one embodiment the CD3 binding antigen binding moiety, particularly Fab molecule, comprises the heavy chain variable region sequence of SEQ ID NO: 126 and the light chain variable region sequence of SEQ ID NO: 127.

(ii) Target Cell Antigen Binding Moiety

In some embodiments, an antibody comprised in the therapeutic agent, particularly a bispecific antibody, comprises at least one antigen binding moiety, particularly a Fab molecule, which specifically binds to a target cell antigen. In certain embodiments, the antibody comprises two antigen binding moieties, particularly Fab molecules, which specifically bind to a target cell antigen. In a particular such embodiment, each of these antigen binding moieties specifically binds to the same antigenic determinant. In an even more particular embodiment, all of these antigen binding moieties are identical, i.e. they comprise the same amino acid sequences including the same amino acid substitutions in the CH1 and CL domain as described herein (if any). In one embodiment, the antibody comprises an immunoglobulin molecule which specifically binds to a target cell antigen. In one embodiment the antibody comprises not more than two antigen binding moieties, particularly Fab molecules, which specifically bind to a target cell antigen.

In particular embodiments, the antigen binding moiety(ies) which specifically bind to a target cell antigen is/are a conventional Fab molecule. In such embodiments, the antigen binding moiety(ies) which specifically binds an activating T cell antigen is a crossover Fab molecule as described herein, i.e. a Fab molecule wherein the variable domains VH and VL or the constant domains CH1 and CL of the Fab heavy and light chains are exchanged/replaced by each other.

In alternative embodiments, the antigen binding moiety(ies) which specifically bind to a target cell antigen is/are a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) which specifically binds an activating T cell antigen is a conventional Fab molecule.

The target cell antigen binding moiety is able to direct the antibody to a target site, for example to a specific type of tumor cell that expresses the target cell antigen.

In one embodiment, the target cell antigen is CEA, particularly human CEA.

In one embodiment, the antigen binding moiety, particularly Fab molecule, which specifically binds to CEA comprises a heavy chain variable region comprising the heavy chain complementarity determining region (CDR) 1 of SEQ ID NO: 14, the heavy chain CDR 2 of SEQ ID NO: 15, and the heavy chain CDR 3 of SEQ ID NO: 16, and a light chain variable region comprising the light chain CDR 1 of SEQ ID NO: 17, the light chain CDR 2 of SEQ ID NO: 18 and the light chain CDR 3 of SEQ ID NO: 19. In a further embodiment, the antigen binding moiety, particularly Fab molecule, which specifically binds to CEA comprises a heavy chain variable region that is at least 95%, 96%, 97%, 98%, or 99% identical to the sequence of SEQ ID NO: 20, and a light chain variable region that is at least 95%, 96%, 97%, 98%, or 99% identical to the sequence of SEQ ID NO: 21. In still a further embodiment, the antigen binding moiety, particularly Fab molecule, which specifically binds to CEA comprises the heavy chain variable region sequence of SEQ ID NO: 20, and the light chain variable region sequence of SEQ ID NO: 21.

In one embodiment, the antigen binding moiety, particularly Fab molecule, which specifically binds to CEA comprises a heavy chain variable region comprising the heavy chain complementarity determining region (CDR) 1 of SEQ ID NO: 136, the heavy chain CDR 2 of SEQ ID NO: 137, and the heavy chain CDR 3 of SEQ ID NO: 138, and a light chain variable region comprising the light chain CDR 1 of SEQ ID NO: 139, the light chain CDR 2 of SEQ ID NO: 140 and the light chain CDR 3 of SEQ ID NO: 141. In a further embodiment, the antigen binding moiety, particularly Fab molecule, which specifically binds to CEA comprises a heavy chain variable region that is at least 95%, 96%, 97%, 98%, or 99% identical to the sequence of SEQ ID NO: 142, and a light chain variable region that is at least 95%, 96%, 97%, 98%, or 99% identical to the sequence of SEQ ID NO: 143. In still a further embodiment, the antigen binding moiety, particularly Fab molecule, which specifically binds to CEA comprises the heavy chain variable region sequence of SEQ ID NO: 142, and the light chain variable region sequence of SEQ ID NO: 143.

In one embodiment, the target cell antigen is a B-cell antigen, particularly a malignant B-cell antigen. In one embodiment, the target cell antigen is a cell surface antigen.

In one embodiment the target cell antigen is selected from the group consisting of CD20, CD19, CD22, ROR-1, CD37 and CD5.

In one embodiment, the target cell antigen is CD20, particularly human CD20.

In one embodiment, the antigen binding moiety, particularly Fab molecule, which specifically binds to CD20 comprises a heavy chain variable region comprising the heavy chain complementarity determining region (CDR) 1 of SEQ ID NO: 4, the heavy chain CDR 2 of SEQ ID NO: 5, and the heavy chain CDR 3 of SEQ ID NO: 6, and a light chain variable region comprising the light chain CDR 1 of SEQ ID NO: 7, the light chain CDR 2 of SEQ ID NO: 8 and the light chain CDR 3 of SEQ ID NO: 9. In a further embodiment, the antigen binding moiety, particularly Fab molecule, which specifically binds to CD20 comprises a heavy chain variable region that is at least 95%, 96%, 97%, 98%, or 99% identical to the sequence of SEQ ID NO: 10, and a light chain variable region that is at least 95%, 96%, 97%, 98%, or 99% identical to the sequence of SEQ ID NO: 11. In still a further embodiment, the antigen binding moiety, particularly Fab molecule, which specifically binds to CD20 comprises the heavy chain variable region sequence of SEQ ID NO: 10, and the light chain variable region sequence of SEQ ID NO: 11.

In one embodiment, the antigen binding moiety, particularly Fab molecule, which specifically binds to CD20 comprises a heavy chain variable region comprising the heavy chain HVR 1 (H1-HVR) of SEQ ID NO: 128, the H2-HVR of SEQ ID NO: 129, and the H3-HVR of SEQ ID NO: 130; and a light chain variable region comprising the light chain HVR 1 (L1-HVR) of SEQ ID NO: 131, the L2-HVR of SEQ ID NO: 132 and the L3-HVR of SEQ ID NO: 133. In a further embodiment, the antigen binding moiety, particularly Fab molecule, which specifically binds to CD20 comprises a heavy chain variable region that is at least 95%, 96%, 97%, 98%, or 99% identical to the sequence of SEQ ID NO: 134, and a light chain variable region that is at least 95%, 96%, 97%, 98%, or 99% identical to the sequence of SEQ ID NO: 135. In still a further embodiment, the antigen binding moiety, particularly Fab molecule, which specifically binds to CD20 comprises the heavy chain variable region sequence of SEQ ID NO: 134, and the light chain variable region sequence of SEQ ID NO: 135.

In one embodiment, the target cell antigen is CD19, particularly human CD19.

In one embodiment, the antigen binding moiety, particularly Fab molecule, which specifically binds to CD19 comprises a heavy chain variable region comprising the heavy chain complementarity determining region (CDR) 1 of SEQ ID NO: 48, the heavy chain CDR 2 of SEQ ID NO: 49, and the heavy chain CDR 3 of SEQ ID NO: 50, and a light chain variable region comprising the light chain CDR 1 of SEQ ID NO: 51, the light chain CDR 2 of SEQ ID NO: 52 and the light chain CDR 3 of SEQ ID NO: 53. In a further embodiment, the antigen binding moiety, particularly Fab molecule, which specifically binds to CD19 comprises a heavy chain variable region that is at least 95%, 96%, 97%, 98%, or 99% identical to the sequence of SEQ ID NO: 54, and a light chain variable region that is at least 95%, 96%, 97%, 98%, or 99% identical to the sequence of SEQ ID NO: 55. In still a further embodiment, the antigen binding moiety, particularly Fab molecule, which specifically binds to CD19 comprises the heavy chain variable region sequence of SEQ ID NO: 54, and the light chain variable region sequence of SEQ ID NO: 55.

In another embodiment, the antigen binding moiety, particularly Fab molecule, which specifically binds to CD19 comprises a heavy chain variable region comprising the heavy chain complementarity determining region (CDR) 1 of SEQ ID NO: 59, the heavy chain CDR 2 of SEQ ID NO: 60, and the heavy chain CDR 3 of SEQ ID NO: 61, and a light chain variable region comprising the light chain CDR 1 of SEQ ID NO: 62, the light chain CDR 2 of SEQ ID NO: 63 and the light chain CDR 3 of SEQ ID NO: 64. In a further embodiment, the antigen binding moiety, particularly Fab molecule, which specifically binds to CD19 comprises a heavy chain variable region that is at least 95%, 96%, 97%, 98%, or 99% identical to the sequence of SEQ ID NO: 65, and a light chain variable region that is at least 95%, 96%, 97%, 98%, or 99% identical to the sequence of SEQ ID NO: 66. In still a further embodiment, the antigen binding moiety, particularly Fab molecule, which specifically binds to CD19 comprises the heavy chain variable region sequence of SEQ ID NO: 65, and the light chain variable region sequence of SEQ ID NO: 66.

In another embodiment, the antigen binding moiety, particularly Fab molecule, which specifically binds to CD19 comprises
  (i) a heavy chain variable region comprising the heavy chain complementarity determining region (CDR) 1 of SEQ ID NO: 67, the heavy chain CDR 2 of SEQ ID NO: 68, and the heavy chain CDR 3 of SEQ ID NO: 69, and a light chain variable region comprising the light chain CDR 1 of SEQ ID NO: 70, the light chain CDR 2 of SEQ ID NO: 71 and the light chain CDR 3 of SEQ ID NO: 72;
  (ii) a heavy chain variable region comprising the heavy chain complementarity determining region (CDR) 1 of SEQ ID NO: 75, the heavy chain CDR 2 of SEQ ID NO: 76, and the heavy chain CDR 3 of SEQ ID NO: 77, and a light chain variable region comprising the light chain CDR 1 of SEQ ID NO: 78, the light chain CDR 2 of SEQ ID NO: 79 and the light chain CDR 3 of SEQ ID NO: 80;
  (iii) a heavy chain variable region comprising the heavy chain complementarity determining region (CDR) 1 of SEQ ID NO: 83, the heavy chain CDR 2 of SEQ ID NO: 84, and the heavy chain CDR 3 of SEQ ID NO: 85, and a light chain variable region comprising the light chain CDR 1 of SEQ ID NO: 86, the light chain CDR 2 of SEQ ID NO: 87 and the light chain CDR 3 of SEQ ID NO: 88;
  (iv) a heavy chain variable region comprising the heavy chain complementarity determining region (CDR) 1 of SEQ ID NO: 91, the heavy chain CDR 2 of SEQ ID NO: 92, and the heavy chain CDR 3 of SEQ ID NO: 93, and a light chain variable region comprising the light chain CDR 1 of SEQ ID NO: 94, the light chain CDR 2 of SEQ ID NO: 95 and the light chain CDR 3 of SEQ ID NO: 96;
  (v) a heavy chain variable region comprising the heavy chain complementarity determining region (CDR) 1 of SEQ ID NO: 99, the heavy chain CDR 2 of SEQ ID NO: 100, and the heavy chain CDR 3 of SEQ ID NO: 101, and a light chain variable region comprising the light chain CDR 1 of SEQ ID NO: 102, the light chain CDR 2 of SEQ ID NO: 103 and the light chain CDR 3 of SEQ ID NO: 104; or
  (vi) a heavy chain variable region comprising the heavy chain complementarity determining region (CDR) 1 of SEQ ID NO: 107, the heavy chain CDR 2 of SEQ ID NO: 108, and the heavy chain CDR 3 of SEQ ID NO: 109, and a light chain variable region comprising the light chain CDR 1 of SEQ ID NO: 110, the light chain CDR 2 of SEQ ID NO: 111 and the light chain CDR 3 of SEQ ID NO: 112.

In a further embodiment, the antigen binding moiety, particularly Fab molecule, which specifically binds to CD19 comprises
  (i) a heavy chain variable region that is at least 95%, 96%, 97%, 98%, or 99% identical to the sequence of SEQ ID NO: 73, and a light chain variable region that is at least 95%, 96%, 97%, 98%, or 99% identical to the sequence of SEQ ID NO: 74;
  (ii) a heavy chain variable region that is at least 95%, 96%, 97%, 98%, or 99% identical to the sequence of SEQ ID NO: 81, and a light chain variable region that is at least 95%, 96%, 97%, 98%, or 99% identical to the sequence of SEQ ID NO: 82;
  (iii) a heavy chain variable region that is at least 95%, 96%, 97%, 98%, or 99% identical to the sequence of SEQ ID NO: 89, and a light chain variable region that is at least 95%, 96%, 97%, 98%, or 99% identical to the sequence of SEQ ID NO: 90;
  (iv) a heavy chain variable region that is at least 95%, 96%, 97%, 98%, or 99% identical to the sequence of SEQ ID NO: 97, and a light chain variable region that is at least 95%, 96%, 97%, 98%, or 99% identical to the sequence of SEQ ID NO: 98;
  (v) a heavy chain variable region that is at least 95%, 96%, 97%, 98%, or 99% identical to the sequence of SEQ ID NO: 105, and a light chain variable region that is at least 95%, 96%, 97%, 98%, or 99% identical to the sequence of SEQ ID NO: 106; or
  (vi) a heavy chain variable region that is at least 95%, 96%, 97%, 98%, or 99% identical to the sequence of SEQ ID NO: 113, and a light chain variable region that is at least 95%, 96%, 97%, 98%, or 99% identical to the sequence of SEQ ID NO: 114.

In still a further embodiment, the antigen binding moiety, particularly Fab molecule, which specifically binds to CD19 comprises
  (i) the heavy chain variable region sequence of SEQ ID NO: 73, and the light chain variable region sequence of SEQ ID NO: 74;
  (ii) the heavy chain variable region sequence of SEQ ID NO: 81, and the light chain variable region sequence of SEQ ID NO: 82;
  (iii) the heavy chain variable region sequence of SEQ ID NO: 89, and the light chain variable region sequence of SEQ ID NO: 90;
  (iv) the heavy chain variable region sequence of SEQ ID NO: 97, and the light chain variable region sequence of SEQ ID NO: 98;
  (v) the heavy chain variable region sequence of SEQ ID NO: 105, and the light chain variable region sequence of SEQ ID NO: 106; or
  (vi) the heavy chain variable region sequence of SEQ ID NO: 113, and the light chain variable region sequence of SEQ ID NO: 114.

Charge Modifications

An antibody, particularly a multispecific antibody, comprised in the therapeutic agent may comprise amino acid substitutions in Fab molecules comprised therein which are particularly efficient in reducing mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody does not comprise both modifications mentioned under i) and ii). The constant domains CL and CH1 of the second Fab molecule are not replaced by each other (i.e. remain unexchanged).

In one embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In particular embodiments, the constant domain CL of the first Fab molecule under a) is of kappa isotype.

Alternatively, the amino acid substitutions according to the above embodiments may be made in the constant domain CL and the constant domain CH1 of the second Fab molecule under b) instead of in the constant domain CL and the constant domain CH1 of the first Fab molecule under a). In particular such embodiments, the constant domain CL of the second Fab molecule under b) is of kappa isotype.

The antibody may further comprise a third Fab molecule which specifically binds to the first antigen. In particular embodiments, said third Fab molecule is identical to the first Fab molecule under a). In these embodiments, the amino acid substitutions according to the above embodiments will be made in the constant domain CL and the constant domain CH1 of each of the first Fab molecule and the third Fab molecule. Alternatively, the amino acid substitutions according to the above embodiments may be made in the constant domain CL and the constant domain CH1 of the second Fab molecule under b), but not in the constant domain CL and the constant domain CH1 of the first Fab molecule and the third Fab molecule.

In particular embodiments, the antibody further comprises an Fc domain composed of a first and a second subunit capable of stable association.

Treatment Regimen

According to the invention, the Type II anti-CD20 antibody and the therapeutic agent may be administered in various ways (e.g. with regard to the route of administration, dose and/or timing), as long as the Type II anti-CD20 antibody is administered prior to the therapeutic agent and that the administration of the Type II anti-CD20 antibody has effectively induced a reduction of the number of B cells in the treated subject by the time the therapeutic agent is administered. Without wishing to be bound by theory, the reduction of the number of B cells in the subject prior to administration of the therapeutic agent will reduce or prevent the formation of anti-drug antibodies (ADAs) to the therapeutic agent and thus reduce or prevent a loss of efficacy of the therapeutic agent and/or adverse events in the subject associated with ADAs, and/or will reduce or prevent cytokine release associated with administration of the therapeutic agent and thus reduce or prevent adverse events (such as IRRs) in the subject associated with the administration of the therapeutic agent.

In one embodiment, the treatment regimen effectively reduces the formation of anti-drug antibodies (ADAs) in the subject in response to the administration of the therapeutic agent as compared to a corresponding treatment regimen without the administration of the Type II anti-CD20 antibody. In one embodiment, the formation of ADAs is reduced at least 2-fold, at least 3-fold, at least 4-fold, at least 5-fold, at least 10-fold, at least 20-fold, at least 50-fold, or at least 100-fold as compared to a corresponding treatment regimen without the administration of the Type II anti-CD20 antibody. In one embodiment, the formation of ADAs is essentially prevented. In one embodiment, the reduction or prevention of the formation of ADAs is 1, 2, 3, 4, 5, 6, 7, 8, 9, 10, 11, 12, 13, 14, 15, 16, 17, 18, 19, 20 or 21 days, or 1 month, 2 months, 3 months, 4 months, 5 months, 6 months, 12 months, or more, after administration of the therapeutic agent. In one embodiment, the reduction or prevention of ADA is about 2 months after administration of the therapeutic agent.

In one embodiment, the ADA titer in the subject after administration of the therapeutic agent does not exceed the ADA titer in the subject prior to administration of the therapeutic agent. In one embodiment, the ADA titer in the subject after administration of the therapeutic agent does not exceed the ADA titer in the subject prior to administration of the therapeutic agent by more than 1.1-fold, more than 1.2-fold, more than 1.5-fold, more than 2-fold, more than 3-fold, more than 4-fold, more than 5-fold, or more than 10-fold. In one embodiment, the ADA titer in the subject after administration of the therapeutic agent is increased less than 1.1-fold, less than 1.2-fold, less than 1.5-fold, less than 2-fold, less than 3-fold, less than 4-fold, less than 5-fold, or less than 10-fold, as compared to the ADA titer in the subject prior to administration of the therapeutic agent. In one embodiment, the ADA titer in the subject after administration of the therapeutic agent is the ADA titer at 1, 2, 3, 4, 5, 6, 7, 8, 9, 10, 11, 12, 13, 14, 15, 16, 17, 18, 19, 20 or 21 days, or 1 month, 2 months, 3 months, 4 months, 5 months, 6 months, 12 months, or more, after administration of the therapeutic agent. In one embodiment, the ADA titer in the subject after administration of the therapeutic agent is the ADA titer at about 2 months after administration of the therapeutic agent.

In one embodiment, essentially no ADAs are detectable in the subject after administration of the therapeutic agent, particularly 1, 2, 3, 4, 5, 6, 7, 8, 9, 10, 11, 12, 13, 14, 15, 16, 17, 18, 19, 20 or 21 days, or 1 month, 2 months, 3 months, 4 months, 5 months, 6 months, 12 months, or more, after administration of the therapeutic agent.

ADAs can be detected by methods known in the art (see e.g. Mire-Sluis et al., J Immunol Methods (2004) 289, 1-16; Nencini et al., Drug Dev Res (2014), 75 Suppl 1, S4-6; Schouwenburg et al., Nat Rev Rheumatol (2015) 9, 164-172). An exemplary method to detect ADAs is a sandwich ELISA, in which the therapeutic agent (e.g. an antibody) is coated to the assay plate, is exposed to serum of the treated subject, and the presence of ADAs is detected by labelled therapeutic agent. Another exemplary method to detect ADAs is an antigen binding test wherein immunoglobulins from the treated subject's serum are aggregated on a protein (e.g. Protein A Sepharose) and the presence of ADAs is detected by labelled therapeutic agent.

ADAs can be detected e.g. in a blood sample taken from the subject. In one embodiment, the ADA titer in the subject (as measured e.g. in a blood sample taken from the subject) does not exceed a titer (i.e. highest possible dilution of the sample giving an assay signal above the assay cut point) of about 10, of about 20, of about 30, of about 40, of about 50, of about 100, of about 200, or about 500, or of about 1000 after the administration of the therapeutic agent, particularly 1, 2, 3, 4, 5, 6, 7, 8, 9, 10, 11, 12, 13, 14, 15, 16, 17, 18, 19, 20 or 21 days, or 1 month, 2 months, 3 months, 4 months, 5 months, 6 months, 12 months, or more, after administration of the therapeutic agent.

In some embodiments, the treatment regimen increases efficacy of the therapeutic agent, as compared to a corresponding treatment regimen without the administration of the Type II anti-CD20 antibody. In some embodiments, the treatment regimen increases overall survival of the subject, as compared to a corresponding treatment regimen without the administration of the Type II anti-CD20 antibody. In some embodiments, the treatment regimen increases progression-free survival of the subject, as compared to a corresponding treatment regimen without the administration of the Type II anti-CD20 antibody.

In one embodiment, the treatment regimen effectively reduces cytokine release in the subject associated with the administration of the therapeutic agent as compared to a corresponding treatment regimen without the administration of the Type II anti-CD20 antibody. In one embodiment, cytokine release is reduced at least 2-fold, at least 3-fold, at least 4-fold, at least 5-fold, at least 10-fold, at least 20-fold, at least 50-fold, or at least 100-fold as compared to a corresponding treatment regimen without the administration of the Type II anti-CD20 antibody.

In one embodiment, cytokine release is essentially prevented. In one embodiment, the reduction or prevention of cytokine release is 1, 2, 3, 4, 5, 6, 7, 8, 9, 10, 11, 12, 13, 14, 15, 16, 17, 18, 19, 20, 21, 22, 23 or 24 hours after administration of the therapeutic agent. In one embodiment, the reduction or prevention of cytokine release is within the first 24 hours after administration of the therapeutic agent.

In one embodiment, the cytokine concentration in the subject (as measured e.g. in a blood sample taken from the subject) after administration of the therapeutic agent does not exceed the cytokine concentration in the subject prior to administration of the therapeutic agent. In one embodiment, the cytokine concentration in the subject after administration of the therapeutic agent does not exceed the cytokine concentration in the subject prior to administration of the therapeutic agent by more than 1.1-fold, more than 1.2-fold, more than 1.5-fold, more than 2-fold, more than 3-fold, more than 4-fold, more than 5-fold, more than 10-fold, more than 20-fold, more than 50-fold or more than 100-fold. In one embodiment, the cytokine concentration in the subject after administration of the therapeutic agent is increased less than 1.1-fold, less than 1.2-fold, less than 1.5-fold, less than 2-fold, less than 3-fold, less than 4-fold, less than 5-fold, less than 10-fold, less than 20-fold, less than 50-fold or less than 100-fold, as compared to the cytokine concentration in the subject prior to administration of the therapeutic agent. In one embodiment, the cytokine concentration in the subject after administration of the therapeutic agent is the cytokine concentration at 1, 2, 3, 4, 5, 6, 7, 8, 9, 10, 11, 12, 13, 14, 15, 16, 17, 18, 19, 20, 21, 22, 23 or 24 hours after administration of the therapeutic agent. In one embodiment, the cytokine concentration in the subject after administration of the therapeutic agent is the cytokine concentration within the first 24 hours after administration of the therapeutic agent.

In one embodiment, essentially no increase in the concentration of cytokines is detectable in the subject after administration of the therapeutic agent, particularly 1, 2, 3, 4, 5, 6, 7, 8, 9, 10, 11, 12, 13, 14, 15, 16, 17, 18, 19, 20, 21, 22, 23 or 24 hours after administration of the therapeutic agent.

Cytokines can be detected by methods known in the art, such as e.g. ELISA, FACS or Luminex® assay.

Cytokines can be detected e.g. in a blood sample taken from the subject. In one embodiment, the cytokine concentration is the blood of the subject.

In some embodiments, the cytokine is one or more cytokine(s) selected from the group consisting of tumor necrosis factor alpha (TNF-α), interferon gamma (IFN-γ), interleukin-6 (IL-6), interleukin-10 (IL-10), interleukin-2 (IL-2) and interleukin-8 (IL-8), particularly the group consisting of TNF-α, IFN-γ and IL-6. In some embodiments, the cytokine is TNF-α. In some embodiments, the cytokine is IFN-γ. In some embodiments, the cytokine is IL-6. In some embodiments, the cytokine is IL-10. In some embodiments, the cytokine is IL-2. In some embodiments, the cytokine is IL-8.

In some embodiments, the treatment regimen increases the safety of the therapeutic agent, as compared to a corresponding treatment regimen without the administration of the Type II anti-CD20 antibody. In some embodiments, the treatment regimen reduces adverse events in the subject, as compared to a corresponding treatment regimen without the administration of the Type II anti-CD20 antibody. In some embodiments, the treatment regimen increases the serum half-life of the therapeutic agent, as compared to a corresponding treatment regimen without the administration of the Type II anti-CD20 antibody. In some embodiments, the treatment regimen reduces toxicity of the therapeutic agent, as compared to a corresponding treatment regimen without the administration of the Type II anti-CD20 antibody.

According to the invention, the period of time between the administration of the Type II anti-CD20 antibody and the administration of the therapeutic agent is sufficient for reduction of the number of B-cells in the subject in response to the administration of the Type II anti-CD20 antibody.

In one embodiment, the period of time is 3 days to 21 days, 5 days to 20 days, 7 days to 21 days, 7 days to 14 days, 5 days to 15 days, 7 days to 15 days, 8 days to 15 days, 10 days to 20 days, 10 days to 15 days, 11 days to 14 days, or 12 days to 13 days. In one embodiment, the period of time is 7 days to 14 days. In a particular embodiment, the period of time is 10 days to 15 days. In one embodiment, the period of time is 8 days to 15 days. In one embodiment, the period of time is 5 days to 10 days. In a particular embodiment, the period of time is 7 days.

In one embodiment, the period of time is about about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

In one embodiment, the period of time is at least 3 days, at least 4 days, at least 5 days, at least 6 days, at least 7 days, at least 8 days, at least 9 days, at least 10 days, at least 11 days, at least 12 days, at least 13 days, at least 14 days, or at least 15 days. In a particular embodiment, the period of time is at least 5 days. In a further particular embodiment, the period of time is at least 7 days.

In one embodiment, the period of time is between the last administration of the Type II anti-CD20 antibody and the (first, if several) administration of the therapeutic agent. In one embodiment, no administration of the therapeutic agent is made during the period of time.

In a particular embodiment, the reduction of the number of B cells is in the blood of the subject. In one embodiment, the B cells are peripheral blood B cells. In one embodiment, the B cells are normal B cells. In one embodiment, the B cells are malignant and normal B cells. In one embodiment, the B cells are malignant B cells.

In some embodiments, the reduction of B cells is in a tissue of the subject. In one embodiment, the tissue is a tumor. In one embodiment, the tissue is a lymph node. In one embodiment, the tissue is spleen. In one embodiment, the tissue is the marginal zone of spleen. In one embodiment, the B cells are lymph node B cells. In one embodiment, the B cells are splenic B cells. In one embodiment, the B cells are splenic marginal zone B cells. In one embodiment, the B cells are CD20-positive B cells, i.e. B cells expressing CD20 on their surface.

In one embodiment, the reduction of the number of B cells is a reduction of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In one embodiment, the reduction of the number of B cells is a complete elimination of B cells. In a particular embodiment, the reduction of the number of B cells is a reduction of at least 90%, particularly at least 95%, of the number of B cells in the (peripheral) blood of the subject. In one embodiment, the reduction of the number of B cells is a reduction as compared to the number of B cells in the subject prior to the (first, if several) administration of the Type II anti-CD20 antibody to the subject.

The number of B cells in the subject may be determined by any method known in the art suitable for quantifying B cells in patient blood or tissue, such as flow cytometric, immunohistochemical or immunofluorescent methods, using antibodies against B cell markers such as CD20, CD19, and/or PAX5.

The number of B cells may also be determined indirectly, by quantification of protein or mRNA levels of B-cell markers in patient blood or tissues. Suitable methods known in the art for the determination of specific protein levels include immunoassay methods such as enzyme-linked immunosorbent assay (ELISA), or Western Blot, methods for determination of mRNA levels include for example quantitative RT-PCR or microaray technologies.

All the above mentioned methods and technologies are well known in the art and can be deduced from standard textbooks such as Lottspeich (Bioanalytik, Spektrum Akademisher Verlag, 1998) or Sambrook and Russell (Molecular Cloning: A Laboratory Manual, CSH Press, Cold Spring Harbor, N.Y., U.S.A., 2001).

In certain embodiments, the reduction of the number of B cells is determined by quantification of B cells in the blood of the subject (e.g. in a blood sample taken from the subject). In one such embodiment, B cells are quantified by flow cytometric analysis. Flow cytometric methods (FACS) are well known in the art for the quantification of cells in blood or tissue samples. In particular, they allow determining the number of cells expressing a specific antigen (e.g. CD20 and/or CD19) among a defined total number of cells in a blood or tissue sample (e.g. a blood sample, or (part of) a tissue biopsy). In one embodiment, B cells are quantified by flow cytometric analysis using an anti-CD19 antibody and/or an anti-CD20 antibody.

In other embodiments, the reduction of the number of B cells is determined by quantification of B cells in a tissue, e.g. a tumor, of said individual (e.g. in a tissue biopsy taken from the subject). In one such embodiment, B cells are quantified by immunohistochemical or immunofluorescent analysis. In one embodiment, B cells are quantified by immunohistochemical analysis using an anti-CD19 antibody, an anti-CD20 antibody and/or an anti-PAX5 antibody.

Methods of the present invention can be applied in the treatment of a variety of diseases, depending on the therapeutic agent(s) used.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a method of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. In some embodiments, the cancer is a solid tumor. In some embodiments, the cancer expresses the target of the therapeutic agent, e.g. an antibody. In one embodiment, the cancer expresses CEA. In another embodiment, the cancer expresses FAP.

In some embodiments, the disease to be treated is an inflammatory disorder. In some embodiments, the disease to be treated is an autoimmune disease (i.e. a non-malignant disease or disorder arising from and directed against an individual's own tissues). Examples of autoimmune diseases or disorders include, but are not limited to, inflammatory responses such as inflammatory skin diseases including psoriasis and dermatitis (e.g. atopic dermatitis); responses associated with inflammatory bowel disease (such as Crohn's disease and ulcerative colitis); dermatitis; allergic conditions such as eczema and asthma; rheumatoid arthritis; systemic lupus erythematosus (SLE) (including but not limited to lupus nephritis, cutaneous lupus); diabetes mellitus (e.g. type 1 diabetes mellitus or insulin dependent diabetes mellitus); multiple sclerosis and juvenile onset diabetes. In one embodiment, the disease is transplant rejection or graft-versus-host disease.

In some embodiments, the disease to be treated is an infectious disease, such as viral infection or a bacterial infection. In other embodiments, the disease to be treated is neurological disorder. In still further embodiments, the disease to be treated is a metabolic disorder.

In relation aspects of the invention concerned with the reduction of cytokine release associated with the administration of a therapeutic agent in a subject, the methods are particularly useful, in the treatment of B-cell proliferative disorders, particularly CD20-positive B-cell disorders, where (CD20-positive) B-cells are present in large quantities (i.e. an increased number of B-cells is present in the subject suffering from the disorder, as compared to a healthy subject).

Thus, in one embodiment, the disease is a B cell proliferative disorder, particularly a CD20-positive B-cell disorder.

In one embodiment, the disease is selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) or Hodgkin lymphoma (HL). In one embodiment, the disease is selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL) and marginal zone lymphoma (MZL).

In a particular embodiment, the disease is NHL, particularly relapsed/refractory (r/r) NHL. In one embodiment, the disease is DLBCL. In one embodiment, the disease is FL. In one embodiment, the disease is MCL. In one embodiment, the disease is MZL.

A skilled artisan readily recognizes that in many cases the therapeutic agent may not provide a cure but may only provide partial benefit. In some embodiments, a physiological change having some benefit is also considered therapeutically beneficial. Thus, in some embodiments, an amount of therapeutic agent that provides a physiological change is considered an "effective amount" or a "therapeutically effective amount".

The subject, patient, or individual in need of treatment is typically a mammal, more specifically a human. In certain embodiments, the subject is a human.

In some embodiments, in particular in relation aspects of the invention concerned with the reduction of the formation of anti-drug antibodies (ADAs) against a therapeutic agent in a subject, the subject suffers from a locally advanced and/or metastatic solid tumor and has progressed on or is intolerant to the standard of care therapy. In one embodiment, the tumor is a CEA-expressing tumor. In another embodiment, the tumor is a FAP-expressing tumor. Expression of CEA and/or FAP in a tumor may be determined for example by immunohistochemical analysis of a tumor biopsy taken from the subject.

In other embodiments, in particular in relation aspects of the invention concerned with the reduction of cytokine release associated with the administration of a therapeutic agent in a subject, the subject suffers from a B-cell proliferative disorder, particularly from Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) or Hodgkin lymphoma (HL). In one embodiment, the subject suffers from relapsed/refractory (r/r) NHL.

Administration of the Type II Anti-CD20 Antibody

According to the invention, the period of time between the administration of the Type II anti-CD20 antibody and the administration of the therapeutic agent and the dose of the Type II anti-CD20 antibody are chosen such as to effectively reduce the number of B cells in the subject prior to administration of the therapeutic agent.

The Type II anti-CD20 antibody can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In one embodiment, the Type II anti-CD20 antibody is administered parenterally, particularly intravenously, e.g. by intravenous infusion.

The Type II anti-CD20 antibody would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one embodiment, the administration of the Type II anti-CD20 antibody is a single administration. In another embodiment, the administration of the Type II anti-CD20 antibody is two or more separate administrations. In one embodiment, the two or more separate administrations are on two or more consecutive days. In one embodiment, no further administration of the Type II anti-CD20 antibody is made to the subject before or after the administration of the therapeutic agent. In one embodiment, the administration of the Type II anti-CD20 antibody is a single administration, or two administrations on two consecutive days, and no further administration of the Type II anti-CD20 antibody is made. In one embodiment, the period of time is between the last administration of the Type II anti-CD20 antibody and the (first, if several) administration of the therapeutic agent.

In one embodiment, the administration of the Type II anti-CD20 antibody is a dose of Type II anti-CD20 antibody effective for the reduction of B cells in the subject. In one embodiment, the dose of Type II anti-CD20 antibody is effective in reducing the number of B cells in the subject within the period of time between the administration of the Type II anti-CD20 antibody and the administration of the therapeutic agent. In one embodiment, the period of time between the administration of the Type II anti-CD20 antibody and the administration of the therapeutic agent and the administered dose of Type II anti-CD20 antibody is sufficient for reduction of the number of B-cells in the subject in response to the administration of the Type II anti-CD20 antibody.

In one embodiment, the administration of the Type II anti-CD20 antibody is a dose of about 2 g Type II anti-CD20 antibody. The dose of about 2 g Type II anti-CD20 antibody may be administered to the subject as a single administration of about 2 g, or as several administrations, e.g. two administrations of about 1 g each or three administrations of e. g. 100 mg, 900 mg and 1000 mg. In one embodiment, one administration of about 2 g Type II anti-CD20 antibody is made to the subject. In another embodiment, two administrations of about 1 g Type II anti-CD20 antibody each are made to the subject on two consecutive days. In still another embodiment, three administrations ((i) to (iii)) of (i) about 100 mg Type II anti-CD20 antibody, (ii) about 900 mg Type II anti-CD20 antibody, and (iii) about 1000 mg Type II anti-CD20 antibody are made to the subject on three consecutive days. In one embodiment, two administration of about 1 g Type II anti-CD20 antibody are made to the subject on two consecutive days, 10 days to 15 days before the administration of the therapeutic agent. In one embodiment, one administration of about 2 g Type II anti-CD20 antibody is made to the subject 10 days to 15 days before the administration of the therapeutic agent. In one embodiment, no further administration of the Type II anti-CD20 antibody is made to the subject. In one embodiment, no administration of the therapeutic agent is made to the subject prior to the administration of the Type II anti-CD20 antibody (at least not within the same course of treatment).

In one embodiment, the administration of the Type II anti-CD20 antibody is a dose of about 1000 mg Type II anti-CD20 antibody. The dose of about 1000 mg Type II anti-CD20 antibody may be administered to the subject as a single administration of about 1000 mg, or as several administrations, e.g. two administrations of about 500 mg each. In a particular embodiment, one administration of about 1000 mg Type II anti-CD20 antibody is made to the subject. In another embodiment, two administrations of about 500 mg Type II anti-CD20 antibody each are made to the subject on two consecutive days. In one embodiment, one administration of about 1000 mg Type II anti-CD20 antibody is made to the subject, 7 days before the administration of the therapeutic agent. In one embodiment, no further administration of the Type II anti-CD20 antibody is made to the subject. In one embodiment, no administration of the therapeutic agent is made to the subject prior to the administration of the Type II anti-CD20 antibody (at least not within the same course of treatment).

In one embodiment, the treatment regimen further comprises administration of premedication prior to the administration of the Type II anti-CD20 antibody. In embodiment the premedication comprises a corticosteroid (such as e.g. prednisolone, dexamethasone, or methylprednisolone), paracetamol/acetaminophen, and/or an anti-histamine (such as e.g. diphenhydramine). In one embodiment, the premedication is administered at least 60 minutes prior to the administration of the Type II anti-CD20 antibody.

In one embodiment, the treatment regimen does not comprise administration of an immunosuppressive agent other than the Type II anti-CD20 antibody (and optionally the above-described premedication) prior to the administration of the therapeutic agent. In one embodiment, the treatment regimen does not comprise administration of an agent selected from the group of methotrexate, azathioprine, 6-mercaptopurine, leflunomide, cyclosporine, tacrolimus/FK506, mycophenolate mofetil and mycophenolate sodium prior to the administration of the therapeutic agent. In one embodiment, the treatment regimen does not comprise administration of a further antibody in addition to the Type II anti-CD20 antibody prior to the administration of the therapeutic agent.

Administration of the Therapeutic Agent

The therapeutic agent can be administered by any suitable means, including parenteral, intrapulmonary, and intranasal, and, if desired for local treatment, intralesional administration. The methods of the present invention are particularly useful, however, in relation to therapeutic agents administered by parenteral, particularly intravenous, infusion. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In one embodiment, the therapeutic agent is administered parenterally, particularly intravenously. In a particular embodiment, the therapeutic agent is administered by intravenous infusion.

The therapeutic agent would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutic agent need not be, but is optionally formulated with one or more agents currently used to prevent or treat the disorder in question. The effective amount of such other agents depends on the amount of therapeutic agent present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the therapeutic agent (when used alone or in combination with one or more other additional therapeutic agents) will depend on the type of disease to be treated, the type of therapeutic agent, the severity and course of the disease, whether the therapeutic agent is administered for preventive or therapeutic purposes, previous therapy, the patient's clinical history and response to the therapeutic agent, and the discretion of the attending physician. The therapeutic agent is suitably administered to the patient at one time or over a series of treatments. Depending on the type and severity of the disease, about 1 µg/kg to 15 mg/kg (e.g. 0.1 mg/kg-10 mg/kg) of therapeutic agent can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the therapeutic agent would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the subject. Such doses may be administered intermittently, e.g. every week, every two weeks, or every three weeks (e.g. such that the subject receives from about two to about twenty, or e.g. about six doses of the therapeutic agent). An initial higher loading dose, followed by one or more lower doses, or an initial lower dose, followed by one or more higher doses may be administered. An exemplary dosing regimen comprises administering an initial dose of about 10 mg, followed by a bi-weekly dose of about 20 mg of the therapeutic agent. However, other dosage regimens may be useful. The progress of this therapy is easily monitored by conventional techniques and assays.

In one embodiment, the administration of the therapeutic agent is a single administration. In certain embodiments, the administration of the therapeutic agent is two or more administrations. In one such embodiment, the therapeutic agent is administered every week, every two weeks, or every three weeks, particularly every two weeks. In one embodiment, the therapeutic agent is administered in a therapeutically effective amount. In one embodiment the therapeutic agent is administered at a dose of 10 mg-20 mg. In one embodiment the administration of the therapeutic agent comprises an initial administration of a dose of about 10 mg therapeutic agent, and one or more subsequent administrations of a dose of about 20 mg therapeutic agent. In one embodiment the therapeutic agent is administered at a dose of about 50 µg/kg, about 100 µg/kg, about 200 µg/kg, about 300 µg/kg, about 400 µg/kg, about 500 µg/kg, about 600 µg/kg, about 700 µg/kg, about 800 µg/kg, about 900 µg/kg or about 1000 µg/kg. In one embodiment, the therapeutic agent is administered at a dose which is higher than the dose of the therapeutic agent in a corresponding treatment regimen without the administration of the Type II anti-CD20 antibody. In one embodiment the administration of the therapeutic agent comprises an initial administration of a first dose of the therapeutic agent, and one or more subsequent administrations of a second dose the therapeutic agent, wherein the second dose is higher than the first dose. In one embodiment, the administration of the therapeutic agent comprises an initial administration of a first dose of the therapeutic agent, and one or more subsequent administrations of a second dose the therapeutic agent, wherein the first dose is not lower than the second dose.

In one embodiment, the administration of the therapeutic agent in the treatment regimen according to the invention is the first administration of that therapeutic agent to the subject (at least within the same course of treatment). In one embodiment, no administration of the therapeutic agent is made to the subject prior to the administration of the Type II anti-CD20 antibody.

In the present invention, the therapeutic agent can be used either alone or in combination with other agents in a therapy. For instance, the therapeutic agent may be co-administered with at least one additional therapeutic agent. In certain embodiments, an additional therapeutic agent is an immunotherapeutic agent. In some embodiment, the additional therapeutic agent comprises an agent as described herein in relation to the therapeutic agent. The invention is particularly useful in relation to combinations of several therapeutic agents which may induce the formation of ADAs or cytokine release in a subject when used in a treatment regimen without the administration of the Type II anti-CD20 antibody. Such combinations may include various therapeutic agents as described herein, and may particularly include one or more immunotherapeutic agents, e.g. for the treatment of cancer (cancer immunotherapy).

Such combination therapies noted above encompass combined administration (where two or more therapeutic agents are included in the same or separate formulations), and separate administration, in which case, administration of the therapeutic agent can occur prior to, simultaneously, and/or following, administration of an additional therapeutic agent or agents. In one embodiment, administration of the therapeutic agent and administration of an additional therapeutic agent occur within about one month, or within about one, two or three weeks, or within about one, two, three, four, five, or six days, of each other.

Articles of Manufacture

In another aspect of the invention, an article of manufacture, e.g. a kit, is provided, containing materials useful for the treatment, prevention and/or diagnosis of a disease, or for the reduction of the formation of anti-drug antibodies (ADAs) and/or the reduction of cytokine release as described herein. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition, or holds a composition which is effective for reducing the formation of ADAs and/or cytokine release, and may have a sterile access port (for example the container may be an intravenous solution bag or a vial having a stopper pierceable by a hypodermic injection needle). At least one active agent in the composition is a Type II anti-CD20 antibody or a therapeutic agent as described herein. The label or package insert indicates that the composition is used for treating the condition of choice and/or to reduce the formation of ADAs and/or cytokine release. Moreover, the article of manufacture may comprise (a) a first container with a composition contained therein, wherein the composition comprises a Type II anti-CD20 antibody as described herein; and (b) a second container with a composition contained therein, wherein the composition comprises a therapeutic agent as described herein. The article of manufacture in this embodiment of the invention may further comprise a package insert indicating that the compositions can be used to treat a particular condition and/or to reduce the formation of ADAs and/or cytokine release. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EMBODIMENTS

In the following, some of the embodiments of the invention are listed.

1. A method of treating a disease in a subject, the method comprising a treatment regimen comprising
   (i) administration to the subject of a Type II anti-CD20 antibody,
   and consecutively after a period of time
   (ii) administration to the subject of a therapeutic agent,
   wherein the period of time between the administration of the Type II anti-CD20 antibody and the administration of the therapeutic agent is sufficient for reduction of the number of B-cells in the subject in response to the administration of the Type II anti-CD20 antibody.

2. The method of embodiment 1, wherein the treatment regimen effectively reduces the formation of anti-drug antibodies (ADAs) in the subject in response to the administration of the therapeutic agent as compared to a corresponding treatment regimen without the administration of the Type II anti-CD20 antibody.

3. A method for reducing the formation of anti-drug antibodies (ADAs) against a therapeutic agent in a subject, comprising administration of a Type II anti-CD20 antibody to the subject prior to administration of the therapeutic agent.

4. The method of embodiment 3, wherein the period of time between the administration of the Type II anti-CD20 antibody and administration of the therapeutic agent is sufficient for reduction of the number of B-cells in the subject in response to the administration of the Type II anti-CD20 antibody.

5. The method of any one of the preceding embodiments, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

6. The method of any one of the preceding embodiments, wherein the Type II anti-CD20 antibody comprises the heavy chain variable region sequence of SEQ ID NO: 10 and the light chain variable region sequence of SEQ ID NO: 11.

7. The method of any one of the preceding embodiments, wherein the Type II anti-CD20 antibody is an IgG antibody, particularly an $IgG_1$ antibody.

8. The method of any one of the preceding embodiments, wherein the Type II anti-CD20 antibody is engineered to have an increased proportion of non-fucosylated oligosaccharides in the Fc region as compared to a non-engineered antibody.

9. The method of any one of the preceding embodiments, wherein at least about 40% of the N-linked oligosaccharides in the Fc region of the Type II anti-CD20 antibody are non-fucosylated.

10. The method of any one of the preceding embodiments, wherein the Type II anti-CD20 antibody is obinutuzumab.

11. The method of any one of the preceding embodiments, wherein the therapeutic agent comprises a polypeptide.

12. The method of any one of the preceding embodiments, wherein the therapeutic agent comprises an antibody.

13. The method of embodiment 12, wherein the antibody comprised in the therapeutic agent specifically binds to carcinoembryonic antigen (CEA).

14. The method of embodiment 13, wherein the antibody comprised in the therapeutic agent comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19.

15. The method of embodiment 13 or 14, wherein the antibody comprised in the therapeutic agent comprises the heavy chain variable region sequence of SEQ ID NO: 20 and the light chain variable region sequence of SEQ ID NO: 21.

16. The method of embodiment 12, wherein the antibody comprised in the therapeutic agent specifically binds to CD3, particularly CD3ε.

17. The method of embodiment 16, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

18. The method of embodiment 16 or 17, wherein the antibody comprised in the therapeutic agent comprises the heavy chain variable region sequence of SEQ ID NO: 38 and the light chain variable region sequence of SEQ ID NO: 39.

19. The method of any one of embodiments 1 to 18, wherein the therapeutic agent comprises a cytokine.

20. The method of embodiment 19, wherein the cytokine is interleukin-2 (IL-2).

21. The method of embodiment 19 or 20, wherein the cytokine is a mutant human IL-2 polypeptide comprising the amino acid substitutions F42A, Y45A and L72G (numbering relative to the human IL-2 sequence SEQ ID NO: 12).

22. The method of any one of the preceding embodiments, wherein the therapeutic agent comprises an immunoconjugate.

23. The method of embodiment 22, wherein the immunoconjugate comprises an antibody as defined in any one of embodiments 13 to 15, and a cytokine as defined in embodiment 20 or 21.

24. The method of any one of the preceding embodiments, wherein the therapeutic agent comprises cergutuzumab amunaleukin (CEA-IL2v).

25. The method of any one of embodiments 1 to 18, wherein the therapeutic agent comprises a bispecific antibody comprising an antibody as defined in any one of embodiments 13 to 15 and an antibody as defined in any one of embodiments 16 to 18.

26. A Type II anti-CD20 antibody for use in a method of treating a disease in a subject, the method comprising a treatment regimen comprising
(i) administration to the subject of the Type II anti-CD20 antibody,
and consecutively after a period of time
(ii) administration to the subject of a therapeutic agent, wherein the period of time between the administration of the Type II anti-CD20 antibody and the administration of the therapeutic agent is sufficient for reduction of the number of B-cells in the subject in response to the administration of the Type II anti-CD20 antibody.

27. The Type II anti-CD20 antibody of embodiment 26, wherein the treatment regimen effectively reduces the formation of anti-drug antibodies (ADAs) in the subject in response to the administration of the therapeutic agent as compared to a corresponding treatment regimen without the administration of the Type II anti-CD20 antibody.

28. A Type II anti-CD20 antibody for use in a method for reducing the formation of anti-drug antibodies (ADAs) against a therapeutic agent in a subject, comprising administration of the Type II anti-CD20 antibody to the subject prior to administration of the therapeutic agent.

29. The Type II anti-CD20 antibody of embodiment 28, wherein the period of time between the administration of the Type II anti-CD20 antibody and administration of the therapeutic agent is sufficient for reduction of the number of B-cells in the subject in response to the administration of the Type II anti-CD20 antibody.

30. The Type II anti-CD20 antibody of any one of embodiments 26 to 29, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

31. The Type II anti-CD20 antibody of any one of embodiments 26 to 30, wherein the Type II anti-CD20 antibody comprises the heavy chain variable region sequence of SEQ ID NO: 10 and the light chain variable region sequence of SEQ ID NO: 11.

32. The Type II anti-CD20 antibody of any one of embodiments 26 to 31, wherein the Type II anti-CD20 antibody is an IgG antibody, particularly an IgG$_1$ antibody.

33. The Type II anti-CD20 antibody of any one of embodiments 26 to 32, wherein the Type II anti-CD20 antibody is engineered to have an increased proportion of non-fucosylated oligosaccharides in the Fc region as compared to a non-engineered antibody.

34. The Type II anti-CD20 antibody of any one of embodiments 26 to 33, wherein at least about 40% of the N-linked oligosaccharides in the Fc region of the anti-CD20 antibody are non-fucosylated.

35. The Type II anti-CD20 antibody of any one of embodiments 26 to 34, wherein the Type II anti-CD20 antibody is obinutuzumab.

36. The Type II anti-CD20 antibody of any one of embodiments 26 to 35, wherein the therapeutic agent comprises a polypeptide.

37. The Type II anti-CD20 antibody of any one of embodiments 26 to 36, wherein the therapeutic agent comprises an antibody.

38. The Type II anti-CD20 antibody of embodiment 37, wherein the antibody comprised in the therapeutic agent specifically binds to carcinoembryonic antigen (CEA).

39. The Type II anti-CD20 antibody of embodiment 38, wherein the antibody comprised in the therapeutic agent comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19.

40. The Type II anti-CD20 antibody of embodiment 38 or 39, wherein the antibody comprised in the therapeutic agent comprises the heavy chain variable region sequence of SEQ ID NO: 20 and the light chain variable region sequence of SEQ ID NO: 21.

41. The Type II anti-CD20 antibody of embodiment 37, wherein the antibody comprised in the therapeutic agent specifically binds to CD3, particularly CD3ε.

42. The Type II anti-CD20 antibody of embodiment 41, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

43. The Type II anti-CD20 antibody of embodiment 41 or 42, wherein the antibody comprised in the therapeutic agent comprises the heavy chain variable region sequence of SEQ ID NO: 38 and the light chain variable region sequence of SEQ ID NO: 39.

44. The Type II anti-CD20 antibody of any one of embodiments 26 to 43, wherein the therapeutic agent comprises a cytokine.

45. The Type II anti-CD20 antibody of embodiment 44, wherein the cytokine is interleukin-2 (IL-2).

46. The Type II anti-CD20 antibody of embodiment 44 or 45, wherein the cytokine is a mutant human IL-2 polypeptide comprising the amino acid substitutions F42A, Y45A and L72G (numbering relative to the human IL-2 sequence SEQ ID NO: 12).

47. The Type II anti-CD20 antibody of any one of embodiments 26 to 46, wherein the therapeutic agent comprises an immunoconjugate.

48. The Type II anti-CD20 antibody of embodiment 47, wherein the immunoconjugate comprises an antibody as defined in any one of embodiments 38 to 40, and a cytokine as defined in embodiment 45 or 46.

49. The Type II anti-CD20 antibody of any one of embodiments 26 to 48, wherein the therapeutic agent comprises cergutuzumab amunaleukin (CEA-IL2v).

50. The Type II anti-CD20 antibody of any one of embodiments 1 to 43, wherein the therapeutic agent comprises a bispecific antibody comprising an antibody as defined in any one of embodiments 38 to 40 and an antibody as defined in any one of embodiments 41 to 43.

51. Use of a Type II anti-CD20 antibody in the manufacture of a medicament for reduction of the formation of anti-drug antibodies (ADAs) against a therapeutic agent in a subject, wherein the medicament is to be used in a treatment regimen comprising (i) administration to the subject of the Type II anti-CD20 antibody, and consecutively after a period of time (ii) administration to the subject of a therapeutic agent, wherein the period of time between the administration of the Type II anti-CD20 antibody and the administration of the therapeutic agent is sufficient for reduction of the number of B-cells in the subject in response to the administration of the Type II anti-CD20 antibody.

52. Use of a therapeutic agent in the manufacture of a medicament for treatment of a disease in a subject, wherein the treatment comprises a treatment regimen comprising (i) administration to the subject of a Type II anti-CD20 antibody, and consecutively after a period of time (ii) administration to the subject of the therapeutic agent, wherein the period of time between the administration of the Type II anti-CD20 antibody and the administration of the therapeutic agent is sufficient for reduction of the number of B-cells in the subject in response to the administration of the Type II anti-CD20 antibody.

53. The use of embodiment 51 or 52, wherein the treatment regimen effectively reduces the formation of anti-drug antibodies (ADAs) against the therapeutic agent in the subject as compared to a corresponding treatment regimen without the administration of the Type II anti-CD20 antibody.

54. The use of any one of embodiments 51 to 53, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

55. The use of any one of embodiments 51 to 54, wherein the Type II anti-CD20 antibody comprises the heavy chain variable region sequence of SEQ ID NO: 10 and the light chain variable region sequence of SEQ ID NO: 11.

56. The use of any one of embodiments 51 to 55, wherein the Type II anti-CD20 antibody is an IgG antibody, particularly an IgG$_1$ antibody.

57. The use of any one of embodiments 51 to 56, wherein the Type II anti-CD20 antibody is engineered to have an increased proportion of non-fucosylated oligosaccharides in the Fc region as compared to a non-engineered antibody.

58. The use of any one of embodiments 51 to 57, wherein at least about 40% of the N-linked oligosaccharides in the Fc region of the Type II anti-CD20 antibody are non-fucosylated.

59. The use of any one of embodiments 51 to 58, wherein the Type II anti-CD20 antibody is obinutuzumab.

60. The use of any one of embodiments 51 to 59, wherein the therapeutic agent comprises a polypeptide.

61. The use of any one of embodiments 51 to 60, wherein the therapeutic agent comprises an antibody.

62. The use of embodiment 61, wherein the antibody comprised in the therapeutic agent specifically binds to carcinoembryonic antigen (CEA).

63. The use of embodiment 62, wherein the antibody comprised in the therapeutic agent comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19.

64. The use of embodiment 62 or 63, wherein the antibody comprised in the therapeutic agent comprises the heavy chain variable region sequence of SEQ ID NO: 20 and the light chain variable region sequence of SEQ ID NO: 21.

65. The use of embodiment 61, wherein the antibody comprised in the therapeutic agent specifically binds to CD3, particularly CD3ε.

66. The use of embodiment 65, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

67. The use of embodiment 65 or 66, wherein the antibody comprised in the therapeutic agent comprises the heavy chain variable region sequence of SEQ ID NO: 38 and the light chain variable region sequence of SEQ ID NO: 39.

68. The use of any one of embodiments 51 to 67, wherein the therapeutic agent comprises a cytokine.

69. The use of embodiment 68, wherein the cytokine is interleukin-2 (IL-2).

70. The use of embodiment 68 or 69, wherein the cytokine is a mutant human IL-2 polypeptide comprising the amino acid substitutions F42A, Y45A and L72G (numbering relative to the human IL-2 sequence SEQ ID NO: 12).

71. The use of any one of embodiments 51 to 70, wherein the therapeutic agent comprises an immunoconjugate.

72. The use of embodiment 71, wherein the immunoconjugate comprises an antibody as defined in any one of embodiments 62 to 64, and a cytokine as defined in embodiment 69 or 70.

73. The use of any one of embodiments 51 to 72, wherein the therapeutic agent comprises cergutuzumab amunaleukin (CEA-IL2v).

74. The use of any one of embodiments 51 to 67, wherein the therapeutic agent comprises a bispecific antibody comprising an antibody as defined in any one of embodiments 62 to 64 and an antibody as defined in any one of embodiments 65 to 67.

75. A kit for the reduction of the formation of anti-drug antibodies (ADAs) against a therapeutic agent in a subject, comprising a package comprising a Type II anti-CD20 antibody composition and instructions for using the Type II anti-CD20 antibody composition in a treatment regimen comprising (iii) administration to the subject of the Type II anti-CD20 antibody composition, and consecutively after a period of time (iv) administration to the subject of a therapeutic agent, wherein the period of time between the administration of the Type II anti-CD20 antibody composition and the administration of the therapeutic agent is sufficient for reduction of the number of B-cells in the subject in response to the administration of the Type II anti-CD20 antibody.

76. The kit of embodiment 75, further comprising a therapeutic agent composition.

77. A kit for the treatment of a disease in a subject, comprising a package comprising a therapeutic agent composition and instructions for using the therapeutic agent composition in a treatment regimen comprising (iii) administration to the subject of a Type II anti-CD20 antibody,
and consecutively after a period of time
(iv) administration to the subject of the therapeutic agent composition,
wherein the period of time between the administration of the Type II anti-CD20 antibody and the administration of the therapeutic agent composition is sufficient for reduction of the number of B-cells in the subject in response to the administration of the Type II anti-CD20 antibody.

78. The kit of embodiment 77, further comprising a Type II anti-CD20 antibody composition.

79. The kit of any one of embodiments 75 to 78, wherein the treatment regimen effectively reduces the formation of anti-drug antibodies (ADAs) against the therapeutic agent in the subject as compared to a corresponding treatment regimen without the administration of the Type II anti-CD20 antibody composition.

80. The kit of any one of embodiments 75 to 79, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

81. The kit of any one of embodiments 75 to 80, wherein the Type II anti-CD20 antibody comprises the heavy chain variable region sequence of SEQ ID NO: 10 and the light chain variable region sequence of SEQ ID NO: 11.

82. The kit of any one of embodiments 75 to 81, wherein the Type II anti-CD20 antibody is an IgG antibody, particularly an $IgG_1$ antibody.

83. The kit of any one of embodiments 75 to 82, wherein the Type II anti-CD20 antibody is engineered to have an increased proportion of non-fucosylated oligosaccharides in the Fc region as compared to a non-engineered antibody.

84. The kit of any one of embodiments 75 to 83, wherein at least about 40% of the N-linked oligosaccharides in the Fc region of the Type II anti-CD20 antibody are non-fucosylated.

85. The kit of any one of embodiments 75 to 84, wherein the Type II anti-CD20 antibody is obinutuzumab.

86. The kit of any one of embodiments 75 to 85, wherein the therapeutic agent comprises a polypeptide.

87. The kit of any one of embodiments 75 to 86, wherein the therapeutic agent comprises an antibody.

88. The kit of embodiment 87, wherein the antibody comprised in the therapeutic agent specifically binds to carcinoembryonic antigen (CEA).

89. The kit of embodiment 88, wherein the antibody comprised in the therapeutic agent comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19.

90. The kit of embodiment 88 or 89, wherein the antibody comprised in the therapeutic agent comprises the heavy chain variable region sequence of SEQ ID NO: 20 and the light chain variable region sequence of SEQ ID NO: 21.

91. The kit of embodiment 87, wherein the antibody comprised in the therapeutic agent specifically binds to CD3, particularly CD3ε.

92. The kit of embodiment 91, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

93. The kit of embodiment 91 or 92, wherein the antibody comprised in the therapeutic agent comprises the heavy chain variable region sequence of SEQ ID NO: 38 and the light chain variable region sequence of SEQ ID NO: 39.

94. The kit of any one of embodiments 75 to 93, wherein the therapeutic agent comprises a cytokine.

95. The kit of embodiment 94, wherein the cytokine is interleukin-2 (IL-2).

96. The kit of embodiment 94 or 95, wherein the cytokine is a mutant human IL-2 polypeptide comprising the amino acid substitutions F42A, Y45A and L72G (numbering relative to the human IL-2 sequence SEQ ID NO: 12).

97. The kit of any one of embodiments 75 to 96, wherein the therapeutic agent comprises an immunoconjugate.

98. The kit of embodiment 97, wherein the immunoconjugate comprises an antibody as defined in any one of embodiments 88 to 90, and a cytokine as defined in embodiment 95 or 96.

99. The kit of any one of embodiments 75 to 98, wherein the therapeutic agent comprises cergutuzumab amunaleukin (CEA-IL2v).

100. The kit of any one of embodiments 75 to 93, wherein the therapeutic agent comprises a bispecific antibody comprising an antibody as defined in any one of embodiments 88 to 90 and an antibody as defined in any one of embodiments 91 to 93.

101. A therapeutic agent for use in a method of treating a disease in a subject, the method comprising a treatment regimen comprising
(i) administration to the subject of a Type II anti-CD20 antibody,
and consecutively after a period of time
(ii) administration to the subject of the therapeutic agent,
wherein the period of time between the administration of the Type II anti-CD20 antibody and the administration of the therapeutic agent is sufficient for reduction of the number of B-cells in the subject in response to the administration of the Type II anti-CD20 antibody.

102. The therapeutic agent of embodiment 101, wherein the treatment regimen effectively reduces the formation of anti-drug antibodies (ADAs) in the subject in response to the administration of the therapeutic agent as compared to a corresponding treatment regimen without the administration of the Type II anti-CD20 antibody.

103. The therapeutic agent of embodiment 101 or 102, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

104. The therapeutic agent of any one of embodiments 101 to 103, wherein the Type II anti-CD20 antibody comprises the heavy chain variable region sequence of SEQ ID NO: 10 and the light chain variable region sequence of SEQ ID NO: 11.

105. The therapeutic agent of any one of embodiments 101 to 104, wherein the Type II anti-CD20 antibody is an IgG antibody, particularly an $IgG_1$ antibody.

106. The therapeutic agent of any one of embodiments 101 to 105, wherein the Type II anti-CD20 antibody is engineered to have an increased proportion of non-fucosylated oligosaccharides in the Fc region as compared to a non-engineered antibody.

107. The therapeutic agent of any one of embodiments 101 to 106, wherein at least about 40% of the N-linked oligosaccharides in the Fc region of the Type II anti-CD20 antibody are non-fucosylated.

108. The therapeutic agent of any one of embodiments 101 to 107, wherein the Type II anti-CD20 antibody is obinutuzumab.

109. The therapeutic agent of any one of embodiments 101 to 108, wherein the therapeutic agent comprises a polypeptide.

110. The therapeutic agent of any one of embodiments 101 to 109, wherein the therapeutic agent comprises an antibody.

111. The therapeutic agent of embodiment 110, wherein the antibody comprised in the therapeutic agent specifically binds to carcinoembryonic antigen (CEA).

112. The therapeutic agent of embodiment 111, wherein the antibody comprised in the therapeutic agent comprises a heavy chain variable region comprising the heavy chain CDR (HCDR) 1 of SEQ ID NO: 14, the HCDR2 of SEQ ID NO: 15, and the HCDR3 of SEQ ID NO: 16; and a light chain variable region comprising the light chain CDR (LCDR) 1 of SEQ ID NO: 17, the LCDR2 of SEQ ID NO: 18 and the LCDR3 of SEQ ID NO: 19.

113. The therapeutic agent of embodiment 110 or 111, wherein the antibody comprised in the therapeutic agent comprises the heavy chain variable region sequence of SEQ ID NO: 20 and the light chain variable region sequence of SEQ ID NO: 21.

114. The therapeutic agent of embodiment 110, wherein the antibody comprised in the therapeutic agent specifically binds to CD3, particularly CD3ε.

115. The therapeutic agent of embodiment 114, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

116. The therapeutic agent of embodiment 114 or 115, wherein the antibody comprised in the therapeutic agent comprises the heavy chain variable region sequence of SEQ ID NO: 38 and the light chain variable region sequence of SEQ ID NO: 39.

117. The therapeutic agent of any one of embodiments 101 to 116, wherein the therapeutic agent comprises a cytokine.

118. The therapeutic agent of embodiment 117, wherein the cytokine is interleukin-2 (IL-2).

119. The therapeutic agent of embodiment 117 or 118, wherein the cytokine is a mutant human IL-2 polypeptide comprising the amino acid substitutions F42A, Y45A and L72G (numbering relative to the human IL-2 sequence SEQ ID NO: 12).

120. The therapeutic agent of any one of embodiments 101 to 119, wherein the therapeutic agent comprises an immunoconjugate.

121. The therapeutic agent of embodiment 120, wherein the immunoconjugate comprises an antibody as defined in any one of embodiments 111 to 113, and a cytokine as defined in embodiment 118 or 119.

122. The therapeutic agent of any one of embodiments 101 to 121, wherein the therapeutic agent comprises cergutuzumab amunaleukin (CEA-IL2v).

123. The therapeutic agent of any one of embodiments 101 to 119, wherein the therapeutic agent comprises a bispecific antibody comprising an antibody as defined in any one of embodiments 111 to 113 and an antibody as defined in any one of embodiments 114 to 116.

In the following, further embodiments of the invention are listed.

1. A method of treating a disease in a subject, the method comprising a treatment regimen comprising
(i) administration to the subject of a Type II anti-CD20 antibody,
and consecutively after a period of time
(ii) administration to the subject of a T-cell activating therapeutic agent,
wherein the period of time between the administration of the Type II anti-CD20 antibody and the administration of the therapeutic agent is sufficient for reduction of the number of B-cells in the subject in response to the administration of the CD20 antibody.

2. The method of embodiment 1, wherein the treatment regimen effectively reduces cytokine release in the subject associated with the administration of the therapeutic agent as compared to a corresponding treatment regimen without the administration of the Type II anti-CD20 antibody.

3. A method for reducing cytokine release associated with the administration of a therapeutic agent in a subject, comprising administration of a Type II anti-CD20 antibody to the subject prior to administration of the therapeutic agent.

4. The method of embodiment 3, wherein the period of time between the administration of the Type II anti-CD20 antibody and administration of the therapeutic agent is sufficient for reduction of the number of B-cells in the subject in response to the administration of the Type II anti-CD20 antibody.

5. The method of any one of the preceding embodiments, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

6. The method of any one of the preceding embodiments, wherein the Type II anti-CD20 antibody comprises the heavy chain variable region sequence of SEQ ID NO: 10 and the light chain variable region sequence of SEQ ID NO: 11.

7. The method of any one of the preceding embodiments, wherein the Type II anti-CD20 antibody is an IgG antibody, particularly an $IgG_1$ antibody.

8. The method of any one of the preceding embodiments, wherein the Type II anti-CD20 antibody is engineered to have an increased proportion of non-fucosylated oligosaccharides in the Fc region as compared to a non-engineered antibody.

9. The method of any one of the preceding embodiments, wherein at least about 40% of the N-linked oligosaccharides in the Fc region of the Type II anti-CD20 antibody are non-fucosylated.

10. The method of any one of the preceding embodiments, wherein the Type II anti-CD20 antibody is obinutuzumab.

11. The method of any one of the preceding embodiments, wherein the therapeutic agent comprises an antibody, particularly a multispecific antibody.

12. The method of embodiment 11, wherein the antibody comprised in the therapeutic agent specifically binds to an activating T cell antigen, particularly an antigen selected from the group consisting of CD3, CD28, CD137 (also known as 4-1BB), CD40, CD226, OX40, GITR, CD27, HVEM, and CD127, more particularly CD3, most particularly CD3ε.

13. The method of embodiment 11 or 12, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

14. The method of any one of embodiments 11 to 13, wherein the antibody comprised in the therapeutic agent comprises the heavy chain variable region sequence of SEQ ID NO: 38 and the light chain variable region sequence of SEQ ID NO: 39.

15. The method of any one of embodiments 11 to 14, wherein the antibody comprised in the therapeutic agent specifically binds to a B-cell antigen, particularly an antigen selected from the group consisting of CD20, CD19, CD22, ROR-1, CD37 and CD5, more particularly CD20 or CD19, most particularly CD20.

16. The method of embodiment 15, wherein the antibody comprised in the therapeutic agent comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

17. The method of embodiment 15 or 16, wherein the antibody comprised in the therapeutic agent comprises the heavy chain variable region sequence of SEQ ID NO: 10 and the light chain variable region sequence of SEQ ID NO: 11.

18. The method of any one of the preceding embodiments, wherein the antibody comprised in the therapeutic agent is a bispecific antibody comprising (i) an antibody as defined in any one of embodiments 12 to 14 and (ii) an antibody as defined in any one of embodiments 15 to 17.

19. The method of any one of the preceding embodiments, wherein the therapeutic agent comprises CD20XCD3 bsAB.

20. The method of any one of embodiments 1 to 10, wherein the therapeutic agent comprises a T cell expressing a chimeric antigen receptor (CAR), particularly a CAR that specifically binds to a B-cell antigen, more particularly a CAR that specifically binds to an antigen selected from the group of CD20. CD19, CD22, ROR-1, CD37 and CD5.

21. The method of any one of the preceding embodiments, wherein the disease is a B cell proliferative disorder, particularly a CD20-positive B-cell disorder, and/or is a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

22. A Type II anti-CD20 antibody for use in a method of treating a disease in a subject, the method comprising a treatment regimen comprising (i) administration to the subject of the Type II anti-CD20 antibody,
and consecutively after a period of time
(ii) administration to the subject of a T-cell activating therapeutic agent,
wherein the period of time between the administration of the Type II anti-CD20 antibody and the administration of the therapeutic agent is sufficient for reduction of the number of B-cells in the subject in response to the administration of the Type II anti-CD20 antibody.

23. The Type II anti-CD20 antibody of embodiment 22, wherein the treatment regimen effectively reduces cytokine release in the subject associated with the administration of the therapeutic agent as compared to a corresponding treatment regimen without the administration of the Type II anti-CD20 antibody.

24. A Type II anti-CD20 antibody for use in a method for reducing cytokine release associated with the administration of a therapeutic agent in a subject, comprising administration of the Type II anti-CD20 antibody to the subject prior to administration of the therapeutic agent.

25. The Type II anti-CD20 antibody of embodiment 24, wherein the period of time between the administration of the Type II anti-CD20 antibody and administration of the therapeutic agent is sufficient for reduction of the number of B-cells in the subject in response to the administration of the Type II anti-CD20 antibody.

26. The Type II anti-CD20 antibody of any one of embodiments 22 to 25, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

27. The Type II anti-CD20 antibody of any one of embodiments 22 to 26, wherein the Type II anti-CD20 antibody comprises the heavy chain variable region sequence of SEQ ID NO: 10 and the light chain variable region sequence of SEQ ID NO: 11.

28. The Type II anti-CD20 antibody of any one of embodiments 22 to 27, wherein the Type II anti-CD20 antibody is an IgG antibody, particularly an IgG$_1$ antibody.

29. The Type II anti-CD20 antibody of any one of embodiments 22 to 28, wherein the Type II anti-CD20 antibody is engineered to have an increased proportion of non-fucosylated oligosaccharides in the Fc region as compared to a non-engineered antibody.

30. The Type II anti-CD20 antibody of any one of embodiments 22 to 29, wherein at least about 40% of the N-linked oligosaccharides in the Fc region of the Type II anti-CD20 antibody are non-fucosylated.

31. The Type II anti-CD20 antibody of any one of embodiments 22 to 30, wherein the Type II anti-CD20 antibody is obinutuzumab.

32. The Type II anti-CD20 antibody of any one of embodiments 22 to 31, wherein the therapeutic agent comprises an antibody, particularly a multispecific antibody.

33. The Type II anti-CD20 antibody of embodiment 32, wherein the antibody comprised in the therapeutic agent specifically binds to an activating T cell antigen, particularly an antigen selected from the group consisting of CD3, CD28, CD137 (also known as 4-1BB), CD40, CD226, OX40. G1TR, CD27. HVEM, and CD127, more particularly CD3, most particularly CD3ε.

34. The Type II anti-CD20 antibody of embodiment 32 or 33, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

35. The Type II anti-CD20 antibody of any one of embodiments 32 to 34, wherein the antibody comprised in the therapeutic agent comprises the heavy chain variable region sequence of SEQ ID NO: 38 and the light chain variable region sequence of SEQ ID NO: 39.

36. The Type II anti-CD20 antibody of any one of embodiments 32 to 35, wherein the antibody comprised in the therapeutic agent specifically binds to a B-cell antigen, particularly an antigen selected from the group consisting of CD20, CD19, CD22, ROR-1, CD37 and CD5, more particularly CD20 or CD19, most particularly CD20.

37. The Type II anti-CD20 antibody of embodiment 36, wherein the antibody comprised in the therapeutic agent comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

38. The Type II anti-CD20 antibody of embodiment 36 or 37, wherein the antibody comprised in the therapeutic agent comprises the heavy chain variable region sequence of SEQ ID NO: 10 and the light chain variable region sequence of SEQ ID NO: 11.

39. The Type II anti-CD20 antibody of any one of embodiments 22 to 38, wherein the antibody comprised in the therapeutic agent is a bispecific antibody comprising (i) an antibody as defined in any one of embodiments 33 to 35 and (ii) an antibody as defined in any one of embodiments 36 to 38.

40. The Type II anti-CD20 antibody of any one of embodiments 22 to 39, wherein the therapeutic agent comprises CD20XCD3 bsAB.

41. The Type II anti-CD20 antibody of any one of embodiments 22 to 31, wherein the therapeutic agent comprises a T cell expressing a chimeric antigen receptor (CAR), particularly a CAR that specifically binds to a B-cell antigen, more particularly a CAR that specifically binds to an antigen selected from the group of CD20, CD19, CD22, ROR-1, CD37 and CD5.

42. The Type II anti-CD20 antibody of any one of embodiments 22 to 41, wherein the disease is a B cell proliferative disorder, particularly a CD20-positive B-cell disorder, and/or is a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

43. Use of a Type II anti-CD20 antibody in the manufacture of a medicament for reduction of cytokine release associated with the administration of a T-cell activating therapeutic agent in a subject, wherein the medicament is to be used in a treatment regimen comprising (i) administration to the subject of the Type II anti-CD20 antibody, and consecutively after a period of time (ii) administration to the subject of a T-cell activating therapeutic agent, wherein the period of time between the administration of the Type II anti-CD20 antibody and the administration of the therapeutic agent is sufficient for reduction of the number of B-cells in the subject in response to the administration of the CD20 antibody.

44. Use of a T-cell activating therapeutic agent in the manufacture of a medicament for treatment of a disease in a subject, wherein the treatment comprises a treatment regimen comprising (iii) administration to the subject of a Type II anti-CD20 antibody, and consecutively after a period of time (iv) administration to the subject of the T-cell activating therapeutic agent, wherein the period of time between the administration of the Type II anti-CD20 antibody and the administration of the therapeutic agent is sufficient for reduction of the number of B-cells in the subject in response to the administration of the CD20 antibody.

45. The use of embodiment 43 or 44, wherein the treatment regimen effectively reduces cytokine release associated with the administration of the therapeutic agent in the subject as compared to a corresponding treatment regimen without the administration of the Type II anti-CD20 antibody.

46. The use of any one of embodiments 43 to 45, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

47. The use of any one of embodiments 43 to 46, wherein the Type II anti-CD20 antibody comprises the heavy chain variable region sequence of SEQ ID NO: 10 and the light chain variable region sequence of SEQ ID NO: 11.

48. The use of any one of embodiments 43 to 47, wherein the Type II anti-CD20 antibody is an IgG antibody, particularly an $IgG_1$ antibody.

49. The use of any one of embodiments 43 to 48, wherein the Type II anti-CD20 antibody is engineered to have an increased proportion of non-fucosylated oligosaccharides in the Fc region as compared to a non-engineered antibody.

50. The use of any one of embodiments 43 to 49, wherein at least about 40% of the N-linked oligosaccharides in the Fc region of the Type II anti-CD20 antibody are non-fucosylated.

51. The use of any one of embodiments 43 to 50, wherein the Type II anti-CD20 antibody is obinutuzumab.

52. The use of any one of embodiments 43 to 51, wherein the therapeutic agent comprises an antibody, particularly a multispecific antibody.

53. The use of embodiment 51, wherein the antibody comprised in the therapeutic agent specifically binds to an activating T cell antigen, particularly an antigen selected from the group consisting of CD3, CD28, CD137 (also known as 4-1BB), CD40, CD226, OX40, GITR, CD27, HVEM, and CD127, more particularly CD3, most particularly CD3E.

54. The use of embodiment 52 or 53, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

55. The use of any one of embodiments 52 to 54, wherein the antibody comprised in the therapeutic agent comprises the heavy chain variable region sequence of SEQ ID NO: 38 and the light chain variable region sequence of SEQ ID NO: 39.

56. The use of any one of embodiments 52 to 55, wherein the antibody comprised in the therapeutic agent specifically binds to a B-cell antigen, particularly an antigen selected from the group consisting of CD20, CD19, CD22, ROR-1, CD37 and CD5, more particularly CD20 or CD19, most particularly CD20.

57. The use of embodiment 56, wherein the antibody comprised in the therapeutic agent comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

58. The use of embodiment 56 or 57, wherein the antibody comprised in the therapeutic agent comprises the heavy chain variable region sequence of SEQ ID NO: 10 and the light chain variable region sequence of SEQ ID NO: 11.

59. The use of any one of embodiments 43 to 58, wherein the antibody comprised in the therapeutic agent is a bispecific antibody comprising (i) an antibody as defined in any one of embodiments 53 to 55 and (ii) an antibody as defined in any one of embodiments 56 to 58.

60. The use of any one of embodiments 43 to 59, wherein the therapeutic agent comprises CD20XCD3 bsAB. 61. The use of any one of embodiments 43 to 51, wherein the therapeutic agent comprises a T cell expressing a chimeric antigen receptor (CAR), particularly a CAR that specifically binds to a B-cell antigen, more particularly a CAR that specifically binds to an antigen selected from the group of CD20, CD19, CD22, ROR-1, CD37 and CD5.

62. The use of any one of embodiments 43 to 61, wherein the disease is a B cell proliferative disorder, particularly a CD20-positive B-cell disorder, and/or is a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

63. A kit for the reduction of cytokine release associated with the administration of a T-cell activating therapeutic agent in a subject, comprising a package comprising a Type II anti-CD20 antibody composition and instructions for using the Type II anti-CD20 antibody composition in a treatment regimen comprising (i) administration to the subject of the Type II anti-CD20 antibody composition, and consecutively after a period of time (ii) administration to the subject of a T-cell activating therapeutic agent, wherein the period of time between the administration of the Type II anti-CD20 antibody composition and the administration of the therapeutic agent is sufficient for reduction of the number of B-cells in the subject in response to the administration of the CD20 antibody.

64. The kit of embodiment 63, further comprising a T-cell activating therapeutic agent composition.

65. A kit for the treatment of a disease in a subject, comprising a package comprising a T-cell activating therapeutic agent composition and instructions for using the therapeutic agent composition in a treatment regimen comprising (i) administration to the subject of a Type II anti-CD20 antibody, and consecutively after a period of time (ii) administration to the subject of the T-cell activating therapeutic agent composition, wherein the period of time between the administration of the Type II anti-CD20 antibody and the administration of the therapeutic agent composition is sufficient for reduction of the number of B-cells in the subject in response to the administration of the CD20 antibody.

66. The kit of embodiment 65, further comprising a Type II anti-CD20 antibody composition.

67. The kit of any one of embodiments 63 to 66, wherein the treatment regimen effectively reduces cytokine release associated with the administration of the therapeutic agent in the subject as compared to a corresponding treatment regimen without the administration of the Type II anti-CD20 antibody composition.

68. The kit of any one of embodiments 63 to 67, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

69. The kit of any one of embodiments 63 to 68, wherein the Type II anti-CD20 antibody comprises the heavy chain variable region sequence of SEQ ID NO: 10 and the light chain variable region sequence of SEQ ID NO: 11.

70. The kit of any one of embodiments 63 to 69, wherein the Type II anti-CD20 antibody is an IgG antibody, particularly an $IgG_1$ antibody.

71. The kit of any one of embodiments 63 to 70, wherein the Type II anti-CD20 antibody is engineered to have an increased proportion of non-fucosylated oligosaccharides in the Fc region as compared to a non-engineered antibody.

72. The kit of any one of embodiments 63 to 71, wherein at least about 40% of the N-linked oligosaccharides in the Fc region of the Type II anti-CD20 antibody are non-fucosylated.

73. The kit of any one of embodiments 63 to 72, wherein the Type II anti-CD20 antibody is obinutuzumab.

74. The kit of any one of embodiments 63 to 73, wherein the therapeutic agent comprises an antibody, particularly a multispecific antibody.

75. The kit of embodiment 74, wherein the antibody comprised in the therapeutic agent specifically binds to an activating T cell antigen, particularly an antigen selected from the group consisting of CD3, CD28, CD137 (also known as 4-1BB), CD40, CD226, OX40, GITR, CD27, HVEM, and CD127, more particularly CD3, most particularly CD3ε.

76. The kit of embodiment 74 or 75, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

77. The kit of any one of embodiments 74 to 76, wherein the antibody comprised in the therapeutic agent comprises the heavy chain variable region sequence of SEQ ID NO: 38 and the light chain variable region sequence of SEQ ID NO: 39.

78. The kit of any one of embodiments 74 to 77, wherein the antibody comprised in the therapeutic agent specifically binds to a B-cell antigen, particularly an antigen selected from the group consisting of CD20, CD19, CD22, ROR-1, CD37 and CD5, more particularly CD20 or CD19, most particularly CD20.

79. The kit of embodiment 78, wherein the antibody comprised in the therapeutic agent comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

80. The kit of embodiment 78 or 79, wherein the antibody comprised in the therapeutic agent comprises the heavy chain variable region sequence of SEQ ID NO: 10 and the light chain variable region sequence of SEQ ID NO: 11.

81. The kit of any one of embodiments 78 to 80, wherein the antibody comprised in the therapeutic agent is a bispecific antibody comprising (i) an antibody as defined in any one of embodiments 75 to 77 and (ii) an antibody as defined in any one of embodiments 78 to 80.

82. The kit of any one of embodiments 63 to 81, wherein the therapeutic agent comprises CD20XCD3 bsAB.

83. The kit of any one of embodiments 63 to 73, wherein the therapeutic agent comprises a T cell expressing a chimeric antigen receptor (CAR), particularly a CAR that specifically binds to a B-cell antigen, more particularly a CAR that specifically binds to an antigen selected from the group of CD20, CD19, CD22, ROR-1, CD37 and CD5.

84. The kit of any one of embodiments 63 to 83, wherein the disease is a B cell proliferative disorder, particularly a CD20-positive B-cell disorder, and/or is a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

85. A T-cell activating therapeutic agent for use in a method of treating a disease in a subject, the method comprising a treatment regimen comprising
(i) administration to the subject of a Type II anti-CD20 antibody,
and consecutively after a period of time
(ii) administration to the subject of the T-cell activating therapeutic agent,
wherein the period of time between the administration of the Type II anti-CD20 antibody and the administration of the therapeutic agent is sufficient for reduction of the number of B-cells in the subject in response to the administration of the CD20 antibody.

86. The T-cell activating therapeutic agent of embodiment 85, wherein the treatment regimen effectively reduces cytokine release in the subject associated with the administration of the therapeutic agent as compared to a corresponding treatment regimen without the administration of the Type II anti-CD20 antibody.

87. The T-cell activating therapeutic agent of embodiment 85 or 86, wherein the Type II anti-CD20 antibody comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

88. The T-cell activating therapeutic agent of any one of embodiments 85 to 87, wherein the Type II anti-CD20 antibody comprises the heavy chain variable region sequence of SEQ ID NO: 10 and the light chain variable region sequence of SEQ ID NO: 11.

89. The T-cell activating therapeutic agent of any one of embodiments 85 to 88, wherein the Type II anti-CD20 antibody is an IgG antibody, particularly an IgG$_1$ antibody.

90. The T-cell activating therapeutic agent of any one of embodiments 85 to 89, wherein the Type II anti-CD20 antibody is engineered to have an increased proportion of non-fucosylated oligosaccharides in the Fc region as compared to a non-engineered antibody.

91. The T-cell activating therapeutic agent of any one of embodiments 85 to 90, wherein at least about 40% of the N-linked oligosaccharides in the Fc region of the Type II anti-CD20 antibody are non-fucosylated.

92. The T-cell activating therapeutic agent of any one of embodiments 85 to 91, wherein the Type II anti-CD20 antibody is obinutuzumab.

93. The T-cell activating therapeutic agent of any one of embodiments 85 to 92, wherein the therapeutic agent comprises an antibody, particularly a multispecific antibody.

94. The T-cell activating therapeutic agent of embodiment 93, wherein the antibody comprised in the therapeutic agent specifically binds to an activating T cell antigen, particularly an antigen selected from the group consisting of CD3, CD28, CD137 (also known as 4-1BB), CD40, CD226, OX40, GITR, CD27, HVEM, and CD127, more particularly CD3, most particularly CD3E.

95. The T-cell activating therapeutic agent of embodiment 93 or 94, wherein the antibody comprised in the therapeutic agent comprises a heavy chain variable region comprising the heavy chain CDR (HCDR) 1 of SEQ ID NO: 32, the HCDR2 of SEQ ID NO: 33, and the HCDR3 of SEQ ID NO: 34; and a light chain variable region comprising the light chain CDR (LCDR) 1 of SEQ ID NO: 35, the LCDR2 of SEQ ID NO: 36 and the LCDR3 of SEQ ID NO: 37.

96. The T-cell activating therapeutic agent of any one of embodiments 93 to 95, wherein the antibody comprised in the therapeutic agent comprises the heavy chain variable region sequence of SEQ ID NO: 38 and the light chain variable region sequence of SEQ ID NO: 39.

97. The T-cell activating therapeutic agent of any one of embodiments 93 to 96, wherein the antibody comprised in the therapeutic agent specifically binds to a B-cell antigen, particularly an antigen selected from the group consisting of CD20, CD19, CD22, ROR-1, CD37 and CD5, more particularly CD20 or CD19, most particularly CD20.

98. The T-cell activating therapeutic agent of embodiment 97, wherein the antibody comprised in the therapeutic agent comprises a heavy chain variable region comprising the heavy chain CDR (HCDR) 1 of SEQ ID NO: 4, the HCDR2 of SEQ ID NO: 5, and the HCDR3 of SEQ ID NO: 6; and a light chain variable region comprising the light chain CDR (LCDR) 1 of SEQ ID NO: 7, the LCDR2 of SEQ ID NO: 8 and the LCDR3 of SEQ ID NO: 9.

99. The T-cell activating therapeutic agent of embodiment 97 or 98, wherein the antibody comprised in the therapeutic agent comprises the heavy chain variable region sequence of SEQ ID NO: 10 and the light chain variable region sequence of SEQ ID NO: 11.

100. The T-cell activating therapeutic agent of any one of embodiments 85 to 99, wherein the antibody comprised in the therapeutic agent is a bispecific antibody comprising (i) an antibody as defined in any one of embodiments 94 to 96 and (ii) an antibody as defined in any one of embodiments 97 to 99.

101. The T-cell activating therapeutic agent of any one of embodiments 85 to 100, wherein the therapeutic agent comprises CD20XCD3 bsAB.

102. The T-cell activating therapeutic agent of any one of embodiments 85 to 92, wherein the therapeutic agent comprises a T cell expressing a chimeric antigen receptor (CAR), particularly a CAR that specifically binds to a B-cell antigen, more particularly a CAR that specifically binds to an antigen selected from the group of CD20, CD19, CD22, ROR-1, CD37 and CD5.

103. The T-cell activating therapeutic agent of any one of embodiments 85 to 102, wherein the disease is a B cell proliferative disorder, particularly a CD20-positive B-cell disorder, and/or is a disease selected from the group consisting of Non-Hodgkin lymphoma (NHL), acute lymphocytic leukemia (ALL), chronic lymphocytic leukemia (CLL), diffuse large B-cell lymphoma (DLBCL), follicular lymphoma (FL), mantle-cell lymphoma (MCL), marginal zone lymphoma (MZL), Multiple myeloma (MM) and Hodgkin lymphoma (HL).

EXAMPLES

The following are examples of methods and compositions of the invention. It is understood that various other embodiments may be practiced, given the general description provided above.

Example 1

Prior Treatment with Obinutuzumab but not Rituximab or Vehicle Results in the Attenuation of Tetanus Toxoid Specific De Novo IgG Antibody Responses in Cynomolgus Monkeys To evaluate the functional impact that B-cell depletion with obinutuzumab or rituximab has on the humoral immune response to foreign antigens, cynomolgus monkeys were immune challenged after treatment with either a novel antigen that the animals had never experienced before (de novo response to tetanus toxoid) or with a booster immune rechallenge with an immunogen that the animals had already encountered prior to the CD20 antibody administration (memory recall response to measles/rubella).

Animals were administered on day −14 and day −7 rituximab or obinutuzumab at a dose of 30 mg/kg or vehicle by i.v. infusion. Immunization with tetanus toxoid was performed on Day 0. Naïve animals from all groups had a baseline anti-tetanus toxoid IgG measurement of around 0.1 IU/ml at day 0. At Day 7, vehicle treated animals and rituximab treated animals mounted robust humoral anti-tetanus toxoid IgG responses, with an increase to around 1.0 IU/ml, while obinutuzumab treated animals showed attenuated responses, resulting in an equal to background signal of 0.1 IU/ml. By Day 21, serological titers in vehicle treated and rituximab treated animals continued to rise to peak levels of 2.5 IU/ml (FIG. 1). The obinutuzumab treated animals began to display a slight increase in titers to 0.5 IU/ml, which was significantly below of that of vehicle and rituximab treated groups. The serum IgG response waned by day 51 and 68 in all groups reaching around 1.5 IU/ml in vehicle, 1.3 IU/ml in rituximab and returning to 0.2 IU/ml in obinutuzumab treated animals.

These results indicate that prior treatment with obinutuzumab, but not rituximab, results in the attenuation of tetanus toxoid specific de novo IgG antibody responses in cynomolgus monkeys.

To investigate the memory recall responses by measles specific IgG antibody production in response to immune re-challenge with a measles/rubella booster vaccination animals that had measurable baseline positive anti-measles titers were selected. Animals were administered rituximab or obinutuzumab at a dose of 30 mg/kg or vehicle by i.v. infusion on day −14 and Day −7. Immune re-challenge with a measles/rubella vaccination was performed on Day 0.

Figure 2:
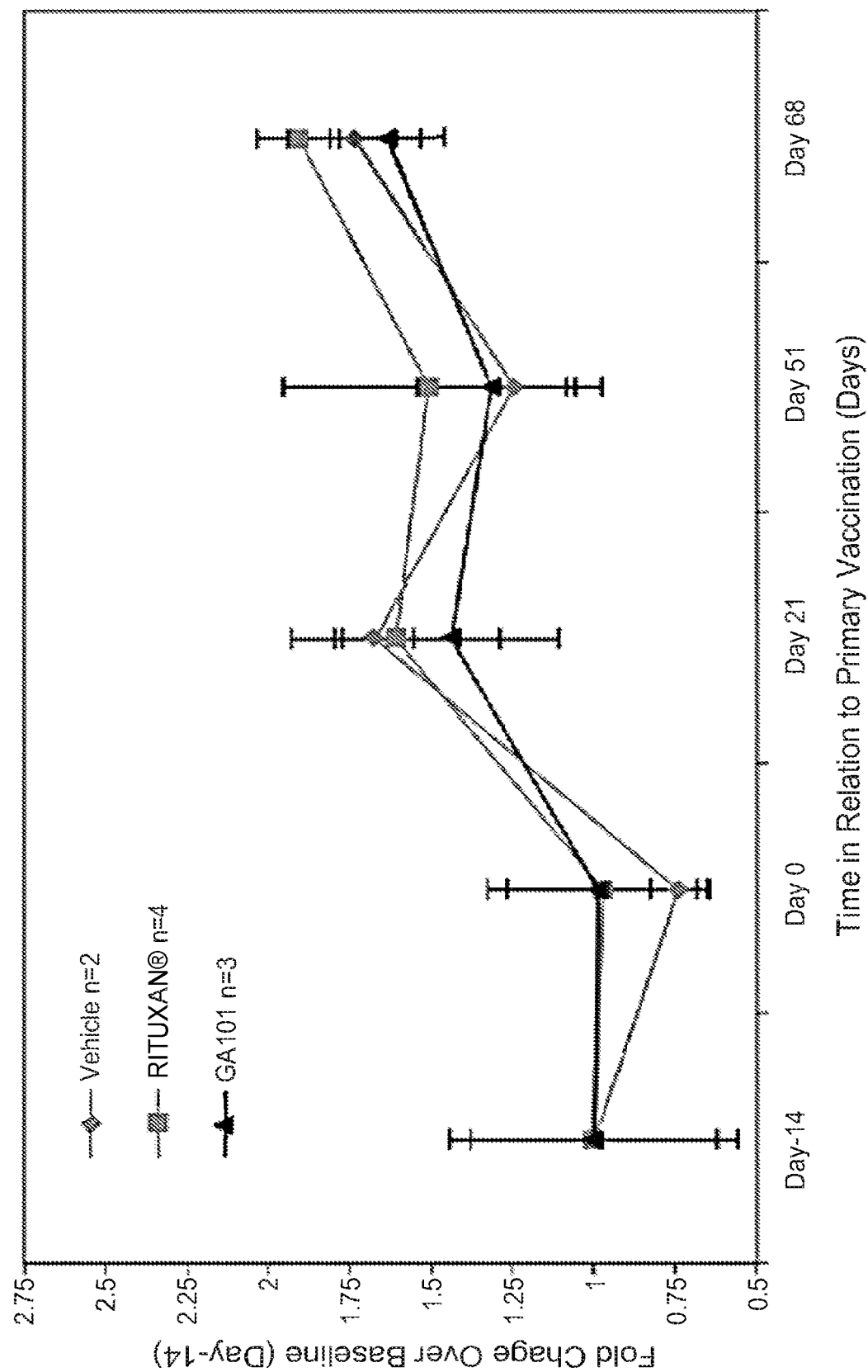
FIG. 2. Memory recall responses by measles specific IgG antibody production in response to immune re-challenge with a measles/rubella booster vaccination in animals with baseline titers to measles is not affected by either obinutuzumab or rituximab in cynomolgus monkeys. RITUXAN® indicates rituximab and GA101 obinutuzumab, respectively.

Measuring the fold change at optical density OD450 nm reading over baseline Day −14 reading, resulted in measurable increase in anti-measles titers in all three groups at Day 21, Day 51 and Day 68 with no significant difference found in the IgG responses to measles amongst the three different treatment groups (FIG. 2). The conclusion is that memory recall responses were left intact regardless of anti-CD20 depletion therapy. The administration of either obinutuzumab or rituximab had no measurable impact on the memory recall responses to a booster immunization against measles/rubella vaccination with established basal titers as a result of prior vaccination.

Overall, these results showed that prior treatment with obinutuzumab led to strong suppression of de novo antibody responses, but left the protective humoral memory responses intact. Without wishing to be bound by theory, the ability to block de novo humoral antibody responses may possibly be attributed to either the increased extent of endogenous B-cell depletion seen with obinutuzumab and/or the enhanced ability of obinutuzumab to deplete activated, CD20 expressing B cells.

Example 2

A Multi-Center, Randomized, Open-Label Phase 1 Study to Evaluate Feasibility, Safety and Pharmacodynamic Effect of Pretreatment with Obinutuzumab Prior to Therapy with RO6895882 (Cergutuzumab Amunaleukin, CEA-IL2v), in Patients with Locally Advanced and/or Metastatic Solid Tumors Methods An open-label, multi-center, randomized Phase 1b clinical sub-study of RO6895882 given with or without obinutuzumab as pre-treatment is performed.

The main objective of this sub-study is to determine if pre-treatment with obinutuzumab prevents the formation of ADAs in patients treated subsequently with RO6895882.

The trial enrolls patients with locally advanced and/or metastatic CEA-positive solid tumors that have progressed on or are intolerant to the standard of care therapy. Obinutuzumab and RO6895882 are administered intravenously (IV).

Fourteen patients were randomized into the obinutuzumab pretreatment arm and five patients to the control arm without obinutuzumab pretreatment. The patients in the obinutuzumab pretreatment arm received 2 g of obinutuzumab, administered on two consecutive days (2×1000 mg), Day −13 and Day −12 (+/−2 days) before the Cycle 1 Day 1 (CD1) R6895882 administration. Pre-medication was given prior to each obinutuzumab dosing. On C1D1 all patients received a fixed and flat 10 mg dose of RO6895882. At subsequent cycles, all patients received 20 mg of RO6895882, administered over a minimum of 2 hour IV infusion bi-weekly (q2W). The patients in the control arm (without obinutuzumab pretreatment) received RO6895882 administrations starting at C1D1 identically to the patients in the obinutuzumab pretreatment arm.

Blood samples were collected before and during the treatment period for the monitoring of B lymphocyte counts. B cell counts were obtained using flow cytometry and staining for CD19. Blood samples for ADA determination were obtained at baseline and thereafter every second week after the RO6895882 administration.

All patients underwent baseline and on-treatment tumor biopsies. For the obinutuzumab pretreated patients, baseline biopsies were taken after randomization, before administration of obinutuzumab. The control patients have tumor biopsies taken prior to the Cycle 1 Day 1 RO6895882 administration. On-treatment tumor biopsies from the first five patients pretreated with obinutuzumab were collected on Cycle 1 Day 1 (+0/−1 days) prior to RO895882 administration in order to confirm tissue B cell depletion before the start of RO895882 treatment. From the remaining obinutuzumab pre-treated patients the repeated tumor biopsies were collected on Cycle 3 Day 14 (+/−2 days), prior to the fourth RO895882 administration on Cycle 4 Day 1. One portion of the biopsy tissue was analyzed by flow cytometry and staining with CD19 for B lymphocyte detection. The second portion was formalin fixed and embedded in paraffin and analyzed for B lymphocytes using CD20 and PAX5 staining.

The primary objectives for this study were to assess the effect of pre-treatment with obinutuzumab on decreasing the proportion of patients with ADA titer at cycle 4, and to evaluate the safety and tolerability of administration of obinutuzumab prior to treatment with RO6895882.

Secondary objectives for this study included characterization of the RO6895882 ADAs (at cycle 4) and investigation and characterization of the B-cell depletion in tissue (tumor and skin) and peripheral blood resulting from obinutuzumab pre-treatment.

Results

RO6895882 (cergutuzumab amunaleukin, CEA-IL2v) has been tested in Study BP28920 EH Study (ClinicalTrials.gov identifier NCT02004106). As of November 2016, preliminary results from Study BP28920 show that in 59 of 74 patients (80%) anti-CEA-IL2v antibodies were detected. Among the 59 ADA-positive patients, 58 (0.98%) showed a persistent immune response while 1 (1.6%) showed a transient immune response. The intensity of ADA responses ranges from low to high titers (10-196.830). 32 out of 59 persistent ADA-positive cases (54%) show high ADA titers (>100). The first onset of an immune response was observed after one dose of RO6895882 (cergutuzumab amunaleukin, CEA-IL2v) as early as on day 5. i.e. 96 h post first dose. No patient with pre-existing ADAs was identified and all ADAs were treatment induced. In five out of 59 patients (8%), in addition to high ADA titres (>100), loss of exposure was observed. Neither hypersensitivity reactions or signs and symptoms suggestive of hypersensitivity, nor evidence of ADA-mediated adverse events were reported in the 108 patients who received RO6895882.

The above-described clinical sub-study was initiated to explore the potential of obinutuzumab (Gazyva®) given as a pre-treatment to administration of RO6895882 (cergutuzumab amunaleukin, CEA-IL2v) to attenuate development of anti-drug antibodies (ADAs). The study has concluded.

Fourteen out of 14 obinutuzumab treated patients remained free of ADAs against RO6895882 on Cycle 2 Day 1 (two weeks after first R6895882 administration) and throughout the entire study period. The longest on-treatment follow up period was up to 10 treatment cycles, i.e. 20 weeks. Four out of five control patients who were not pre-treated with obinutuzumab developed ADAs with titers of 10 to 270 after 1 dose of R6895882.

The safety profile of obinutuzumab pre-treatment was acceptable in patients with locally advanced and/or metastatic solid tumors. Patients receiving obinutuzumab/CEA-IL2v treatment did not experience unexpected AEs compared to the CEA-IL2v monotherapy. No fatal outcome due to adverse event was reported.

Figure 3:
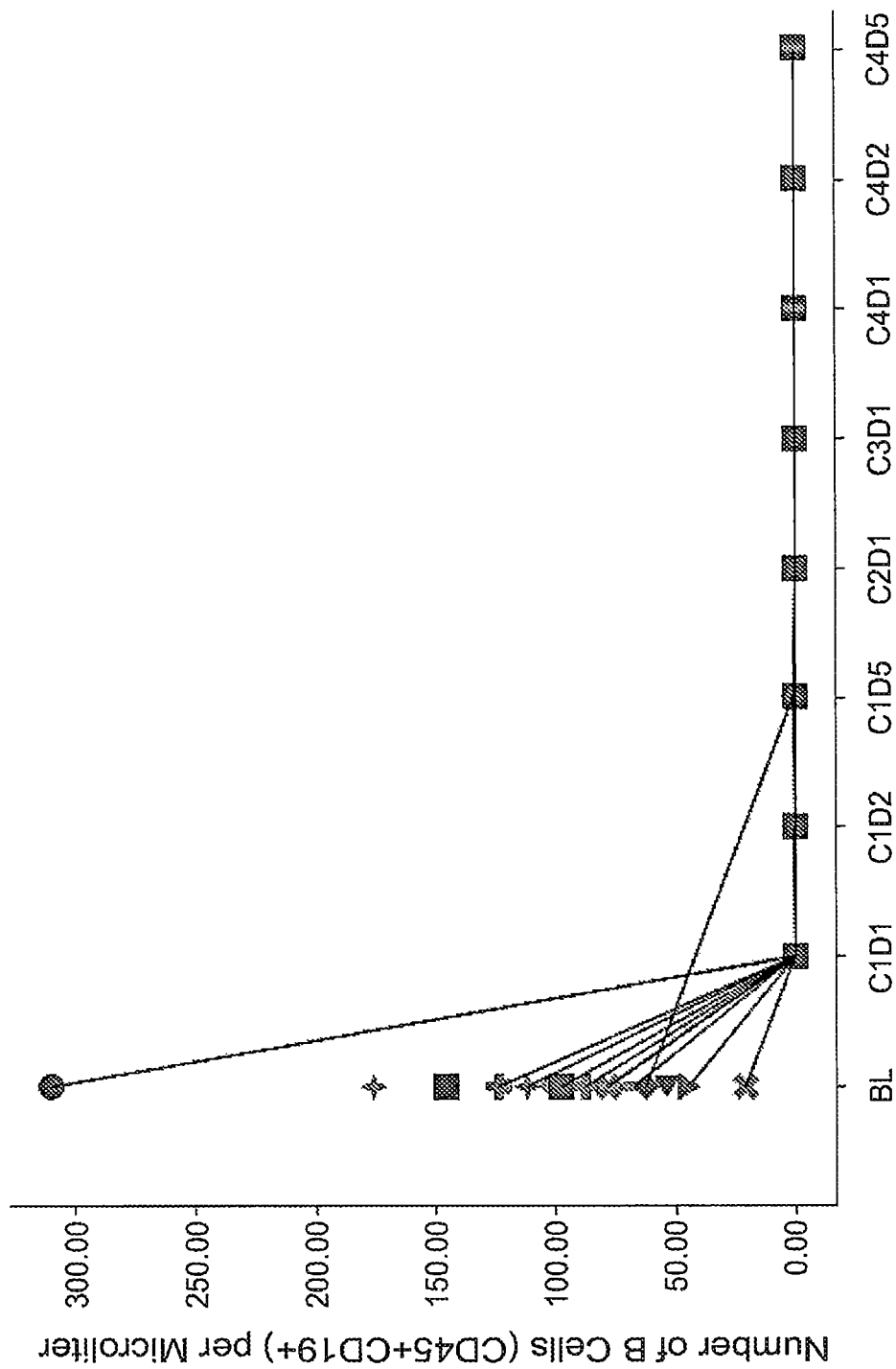
FIG. 3. B cell counts (CD45+CD19+) in peripheral blood samples before start of obinutuzumab pre-treatment (BL=baseline), before start of treatment with R06895882 (C1D1=Cycle 1 Day 1) and during treatment with R06895882. Lines/symbols represent individual patients. From the C1D1 time points onwards, no B cells were detectable in the peripheral blood samples.

Flow cytometric analysis of peripheral blood indicated complete depletion of B cells after obinutuzumab treatment. Before the start of treatment with RO6895882 (C1D1), no B cells were detectable in the collected blood samples (FIG. 3).

Figure 4A:
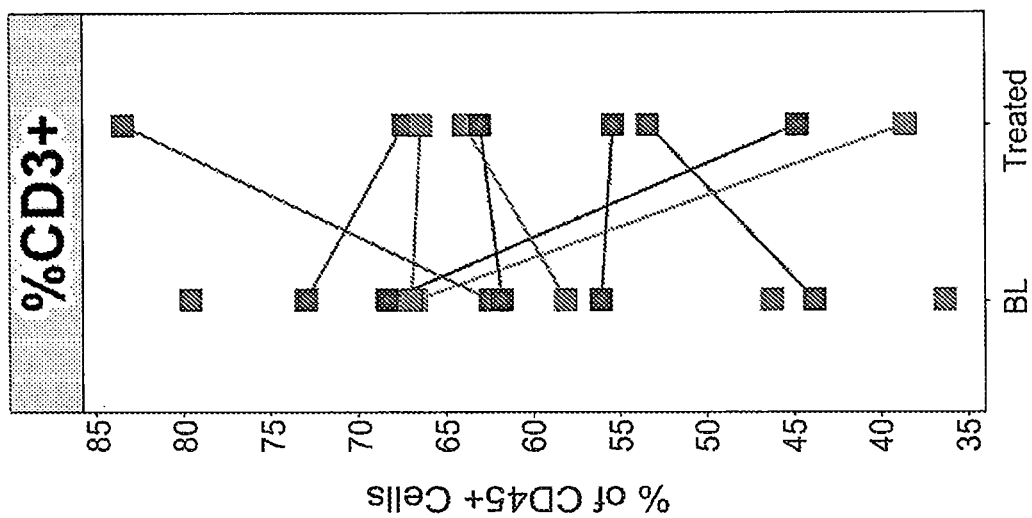
FIGS. 4A-4C. Reduction of CD19+ cells (B cells) detected by flow cytometry in tumor biopsies collected at baseline (BL) and after treatment with obinutuzumab (treated). On-treatment samples were obtained either before or during treatment with R06895882. The percentage of CD45+ cells (lymphocytes) staining positive for CD19 (B lymphocytes) was strongly reduced (FIG. 4B). No clear change was observed for the percentage of CD16+ cells (Natural Killer Cells) (FIG. 4A) or CD3+ cells (T lymphocytes) (FIG. 4C). Lines represent individual patients.
Figure 4B:
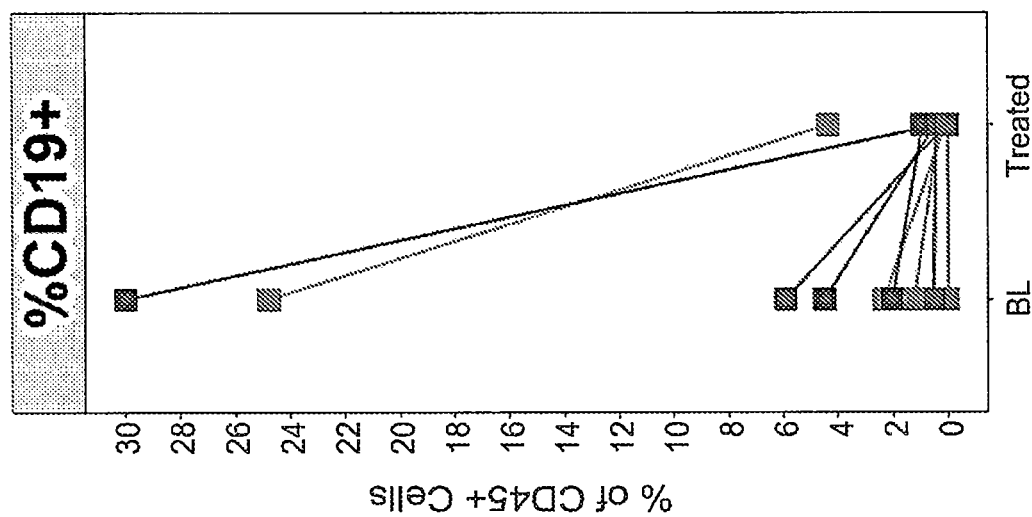
Figure 4C:
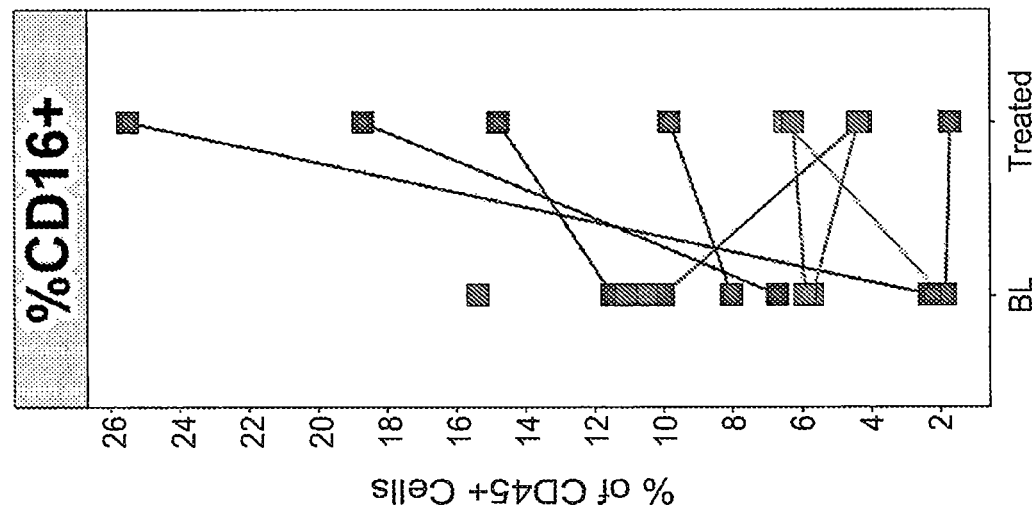
Figure 5B:
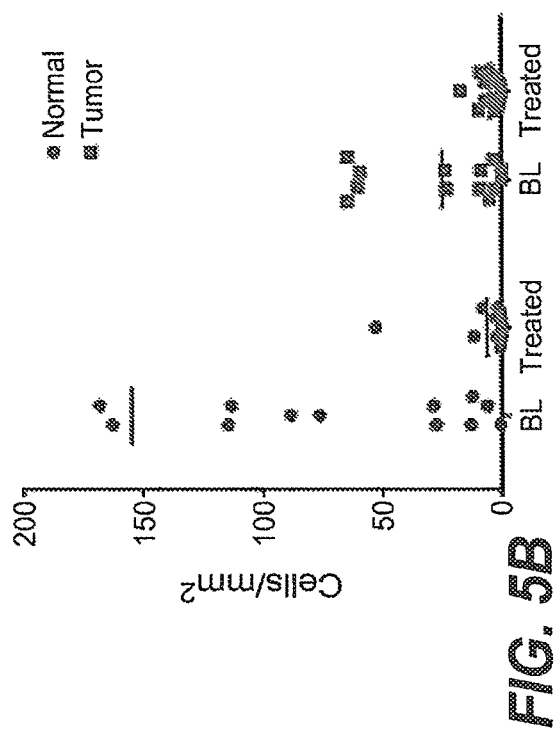
FIGS. 5A-5D. Reduction of B cells in tumor biopsies collected at baseline (BL) and after treatment (treated) with obinutuzumab measured by immunohistochemistry. On-treatment samples were obtained either before or during treatment with R06895882. The density of B lymphocytes was measured by staining with CD20 (FIG. 5A, FIG. 5B) and PAX 5 (FIG. 5C, FIG. 5D). Both methods detected a depletion of B lymphocytes in tumor and surrounding normal tissue. Lines represent individual patients.
Figure 5D:
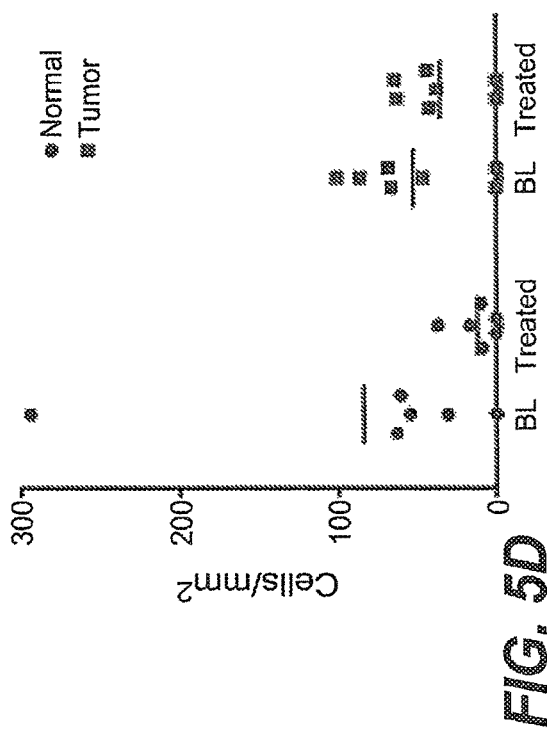
Figure 5A:
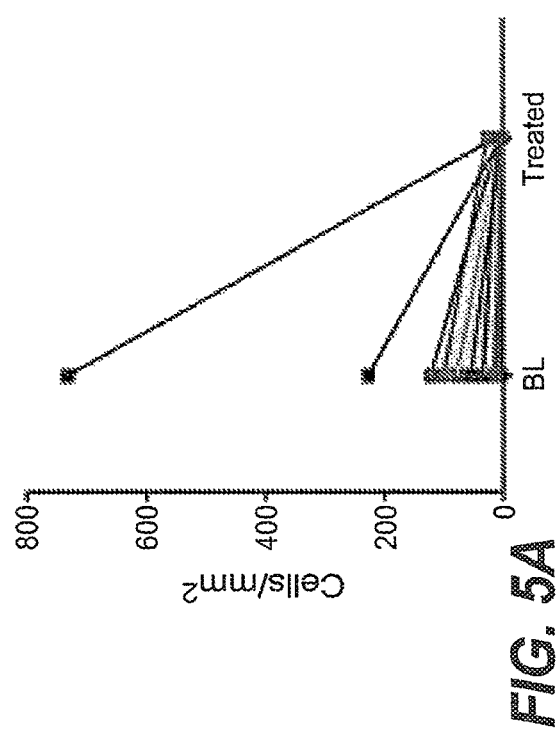
Figure 5C:
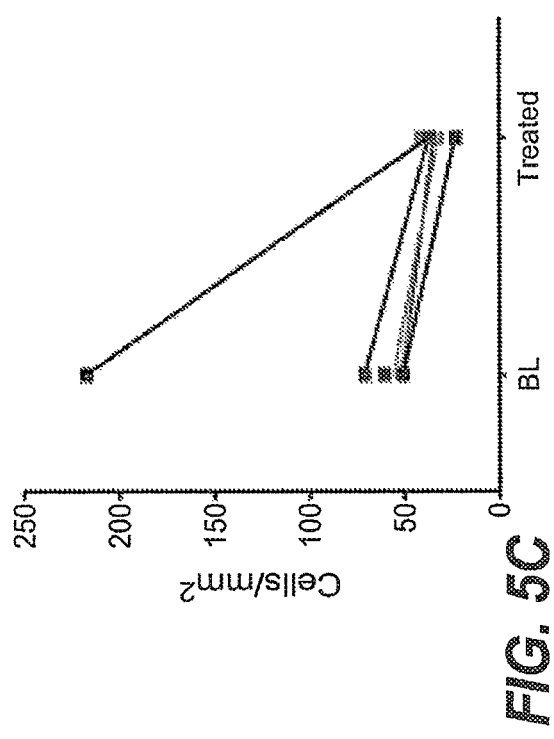

The tumor biopsy samples from obinutuzumab pre-treatment patients were analyzed by both flow cytometry and immunohistochemistry (IHC) for the frequency of B cells. Flow cytometric analysis (FIG. 4) showed a strong reduction in the number and percentage of cells that stain positive for CD19, a surface protein expressed on B lymphocytes. IHC analysis of a different portion of the paired tumor biopsy samples detected a decrease in cells staining positive for CD20, a second antigen expressed on B cells (FIGS. 5 A and B). In order to exclude that the reduction in CD20 staining was caused by obinutuzumab which may compete with anti-CD20 staining, the results were confirmed by staining with PAX5, a B cell specific transcription factor, which was also strongly reduced (FIGS. 5 C and D). Taken together, these results indicate an effective reduction of B cells in the tumor and adjacent normal tissue.

In conclusion, the above data from this sub-study strongly suggest that obinutuzumab is efficacious in mitigating ADAs.

Example 3

Clinical Evaluation of Feasibility, Safety and Pharmacodynamic Effect of Pre-Treatment with Obinutuzumab Prior to Therapy with CEA TCB An ongoing phase I clinical trial with CEA TCB (ClinicalTrials.gov identifier: NCT02324257) enrolls patients with locally advanced and/or metastatic CEA-positive solid tumors who have progressed on standard treatment, are intolerant to standard of care (SOC), and/or are non-amenable to SOC.

Parallel cohorts of patients are opened to enroll patients that will be pretreated with obinutuzumab. The main objective of these cohorts is to determine if pre-treatment with obinutuzumab prevents the formation of ADAs in patients treated subsequently with CEA TCB. Obinutuzumab and CEA TCB are administered intravenously (IV). The patients in the obinutuzumab pre-treatment cohorts receive 2000 mg of obinutuzumab, either 2000 mg of obinutuzumab IV on Day-13 or 1000 mg of obinutuzumab IV on two consecutive days, Day-13 and Day-12 (±2 days) before the Cycle 1 Day 1 (CD1) of CEA TCB administration. Pre-medication including analgesic, anti-histamine and corticosteroid is given prior to each obinutuzumab dosing. On C1D1, all patients receive a flat dose (depending on the dose cohort they are allocated to, as defined in the ongoing clinical trial) of CEA TCB over a minimum of 120-minute IV infusion. At subsequent cycles, all patients receive the same dose of CEA TCB, administered over a minimum of 90-minute IV infusion at C2D1 and over a minimum of 60-minute IV infusion from C3D1 onwards weekly (QW). The patients not receiving obinutuzumab pre-treatment receive CEA TCB administrations starting at C1D1 identically to the patients in the obinutuzumab pre-treatment cohorts. Blood samples are collected before and during the treatment period for the monitoring of B lymphocyte counts. B cell counts are obtained using flow cytometry and staining for CD19. Blood samples for PK to evaluate the serum levels of CEA TCB and for ADA determination are obtained at baseline and thereafter at each cycle of CEA TCB administration. The primary objectives for these cohorts of patients receiving obinutuzumab pre-treatment is the effect of obinutuzumab pretreatment in decreasing the rate of patients with positive Anti-Drug Antibodies (ADA) titer against CEA TCB at week 8 and/or delaying the time of onset of ADA against CEA TCB, and to evaluate the safety and tolerability of administration of obinutuzumab prior to treatment with CEA TCB. The study will also be looking at the characterization of the ADA directed against CEA TCB; it includes as well investigation and characterization of the B-cell depletion in tissue (tumor biopsies are undertaken at Baseline and at week 7 after CD1 with CEA TCB) and peripheral blood resulting from obinutuzumab pre-treatment.

Preliminary Results

CEA TCB is being tested in a EIH Study (ClinicalTrials.gov identifier: NCT02324257). As of 27 Oct. 2016 (ADA data cutoff), preliminary results from Study BP29541 show that in 40 of 77 patients (52%) anti-CEA TCB antibodies were detected, none of these patients received obinutuzumab pre-treatment, except for two patients with transient positive titers (one had a titer of 30 at Cycle 2 Day 1 but became then negative up to Cycle 24 and another one had a titer of 270 at Cycle 3 Day 1 and 90 at Cycle 4 Day 1 but became then negative up to Cycle 8). Except for these two patients, all the 38 other ADA-positive patients showed a persistent immune response. The intensity of ADA responses ranged from low to high titers (10-21870). 17 out of 38 persistent ADA-positive cases (45%) showed moderate ADA titers (≤810), while 21 out of 28 persistent ADA-positive cases (55%) showed high ADA titers (>810). The first onset of an immune response was observed after one dose of CEA TCB at day 8 (C2D pre-dose), however 3 patients had positive titers at Cycle 1 Day 1 pre-dose. Three patients with pre-existing ADAs were identified and in all other patients ADAs were treatment-induced. In 24 out of 38 patients (63%) with a persistent immune response, the sustained ADA presence correlated with total loss of exposure (ranges from Cycle 3 Day 1 and Cycle 13 Day 1 (PK data cutoff: 7 Nov. 2016)). So far no hypersensitivity reactions or signs and symptoms suggestive of hypersensitivity, or evidence of ADA-mediated adverse events have been reported in the 77 patients who received CEA TCB. The above-described clinical study with parallel cohorts of patients receiving obinutuzumab pre-treatment was initiated to explore the potential of obinutuzumab (Gazyva®/Gazyvaro®) given as a pre-treatment to administration of CEA TCB to attenuate development of anti-drug antibodies (ADAs). The study is ongoing. According to the preliminary data, as of the clinical cutoff date of 27 Oct. 2016 (ADA data cutoff), the 12 obinutuzumab pre-treated patients for which ADA data is available so far (2 of the patients only received obinutuzumab as they clinically deteriorated in the meantime and did not receive any CEA TCB infusion) remained free of ADAs against CEA TCB at the following time points: 1 patient up to C1, 1 patient up to C3, 1 patient up to C4, 1 patient up to C6, 1 patient up to C8, 1 patient up to C10, 2 patients up to C12, 1 patient up to C16, and 1 patient up to C25.

Eight out of sixty-five patients who were not pre-treated with obinutuzumab developed ADAs with titers of 10 to 810 after 1 dose of CEA TCB. Based on a preliminary safety analysis, the safety profile of obinutuzumab pre-treatment was acceptable in patients with locally advanced and/or metastatic solid tumors. Patients receiving obinutuzumab pre-treatment prior to receiving weekly doses of CEA TCB did not experience unexpected adverse events (AEs) compared to the ones who did not receive obinutuzumab pre-treatment. Flow cytometric analysis of peripheral blood indicated complete depletion of B cells after obinutuzumab treatment. Before the start of treatment with CEA TCB (C1D1), no B cells were detectable in the collected blood samples. The tumor biopsy samples from obinutuzumab pre-treatment patients were undertaken at Baseline prior to receiving obinutuzumab pre-treatment and on treatment at Cycle 7 Day 1. The analyses are still ongoing.

Example 4

Assessment of the Anti-Tumour Activity and Cytokine Release Mediated by CD20XCD3 bsAB±Obinutuzumab Pre-Treatment (Gpt) in Fully Humanized Mice We investigated whether Gpt could prevent the cytokine release associated with the first administration of CD20XCD3 bsAB in fully humanized NOG mice.

Figure 7A:
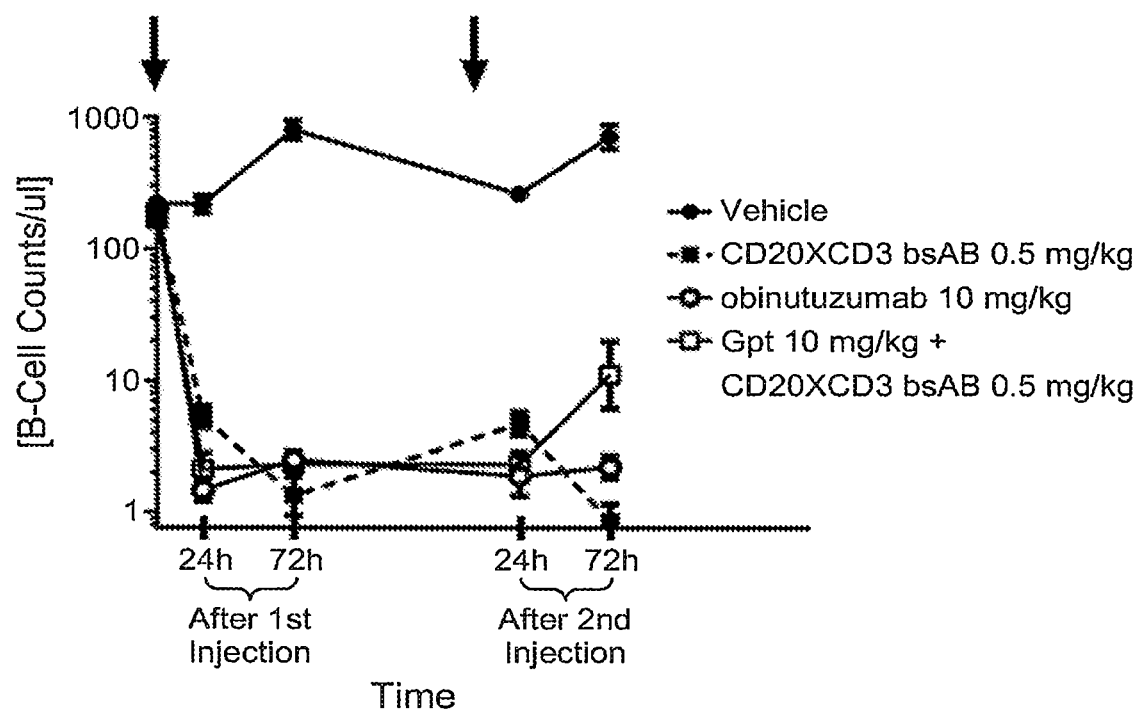
FIGS. 7A and 7B. B cell and T cell counts in the peripheral blood in the different treatment groups. Flow cytometry analysis of CD19$^+$ B cells (FIG. 7A) and CD3$^+$ T cells (FIG. 7B) in the peripheral blood of vehicle and CD20XCD3 bsAB-treated fully humanized NOG mice, 24 hours and 72 hours after first and second CD20XCD3 bsAB administration. Black arrows indicate days of CD20XCD3 bsAB administration.
Figure 7B:
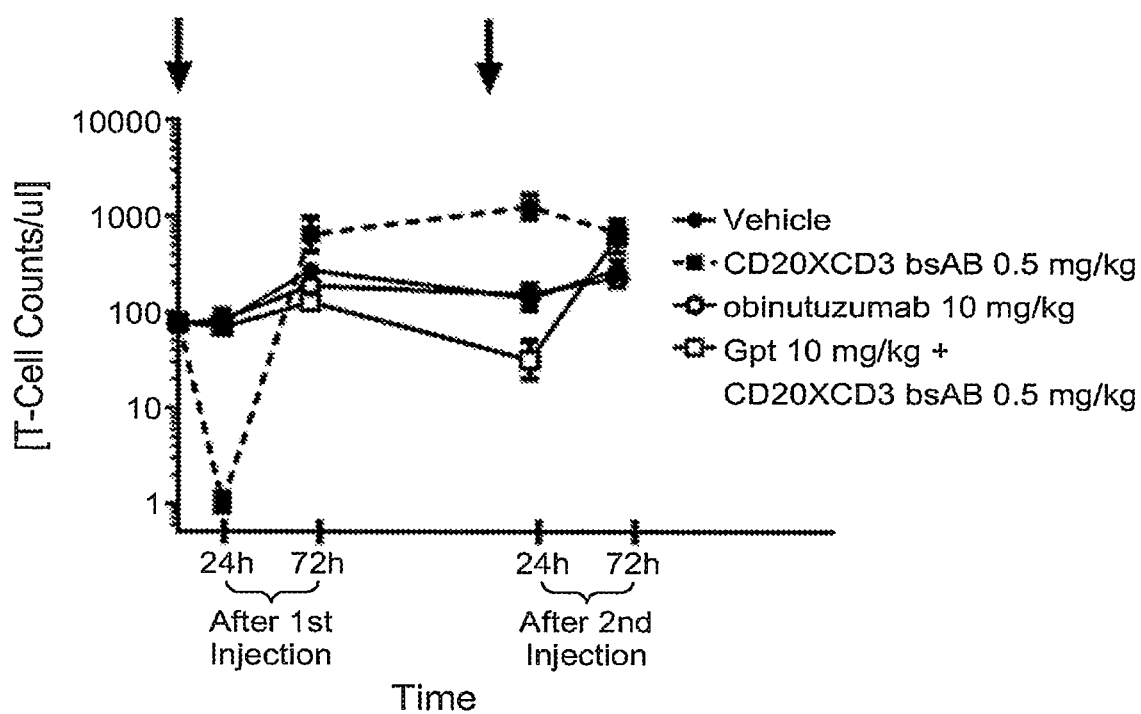

All treatment options (obinutuzumab, CD20XCD3 bsAB and Gpt+CD20XCD3 bsAB) led to efficient peripheral blood B-cell depletion detected already 24 hours after the first therapy administration (FIG. 7A). T cell counts revealed a transient decrease in the peripheral blood 24 hours after the first administration of CD20XCD3 bsAB but not following obinutuzumab or Gpt+CD20XCD3 bsAB (FIG. 7B). Therefore, when administered prior to CD20XCD3 bsAB, a single administration of obinutuzumab abrogates CD20XCD3 bsAB-mediated T cell decrease in the peripheral blood.

Figure 8A:
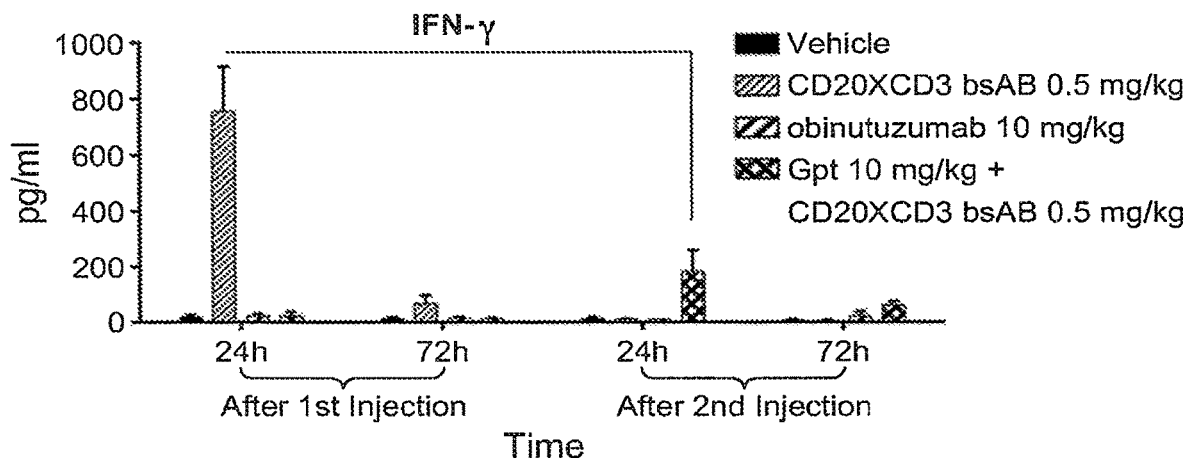
FIGS. 8A-8C. Cytokines released in peripheral blood among the different treatment groups. Multiplex analysis of cytokines in blood of vehicle and treated mice, 24 hours and 72 hours after the first and second administration of CD20XCD3 bsAB. Histogram bars represent the mean of 5 animals with error bars indicating the standard deviation. Representative graphs for IFNγ (FIG. 8A), TNFα (FIG. 8B) and IL-6 (FIG. 8C) are shown. Compare the cytokine release of the first injection of CD20XCD3 bsAB with and without obinutuzumab pre-treatment (bars to be compared are indicated by connecting lines).
Figure 8B:
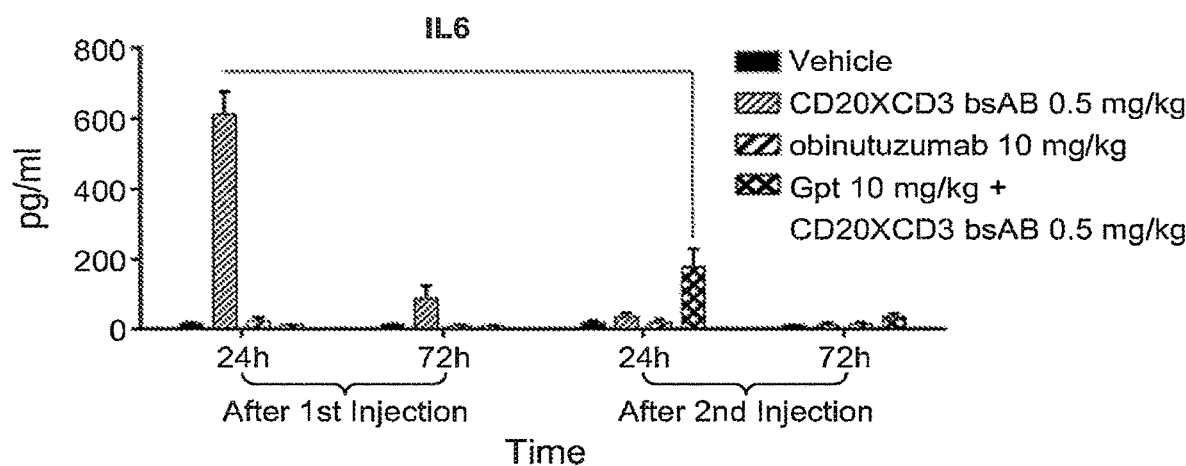
Figure 8C:
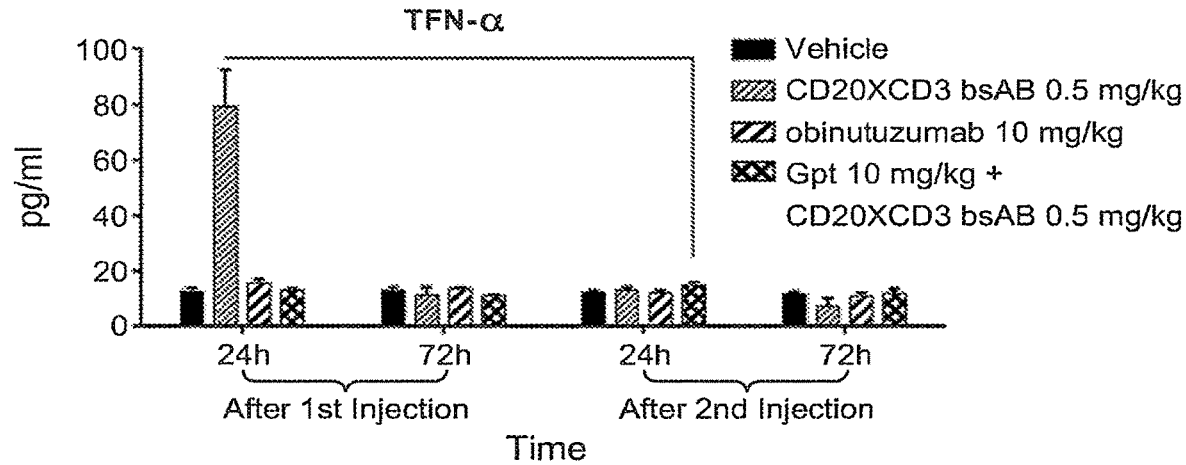

The analysis of cytokines released in blood of treated mice in the different experimental groups revealed that CD20XCD3 bsAB treatment induces a transient elevation of several cytokines in the blood, with a peak at 24 hours after the first administration and a return to near baseline levels by 72 hours (FIG. 8). MIP-1b, IL-5, IL-10, MCP-1 show a similar trend to IFNγ, TNFα and IL-6 (not shown). Gpt strongly reduced the cytokine release in the peripheral blood associated with the first CD20XCD3 bsAB injection (Table 2).

TABLE 2

Cytokines Released in the Peripheral Blood of Fully Humanized NOG Mice upon CD20XCD3 bsAB and Gpt + CD20XCD3 bsAB Treatments

| | Treatment | | |
|---|---|---|---|
| Cytokine | Vehicle (pg/ml) | CD20XCD3 bsAB (pg/ml) | Gpt + CD20XCD3 bsAB (pg/ml) |
| IFN-g | 18.50 (18.07) | 756.95 (357.30) | 183.134 (171.91) |
| TNF-a | 12.47 (2.95) | 79.56 (28.98) | 14.89 (2.56) |
| IL-6 | 15.39 (7.15) | 613.27 (140.60) | 178.34 (117.85) |
| IL-8 | 11.44 (2.64) | 292.68 (132.36) | 150.58 (96.76) |

TABLE 2-continued

Cytokines Released in the Peripheral Blood of Fully
Humanized NOG Mice upon CD20XCD3 bsAB and
Gpt + CD20XCD3 bsAB Treatments

| | Treatment | | |
|---|---|---|---|
| Cytokine | Vehicle (pg/ml) | CD20XCD3 bsAB (pg/ml) | Gpt + CD20XCD3 bsAB (pg/ml) |
| MIP-1b | 272.70 (97.05) | 2129.44 (132.36) | 338.95 (71.25) |
| MCP-1 | 73.49 (13.89) | 2146.31 (672.69) | 393.29 (188.86) |
| IL-10 | 223.48 (62.48) | 15,278.89 (6584.50) | 945.04 (604.89) |
| IL-4 | 0.75 (0.14) | 1.99 (0.77) | 0.81 (0.02) |
| G-CSF | 14.60 (5.14) | 21.23 (16.36) | 3.82 (2.02) |
| GM-CSF | 945.97 (155.74) | 1207.48 (299.83) | 626.18 (282.46) |
| IL-5 | 10.42 (3.35) | 162.33 (140.82) | 13.58 (8.44) |
| IL-2 | 19.1 (8.42) | 369.70 (360.64) | 19.59 (17.64) |
| IL-13 | 5.39 (3.66) | 15.42 (11.18) | 2.96 (1.11) |
| IL-1b | 1.48 (0.2) | 6.40 (1.94) | 3.47 (1.88) |
| IL-7 | 6.98 (0) | 4.27 (2.55) | 6.17 (1.79) |
| IL-12p40 | 43.59 (19.45) | 51.31 (23.12) | 17.05 (2.62) |
| IL-17 | 194.40 (96.32) | 274.79 (112.20) | 73.33 (32.43) |

Notes:
Data are displayed as the arithmetic mean (SD).
N = 5 in both treatments.

Figure 9:
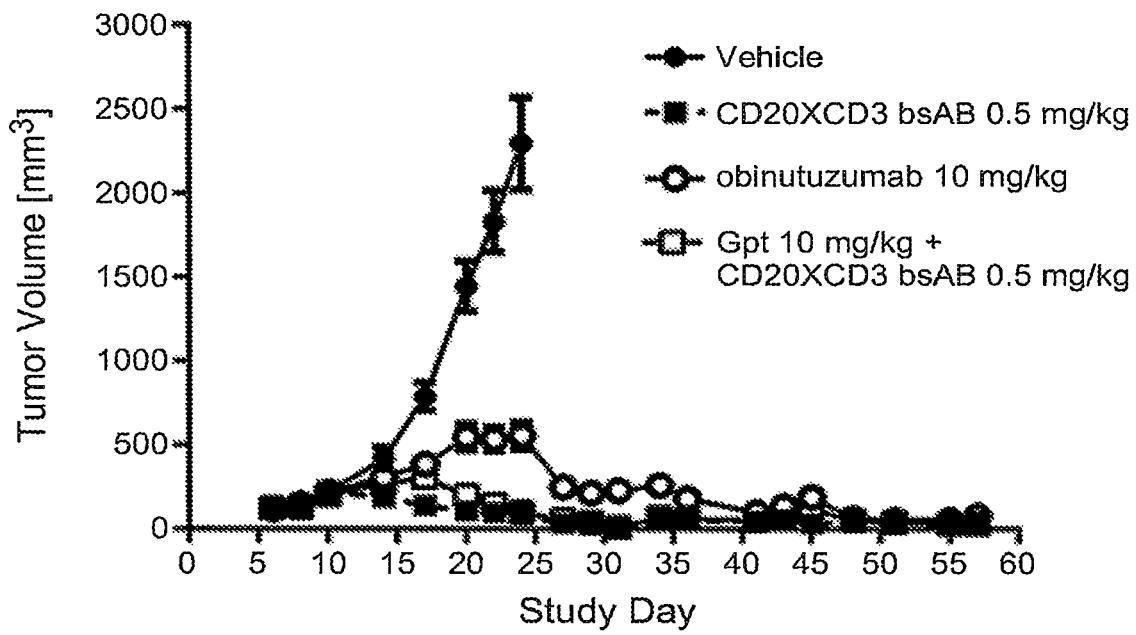
FIG. 9. Anti-tumour activity of CD20XCD3 bsAB, obinutuzumab, and obinutuzumab pretreatment (Gpt)+ CD20XCD3 bsAB. Anti-tumour activity of CD20XCD3 bsAB and obinutuzumab as monotherapy or Gpt+ CD20XCD3 bsAB in fully humanized NOG mice. Black arrow indicates start of therapy. (8<n<10). Tumour model: WSU-DLCL2.

The anti-tumour activity of CD20XCD3 bsAB was not affected by pre-treatment with obinutuzumab (FIG. 9). Obinutuzumab treatment, as monotherapy, showed a strong anti-tumour activity, although with slower kinetics when compared to CD20XCD3 bsAB in this tumour and mouse model.

The data therefore indicate that Gpt reduces the cytokine release associated with the first CD20XCD3 bsAB injection, however, despite targeting the same antigen on tumour cells, the anti-tumour activity of CD20XCD3 bsAB is not affected by Gpt.

Example 5

Obinutuzumab Pre-Treatment Study in Cynomolgus Monkeys

A mechanistic study (non-GLP) in male cynomolgus monkeys was performed to investigate the effects of pre-treatment with obinutuzumab on response to CD20XCD3 bsAB at doses of 0.1, 0.3 and 1 mg/kg) (Table 3). In this study, 6 naïve cynomolgus male monkeys/group (4 for Group 1), received an IV dose of either control article 1 (Groups 1 and 2) or obinutuzumab (50 mg/kg, Groups 3, 4, 5), followed 4 days later by treatment with control article 2 (Group 1), CD20XCD3 bsAB, 0.1 mg/kg (Group 2, Group 3), CD20XCD3 bsAB, 0.3 mg/kg (Group 4) or CD20XCD3 bsAB, 1 mg/kg (Group 5). Four days between the obinutuzumab and CD20XCD3 bsAB dosing was considered sufficient to allow depletion of B cells in peripheral blood, lymph nodes and spleen by obinutuzumab. On Day 12, 2 animals from Group 1, and 4 from Groups 2 to 5 were necropsied (terminal necropsy). Two animals from each group were retained for an 8-week recovery period.

TABLE 3

Study Design: Obinutuzumab Pre-Treatment in Cynomolgus Monkeys.

| Group No. | Test Article | Dosing Day | Dose Level (mg/kg) | Number of Males | |
|---|---|---|---|---|---|
| | | | | Main[a] | Recovery[b] |
| 1 | Control Article 1 | 1 | 0 | 2 | 2 |
| | Control Article 2 | 5 | 0 | | |
| 2 | Control Article 1 | 1 | 0 | 4 | 2 |
| | CD20XCD3 bsAB | 5 | 0.1 | | |
| 3 | obinutuzumab | 1 | 50 | 4 | 2 |
| | CD20XCD3 bsAB | 5 | 0.1 | | |
| 4 | obinutuzumab | 1 | 50 | 4 | 2 |
| | CD20XCD3 bsAB | 5 | 0.3 | | |
| 5 | obinutuzumab | 1 | 50 | 4 | 2 |
| | CD20XCD3 bsAB | 5 | 1 | | |

Note:
Control Article 1 = Control for obinutuzumab: Control article 2 = Control for CD20XCD3 bsAB.
[a]Main group animals, terminal necropsy Day 12.
[b]Recovery animals, necropsy week 8 (Day 61).

The following data are available from this study:
Following pretreatment with obinutuzumab (50 mg/kg, Gpt), IV administration of CD20XCD3 bsAB was tolerated up to 1 mg/kg, the highest tested dose. Clinical signs, observed with CD20XCD3 bsAB alone (emesis, hunched posture and hypoactivity) were markedly reduced by Gpt at all doses of CD20XCD3 bsAB.
CD20XCD3 bsAB administration alone resulted in the reduction of B lymphocytes and the activation and expansion of T-lymphocyte (CD4+ and CD8+) subsets and NK cells. In contrast, the administration of obinutuzumab prior to CD20XCD3 bsAB administration resulted in B-lymphocyte depletion, as well as the subsequent attenuation of T-lymphocyte activation as demonstrated by reductions in the transient reductions of lymphocyte and monocyte populations after CD20XCD3 bsAB administration, as well as reductions in T-cell activation marker up-regulation and expansion, relative to changes present for animals that were treated with CD20XCD3 bsAB alone.
The release of IFNγ, IL-8, TNFα, IL-2 and IL-6, 4-hour post-0.1 mg/kg CD20XCD3 bsAB treatment, was markedly reduced in the Gpt groups. Similarly, low levels of cytokine release were noted at higher doses of CD20XCD3 bsAB in Gpt groups (FIG. 10).
CD20XCD3 bsAB-related histopathologic findings were restricted to the lymphoid organs (e.g. decreased cellularity specifically affecting the CD20-positive cells was present in the lymphoid follicles of the spleen). The CD20-positive cell decreases were almost completely reversed after the 8 week treatment-free period. No other histopathological changes were present, including in brain, spinal cord and sciatic nerve in monkeys treated with CD20XCD3 bsAB at 0.1 mg/kg and in animals administered CD20XCD3 bsAB at 0.1, 0.3 or 1 mg/kg following Gpt.

Example 6

Clinical Evaluation of Safety, Tolerability and Pharmacokinetics of CD20XCD3 bsAB with Obinutuzumab Pre-Treatment in Patients with r/r NHL A phase I dose-escalation study will be performed, the primary objectives of which include evaluation of the safety, tolerability and pharmacokinetics CD20XCD3 bsAB with obinutuzumab pre-treatment in patients with relapsed/refractory (r/r) NHL.

The study will enroll patients with r/r NHL, whose tumours are expected to express CD20 in B cells. Patients with CLL will not be enrolled. Patients are expected to have relapsed after or failed to respond to at least one prior treatment regimen.

Obinutuzumab and CD20XCD3 bsAB will be administered intravenously (IV).

Prior to administration of obinutuzumab and CD20XCD3 bsAB, premedication with corticosteroids (e.g., 20 mg IV dexamethasone, 80 mg IV methylprednisone, or equivalent) will be administered, along with anti-histamines and acetaminophen. Prophylactic measures for other events, such as tumor lysis syndrome will also be either recommended as needed or mandated.

CD20XCD3 bsAB will be initiated on Cycle 1/Day 1 (C1/D1) as a single agent by intravenous (IV) infusion, following pre-treatment with a single dose of obinutuzumab (1000 mg; IV) seven days in advance (Cycle 1/Day −7) of the first CD20XCD3 bsAB dose (Cycle 1/Day 1). The anticipated starting dose of CD20XCD3 bsAB will be 5 micrograms (flat dosing). All dosing cycles are 14 days (Q2W) long, with one additional dose given in Cycle 1 only. Thus, the dosing scheme is for administration of CD20XCD3 bsAB on Days 1 and 8 in Cycle 1 (C1/D1; C1/D8), followed by dosing in all subsequent Cycles on Day 1 only (Q2W) for a total of 12 cycles (24 weeks) of treatment or until unacceptable toxicity or progression occurs.

Blood samples will be collected at appropriate timepoints to determine the relevant PK properties of CD20XCD3 bsAB, as well as a range of PD markers in blood, to assess e.g. magnitude and kinetics of B-cell depletion following Gpt and CD20XCD3 bsAB dose initiation, T-cell phenotypes, and to assess soluble mediator release (cytokines and chemokines), following administration of Gpt and CD20XCD3 bsAB at selected timepoints.

Example 7

Comparison of the Anti-Tumor Activity of Step-Up Dosing (SUD) and Obinutuzumab Pretreatment (Gpt)

As shown in this example, Gpt is a superior approach to step-up dosing (SUD) in terms of anti-tumor activity and T-cell redistribution in peripheral tissues.

Fully humanized NOG female mice (Taconic) were generated in house. Age was 20 weeks at start of experiment. All mice were injected s.c. on study day 0 with $1.5 \times 10^6$ of WSU-DLCL2 cells (human diffuse large B cell lymphoma). Seven days after tumor cell administration (Day 7), mice were administered i.v. with the first treatment as indicated in Table 4. The second treatment as indicated in Table 4 was administered on Day 14.

Figure 11:
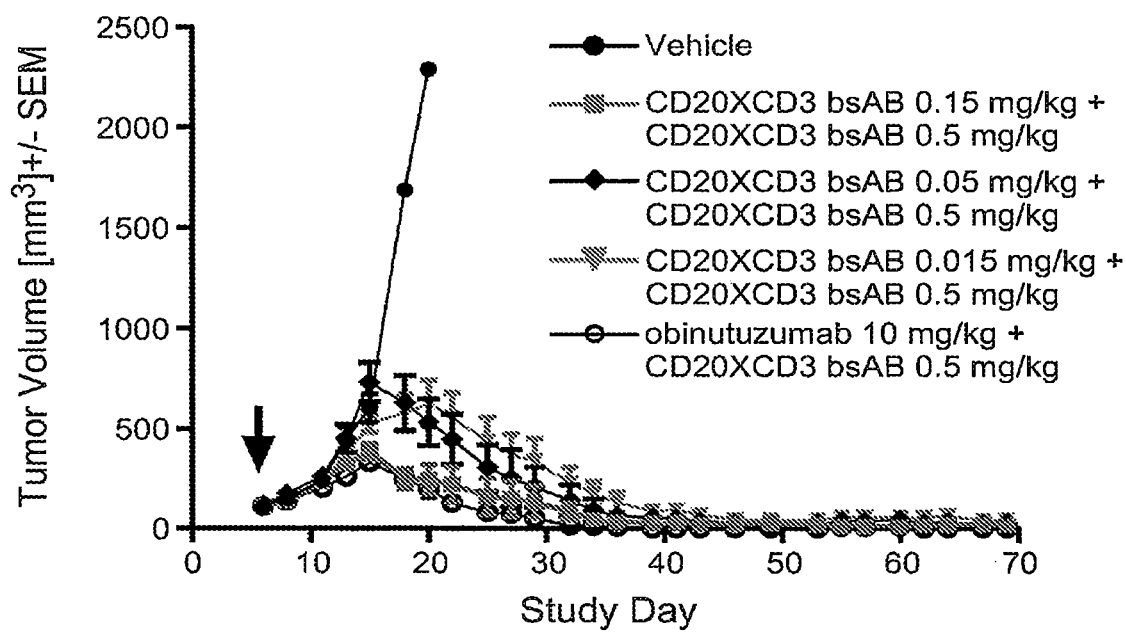
FIG. 11. Anti-tumor activity upon step-up dosing of CD20XCD3 bsAB and obinutuzumab pretreatment (Gpt) in fully humanized NOG mice bearing WSU-DLCL2 tumors. Mice received a first therapy (arrow) either as a fractionated dose of CD20XCD3 bsAB (0.15, 0.05, 0.015 mg/kg IV) or Gpt (10 mg/kg obinutuzumab), followed by weekly intravenous injections of CD20XCD3 bsAB at 0.5 mg/kg (full dose) for 9 treatment cycles (i.e., 9 weeks). In the vehicle group, one single mouse is shown from day 18. For the other groups, n=9 or 10. Tumor model: WSU-DLCL2 injected subcutaneously. [CD20XCD3 bsAB 0.05 mg/kg+ CD20XCD3 bsAB 0.05 mg/kg] vs [obinutuzumab 10 mg/kg+CD20XCD3 bsAB 0.5 mg/kg] *p=0.018 (One-way ANOVA analysis of sAUC with Dunnet's method).
Figure 12A:
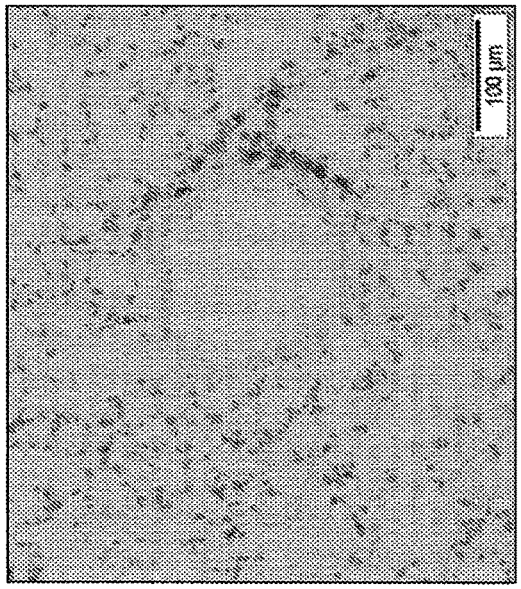
FIGS. 12A-12H. T-cell staining in lungs from fully humanized NOG mice bearing WSU-DLCL2 tumors, (FIGS. 12A-12D) 7 days after the first treatment, and (FIGS. 12E-12H) 24 hours after the second treatment. Treatment groups are as follows (single treatment or first+second treatment)
Figure 12B:
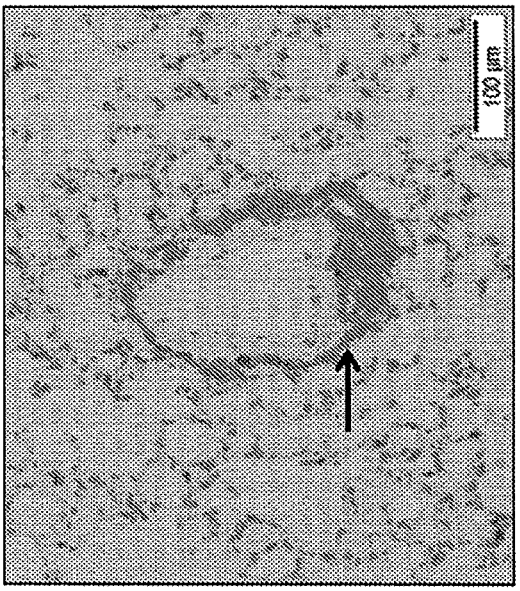
Figure 12C:
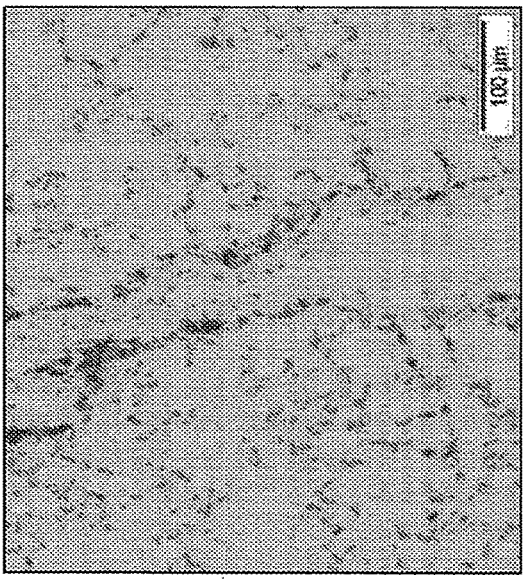
Figure 12D:
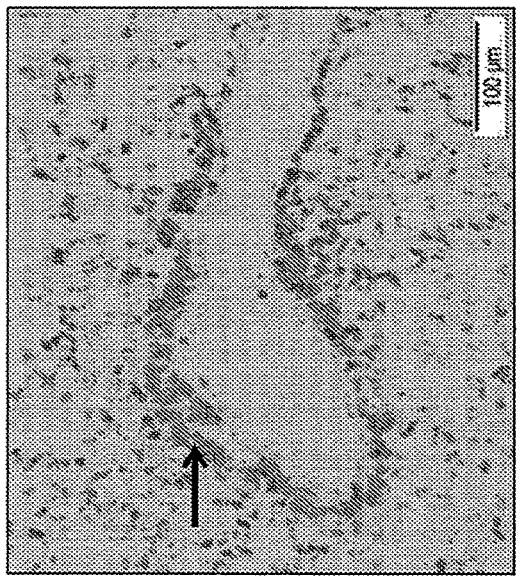
Figure 12E:
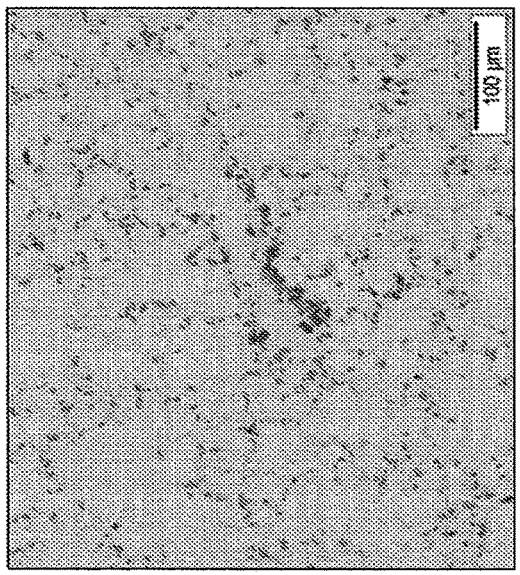
Figure 12F:
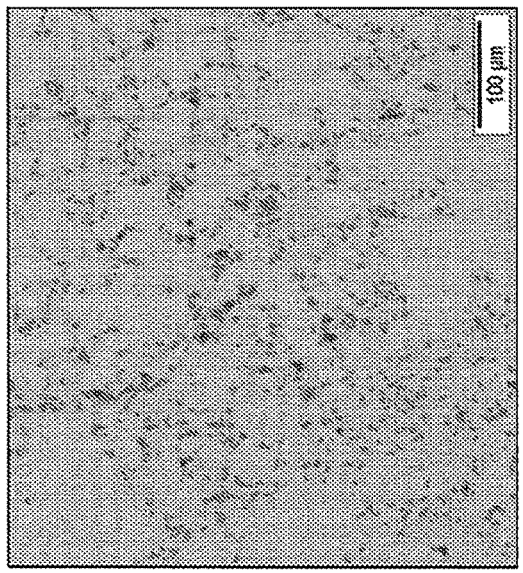
Figure 12G:
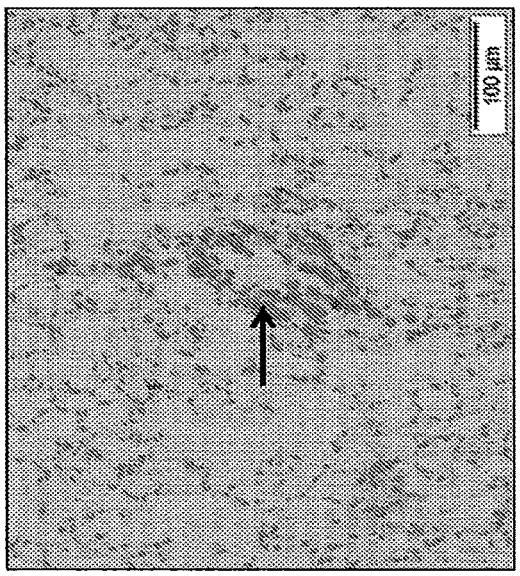
Figure 12H:
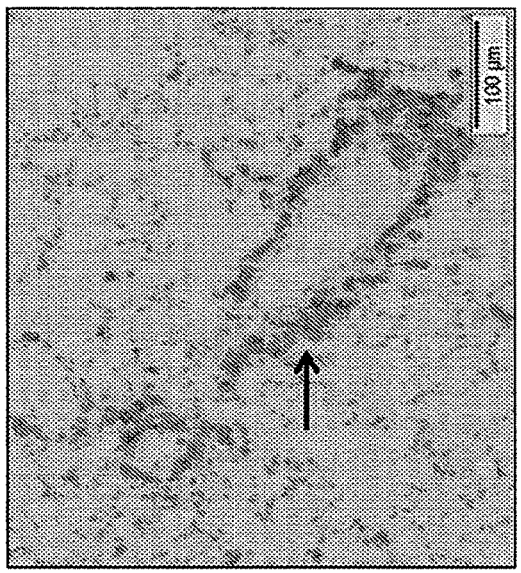

Following 9 weeks of CD20XCD3 bsAB treatment, the number of tumor-free mice at study termination (Day 69) was higher when treatment was preceded by obinutuzumab (Gpt) than when preceded by any of three single fractionated doses of CD20XCD3 bsAB (SUD) (FIG. 11, Table 4).

TABLE 4

Anti-tumor activity upon step-up dosing of CD20XCD3 BSAB and obinutuzumab pretreatment (Gpt) in fully humanized NOG mice bearing WSU-DLCL2 tumors.

| 1st Treatment (Dose) | 2nd Treatment (Dose) | Tumor-Free Mice at Termination (Day 69) |
| --- | --- | --- |
| CD20XCD3 bsAB (0.15 mg/kg) | CD20XCD3 bsAB (0.5 mg/kg) | 4/9 |
| CD20XCD3 bsAB (0.05 mg/kg) | CD20XCD3 bsAB (0.5 mg/kg) | 2/9 |
| CD20XCD3 bsAB (0.015 mg/kg) | CD20XCD3 bsAB (0.5 mg/kg) | 3/10 |
| Obinutuzumab (10 mg/kg) | CD20XCD3 bsAB (0.5 mg/kg) | 7/10 |

In addition to superior anti-tumor efficacy, seven days following the first (pre-)treatment (corresponding to study Day 14), an increase in perivascular CD3 positive T cells was observed in the lungs of CD20XCD3 bsAB-treated mice (full dose or fraction of the full dose) but not with obinutuzumab (10 mg/kg)-treated mice (FIG. 12 A-D). The same was true for the analysis at a later time point corresponding to 24 hours after the second treatment (study Day 15) (FIG. 12 E-H).

For this experiment, mice were generated and injected with tumor cells as described above. Seven days after tumor cell administration, mice were administered i.v. with the treatments as indicated in Table 5A.

Four animals/group were sacrificed 7 days after receiving a single dose of CD20XCD3 bsAB, obinutuzumab or vehicle. The remaining four animals/group were sacrificed 24 hours after receiving the second treatment on Day 14, as indicated in Table 5B. Controls received the vehicle buffer.

Lung, liver and kidney were collected at necropsy and serial sections were stained with immunohistochemistry (IHC) for human CD3 according to established protocols. Sections stained immunohistochemically for CD3 were evaluated blinded by a Board Certified Veterinary Pathologist using a score from 0 (no or rare CD3 positive cells in the section) to 3 (many CD3 positive cells surrounding the vessels/ducts).

Representative results from lung sections are shown in FIG. 12, Table 5.

A dose dependent increase in perivascular CD3 positive T cells was observed in the lung of mice seven days after single dose of ≥0.05 mg/kg CD20XCD3 bsAB (full dose or fraction of the full dose), but not in obinutuzumab-treated mice (FIG. 12 A-D, Table 5A).

TABLE 5A

Lung IHC for CD3 - animals sacrificed 7 days after first treatment. Table shows the average score of perivascular CD3 positive T cells in the lung (performed by blinded pathologist analysis).

| Treatment (dose) | Average Score |
| --- | --- |
| Vehicle (-) | 0.75 |
| CD20XCD3 bsAB (0.5 mg/kg) | 3 |
| CD20XCD3 bsAB (0.15 mg/kg) | 1.75 |
| CD20XCD3 bsAB (0.05 mg/kg) | 1.5 |
| CD20XCD3 bsAB | |

TABLE 5A-continued

Lung IHC for CD3 - animals sacrificed 7
days after first treatment. Table shows
the average score of perivascular
CD3 positive T cells in the lung
(performed by blinded
pathologist analysis).

| Treatment (dose) | Average Score |
|---|---|
| (0.015 mg/kg) | 0.5 |
| Obinutuzumab (10 mg/kg) | 0.25 |

An increase in perivascular T cells was also observed in mice 24 hours after a single or a repeated dose of CD20XCD3 bsAB, but not in mice pretreated with obinutuzumab (FIG. 12 E-H, Table 5B).

TABLE 5B

Lung IHC for CD3 - nimals sacrificed 24
hours after 2nd treatment. Table
shows the average score of perivascular
CD3 positive T cells in the lung
(performed by blinded pathologist analysis).

| First Treatment (dose) | Second Treatment (dose) | Average Score |
|---|---|---|
| Vehicle (-) | Vehicle (-) | 0 |
| Vehicle (-) | CD20XCD3 bsAB (0.5 mg/kg) | 1.5 |
| CD20XCD3 bsAB (0.15 mg/kg) | CD20XCD3 bsAB (0.5 mg/kg) | 1.7 |
| CD20XCD3 bsAB (0.05 mg/kg) | CD20XCD3 bsAB (0.5 mg/kg) | 2.5 |
| CD20XCD3 bsAB (0.015 mg/kg) | CD20XCD3 bsAB (0.5 mg/kg) | 2.3 |
| Obinutuzumab (10 mg/kg) | CD20XCD3 bsAB (0.5 mg/kg) | 0.5 |

In animals receiving a single dose of 0.5 mg/kg of CD20XCD3 bsAB sacrificed 24 hours after treatment, margination and adhesion of CD3 positive T cells was present in lung vessels (FIG. 13), suggesting an early activation of T cells with transmigration into the perivascular space.

In conclusion, single or repeated treatment with full dose or fraction of the full dose of CD20XCD3 bsAB resulted in an increase in CD3 positive T cells compared to controls with perivascular distribution in the lung, perivascular/periductal in the liver and in the glomeruli in the kidneys (liver and kidney data not shown). These changes were not occurring in animals pretreated with obinutuzumab.

Example 8

Comparison of CD20XCD3 bsAB Exposure in Cynomolgus Monkeys with or without Gpt

In this example, Gpt is shown to increase CD20XCD3 bsAB exposure. Cynomolgus monkeys were administered a single IV dose of 100-1000 µg/kg CD20XCD3 bsAB with or without obinutuzumab pretreatment (Gpt) (50 mg/kg, 4 days prior to CD20XCD3 bsAB administration).

Figure 14:
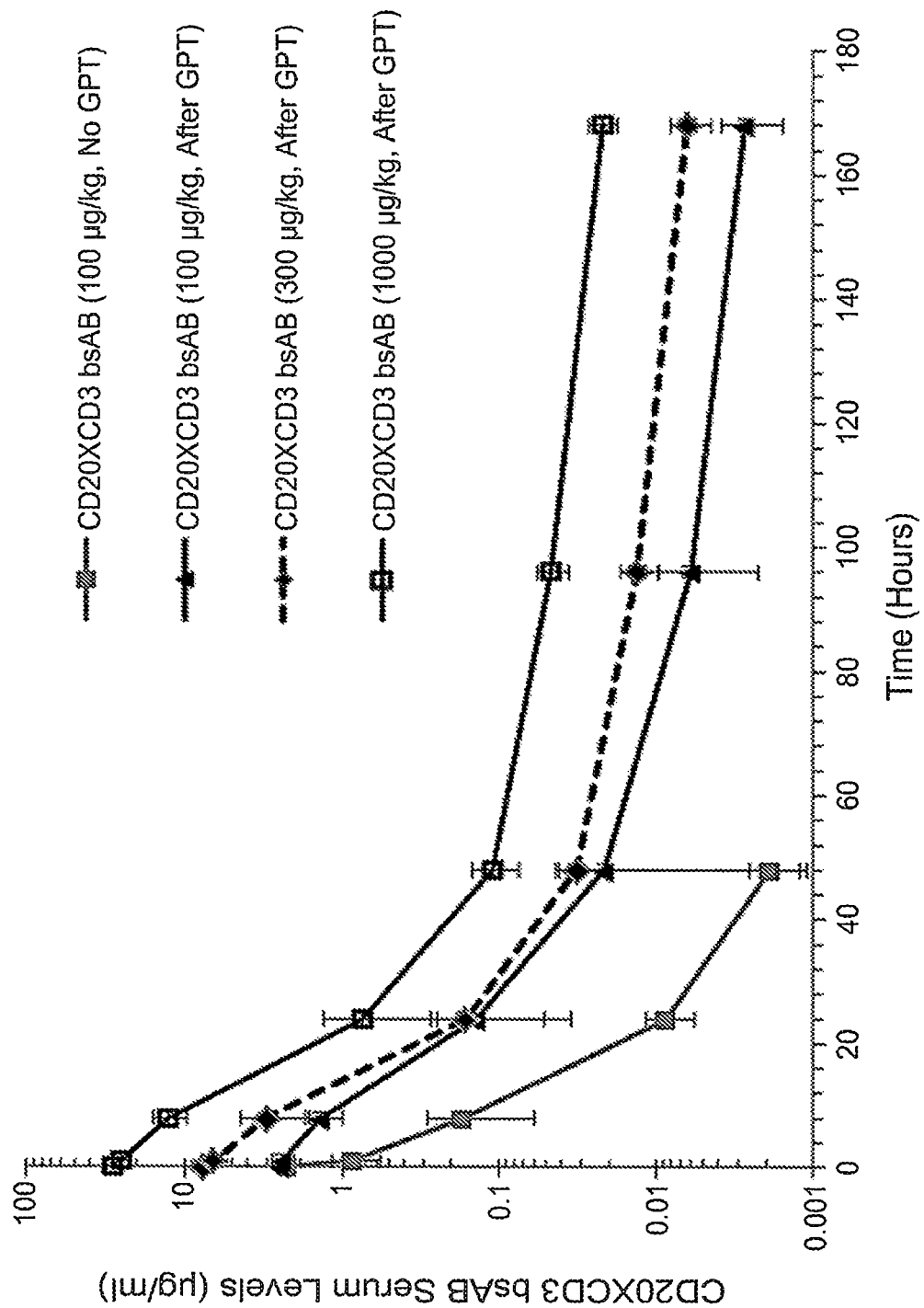
FIG. 14. Serum concentration-time curves of CD20XCD3 bsAB following a single intravenous administration with or without obinutuzumab Pretreatment in cynomolgus monkeys. Cynomolgus monkeys were administered a single IV dose of 100-1000 μg/kg CD20XCD3 bsAB with or without obinutuzumab pretreatment (Gpt) (50 mg/kg, 4 days prior to CD20XCD3 bsAB administration). Six animals are represented in each dose group and the data is presented as mean±SD.

The increased exposure resulting from the depletion of CD20+B cells by obinutuzumab (50 mg/kg) is shown by the CD20XCD3 bsAB serum levels following a single dose of 100 µg/kg CD20xCD3 bsAB with or without Gpt (FIG. 14). Clearance of CD20XCD3 bsAB following Gpt was markedly reduced to about one fourth of the clearance observed in the group without Gpt (Table 6). By the time of CD20XCD3 bsAB dosing, B cells were reduced by Gpt to about 1-5% of baseline levels. The reduction in clearance is consistent with the Gpt-induced B-cell depletion and the resulting reduction of target-mediated clearance from B-cell binding.

Following Gpt, clearance and the central volume of distribution (Vc) were independent of dose in the dose range studied, with clearance values around 90 mL/day/kg and Vc values around 40 mL/kg, which is similar to the serum volume.

TABLE 6

Mean Pharmacokinetic parameters of CD2OXCD3 bsAB following a single intravenous administration with or without obinutuzumab pretreatment in cynomolgus monkeys.

| Dose (m/kg) | Obinutuzumab pretreatment | CL (mL/day/kg) | $V_c$ (mL/kg) | $T_{1/2}{}^a$ (h) | $C_{max}$ (µg/mL) | $AUC_{inf}$/Dose (µg · h/mL/µg/kg) |
|---|---|---|---|---|---|---|
| 100 | No | 384 (27.7) | 43.2 (16.8) | 7.53 (50.3) | 2.22 (17.3) | 0.0679 (36.3) |
| 100 | Yes | 81.7 (22.4) | 41.1 (13.6) | 67.7 (34.0) | 2.56 (12.5) | 0.308 (25.1) |
| 300 | Yes | 110 (28.8) | 37.9 (5.2) | 53.4 (10.4) | 7.63 (7.8) | 0.234 (29.4) |
| 1000 | Yes | 87.5 (19.0) | 34.9 (10.0) | 54.6 (17.6) | 28.7 (9.8) | 0.283 (19.7) |

$AUC_{inf}$ = area under the concentration-time curve from Time 0 to infinity;

CL = clearance;

$C_{max}$ = maximum concentration;

$T_{1/2}$ = half-life;

$V_c$ = central volume of distribution.

Notes:

Cynomolgus monkeys were administered a single IV dose of 100-1000 µg/kg CD2OXCD3 bsAB with or without obinutuzumab pretreatment (Gpt) (50 mg/kg, 5 days prior to CD2OXCD3 bsAB administration) in a Mechanistic Safety Study. Values are averages of six animals per group ( ± % CV).

[a] Apparent $T_{1/2}$ (due to non-linear pharmacokinetics)

Example 9

Obinutuzumab Pre-Treatment to Avoid Cytokine Release after Adoptive T Cell Therapy with CAR-T Cells Cytokine release syndrome (CRS) is a very frequent phenomenon following treatment with CD19 CAR-T cells as well as CAR-T cells directed against CD20 or CD22 that can result in lethal side effects. Strategies to avoid or reduce CRS focus on various aspects of CAR-T therapy (reviewed in Xu and Tang, Cancer Letters (2014) 343, 172-178).

We suggest a novel approach to avoid CRS following treatment with CAR-T cells in B cell proliferative disorders, by depletion of peripheral and malignant B cells using obinutuzumab pre-treatment.

For this purpose, patients with a B-cell proliferative disorder (e.g. NHL) are randomized into an obinutuzumab pre-treatment arm and a control arm without obinutuzumab pre-treatment. The patients in the obinutuzumab pre-treatment arm receive 1 g of obinutuzumab, administered on Day −7 (+/−2 days) before administration of CD19, CD20 or CD22 CAR-T cells.

Patients are infused with autologous T cells transduced with a CAR lentiviral vector at an appropriate dose for the specific CAR-T cell used, the patient and the disease to be treated (e.g. $0.76 \times 10^6$ to $20.6 \times 10^6$ CAR-T cells per kilogram of body weight as described in Maude et al., N Engl J Med (2014) 371, 1507-1517; $1.4 \times 10^6$ to $1.2 \times 10^7$ CAR-T cells per kilogram of body weight as described in Grupp et al., New Engl J Med (2013) 368, 1509-1518; or $0.14 \times 10^8$ to $11 \times 10^8$ CAR-T cells as described in Porter et al., Sci Transl Med (2015) 7, 303ra139). Patients are monitored for a response, toxic effects, and the expansion and persistence of circulating CAR-T cells.

Pre-medication is given prior to each obinutuzumab dosing. Blood samples are collected before and during the treatment period for the monitoring of B lymphocyte counts. B cell counts are obtained using flow cytometry and staining for CD19. In addition, incidence of CRS is screened by measuring cytokines including IL-6.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a carcinoembryonic antigen (CEA)-expressing cancer in a subject, the method comprising a treatment regimen comprising:
   (i) administering to the subject a Type II anti-CD20 antibody comprising a heavy chain variable region comprising a heavy chain CDR (HCDR) 1 comprising the amino acid sequence of SEQ ID NO: 4, an HCDR2 comprising the amino acid sequence of SEQ ID NO: 5, and an HCDR3 comprising the amino acid sequence of SEQ ID NO: 6; and a light chain variable region comprising a light chain CDR (LCDR) 1 comprising the amino acid sequence of SEQ ID NO: 7, an LCDR2 comprising the amino acid sequence of SEQ ID NO: 8, and an LCDR3 comprising the amino acid sequence of SEQ ID NO: 9, and consecutively, after a period of time,
   (ii) administering to the subject a therapeutic agent comprising a bispecific antibody, wherein the bispecific antibody specifically binds to CD3 and CEA,
   wherein the period of time between step (i) and step (ii) is sufficient for the Type II anti-CD20 antibody to reduce the number of B cells in the subject.

2. The method of claim 1, wherein the treatment regimen effectively reduces the formation of anti-drug antibodies (ADAs) in the subject against the therapeutic agent, as compared to a corresponding treatment regimen without the administration of the Type II anti-CD20 antibody.

3. The method of claim 1, wherein the treatment regimen effectively reduces cytokine release in the subject associated with the administration of the therapeutic agent, as compared to a corresponding treatment regimen without the administration of the Type II anti-CD20 antibody.

4. The method of claim 1, wherein the Type II anti-CD20 antibody comprises a heavy chain variable region comprising the amino acid sequence of SEQ ID NO: 10 and a light chain variable region comprising the amino acid sequence of SEQ ID NO: 11.

5. The method of claim 1, wherein the Type II anti-CD20 antibody is an IgG antibody, and wherein at least about 40% of the N-linked oligosaccharides in the Fc region of the Type II anti-CD20 antibody are non-fucosylated.

6. The method of claim 4, wherein the Type II anti-CD20 antibody is obinutuzumab.

7. The method of claim 1, wherein the bispecific antibody comprises a CEA-binding moiety comprising a heavy chain variable region comprising an HCDR 1 comprising the amino acid sequence of SEQ ID NO: 14, an HCDR2 comprising the amino acid sequence of SEQ ID NO: 15, and an HCDR3 comprising the amino acid sequence of SEQ ID NO: 16; and a light chain variable region comprising an LCDR 1 comprising the amino acid sequence of SEQ ID NO: 17, an LCDR2 comprising the amino acid sequence of SEQ ID NO: 18, and an LCDR3 comprising the amino acid sequence of SEQ ID NO: 19.

8. The method of claim 1, wherein the bispecific antibody comprises a CD3-binding moiety comprising a heavy chain variable region comprising an HCDR 1 comprising the amino acid sequence of SEQ ID NO: 32, an HCDR2 comprising the amino acid sequence of SEQ ID NO: 33, and an HCDR3 comprising the amino acid sequence of SEQ ID NO: 34; and a light chain variable region comprising an LCDR 1 comprising the amino acid sequence of SEQ ID NO: 35, an LCDR2 comprising the amino acid sequence of SEQ ID NO: 36, and an LCDR3 comprising the amino acid sequence of SEQ ID NO: 37.

9. The method of claim 7, wherein the CEA-binding moiety comprises
   a heavy chain variable region comprising the amino acid sequence of SEQ ID NO: 20 and a light chain variable region comprising the amino acid sequence of SEQ ID NO: 21.

10. The method of claim 5, wherein the IgG antibody is an IgG$_1$ antibody.

11. The method of claim 1, wherein the CD3 is CD3ε.

12. The method of claim 1, wherein the bispecific antibody comprises a CD3-binding moiety and a CEA-binding moiety, wherein:
   (i) the CD3-binding moiety comprises a heavy chain variable region comprising the amino acid sequence of SEQ ID NO: 38 and a light chain variable region comprising the amino acid sequence of SEQ ID NO: 39; and
   (ii) the CEA-binding moiety comprises a heavy chain variable region comprising the amino acid sequence of SEQ ID NO: 20 and a light chain variable region comprising the amino acid sequence of SEQ ID NO: 21.

13. The method of claim 1, wherein:
   (a) the bispecific antibody comprises a CD3-binding moiety and a CEA-binding moiety, wherein:
      (i) the CD3-binding moiety comprises a heavy chain variable region comprising the amino acid sequence of SEQ ID NO: 38 and a light chain variable region comprising the amino acid sequence of SEQ ID NO: 39; and
      (ii) the CEA-binding moiety comprises a heavy chain variable region comprising the amino acid sequence of SEQ ID NO: 20 and a light chain variable region comprising the amino acid sequence of SEQ ID NO: 21; and (b) the Type II anti-CD20 antibody comprises a heavy chain variable region comprising the amino acid sequence of SEQ ID NO: 10 and a light chain variable region comprising the amino acid sequence of SEQ ID NO: 11.

14. The method of claim 8, wherein the CD3-binding moiety comprises a heavy chain variable region comprising the amino acid sequence of SEQ ID NO: 38 and a light chain variable region comprising the amino acid sequence of SEQ ID NO: 39.

15. A method of treating a CD20-positive B-cell disorder in a subject, the method comprising a treatment regimen comprising:
   (i) administering to the subject a Type II anti-CD20 antibody comprising a heavy chain variable region comprising an HCDR1 comprising the amino acid sequence of SEQ ID NO: 4, an HCDR2 comprising the amino acid sequence of SEQ ID NO: 5, and an HCDR3 comprising the amino acid sequence of SEQ ID NO: 6; and a light chain variable region comprising an LCDR1 comprising the amino acid sequence of SEQ ID NO: 7, an LCDR2 comprising the amino acid sequence of SEQ ID NO: 8, and an LCDR3 comprising the amino acid sequence of SEQ ID NO: 9, and consecutively, after a period of time,
   (ii) administering to the subject a therapeutic agent comprising a bispecific antibody, wherein the bispecific antibody specifically binds to CD3 and CD20,
   wherein the period of time between step (i) and step (ii) is sufficient for the Type II anti-CD20 antibody to reduce the number of B cells in the subject.

16. The method of claim 15, wherein the CD3 is CD3ε.

17. The method of claim 15, wherein the treatment regimen effectively reduces the formation of ADAs in the subject against the therapeutic agent, as compared to a corresponding treatment regimen without the administration of the Type II anti-CD20 antibody.

18. The method of claim 15, wherein the treatment regimen effectively reduces cytokine release in the subject associated with the administration of the therapeutic agent, as compared to a corresponding treatment regimen without the administration of the Type II anti-CD20 antibody.

19. The method of claim 15, wherein the Type II anti-CD20 antibody comprises a heavy chain variable region comprising the amino acid sequence of SEQ ID NO: 10 and a light chain variable region comprising the amino acid sequence of SEQ ID NO: 11.

20. The method of claim 15, wherein the Type II anti-CD20 antibody is an IgG antibody, and wherein at least about 40% of the N-linked oligosaccharides in the Fc region of the Type II anti-CD20 antibody are non-fucosylated.

21. The method of claim 20, wherein the IgG antibody is an $IgG_1$ antibody.

22. The method of claim 19, wherein the Type II anti-CD20 antibody is obinutuzumab.

23. The method of claim 15, wherein the bispecific antibody comprises a CD3-binding moiety comprising a heavy chain variable region comprising an HCDR1 comprising the amino acid sequence of SEQ ID NO: 32, an HCDR2 comprising the amino acid sequence of SEQ ID NO: 33, and an HCDR3 comprising the amino acid sequence of SEQ ID NO: 34; and a light chain variable region comprising an LCDR1 comprising the amino acid sequence of SEQ ID NO: 35, an LCDR2 comprising the amino acid sequence of SEQ ID NO: 36, and an LCDR3 comprising the amino acid sequence of SEQ ID NO: 37.

24. The method of claim 23, wherein the CD3-binding moiety comprises a heavy chain variable region comprising the amino acid sequence of SEQ ID NO: 38 and a light chain variable region comprising the amino acid sequence of SEQ ID NO: 39.

25. The method of claim 15, wherein the bispecific antibody comprises a CD20-binding moiety comprising a heavy chain variable region comprising an HCDR 1 comprising the amino acid sequence of SEQ ID NO: 4, an HCDR2 comprising the amino acid sequence of SEQ ID NO: 5, and an HCDR3 comprising the amino acid sequence of SEQ ID NO: 6; and a light chain variable region comprising an LCDR 1 comprising the amino acid sequence of SEQ ID NO: 7, an LCDR2 comprising the amino acid sequence of SEQ ID NO: 8, and an LCDR3 comprising the amino acid sequence of SEQ ID NO: 9.

26. The method of claim 25, wherein the CD20-binding moiety comprises a heavy chain variable region comprising the amino acid sequence of SEQ ID NO: 10 and a light chain variable region comprising the amino acid sequence of SEQ ID NO: 11.

27. The method of claim 15, wherein the bispecific antibody comprises a CD3-binding moiety and a CD20-binding moiety, wherein:
   (i) the CD3-binding moiety comprises a heavy chain variable region comprising the amino acid sequence of SEQ ID NO: 38 and a light chain variable region comprising the amino acid sequence of SEQ ID NO: 39; and
   (ii) the CD20-binding moiety comprises a heavy chain variable region comprising the amino acid sequence of SEQ ID NO: 10 and a light chain variable region comprising the amino acid sequence of SEQ ID NO: 11.

28. The method of claim 15, wherein:
(a) the bispecific antibody comprises a CD3-binding moiety and a CD20-binding moiety, wherein:
   (i) the CD3-binding moiety comprises a heavy chain variable region comprising the amino acid sequence of SEQ ID NO: 38 and a light chain variable region comprising the amino acid sequence of SEQ ID NO: 39; and
   (ii) the CD20-binding moiety comprises a heavy chain variable region comprising the amino acid sequence of SEQ ID NO: 10 and a light chain variable region comprising the amino acid sequence of SEQ ID NO: 11; and
(b) the Type II anti-CD20 antibody comprises a heavy chain variable region comprising the amino acid sequence of SEQ ID NO: 10 and a light chain variable region comprising the amino acid sequence of SEQ ID NO: 11.

* * * * *

UNITED STATES PATENT AND TRADEMARK OFFICE
CERTIFICATE OF CORRECTION

PATENT NO. : 11,013,801 B2
APPLICATION NO. : 15/371891
DATED : May 25, 2021
INVENTOR(S) : Marina Bacac et al.

It is certified that error appears in the above-identified patent and that said Letters Patent is hereby corrected as shown below:

On the Title Page

Page 4, under OTHER PUBLICATIONS, Line 30, in Klein et al., replace "Dubel" with --Dübel--.

In the Specification

Column 1, Line 49, replace "[Suppl 2]II" with --[Suppl 2]:II--.

Column 3, Line 26, replace "CD20+B cells" with --$CD20^+$ B cells--.

Column 10, Line 11, replace "CDR" with --$CD3\varepsilon$--.

Column 11, Line 44, replace "R06895882" with --RO6895882--;
    Line 46, replace "R06895882" with --RO6895882--;
    Line 53, replace "R06895882" with --RO6895882--;
    Line 63, replace "R06895882" with --RO6895882--.

Column 13, Line 7, replace "mg/kg+CD20XCD3" with --mg/kg + CD20XCD3--;
    Line 49, replace "BMS" with --BM5--;
    Line 50, replace "LFS" with --LF5--.

Column 15, Line 21, replace "Sauve" with --Sauvé--;
    Line 44, replace "Sauve" with --Sauvé--.

Column 16, Line 6, replace "A42, A42" with --A42, $A_{42}$--.

Column 20, Line 58, replace "lambda (k)" with --lambda ($\lambda$)--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,013,801 B2

Column 30, Line 19, replace "(CD3c)" with --(CD3ε)--;
    Line 20, replace "CD3c" with --CD3ε--;
    Line 24, replace "CD3c" with --CD3ε--.

Column 32, Line 41, replace "p.'75-'76" with --p.75-76--.

Column 33, Line 29, replace "CytoTox 96®" with --CytoTox 96®--.

Column 35, Line 16, replace "13(1,2)" with --β(1,2)--.

Column 36, Line 6, replace "E4-PHA" with --E$_4$-PHA--.

Column 37, Line 37, replace "F(ab')2" with --F(ab')$_2$--.

Column 38, Line 66, replace "HuMAB®" with --HUMAB®--.

Column 39, Lines 1-2, replace "VELOCIMOuSE®" with --VELOCIMOUSE®--.

Column 42, Line 50, replace "Carbon-4-labeled" with --Carbon-14-labeled--.

Column 43, Line 59, replace "CD40. CD226. CD28, OX40." with --CD40, CD226, CD28, OX40,--;
    Lines 62-63, replace "CD226. CD28. OX40, GITR. CD137" with
    --CD226, CD28, OX40, GITR, CD137--.

Column 44, Lines 3-4, replace "VISTA. LAG-3. B7-H3, B7-H4, IDO, TIGIT, MICA/B. or arginase"
with --VISTA, LAG-3, B7-H3, B7-H4, IDO, TIGIT, MICA/B, or arginase--;
    Line 7, replace "PD-1 TIM-3" with --PD-1, TIM-3--;
    Line 8, replace "MICA/B. or arginase" with --MICA/B, or arginase--;
    Line 13, replace "CT-01" with --CT-011--;
    Line 32, replace "YW243.55.S70. MPDL3280A. MDX-1105" with
    --YW243.55.S70, MPDL3280A, MDX-1105--.

Column 46, Line 19, replace "MM-11" with --MM-111--;
    Line 44, replace "AMG212. MT112" with --AMG212, MT112--;
    Line 62, replace "XmAb®13676" with --XmAb®13676--.

Column 47, Line 56, replace "CD3E" with --CD3ε--.

Column 48, Line 38, replace "XmAb®13676" with --XmAb®13676--;
    Line 50, replace "XmAb®13551, XmAb®15426, or XmAb®14702" with
    --XmAb®13551, XmAb®15426, or XmAb®14702--;
    Line 60, replace "XmAb®14045" with --XmAb®14045--.

Column 51, Line 31, replace "IFN-βP" with --IFN-β--;
    Line 51, replace "T (T) cells" with --T (T$_{reg}$) cells--.

CERTIFICATE OF CORRECTION (continued)
U.S. Pat. No. 11,013,801 B2

Column 52, Line 11, replace "IFN-7" with --IFN-γ--.

Column 65, Line 30, replace "FIGS. 6" with --FIGS. 6I--.

Column 77, Line 14, replace "F405" with --F405I--.

Column 80, Line 66, replace "P329G. or a" with --P329G, or a--.

Column 81, Line 49, replace "CytoTox 96®" with --CytoTox 96®--.

Column 93, Line 15, replace "(IFN-7)" with --IFN-γ--.

Column 111, Line 55, replace "CD20. CD19" with --CD20, CD19--.

Column 112, Line 61, replace "OX40. G1TR, CD27. HVEM" with --OX40, GITR, CD27, HVEM--.

Column 114, Line 59, replace "CD3E" with --CD3ε--.

Column 115, Line 31, replace "bsAB. 61. The" with --bsAB. ¶ 61. The--.

Column 118, Line 33, replace "CD3E" with --CD3ε--.

Column 120, Line 63, replace "CD1 R68955882" with --C1D1 RO6895882--.

Column 121, Line 10, replace "R0689588" with --RO6895882--;
    Line 18, replace "RO895882" with --RO6895882--;
    Line 20, replace "RO895882" with --RO6895882--;
    Line 23, replace "RO895882" with --RO6895882--;
    Line 41, replace "EH" with --EIH--;
    Line 45, replace "(0.98%)" with --(98%)--;
    Line 48, replace "(10-196.830). 32 out of" with --(10 — 196.830), 32 out of--;
    Line 52, replace "day 5. i.e. 96" with --day 5, i.e. 96--;
    Line 59, replace "R06895882" with --RO6895882--;
    Line 62, replace "R06895882" with --RO6895882--;
    Line 67, replace "R06895882" with --RO6895882--.

Column 122, Line 1, replace "R6895882" with --RO6895882--;
    Line 6, replace "R6895882" with --RO6895882--;
    Line 15, replace "R06895882" with --RO6895882--;
    Line 60, replace "(CD1)" with --(C1D1)--.

Column 123, Line 24, replace "CD1 with CEA" with --C1D1 with CEA--;
    Line 44, replace "C2D pre-dose" with --C2D1 pre-dose--.

Column 129, Line 22, replace "CD3 - nimals" with --CD3 - animals--.

CERTIFICATE OF CORRECTION (continued)
U.S. Pat. No. 11,013,801 B2

Column 130, Line 24, replace "CD20+B" with --CD20$^+$ B--;
    Line 26, replace "CD20×CD3" with --CD20XCD3--;
    Table 6, replace "parameters of CD2OXCD3" with --parameters of CD20XCD3--;
    Table 6, replace "Dose (m/kg)" with --Dose (μg/kg)--;
    Table 6, replace "100-1000 μg/kg CD2OXCD3" with --100-1000 μg/kg CD20XCD3--;
    Table 6, replace "5 days prior to CD2OXCD3" with --5 days prior to CD20XCD3--.

Column 253, Line 32, replace "CD3c" with --CD3ε--.